US009957505B2

(12) United States Patent
Hauser

(10) Patent No.: US 9,957,505 B2
(45) **Date of Patent: *May 1, 2018**

(54) POLYNUCLEOTIDES FOR MULTIVALENT RNA INTERFERENCE, COMPOSITIONS AND METHODS OF USE THEREOF

(71) Applicant: HALO-BIO RNAI THERAPEUTICS, INC., Seattle, WA (US)

(72) Inventor: Todd M. Hauser, Seattle, WA (US)

(73) Assignee: HALO-BIO RNAI THERAPEUTICS, INC., Seattle, WA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/954,653

(22) Filed: Nov. 30, 2015

(65) Prior Publication Data

US 2016/0160215 A1 Jun. 9, 2016

Related U.S. Application Data

(63) Continuation of application No. 13/375,460, filed as application No. PCT/US2010/036962 on Jun. 1, 2010, now Pat. No. 9,200,276.

(Continued)

(51) Int. Cl.

*C12N 15/113* (2010.01)
*C12N 15/11* (2006.01)

(52) U.S. Cl.

CPC .......... *C12N 15/113* (2013.01); *C12N 15/111* (2013.01); *C12N 15/1131* (2013.01);

(Continued)

(58) Field of Classification Search

None

See application file for complete search history.

(56) References Cited

U.S. PATENT DOCUMENTS

| | | | |
|---|---|---|---|
| 5,034,506 | A | 7/1991 | Summerton et al. |
| 5,142,047 | A | 8/1992 | Summerton et al. |

(Continued)

FOREIGN PATENT DOCUMENTS

| | | |
|---|---|---|
| AU | 2002326410 B2 | 7/2002 |
| AU | 2004263830 B2 | 6/2004 |

(Continued)

OTHER PUBLICATIONS

Pertzev, A. V. et al., "Characterization of RNA sequence determinants and antideterminants of processing reactivity for a minimal substrate of *Escherichia coli* ribonuclease 111," Nucleic Acids Research, 34(13):3708-3721 (2006).

(Continued)

*Primary Examiner* — Jennifer Pitrak McDonald

(74) *Attorney, Agent, or Firm* — Perkins Coie LLP; Patrick D. Morris

(57) ABSTRACT

The present invention includes bivalent or multivalent nucleic acid molecules or complexes of nucleic acid molecules having two or more target-specific regions, in which the target-specific regions are complementary to a single target gene at more than one distinct nucleotide site, and/or in which the target regions are complementary to more than one target gene or target sequence. Also included are compositions comprising such nucleic acid molecules and methods of using the same for multivalent RNA interference and the treatment of a variety of diseases and infections.

17 Claims, 23 Drawing Sheets

Related U.S. Application Data

(60) Provisional application No. 61/183,011, filed on Jun. 1, 2009.

(52) U.S. Cl.
CPC ...... *C12N 2310/14* (2013.01); *C12N 2310/51* (2013.01); *C12N 2310/52* (2013.01); *C12N 2310/53* (2013.01); *C12N 2320/30* (2013.01)

(56) References Cited

U.S. PATENT DOCUMENTS

| | | | |
|---|---|---|---|
| 5,166,315 | A | 11/1992 | Summerton et al. |
| 5,217,866 | A | 6/1993 | Summerton et al. |
| 5,445,934 | A | 8/1995 | Fodor et al. |
| 5,506,337 | A | 4/1996 | Summerton et al. |
| 5,521,063 | A | 5/1996 | Summerton et al. |
| 5,539,082 | A | 7/1996 | Nielsen et al. |
| 5,650,298 | A | 7/1997 | Bujard et al. |
| 5,698,685 | A | 12/1997 | Summerton et al. |
| 5,714,331 | A | 2/1998 | Buchardt et al. |
| 5,719,262 | A | 2/1998 | Buchardt et al. |
| 5,856,174 | A | 1/1999 | Lipshutz et al. |
| 5,874,554 | A | 2/1999 | Gamble et al. |
| 5,898,031 | A | 4/1999 | Crooke |
| 5,922,927 | A | 7/1999 | Bujard et al. |
| 6,013,516 | A | 1/2000 | Verma et al. |
| 6,107,094 | A | 8/2000 | Crooke |
| 6,218,181 | B1 | 4/2001 | Verma et al. |
| 6,271,348 | B1 | 8/2001 | Bujard et al. |
| 6,506,559 | B1 | 1/2003 | Fire et al. |
| 6,670,461 | B1 | 12/2003 | Wengel et al. |
| 6,794,499 | B2 | 9/2004 | Wengel et al. |
| 6,969,766 | B2 | 11/2005 | Kim et al. |
| 7,022,851 | B2 | 4/2006 | Kim et al. |
| 7,034,133 | B2 | 4/2006 | Wengel et al. |
| 7,053,207 | B2 | 5/2006 | Wengel |
| 7,056,704 | B2 | 6/2006 | Tuschl et al. |
| 7,060,809 | B2 | 6/2006 | Wengel et al. |
| 7,078,196 | B2 | 7/2006 | Kim et al. |
| 7,084,125 | B2 | 8/2006 | Wengel |
| 7,125,994 | B2 | 10/2006 | Kim et al. |
| 7,145,006 | B2 | 12/2006 | Kim et al. |
| 7,179,896 | B2 | 2/2007 | Kim et al. |
| 7,196,187 | B2 | 3/2007 | Frenken et al. |
| 7,211,668 | B2 | 5/2007 | Kim et al. |
| 7,320,965 | B2 | 1/2008 | Sah et al. |
| 7,348,314 | B2 | 3/2008 | John et al. |
| 7,361,752 | B2 | 4/2008 | Heidenreich et al. |
| 7,423,142 | B2 | 9/2008 | Vornlocher |
| 7,432,250 | B2 | 10/2008 | Crooke |
| 7,473,525 | B2 | 1/2009 | Kreutzer et al. |
| 7,507,809 | B2 | 3/2009 | Meyers |
| 7,517,865 | B2 | 4/2009 | Meyers |
| 7,528,118 | B2 | 5/2009 | Soutschek et al. |
| 7,569,575 | B2 | 8/2009 | Sorensen et al. |
| 7,572,582 | B2 | 8/2009 | Wengel et al. |
| 7,579,451 | B2 | 8/2009 | Manoharan et al. |
| 7,582,744 | B2 | 9/2009 | Manoharan et al. |
| 7,595,306 | B2 | 9/2009 | Bumerot |
| 7,615,618 | B2 | 11/2009 | Manoharan et al. |
| 7,626,014 | B2 | 12/2009 | Manoharan et al. |
| 7,629,321 | B2 | 12/2009 | Crooke |
| 7,632,932 | B2 | 12/2009 | Manoharan et al. |
| 7,674,778 | B2 | 3/2010 | Manoharan et al. |
| 7,674,779 | B2 | 3/2010 | Heidenreich et al. |
| 7,695,902 | B2 | 4/2010 | Crooke |
| 2002/0086356 | A1 | 7/2002 | Tuschl et al. |
| 2003/0027783 | A1 | 2/2003 | Zernicka-Goetz et al. |
| 2003/0108923 | A1 | 6/2003 | Tuschl et al. |
| 2003/0139363 | A1 | 7/2003 | Kay et al. |
| 2003/0153519 | A1 | 8/2003 | Kay et al. |
| 2004/0053875 | A1 | 3/2004 | Kreutzer et al. |
| 2004/0072779 | A1 | 4/2004 | Kreutzer et al. |
| 2004/0102408 | A1 | 5/2004 | Kreutzer et al. |
| 2004/0171031 | A1 | 9/2004 | Baker et al. |
| 2004/0259247 | A1 | 12/2004 | Tuschl et al. |
| 2005/0026278 | A1 | 2/2005 | Tuschl et al. |
| 2005/0100907 | A1 | 5/2005 | Kreutzer et al. |
| 2005/0107325 | A1 | 5/2005 | Manoharan et al. |
| 2005/0142114 | A1 | 6/2005 | Gieseler et al. |
| 2005/0153337 | A1 | 7/2005 | Manoharan |
| 2005/0164235 | A1 | 7/2005 | Manoharan et al. |
| 2005/0176667 | A1 | 8/2005 | Vornlocher |
| 2005/0191618 | A1 | 9/2005 | McSwiggen et al. |
| 2005/0196781 | A1 | 9/2005 | Robin et al. |
| 2005/0233342 | A1 | 10/2005 | Manoharan et al. |
| 2005/0234006 | A1 | 10/2005 | Tuschl et al. |
| 2005/0234007 | A1 | 10/2005 | Tuschl et al. |
| 2006/0094678 | A1 | 5/2006 | Vornlocher et al. |
| 2006/0166913 | A1 | 7/2006 | Suzuki |
| 2006/0166922 | A1 | 7/2006 | Eichler et al. |
| 2007/0003960 | A1 | 1/2007 | Tuschl et al. |
| 2007/0003961 | A1 | 1/2007 | Tuschl et al. |
| 2007/0003962 | A1 | 1/2007 | Tuschl et al. |
| 2007/0003963 | A1 | 1/2007 | Tuschl et al. |
| 2007/0093445 | A1 | 4/2007 | Tuschl et al. |
| 2007/0123482 | A1 | 5/2007 | Stoffel et al. |
| 2007/0141610 | A1 | 6/2007 | Spier |
| 2007/0148246 | A1 | 6/2007 | Luo et al. |
| 2007/0155686 | A1 | 7/2007 | Akinc et al. |
| 2007/0173473 | A1 | 7/2007 | McSwiggen et al. |
| 2007/0179100 | A1 | 8/2007 | Manoharan |
| 2007/0185050 | A1 | 8/2007 | Heidenreich et al. |
| 2007/0197460 | A1 | 8/2007 | Fougerolles et al. |
| 2007/0213292 | A1 | 9/2007 | Stoffel et al. |
| 2007/0264265 | A1 | 11/2007 | Goldenberg et al. |
| 2007/0270579 | A1 | 11/2007 | Jadhav et al. |
| 2007/0275465 | A1 | 11/2007 | Woppmann et al. |
| 2007/0275914 | A1 | 11/2007 | Manoharan et al. |
| 2008/0009457 | A1 | 1/2008 | Gould-Fogerite et al. |
| 2008/0039415 | A1 | 2/2008 | Stewart et al. |
| 2008/0132461 | A1 | 6/2008 | Tuschi et al. |
| 2008/0166800 | A1 | 7/2008 | Kreutzer et al. |
| 2008/0171861 | A1 | 7/2008 | Kreutzer et al. |
| 2008/0171862 | A1 | 7/2008 | Kreutzer et al. |
| 2008/0182981 | A1 | 7/2008 | Kreutzer et al. |
| 2008/0194512 | A1 | 8/2008 | John et al. |
| 2008/0213891 | A1 | 9/2008 | Manoharan et al. |
| 2008/0221054 | A1 | 9/2008 | Zernicka-Goetz et al. |
| 2008/0221055 | A1 | 9/2008 | Sah et al. |
| 2008/0233651 | A1 | 9/2008 | Kreutzer et al. |
| 2008/0242628 | A1 | 10/2008 | Zernicka-Goetz et al. |
| 2008/0255345 | A1 | 10/2008 | Manoharan et al. |
| 2008/0261303 | A1 | 10/2008 | Kreutzer et al. |
| 2008/0269147 | A1 | 10/2008 | Tuschl et al. |
| 2008/0311630 | A1 | 12/2008 | Schroff et al. |
| 2009/0005549 | A1 | 1/2009 | Manoharan et al. |
| 2009/0023673 | A1 | 1/2009 | Manoharan et al. |
| 2009/0143323 | A1 | 6/2009 | Bavari et al. |
| 2010/0016405 | A1 | 1/2010 | Bumcrot et al. |
| 2010/0069461 | A1 | 3/2010 | Vornlocher et al. |
| 2010/0240730 | A1 | 9/2010 | Beigelman et al. |
| 2012/0016007 | A1 | 1/2012 | Lee et al. |

FOREIGN PATENT DOCUMENTS

| | | | |
|---|---|---|---|
| EP | 1144623 | B1 | 8/2002 |
| EP | 0928290 | B1 | 3/2005 |
| EP | 1214945 | B1 | 6/2005 |
| EP | 1230375 | B1 | 7/2005 |
| EP | 1600506 | A2 | 11/2005 |
| EP | 1621545 | A2 | 2/2006 |
| EP | 1633770 | A2 | 3/2006 |
| EP | 1407044 | B1 | 9/2007 |
| EP | 1550719 | B1 | 12/2008 |
| EP | 1309726 | B1 | 12/2009 |
| EP | 1605978 | B1 | 9/2010 |
| EP | 1873259 | B1 | 1/2012 |
| EP | 1409506 | B1 | 5/2012 |
| JP | 4095895 | B2 | 6/2008 |
| WO | 2009/018332 | A1 | 2/1909 |
| WO | 97/46570 | | 12/1997 |
| WO | 02/044321 | A2 | 6/2002 |

(56) References Cited

FOREIGN PATENT DOCUMENTS

| | | | |
|---|---|---|---|
| WO | 2004/030634 | A2 | 4/2004 |
| WO | 2004/035765 | A2 | 4/2004 |
| WO | 2004/064737 | A2 | 8/2004 |
| WO | 2004/080406 | A2 | 9/2004 |
| WO | 2004/090108 | A2 | 10/2004 |
| WO | 2004/091515 | A2 | 10/2004 |
| WO | 2004/094345 | A2 | 11/2004 |
| WO | 2004/094595 | A2 | 11/2004 |
| WO | 2005/004794 | A2 | 1/2005 |
| WO | 2005/014782 | A2 | 2/2005 |
| WO | 2005/089224 | A2 | 9/2005 |
| WO | 2005/097817 | A2 | 10/2005 |
| WO | 2005/115481 | A2 | 12/2005 |
| WO | 2006/020768 | A2 | 2/2006 |
| WO | 2006/032041 | A2 | 3/2006 |
| WO | 2006/036916 | A2 | 4/2006 |
| WO | 2006/063252 | A2 | 6/2006 |
| WO | 2006/066158 | A2 | 6/2006 |
| WO | 2006/073458 | A2 | 7/2006 |
| WO | 2006/073602 | A2 | 7/2006 |
| WO | 2006/073727 | A2 | 7/2006 |
| WO | 2006/074346 | A2 | 7/2006 |
| WO | 2006/078278 | A2 | 7/2006 |
| WO | 2006/081192 | A2 | 8/2006 |
| WO | 2006/084209 | A2 | 8/2006 |
| WO | 2006/088490 | A2 | 8/2006 |
| WO | 2006/093526 | A2 | 9/2006 |
| WO | 2006/0112872 | A2 | 10/2006 |
| WO | 2007/002718 | A2 | 1/2007 |
| WO | 2007/014077 | A2 | 2/2007 |
| WO | 2007/021896 | A2 | 2/2007 |
| WO | 2007/022470 | A2 | 2/2007 |
| WO | 2007/051045 | A2 | 5/2007 |
| WO | 2007/053696 | A2 | 5/2007 |
| WO | 2007/056326 | A2 | 5/2007 |
| WO | 2007/056331 | A2 | 5/2007 |
| WO | 2007/056859 | A1 | 5/2007 |
| WO | 2007/091269 | A2 | 8/2007 |
| WO | 2007/109097 | A2 | 9/2007 |
| WO | 2007/115168 | A2 | 10/2007 |
| WO | 2007/127919 | A2 | 11/2007 |
| WO | 2007/134161 | A2 | 11/2007 |
| WO | 2007/137156 | A2 | 11/2007 |
| WO | 2007/137220 | A2 | 11/2007 |
| WO | 2007/137239 | A2 | 11/2007 |
| WO | 2008/008719 | A2 | 1/2008 |
| WO | 2008/021157 | A1 | 2/2008 |
| WO | 2008/036127 | A2 | 3/2008 |
| WO | 2008/036638 | A2 | 3/2008 |
| WO | 2008/036929 | A2 | 3/2008 |
| WO | 2008/036933 | A2 | 3/2008 |
| WO | 2008/042973 | A2 | 4/2008 |
| WO | 2008/091703 | A2 | 7/2008 |
| WO | 2008/121604 | A2 | 10/2008 |
| WO | 2008/131419 | A2 | 10/2008 |
| WO | 2009/020771 | A2 | 2/2009 |
| WO | 2009/064471 | A1 | 5/2009 |
| WO | 2009/073809 | A2 | 6/2009 |
| WO | 2010/078516 | A2 | 7/2010 |
| WO | 2010/135716 | A1 | 11/2010 |
| WO | 2010/141511 | A2 | 12/2010 |

OTHER PUBLICATIONS

Nielsen, P. E. et al., "Sequence-selective recognition of DNA by strand displacement with a thyminesubstituted polyamide," Science, 254(5037):1497-1500 (1991).

Obika, S., et al., "Synthesis of 2'-0,4'-C-methyleneuridine and-cytidine. Novel bicyclic nucleosides having a Fixed C3-endo sugar puckering," Tetrahedron Letters, 38(50):8735-8738 (1997).

Obika, S. et al., "Stability and structural features of the duplexes containing necleoside analogues with a fixed N-type conformation, 2'-0,4'-C-methyleneribonucleosides," Tetrahedron Letters, 39(30):5401-5404 (1998).

Obika, S. et al., "Synthesis and properties of 3'-amino-2',4'-SNA, a bridged nucleic acid with a N3'-4P5' phosphoramidate linkage," Bioorganic & Medicinal Chemistry, 16(20):9230-9237 (2008).

Ohkawa, J. et al., "Control of the functional activity of an antisense RNA by a tetracycline-responsive derivative of the human U6 snRNA promoter," Human Gene Therapy, 11 :577-585 (2000).

Paule, M. R. et al., "Transcription by RNA polymerases I and III," Nucleic Acids Research, 28(6):1283-1298 (2000).

Santini, G. P. H. et al., "DNA tri-and tetra-loops and RNA tetra-loops hairpins fold as elastic biopolymer chains in agreement with PDS coordinates," Nucleic Acids Research, 31(3):1086-1096 (2003).

Sharp, P.A., "RNAi and double-strand RNA," Genes & Development, 13:139-141 (1999).

Sharp, P.A., "RNA interference—2001," Genes & Development, 15:485-490 (2001).

Singer-Sam, J. et al., "Sequence of the promoter region of the gene for human X-linked 3-phosphoglycerate kinase," Gene, 32:409-417 (1984).

Stamato, T. D. et al., "Mutagen treatment of single Chinese hamster ovary cells produces colonies mosaic for Glucose-6-phosphate dehydrogenase activity," Somatic Cell Genetics, 8(5):643-651 (1982).

Sutton, R. E. et al., "Human immunodeficiency virus type 1 vectors efficiently transduce human hematopoietic stem cells," Journal of Virology, 72(7):5781-5788 (1998).

Tabara, H. et al., "The rde-1 gene, RNA interference, and transposon silencing in C.elegans," Cell, 99:123-132 (1999).

Takadera, T. et al., "Structure of the two promoters of the human Ick gene: differential accumulation of two classes of Ick transcripts in T cells," Molecular and Cellular Biology, 9(5):2173-2180 (1989).

Uchida, N. et al., "HIV, but not murine leukemia virus, vectors mediate high efficiency gene transfer into freshly isolated Go/G1 human hematopoietic stem cells," Proc. Natl. Acad. Sci. USA, 95:11939-11944 (1998).

Uhlmann, E. et al., "Antisense: Chemical Modifications," In Encyclopedia of Cancer, vol. X, pp. 64-81, Academic Press Inc. (1997).

Wargelius, A. et al., "Double stranded RNA induces specific developmental defects in zebrafish embyos," Biochemical and Biophysical Research Communication, 263:156-161 (1999).

Singh, S. K. et al., "LNA (locked nucleic acids): synthesis and high-affinity necleic acid recognition," Chemical Communications, 3:455-456 (1998).

Wengel, J., "Synthesis of 3'-C- and 4'-C-branched oligodeoxynucleotides and the development of locked nucleic acid (LNA)," Accounts of Chemical Research, 32(4):301-310 (1999).

Wu, H. et al., "A novel family of RNA tetraloop structure forms the recognition site for *Saccharomyces cerevisiae* RNase III," The EMBO Journal, 20(24):7240-7249 (2001).

Yee, S-P et al. "The regulation of myogenin gene expression during the embryonic development of the mouse," Genes & Development, 7:1277-1289 (1993).

Zamore, P. D. et al., "RNAi: Double-stranded RNA directs the ATP-dependent cleavage of mRNA at 21 to 23 nucleotide intervals," Cell, 101:25-33 (2000).

Zufferey, R. et al., "Self-inactivating lentivirus vector for safe and efficient in vivo gene delivery," Journal of Virology, 72(12):9873-9880 (1998).

Gan, J., et al., "Structural Insight into the Mechanism of Double-Stranded RNA Processing by Ribonuclease III," Cell 124:355-366 (2006).

Anderson, J., et al., "Bispecific Short Hairpin siRNA Constructs Targeted to CD4, CXCR4, and CCR5 Confer HIV-1 Resistance," Oligonucleotides 13:303-312 (2003).

Cheng, T.L., et al., "Multitarget Therapy of Malignant Cancers by the Head-to-Tail Tandem Array Multiple shRNAs Expression System," Cancer Gene Therapy 16:516-531 (2009).

Hong, C. A., et al., "Gene Silencing by siRNA Microhydrogels via Polymeric Nanoscale Condensation," Journal of the American Chemical Society 133:13914-13917 (2011).

Stove, V., et al., "Multiple Gene Knock-Down by a Single Lentiviral Vector Expressing and Array of Short Hairpin RNAs," Electronic Journal of Biotechnology 9(5):573-579 (2006).

(56) References Cited

OTHER PUBLICATIONS

Um, S. H., et al., "Enzyme-Catalysed Assembly of DNA Hydrogel," Nature Materials 5:797-801 (2006).
Altschul, S. F., et al., "Gapped BLAST and PSI-BLAST: a new generation of protein database search programs," Nucleic Acids Research 25(17):3389-3402 (1997).
International Preliminary Report on Patentability for International Application No. PCT/US2010/036962, dated Dec. 6, 2011.
Adra, C. N. et al., "Cloning and expression of the mouse pgk-1 gene and the nucleotide sequence of its promoter," Gene, 60(1):65-74 (1987).
Bass, B. L., "The short answer," Nature, 411:428-429 (2001).
Bernstein, E. et al., "Role for a bidentate ribonuclease in the initiation step of RNA interference," Nature, 409:363-366 (2001).
Blaszczyk, J. et al., "Noncatalytic assembly of ribonuclease III with double-stranded RNA," Structure, 12(3):457-466 (2004).
Bosher, J. M. et al., "RNA interference can target pre-mRNA: consequences for gene expression in Caenorhabditis elegans operon," Genetics, 153(3):1245-1256 ( 1999).
Brummelkamp, T. R. et al., "A system for stable expression of short interfering RNAs in mammalian cells," Science, 296:550-552 (2002).
Brummelkamp, T. R. et al., "Stable suppression of tumorigenicity by virus-mediated RNA interference," Cancer Cell, 2(3):243-247 (2002).
Burgin, A. B., Jr. et al., "Chemically modified hammerhead ribozymes with improved catalytic rates," Biochemistry, 35(45):14090-14097 (1996).
Carson, P. E. et al., "Glucose-6-phosphate dehydrogenase deficiency and related disorders of the pentose phosphate pathway," The American Journal of Medicine, 41:744-764 (1966).
Case, S.S. et al., "Stable transduction of quiescent CD34+CD38-human hematopoietic cells by HIV-1-based lentiviral vectors," Proc. Natl. Acad. Sci. USA, 96:2988-2993 (1999).
Chang, C. I. et al., "Branched, tripartite-interfering RNAs silence multiple target genes with long guid strands," Nucleic Acid Therapeutics, 22(1):30-39 (2012).
Dobson, M. J. et al., "Conservation of high efficiency promoter sequences in *Saccharomyces cerevisiae*," Nucleic Acids Research, 10(8):2625-2637 (1982).
Egholm, M. et al., "PNA hybridizes to complementary oligonucleotides obeying the Watson-Crick hydrogenbonding rules," Nature, 365:566-568 (1993).
Elbashir, S. M. et al., "RNA interference is mediated by 21- and 22-nucleotide RNAs," Genes and Development, 15: 188-200 (2001).
Elbashir, S. M. et al., "Duplexes of 21-nucleotide RNAs mediate RNA interference in cultured mammalian cells," Nature, 411:494-498 (2001).
Evans, J. T. et al., "Human cord blood CD34+CD38-cell transduction via lentivirus-based gene transfer vectors," Human Gene Therapy, 10:1479-1489 (1999).
Fire, A. et al., "Potent and specific genetic interference by double-stranded RNA in Caenorhabditis elegans," Nature, 391(6669):806-810 (1998).
Fire, A., "RNA-triggered gene silencing," Trends in Genetics, 15(9):358-363 (1999).
Frecha, C. et al., "Stable transduction of quiescent T cells without induction of cycle progression by a novel lentiviral vector pseudotyped with measles virus glycoproteins," Blood, 112(13):4843-4852 (2008).
Gan, J. et al., "Intermediate states of ribonuclease III in complex with double-stranded RNA," Structure, 13(10):1435-1442 (2005).
Gan, J. et al., "A stepwise model for double-stranded RNA processing by ribonuclease III," Molecular Microbiology, 67(1):143-154 (2008).
Garvin, A. M. et al., "Structure of the murine Ick gene and its rearrangement in a murine lymphoma cell line," Molecular and Cellular Biology, 8(8):3058-3064 (1988).
Gundersen, G. et al., "Tissue-specific methylation of a CpG island in transgenic mice," Gene, 113:207-214 (1992).
Gunning, P. et al., "A human beta-actin expression vector system directs high-level accumulation of antisense transcripts," Proc. Natl. Acad. Sci. USA, 84:4831-4835 (1987).
Hammond, S. M. et al., "An RNA-directed nuclease mediates post transcriptional gene silencing in *Drosophila* cells," Nature, 404(6775):293-296 (2000).
Hiramatsu, K. et al., "Genetic characterization of methicillin-resistant *Staphylococcus aureus*," Vaccine, 225:S5-S8 (2004).
Hunter, T. et al., "The characteristics of inhibition of protein synthesis by double-stranded ribonucleic acid in reticulocyte lysates," The Journal of Biological Chemistry, 250(2):409-417 (1975).
Iwakuma, T. et al., "Self-inactivating lentiviral vectors and U3 and U5 modifications," Virology, 261:120-132 (1999).
Ji, X., "Structural basis for non-catalytic and catalytic activities of ribonuclease III," Biological Crystallography, Acta Crystallographica Section D, 62(8):933-940 (2006).
Ji, X., "The mechanism of RNase III action: how dicer dices," Current Topics in Microbiology and Immunology, 320:99-116 (2008).
Karasuyama, H. et al., "Autocrine growth and tumorigenicity of interleukin 2-dependent helper T cells transfected with IL-2 gene," J. Exp. Med., 169:13-25 (1989).
Kennerdell, J. R. et al., "Use of dsRNA-mediated genetic interference to demonstrate that frizzled and frizzled 2 act in the wingless pathway," Cell, 95:1017-1026 (1998).
Ketting, R. F. et al., "Mut-7 of C. elegans, required for transposon silencing and RNA interference, is a homolog of Werner syndrome helicase and RnaseD," Cell, 99:133-141 (1999).
Koshkin, A. A. et al., "LNA (locked nucleic acids): synthesis of the adenine, cytosine, guanine, 5-methylcytosine, thymine and uracil bicyclonucleoside monomers, oligomerisation, and unprecedented nucleic acid recognition" Tetrahedron 54(14):3607-3630 (1998).
Lamontagne, B. et al., "The RNase III family: a conserved structure and expanding functions in eukaryotic dsRNA metabolism," Curr. Issues Mol. Biol., 3(4):71-78 (2001).
Lamontagne, B. et al., "Sequence dependence of substrate recognition and cleavage by yeast RNase III," Journal of Molecular Biology, 327(5):985-1000 (2003).
Lamontagne, B et al., Short RNA guides cleavage by eukaryotic Rnase iII, PLoS ONE, 2(5):e472 (2007).
Lebars, I. et al., "Solution structure of conserved AGNN tetraloops: insights into Rnt1p RNA processing," The EMBO Journal, 20(24):7250-7258 (2001).
Logan, J. et al., "Adenovirus tripartite leader sequence enhances translation of mRNAs late after infection," Proc. Natl. Acad. Sci. USA, 81:3655-3659 ( 1984).
Lohmann, J. U. et al., "Silencing of developmental genes in Hydra," Developmental Biology, 214:211-214 (1999).
Luo, X. M. et al. "Engineering human hematopoietic stem/progenitor cells to produce a broadly neutralizing anti-HIV antibody after in vitro maturation to human B lymphocytes," Blood, 113(7):1422-1431 (2009).
Macrae, I. J. et al., "Ribonuclease revisited: structural insights into ribonuclease III family enzymes," Current Opinion in Structural Biology, 17(1):138-145 (2007).
Meissner, W. et al., "Development of an inducible pol III transcription system essentially requiring a mutated form of the TATA-binding protein," Nucleic Acids Research, 29(8):1672-1682 (2001).
Misquitta, L. et al., "Targeted disruption of gene function in *Drosophila* by RNA interference (RNA-i): a role for nautilus in embryonic somatic muscle formation," Proc. Natl. Acad. Sci. USA., 96:1451-1456 (1999).
Miyoshi, H. et al., "Development of a self-inactivating lentivirus vector," Journal of Virology, 72(10):8150-8157 (1998).
Miyoshi, H. et al., "Transduction of human CD34+ cells that mediate long-term engraftment of NOD/SCIO mice by HIV vectors," Science, 283:682-686 (1999).
Montgomery, M. K. et al., "RNA as a target of double-stranded RNA-mediated genetic interference in Caenorhabiditis elegans," Proc. Natl. Acad. Sci. USA. 95:15502-15507 (1998).

(56) References Cited

OTHER PUBLICATIONS

Narayan, O. et al., "Biology and pathogenesis of lentiviruses," J. Gen. Virology, 70:1617-1639 (1989).
Ngo, H. et al., "Double-stranded RNA induces gene degradation in Trypanosoma brucei," Proc. Natl. Acad. Sci. USA, 95:14687-14692 (1998).
European Patent Office, Official Communication for EP10783959.9, dated Jun. 12, 2017. 7 pages.

SEQ ID NO: 8 GFP Targeting

AUGGUGAGCAAGGGCGAGGAGCUGUUCACCGGGGUGGUGCCCAUCCUGGUCGAGCUGGACGGCGACGUAAACGGCC
ACAAGUUCAGCGUGUCCGGCGAGGGCGAGGGCGAUGCCACCUACGGCAAGCUGACCCUGAAGUUCAUCUGCACCAC
CGGCAAGCUGCCCGUGCCCUGGCCCACCCUCGUGACCACCCUGACCUACGGCGUGCAGUGCUUCAGCCGCUACCCCG
ACCACAUGAAGCAGCACGACUUCUUCAAGUCCGCCAUGCCCGAAGGCUACGUCCAGGAGCGCACCAUCUUCUUCAA
GGACGACGGCAACUACAAGACCCGCGCCGAGGUGAAGUUCGAGGGCGACACCCUGGUGAACCGCAUCGAGCUGAAG
GGCAUCGACUUCAAGGAGGACGGCAACAUCCUGGGGCACAAGCUGGAGUACAACUACAACAGCCACAACGUCUAUA
UCAUGGCCGACAAGCAGAAGAACGGCAUCAAGGUGAACUUCAAGAUCCGCCACAACAUCGAGGACGGCAGCGUGCA
GCUCGCCGACCACUACCAGCAGAACACCCCCAUCGGCGACGGCCCCGUGCUGCUGCCCGACAACCACUACCUGAGCA
CCCAGUCCGCCCUGAGCAAAGACCCCAACGAGAAGCGCGAUCACAUGGUCCUGCUGGAGUUCGUGACCGCCGCCGG
GAUCACUCUCGGCAUGGACGAGCUGUACAAGUAAA

FIG. 8A

SEQ ID NO: 8 GFP Targeting

AUGGUGAGCAAGGGCGAGGAGCUGUUCACCGGGGUGGUGCCCAUCCUGGUCGAGCUGGACGGCGACGUAAACGGCC
ACAAGUUCAGCGUGUCCGGCGAGGGCGAGGGCGAUGCCACCUACGGCAAGCUGACCCUGAAGUUCAUCUGCACCAC
CGGCAAGCUGCCCGUGCCCUGGCCCACCCUCGUGACCACCCUGACCUACGGCGUGCAGUGCUUCAGCCGCUACCCCG
ACCACAUGAAGCAGCACGACUUCUUCAAGUCCGCCAUGCCCGAAGGCUACGUCCAGGAGCGCACCAUCUUCUUCAA
GGACGACGGCAACUACAAGACCCGCGCCGAGGUGAAGUUCGAGGGCGACACCCUGGUGAACCGCAUCGAGCUGAAG
GGCAUCGACUUCAAGGAGGACGGCAACAUCCUGGGGCACAAGCUGGAGUACAACUACAACAGCCACAACGUCUAUA
UCAUGGCCGACAAGCAGAAGAACGGCAUCAAGGUGAACUUCAAGAUCCGCCACAACAUCGAGGACGGCAGCGUGCA
GCUCGCCGACCACUACCAGCAGAACACCCCCAUCGGCGACGGCCCCGUGCUGCUGCCCGACAACCACUACCUGAGCA
CCCAGUCCGCCCUGAGCAAAGACCCCAACGAGAAGCGCGAUCACAUGGUCCUGCUGGAGUUCGUGACCGCCGCCGG
GAUCACUCUCGGCAUGGACGAGCUGUACAAGUAAA

FIG. 8B

SEQ ID NO: 8 GFP Targeting

AUGGUGAGCAAGGGCGAGGAGCUGUUCACCGGGGUGGUGCCCAUCCUGGUCGAGCUGGACGGCGACGUAAACGGCC
ACAAGUUCAGCGUGUCCGGCGAGGGCGAGGGCGAUGCCACCUACGGCAAGCUGACCCUGAAGUUCAUCUGCACCAC
CGGCAAGCUGCCCGUGCCCUGGCCCACCCUCGUGACCACCCUGACCUACGGCGUGCAGUGCUUCAGCCGCUACCCCG
ACCACAUGAAGCAGCACGACUUCUUCAAGUCCGCCAUGCCCGAAGGCUACGUCCAGGAGCGCACCAUCUUCUUCAA
GGACGACGGCAACUACAAGACCCGCGCCGAGGUGAAGUUCGAGGGCGACACCCUGGUGAACCGCAUCGAGCUGAAG
GGCAUCGACUUCAAGGAGGACGGCAACAUCCUGGGGCACAAGCUGGAGUACAACUACAACAGCCACAACGUCUAUA
UCAUGGCCGACAAGCAGAAGAACGGCAUCAAGGUGAACUUCAAGAUCCGCCACAACAUCGAGGACGGCAGCGUGCA
GCUCGCCGACCACUACCAGCAGAACACCCCCAUCGGCGACGGCCCCGUGCUGCUGCCCGACAACCACUACCUGAGCA
CCCAGUCCGCCCUGAGCAAAGACCCCAACGAGAAGCGCGAUCACAUGGUCCUGCUGGAGUUCGUGACCGCCGCCGG
GAUCACUCUCGGCAUGGACGAGCUGUACAAGUAAA

FIG. 8C

SEQ ID NO:9 EXEMPLARY HIV GENOME:

GUCUCUCUGGUUAGACCAGAUCUGAGCCUGGGAGCUCUCUGGCUAACUAGGGAACCCACUGCUUAAGCCUCAAUAAAGCUU
GCCUUGAGUGCUUCAAGUAGUGUGUGCCCGUCUGUUGUGUGACUCUGGUAACUAGAGAUCCCUCAGACCCUUUUAGUCAGU
GUGGAAAAUCUCUAGCAGUGGCGCCCGAACAGGGACAUGAAAGCGAAAGGGAAACCAGAGGAGCUCUCUCGACGCAGGACU
CGGCUUGCUGAAGCGCGCACGGCAAGAGGCGAGGGGCGGCGACUGGUGAGUACGCCAAAAAUUUUGACUAGCGGAGGCUA
GAAGGAGAGAGAUGGGUGCGAGAGCGUCAGUAUUAAGCGGGGGAAAAUUAGAUCGAUGGGAAAAAAUUCGGUUAAGGCCAG
GGGGAAAGAAAAAAUAUAAAUUAAAACAUAUAGUAUGGGCAAGCAGGGAGCUAGAACGAUUCGCAGUUAAUCCUGGCCUGUU
AGAAACAUCAGAAGGCUGUAGACAAAUACUGGGACAGCUACAACCAUCCCUUCAGACAGGAUCAGAAGAACGUAGAUCAUUA
UAUAAUACAGUAGCAACCCUCUAUUGUGUGCAUCAAAGGAUAGAGAUAAAAGACACCAAGGAAGCUUUAGACAAGAUAGAGG
AAGAGCAAAACAAAAGUAAGAAAAAAGCACAGCAAGCAGCAGCUGACACAGGACACAGCAGCCAGGUCAGCCAAAAUUACCCU
AUAGUGCAGAACAUCCAGGGGCAAAUGGUACAUCAGGCCAUAUCACCUAGAACUUUAAAUGCAUGGGUAAAAGUAGUAGAAG
AGAAGGCUUUCAGCCCAGAAGUGAUACCCAUGUUUUCAGCAUUAUCAGAAGGAGCCACCCCACAAGAUUUAAACACCAUGCU
AAACACAGUGGGGGGACAUCAAGCAGCCAUGCAAAUGUUAAAAGAGACCAUCAAUGAGGAAGCUGCAGAAUGGGAUAGAGUG
CAUCCAGUGCAUGCAGGGCCUAUUGCACCAGGCCAGAUGAGAGAACCAAGGGGAAGUGACAUAGCAGGAACUACUAGUACC
CUUCAGGAACAAAUAGGAUGGAUGACACAUAAUCCACCUAUCCCAGUAGGAGAAAUCUAUAAAAGAUGGAUAAUCCUGGGAU
UAAAUAAAAUAGUAAGAAUGUAUAGCCCUACCAGCAUUCUGGACAUAAGACAAGGACCAAAGGAACCCUUUAGAGACUAUGUA
GACCGAUUCUAUAAAACUCUAAGAGCCGAGCAAGCUUCACAAGAGGUAAAAAAUUGGAUGACAGAAACCUUGUUGGUCCAAA
AUGCGAACCCAGAUUGUAAGACUAUUUUAAAAGCAUUGGGACCAGGAGCGACACUAGAAGAAAUGAUGACAGCAUGUCAGGG
AGUGGGGGGACCCGGCCAUAAAGCAAGAGUUUUGGCUGAAGCAAUGAGCCAAGUAACAAAUCCAGCUACCAUAAUGAUACAG
AAAGGCAAUUUUAGGAACCAAAGAAAGACUGUUAAGUGUUUCAAUUGUGGCAAAGAAGGGCACAUAGCCAAAAAUUGCAGGG
CCCCUAGGAAAAAGGGCUGUUGGAAAUGUGGAAAGGAAGGACACCAAAUGAAAGAUUGUACUGAGAGACAGGCUAAUUUUUU
AGGGAAGAUCUGGCCUUCCCACAAGGGAAGGCCAGGGAAUUUUCUUCAGAGCAGACCAGAGCCAACAGCCCCACCAGAAGA
GAGCUUCAGGUUUGGGGAAGAGACAACAACUCCCUCUCAGAAGCAGGAGCCGAUAGACAAGGAACUGUAUCCUUUAGCUUC
CCUCAGAUCACUCUUUGGCAGCGACCCCUCGUCACAAUAAAGAUAGGGGGGCAAUUAAAGGAAGCUCUAUUAGAUACAGGAG
CAGAUGAUACAGUAUUAGAAGAAAUGAAUUUGCCAGGAAGAUGGAAACCAAAAAUGAUAGGGGGAAUUGGAGGUUUUAUCAA
AGUAAGACAGUAUGAUCAGAUACUCAUAGAAAUCUGCGGACAUAAAGCUAUAGGUACAGUAUUAGUAGGACCUACACCUGUC
AACAUAAUUGGAAGAAAUCUGUUGACUCAGAUUGGCUGCACUUUAAAUUUUCCCAUUAGUCCUAUUGAGACUGUACCAGUAA
AAUUAAAGCCAGGAAUGGAUGGCCCAAAAGUUAAACAAUGGCCAUUGACAGAAGAAAAAAUAAAAGCAUUAGUAGAAAUUUGU
ACAGAAAUGGAAAAGGAAGGAAAAAUUUCAAAAAUUGGGCCUGAAAAUCCAUACAAUACUCCAGUAUUUGCCAUAAAGAAAAA
AGACAGUACUAAAUGGAGAAAAUUAGUAGAUUUCAGAGAACUUAAUAAGAGAACUCAAGAUUUCUGGGAAGUUCAAUUAGGA
AUACCACAUCCUGCAGGGUUAAAACAGAAAAAAUCAGUAACAGUACUGGAUGUGGGCGAUGCAUAUUUUUCAGUUCCCUUAG
AUAAAGACUUCAGGAAGUAUACUGCAUUUACCAUACCUAGU

FIG. 10A

SEQ ID NO:9 (CONTINUED)

AUAAACAAUGAGACACCAGGGAUUAGAUAUCAGUACAAUGUGCUUCCACAGGGAUGGAAAGGAUCACCAGCAAUAUUCCAGU
GUAGCAUGACAAAAAUCUUAGAGCCUUUUAGAAAACAAAAUCCAGACAUAGUCAUCUAUCAAUACAUGGAUGAUUUGUAUGUA
GGAUCUGACUUAGAAAUAGGGCAGCAUAGAACAAAAAUAGAGGAACUGAGACAACAUCUGUUGAGGUGGGGAUUUACCACAC
CAGACAAAAAACAUCAGAAAGAACCUCCAUUCCUUUGGAUGGGUUAUGAACUCCAUCCUGAUAAAUGGACAGUACAGCCUAU
AGUGCUGCCAGAAAAGGACAGCUGGACUGUCAAUGACAUACAGAAAUUAGUGGGAAAAUUGAAUUGGGCAAGUCAGAUUUAU
GCAGGGAUUAAAGUAAGGCAAUUAUGUAAACUUCUUAGGGGAACCAAAGCACUAACAGAAGUAGUACCACUAACAGAAGAAG
CAGAGCUAGAACUGGCAGAAAACAGGGAGAUUCUAAAAGAACCGGUACAUGGAGUGUAUUAUGACCCAUCAAAAGACUUAAU
AGCAGAAAUACAGAAGCAGGGGCAAGGCCAAUGGACAUAUCAAAUUUAUCAAGAGCCAUUUAAAAAUCUGAAAACAGGAAAGU
AUGCAAGAAUGAAGGGUGCCCACACUAAUGAUGUGAAACAAUUAACAGAGGCAGUACAAAAAAUAGCCACAGAAAGCAUAGUA
AUAUGGGGAAAGACUCCUAAAUUUAAAUUACCCAUACAAAAGGAAACAUGGGAAGCAUGGUGGACAGAGUAUUGGCAAGCCA
CCUGGAUUCCUGAGUGGGAGUUUGUCAAUACCCCUCCCUUAGUGAAGUUAUGGUACCAGUUAGAGAAAGAACCCAUAAUAG
GAGCAGAAACUUUCUAUGUAGAUGGGGCAGCCAAUAGGGAAACUAAAUUAGGAAAAGCAGGAUAUGUAACUGACAGAGGAAG
ACAAAAAGUUGUCCCCCUAACGGACACAACAAAUCAGAAGACUGAGUUACAAGCAAUUCAUCUAGCUUUGCAGGAUUCGGGA
UUAGAAGUAAACAUAGUGACAGACUCACAAUAUGCAUUGGGAAUCAUUCAAGCACAACCAGAUAAGAGUGAAUCAGAGUUAG
UCAGUCAAAUAAUAGAGCAGUUAAUAAAAAAGGAAAAAGUCUACCUGGCAUGGGUACCAGCACACAAAGGAAUUGGAGGAAA
UGAACAAGUAGAUAAAUUGGUCAGUGCUGGAAUCAGGAAAGUACUAUUUUUAGAUGGAAUAGAUAAGGCCCAAGAAGAACAU
GAGAAAUAUCACAGUAAUUGGAGAGCAAUGGCUAGUGAUUUUAACCUACCACCUGUAGUAGCAAAAGAAAUAGUAGCCAGCU
GUGAUAAAUGUCAGCUAAAAGGGGAAGCCAUGCAUGGACAAGUAGACUGUAGCCCAGGAAUAUGGCAGCUAGAUUGUACACA
UUUAGAAGGAAAAGUUAUCUUGGUAGCAGUUCAUGUAGCCAGUGGAUAUAUAGAAGCAGAAGUAAUUCCAGCAGAGACAGGG
CAAGAAACAGCAUACUUCCUCUUAAAAUUAGCAGGAAGAUGGCCAGUAAAAACAGUACAUACAGACAAUGGCAGCAAUUUCAC
CAGUACUACAGUUAAGGCCGCCUGUUGGUGGGCGGGGAUCAAGCAGGAAUUUGGCAUUCCCUACAAUCCCCAAAGUCAAGG
AGUAAUAGAAUCUAUGAAUAAAGAAUUAAAGAAAAUUAUAGGACAGGUAAGAGAUCAGGCUGAACAUCUUAAGACAGCAGUAC
AAAUGGCAGUAUUCAUCCACAAUUUUAAAAGAAAAGGGGGGAUUGGGGGGUACAGUGCAGGGGAAAGAAUAGUAGACAUAAU
AGCAACAGACAUACAAACUAAAGAAUUACAAAAACAAAUUACAAAAAUUCAAAAUUUUCGGGUUUAUUACAGGGACAGCAGAG
AUCCAGUUUGGAAAGGACCAGCAAAGCUCCUCUGGAAAGGUGAAGGGGCAGUAGUAAUACAAGAUAAUAGUGACAUAAAAGU
AGUGCCAAGAAGAAAAGCAAAGAUCAUCAGGGAUUAUGGAAAACAGAUGGCAGGUGAUGAUUGUGUGGCAAGUAGACAGGAU
GAGGAUUAACACAUGGAAAAGAUUAGUAAAACACCAUAUGUAUAUUUCAAGGAAAGCUAAGGACUGGUUUUAUAGACAUCAC
UAUGAAAGUACUAAUCCAAAAAUAAGUUCAGAAGUACACAUCCCACUAGGGGAUGCUAAAUUAGUAAUAACAACAUAUUGGGG
UCUGCAUACAGGAGAAAGAGACUGGCAUUUGGGUCAGGG

FIG. 10B

SEQ ID NO:9 (CONTINUED)
AGUCUCCAUAGAAUGGAGGAAAAAGAGAUAUAGCACACAAGUAGACCCUGACCUAGCAGACCAACUAAUUCAUCUGCACUAU
UUUGAUUGUUUUUCAGAAUCUGCUAUAAGAAAUACCAUAUUAGGACGUAUAGUUAGUCCUAGGUGUGAAUAUCAAGCAGGAC
AUAACAAGGUAGGAUCUCUACAGUACUUGGCACUAGCAGCAUUAAUAAAACCAAAACAGAUAAAGCCACCUUUGCCUAGUGU
UAGGAAACUGACAGAGGACAGAUGGAACAAGCCCCAGAAGACCAAGGGCCACAGAGGGAGCCAUACAAUGAAUGGACACUAG
AGCUUUUAGAGGAACUUAAGAGUGAAGCUGUUAGACAUUUUCCUAGGAUAUGGCUCCAUAACUUAGGACAACAUAUCUAUGA
AACUUACGGGGAUACUUGGGCAGGAGUGGAAGCCAUAAUAAGAAUUCUGCAACAACUGCUGUUUAUCCAUUUCAGAAUUGG
GUGUCGACAUAGCAGAAUAGGCGUUACUCGACAGAGGAGAGCAAGAAAUGGAGCCAGUAGAUCCUAGACUAGAGCCCUGGA
AGCAUCCAGGAAGUCAGCCUAAAACUGCUUGUACCAAUUGCUAUUGUAAAAAGUGUUGCUUUCAUUGCCAAGUUUGUUUCAU
AACAAAAGCCUUAGGCAUCUCCUAUGGCAGGAAGAAGCGGAGACAGCGACGAAGACCUCCUCAAGGCAGUCAGACUCAUCAA
GUUUCUCUAUCAAAGCAGUAAGUAAUACAUGUAAUGCAACCUAUACAAAUAGCAAUAGUAGCAUUAGUAGUAGCAAUAAUAAU
AGCAAUAGUUGUGUGGUCCAUAGUAAUCAUAGAAUAUAGGAAAAUAUUAAGACAAAGAAAAAUAGACAGGUUAAUUGAUAGAC
UAAUAGAAAGAGCAGAAGACAGUGGCAAUGAGAGUGAAGGAGAAAUAUCAGCACUUGUGGAGAUGGGGGUGGAGAUGGGGC
ACCAUGCUCCUUGGGAUGUUGAUGAUCUGUAGUGCUACAGAAAAAUUGUGGGUCACAGUCUAUUAUGGGGUACCUGUGUGG
AAGGAAGCAACCACCACUCUAUUUUGUGCAUCAGAUGCUAAAGCAUAUGAUACAGAGGUACAUAAUGUUUGGGCCACACAUG
CCUGUGUACCCACAGACCCCAACCCACAAGAAGUAGUAUUGGUAAAUGUGACAGAAAAUUUUAACAUGUGGAAAAAUGACAU
GGUAGAACAGAUGCAUGAGGAUAUAAUCAGUUUAUGGGAUCAAAGCCUAAAGCCAUGUGUAAAAUUAACCCCACUCUGUGUU
AGUUUAAAGUGCACUGAUUUGAAGAAUGAUACUAAUACCAAUAGUAGUAGCGGGAGAAUGAUAAUGGAGAAAGGAGAGAUAA
AAAACUGCUCUUUCAAUAUCAGCACAAGCAUAAGAGGUAAGGUGCAGAAAGAAUAUGCAUUUUUUUAUAAACUUGAUAUAAUA
CCAAUAGAUAAUGAUACUACCAGCUAUACGUUGACAAGUUGUAACACCUCAGUCAUUACACAGGCCUGUCCAAAGGUAUCCU
UUGAGCCAAUUCCCAUACAUUAUUGUGCCCCGGCUGGUUUUGCGAUUCUAAAAUGUAAUAAUAAGACGUUCAAUGGAACAGG
ACCAUGUACAAAUGUCAGCACAGUACAAUGUACACAUGGAAUUAGGCCAGUAGUAUCAACUCAACUGCUGUUAAAUGGCAGU
CUAGCAGAAGAAGAGGUAGUAAUUAGAUCUGUCAAUUUCACGGACAAUGCUAAAACCAUAAUAGUACAGCUGAACACAUCUG
UAGAAAUUAAUUGUACAAGACCCAACAACAAUACAAGAAAAAAAAUCCGUAUCCAGAGGGGACCAGGGAGAGCAUUUGUUACA
AUAGGAAAAAUAGGAAAUAUGAGACAAGCACAUUGUAACAUUAGUAGAGCAAAAUGGAAUGCCACUUUAAAACAGAUAGCUAG
CAAAUUAAGAGAACAAUUUGGAAAUAAUAAAACAAUAAUCUUUAAGCAAUCCUCAGGAGGGGACCCAGAAAUUGUAACGCACA
GUUUUAAUUGUGGAGGGGAAUUUUUCUACUGUAAUUCAACACAACUGUUUAAUAGUACUUGGUUUAAUAGUACUUGGAGUAC
UGAAGGGUCAAAUAACACUGAAGGAAGUGACACAAUCACACUCCCAUGCAGAAUAAAACAAUUUAUAAACAUGUGGCAGGAAG
UAGGAAAAGCAAUGUAUGCCCCUCCCAUCAGCGGACAAAUUAGAUGUUCAUCAAAUAUUACAGGGCUGCUAUUAACAAGAGA
UGGUGGUAAUAACAACAAUGGGUCCGAGAUCUUCAGACCUGGAGGAGGAGAUAUGAGGGACAAUUGGAGAAGUGAAUUAUA
UAAAUAUAAAGUAGUAAAAAUUGAACCAUUAGGAGUAGCACCCACCAAGGCAAAGAGAAGAGUGGUGCAGAGAGAAAAAAGAG
CAGUGGGAAUAGGAGCUUUGUUCCUUGGGUUCUUGGGAGCAGCAGGAAGCACUAUGGGCGCAGCGUCAAUGACGCUGACG
GUACAGGCCAGACAAUUAUUGUCUGGUAUAGUGCAGCAGCAGAACAAUUUGCUGAGGGCUAUUGAGGCGCAACAGCAUCUG
UUGCAACUCACAGUCUGGGGCAUCAAGCAGCUCCAGGCAAGAAUCCUGGCUGUGGAAAGAUACCUAAAGGAUCAACAGCUC
CUGGGGAUUUGGGGUUGCUCUGGAA

FIG. 10C

SEQ ID NO:9 (CONTINUED)

AACUCAUUUGCACCACUGCUGUGCCUUGGAAUGCUAGUUGGAGUAAUAAAUCUCUGGAACAGAUUUGGAAUCACA
CGACCUGGAUGGAGUGGGACAGAGAAAUUAACAAUUACACAAGCUUAAUACACUCCUUAAUUGAAGAAUCGCAAA
ACCAGCAAGAAAAGAAUGAACAAGAAUUAUUGGAAUUAGAUAAAUGGGCAAGUUUGUGGAAUUGGUUUAACAUAA
CAAAUUGGCUGUGGUAUAUAAAAUUAUUCAUAAUGAUAGUAGGAGGCUUGGUAGGUUUAAGAAUAGUUUUUGCUG
UACUUUCUGUAGUGAAUAGAGUUAGGCAGGGAUAUUCACCAUUAUCGUUUCAGACCCACCUCCCAAUCCCGAGG
GGACCCGACAGGCCCGAAGGAAUAGAAGAAGAAGGUGGAGAGAGAGACAGAGACAGAUCCAUUCGAUUAGUGAAC
GGAUCCUUAGCACUUAUCUGGGACGAUCUGCGGAGCCUGUGCCUCUUCAGCUACCACCGCUUGAGAGACUUACU
CUUGAUUGUAACGAGGAUUGUGGAACUUCUGGGACGCAGGGGGUGGGAAGCCCUCAAAUAUUGGUGGAAUCUCC
UACAAUAUUGGAGUCAGGAGCUAAAGAAUAGUGCUGUUAGCUUGCUCAAUGCCACAGCUAUAGCAGUAGCUGAG
GGGACAGAUAGGGUUAUAGAAGUAGUACAAGAAGCUUAUAGAGCUAUUCGCCACAUACCUAGAAGAAUAGGACAG
GGCUUGGAAAGGAUUUUGCUAUAAGAUGGGUGGCAAGUGGUCAAAAAGUAGUGUGGUUGGAUGGCCUGCUGUAA
GGGAAAGAAUGAGACGAGCUGAGCCAGCAGCAGAUGGGGUGGGAGCAGCAUCUCGAGACCUAGAAAAACAUGGA
GCAAUCACAAGUAGCAACACAGCAGCUAACAAUGCUGCUUGUGCCUGGCUAGAAGCACAAGAGGAGGAGAAGGUG
GGUUUUCCAGUCACACCUCAGGUACCUUUAAGACCAAUGACUUACAAGGCAGCUGUAGAUCUUAGCCACUUUUUA
AAAGAAAAGGGGGGACUGGAAGGGCUAAUUCACUCCCAACGAAGACAAGAUAUCCUUGAUCUGUGGAUCUACCAC
ACACAAGGCUACUUCCCUGAUUGGCAGAACUACACACCAGGACCAGGGAUCAGAUAUCCACUGACCUUUGGAUGG
CGCUACAAGCUAGUACCAGUUGAGCCAGAGAAGUUAGAAGAAGCCAACAAAGGAGAGAACACCAGCUUGUUACAC
CCUGUGAGCCUGCAUGGAAUGGAUGACCCGGAGAGAGAAGUGUUAGAGUGGAGGUUUGACAGCCGCCUAGCAUU
UCAUCACGUGGCCCGAGAGCUGCAUCCGGAGUACUUCAAGAACUGCUGAUAUCGAGCUUGCUACAAGGGACUUU
CCGCUGGGGACUUUCCAGGGAGGCGUGGCCUGGGCGGGACUGGGGAGUGGCGAGCCCUCAGAUCCUGCAUAUA
AGCAGCUGCUUUUUGCCUGUACUGGGUCUCUCUGGUUAGACCAGAUCUGAGCCUGGGAGCUCUCUGGCUAACUA
GGGAACCCACUGCUUAAGCCUCAAUAAAGCUUGCCUUGAGUGCUUCAAGUAGUGUGUGCCCGUCUGUUGUGUGA
CUCUGGUAACUAGAGAUCCCUCAGACCCUUUUAGUCAGUGUGGAAAAUCUCUAGCAGU

FIG. 10D

SEQ ID NO:4
>gi / 9629357:5771-8341 Human immunodeficiency virus 1, complete genome (ENV gene)

ATGAGAGTGAAGGAGAAATATCAGCACTTGTGGAGATGGGGGTGGAGATGGGGCACCATGCTCCTTGGGATGTTGATGATCTG
TAGTGCTACAGAAAAATTGTGGGTCACAGTCTATTATGGGGTACCTGTGTGGAAGGAAGCAACCACCACTCTATTTTGTGCATCA
GATGCTAAAGCATATGATACAGAGGTACATAATGTTTGGGCCACACATGCCTGTGTACCCACAGACCCCAACCCACAAGAAGTA
GTATTGGTAAATGTGACAGAAAATTTTAACATGTGGAAAAATGACATGGTAGAACAGATGCATGAGGATATAATCAGTTTATGGGA
TCAAAGCCTAAAGCCATGTGTAAAATTAACCCCACTCTGTGTTAGTTTAAAGTGCACTGATTTGAAGAATGATACTAATACCAATA
GTAGTAGCGGGAGAATGATAATGGAGAAAGGAGAGATAAAAAACTGCTCTTTCAATATCAGCACAAGCATAAGAGGTAAGGTGC
AGAAAGAATATGCATTTTTTTATAAACTTGATATAATACCAATAGATAATGATACTACCAGCTATAAGTTGACAAGTTGTAACACCT
CAGTCATTACACAGGCCTGTCCAAAGGTATCCTTTGAGCCAATTCCCATACATTATTGTGCCCCGGCTGGTTTTGCGATTCTAAA
ATGTAATAATAAGACGTTCAATGGAACAGGACCATGTACAAATGTCAGCACAGTACAATGTACACATGGAATTAGGCCAGTAGTA
TCAACTCAACTGCTGTTAAATGGCAGTCTAGCAGAAGAAGAGGTAGTAATTAGATCTGTCAATTTCACGGACAATGCTAAAACCAT
AATAGTACAGCTGAACACATCTGTAGAAATTAATTGTACAAGACCCAACAACAATACAAGAAAAAGAATCCGTATCCAGAGAGGA
CCAGGGAGAGCATTTGTTACAATAGGAAAAATAGGAAATATGAGACAAGCACATTGTAACATTAGTAGAGCAAAATGGAATAACA
CTTTAAAACAGATAGCTAGCAAATTAAGAGAACAATTTGGAAATAATAAAACAATAATCTTTAAGCAATCCTCAGGAGGGGACCCA
GAAATTGTAACGCACAGTTTTAATTGTGGAGGGGAATTTTTCTACTGTAATTCAACACAACTGTTTAATAGTACTTGGTTTAATAGT
ACTTGGAGTACTGAAGGGTCAAATAACACTGAAGGAAGTGACACAATCACCCTCCCATGCAGAATAAAACAAATTATAAACATGT
GGCAGAAAGTAGGAAAAGCAATGTATGCCCCTCCCATCAGTGGACAAATTAGATGTTCATCAAATATTACAGGGCTGCTATTAAC
AAGAGATGGTGGTAATAGCAACAATGAGTCCGAGATCTTCAGACCTGGAGGAGGAGATATGAGGGACAATTGGAGAAGTGAATT
ATATAAATATAAAGTAGTAAAAATTGAACCATTAGGAGTAGCACCCACCAAGGCAAAGAGAAGAGTGGTGCAGAGAGAAAAAAGA
GCAGTGGGAATAGGAGCTTTGTTCCTTGGGTTCTTGGGAGCAGCAGGAAGCACTATGGGCGCAGCCTCAATGACGCTGACGGT
ACAGGCCAGACAATTATTGTCTGGTATAGTGCAGCAGCAGAACAATTTGCTGAGGGCTATTGAGGCGCAACAGCATCTGTTGCA
ACTCACAGTCTGGGGCATCAAGCAGCTCCAGGCAAGAATCCTGGCTGTGGAAAGATACCTAAAGGATCAACAGCTCCTGGGGAT
TTGGGGTTGCTCTGGAAAACTCATTTGCACCACTGCTGTGCCTTGGAATGCTAGTTGGAGTAATAAATCTCTGGAACAGATTTGG
AATCACACGACCTGGATGGAGTGGGACAGAGAAATTAACAATTACACAAGCTTAATACACTCCTTAATTGAAGAATCGCAAAACC
AGCAAGAAAAGAATGAACAAGAATTATTGGAATTAGATAAATGGGCAAGTTTGTGGAATTGGTTTAACATAACAAATTGGCTGTGG
TATATAAAATTATTCATAATGATAGTAGGAGGCTTGGTAGGTTTAAGAATAGTTTTTGCTGTACTTTCTATAGTGAATAGAGTTAGG
CAGGGATATTCACCATTATCGTTTCAGACCCACCTCCCAACCCCGAGGGGACCCGACAGGCCCGAAGGAATAGAAGAAGAAGG
TGGAGAGAGAGACAGAGACAGATCCATTCGATTAGTGAACGGATCCTTGGCACTTATCTGGGACGATCTGCGGAGCCTGTGCCT
CTTCAGCTACCACCGCTTGAGAGACTTACTCTTGATTGTAACGAGGATTGTGGAACTTCTGGGACGCAGGGGGTGGGAAGCCCT
CAAATATTGGTGGAATCTCCTACAGTATTGGAGTCAGGAACTAAAGAATAGTGCTGTTAGCTTGCTCAATGCCACAGCCATAGCA
GTAGCTGAGGGGACAGATAGGGTTATAGAAGTAGTACAAGGAGCTTGTAGAGCTATTCGCCACATACCTAGAAGAATAAGACAG
GGCTTGGAAAGGATTTTGCTATAA

FIG. 11

SEQ ID NO:2
>gi / 9629357:336-1838 Human immunodeficiency virus 1, complete genome (GAG gene)
ATGGGTGCGAGAGCGTCAGTATTAAGCGGGGGAGAATTAGATCGATGGGAAAAAATTCGGTTAAGGCCAGGGGGAA
AGAAAAAATATAAATTAAAACATATAGTATGGGCAAGCAGGGAGCTAGAACGATTCGCAGTTAATCCTGGCCTGTTAG
AAACATCAGAAGGCTGTAGACAAATACTGGGACAGCTACAACCATCCCTTCAGACAGGATCAGAAGAACTTAGATCAT
TATATAATACAGTAGCAACCCTCTATTGTGTGCATCAAAGGATAGAGATAAAAGACACCAAGGAAGCTTTAGACAAGA
TAGAGGAAGAGCAAAACAAAAGTAAGAAAAAAGCACAGCAAGCAGCAGCTGACACAGGACACAGCAATCAGGTCAG
CCAAAATTACCCTATAGTGCAGAACATCCAGGGGCAAATGGTACATCAGGCCATATCACCTAGAACTTTAAATGCATG
GGTAAAAGTAGTAGAAGAGAAGGCTTTCAGCCCAGAAGTGATACCCATGTTTTCAGCATTATCAGAAGGAGCCACCC
CACAAGATTTAAACACCATGCTAAACACAGTGGGGGGACATCAAGCAGCCATGCAAATGTTAAAAGAGACCATCAAT
GAGGAAGCTGCAGAATGGGATAGAGTGCATCCAGTGCATGCAGGGCCTATTGCACCAGGCCAGATGAGAGAACCAA
GGGGAAGTGACATAGCAGGAACTACTAGTACCCTTCAGGAACAAATAGGATGGATGACAAATAATCCACCTATCCCA
GTAGGAGAAATTTATAAAAGATGGATAATCCTGGGATTAAATAAAATAGTAAGAATGTATAGCCCTACCAGCATTCTGG
ACATAAGACAAGGACCAAAGGAACCCTTTAGAGACTATGTAGACCGGTTCTATAAAACTCTAAGAGCCGAGCAAGCTT
CACAGGAGGTAAAAAATTGGATGACAGAAACCTTGTTGGTCCAAAATGCGAACCCAGATTGTAAGACTATTTTAAAAG
CATTGGGACCAGCGGCTACACTAGAAGAAATGATGACAGCATGTCAGGGAGTAGGAGGACCCGGCCATAAGGCAAG
AGTTTTGGCTGAAGCAATGAGCCAAGTAACAAATTCAGCTACCATAATGATGCAGAGAGGCAATTTTAGGAACCAAAG
AAAGATTGTTAAGTGTTTCAATTGTGGCAAAGAAGGGCACACAGCCAGAAATTGCAGGGCCCCTAGGAAAAAGGGCT
GTTGGAAATGTGGAAAGGAAGGACACCAAATGAAAGATTGTACTGAGAGACAGGCTAATTTTTTAGGGAAGATCTGG
CCTTCCTACAAGGGAAGGCCAGGGAATTTTCTTCAGAGCAGACCAGAGCCAACAGCCCCACCAGAAGAGAGCTTCA
GGTCTGGGGTAGAGACAACAACTCCCCCTCAGAAGCAGGAGCCGATAGACAAGGAACTGTATCCTTTAACTTCCCTC
AGGTCACTCTTTGGCAACGACCCCTCGTCACAATAA

FIG. 12A

SEQ ID NO:3
>(gi / 9629357:5377-5591, 7925-7970) Human immunodeficiency virus 1, complete genome (TAT gene)
ATGGAGCCAGTAGATCCTAGACTAGAGCCCTGGAAGCATCCAGGAAGTCAGCCTAAAACTGCTTGTACCAATTGCTA
TTGTAAAAAGTGTTGCTTTCATTGCCAAGTTTGTTTCATAACAAAAGCCTTAGGCATCTCCTATGGCAGGAAGAAGCG
GAGACAGCGACGAAGAGCTCATCAGAACAGTCAGACTCATCAAGCTTCTCTATCAAAGCAACCCACCTCCCAACCCC
GAGGGGACCCGACAGGCCCGAAGGAATAG

FIG. 12B

SEQ ID NO:10 >NM_009693 (MM ApoB)

UACCUGCCUGAGCUCCGCCUCCGAAGACCCUGUAGAGCAAGCAGCAGGGGCUAGGCCCGUGGCCAGGCCACAGCCAGGAA
GCCACCCCACCAUCCAUCCGCCAUGGGCCCACGAAAGCCUGCCCUGCGGACGCCGUUACUGCUGCUGUUCCUGCUACUGUU
CUUGGACACCAGCGUCUGGGCUCAAGAUGAAGUCCUGGAAAACUUAAGCUUCAGCUGUCCAAAAGAUGCAACUCGAUUCAAG
CACCUCCGAAAGUACGUGUACAACUAUGAAGCUGAAAGUUCCAGCGGUGUCCAGGGCACAGCUGACUCCAGAAGCGCCACC
AAGAUCAACUGUAAGGUAGAGCUGGAGGUCCCCCAAAUCUGUGGUUUCAUCAUGAGGACCAACCAGUGUACCCUUAAAGAG
GUGUAUGGCUUCAACCCUGAGGGCAAGGCCUUGAUGAAGAAAACCAAGAACUCUGAAGAGUUUGCAGCUGCCAUGUCCAGG
UACGAACUCAAGCUGGCCAUUCCUGAAGGGAAACAAAUUGUUCUUUACCCUGACAAGGAUGAACCUAAAUAUAUCCUGAACA
UCAAGAGGGGCAUCAUCUCUGCUCUUCUGGUUCCCCCAGAGACAGAAGAGGACCAACAAGAGUUGUUCCUGGAUACCGUGU
AUGGAAACUGCUCAACUCAGGUUACCGUGAAUUCAAGAAAGGGAACCGUACCAACAGAAAUGUCCACAGAGAGAAACCUGCA
GCAAUGUGACGGCUUCCAGCCCAUCAGUACAAGUGUCAGCCCUCUCGCUCUCAUCAAAGGCCUGGUCCACCCCUUGUCAAC
UCUUAUCAGCAGCAGCCAAACUUGCCAGUACACCCUGGAUCCUAAGAGGAAGCAUGUGUCUGAAGCUGUCUGUGAUGAGCA
GCAUCUUUUCCUGCCUUUCUCCUACAAGAAUAAGUAUGGGAUCAUGACACGUGUUACACAGAAACUGAGUCUUGAAGACACA
CCUAAGAUCAACAGUCGCUUCUUCAGUGAAGGUACCAACCGGAUGGGUCUGGCCUUUGAGAGCACCAAGUCCACGUCAUCC
CCAAAGCAGGCUGAUGCUGUUUUGAAGACCCUUCAAGAACUGAAAAAAUUGUCCAUCUCAGAGCAGAAUGCUCAGAGAGCAA
AUCUCUUCAAUAAACUGGUUACUGAGCUGAGAGGCCUCACUGGUGAAGCAAUCACAUCCCUCUUGCCACAGCUGAUUGAAG
UGUCCAGCCCCAUCACUUUACAAGCCUUGGUUCAGUGUGGACAGCCACAGUGCUAUACUCACAUCCUCCAGUGGCUGAAAA
CUGAGAAGGCUCACCCCCUCCUGGUUGACAUUGUCACCUACCUGAUGGCUCUGAUCCCAAAUCCCUCAACACAGAGGCUGC
AGGAAAUCUUUAAUACUGCCAAGGAGCAGCAGAGCCGAGCCACUCUGUAUGCACUGAGCCACGCAGUUAACAGCUAUUUUGA
UGUGGACCAUUCAAGGAGCCCAGUUCUGCAGGAUAUCGCUGGUUACCUGUUGAAACAGAUCGACAAUGAAUGCACGGGCAA
UGAAGACCACACCUUCUUGAUUCUGAGGGUCAUUGGAAAUAUGGGAAGAACCAUGGAACAAGUAAUGCCAGCCCUCAAGUCC
UCAGUCCUGAGCUGUGUACGAAGUACAAAACCAUCUCUGCUGAUUCAGAAAGCUGCUCUCCAGGCCCUGAGGAAGAUGGAA
CUGGAAGAUGAGGUCCGGACGAUCCUUUUUGAUACAUUUGUAAAUGGUGUCGCUCCCGUGGAGAAGAGACUGGCUGCCUAU
CUCUUGCUGAUGAAGAACCCUUCCUCAUCAGAUAUUAACAAAAUUGCCCAACUUCUCCAAUGGGAACAGAGUGAGCAGGUGA
AGAACUUCGUGGCAUCUCACAUUGCCAACAUCUUGAACUCGGAAGAACUGUAUGUCCAAGAUCUGAAAGUUUUGAUCAAAAA
UGCUCUGGAGAAUUCUCAAUUUCCAACGAUCAUGGACUUCAGAAAAUUUUCCCGAAACUAUCAGAUUUCCAAAUCUGCUUCU
CUCCCAAUGUUCGACCCAGUCUCAGUCAAAAUAGAAGGGAAUCUUAUAUUUGAUCCAAGCAGUUAUCUUCCCAGAGAAAGCU
UGCUGAAAACAACCCUCACAGUCUUUGGACUUGCUUCACUUGAUCUCUUUGAGAUUGGUUUAGAAGGAAAAGGGUUUGAGC
CAACACUAGAAGCUCUUUUUGGUAAGCAAGGAUUCUUCCCAGACAGUGUCAACAAGGCUUUGUAUUGGGUCAAUGGCCGAG
UUCCAGAUGGUGUCUCCAAGGUCUUGGUGGACCACUUUGGCUAUACUACAGAUGGCAAGCAUGAACAGGACAUGGUGAAUG
GAAUCAUGCCCAUUGUGGACAAGUUGAUCAAAGAUCUGAAAUCUAAAGAAAUUCCUGAAGCCAGGGCCUAUCUCCGCAUCCU
AGGAAAAGAGCUAAGCUUUGUCAGACUCCAAGACCUCCAAGUCCUGGGGAAGCUGUUGCUGAGUGGUGCACAAACUUUGCA
GGGAAUCCCCCAGAUGGUUGUACAGGCCAUCAGAGAAGGGUCAAAGAAUGACUUGUUUCUCCACUACAUCUUCAUGGACAA
UGCCUUUGAGCUCCCCACUGGAGCAGGGUUACAGCUGCAAGUGUCCUCGUCUGGAGUCUUCACCCCCGGGAUCAAGGCUG
GUGUAAGACUGGAAUUAGCCAACAUACAGGCAGAGCUAGUGGCAAAGCCCUCUGUGUCCUUGGAGUUUGUGACAAAUAUGG

FIG. 13A

SEQ ID NO:10 (CONTINUED)
GCAUCAUCAUCCCAGACUUCGCUAAGAGCAGUGUCCAGAUGAACACCAACUUCUUCCACGAGUCAGGCCUGGAGGCGCGAG
UGGCCCUGAAGGCUGGGCAGCUGAAGGUCAUCAUUCCUUCUCCAAAGAGGCCAGUCAAGCUGUUCAGUGGCAGCAACACAC
UGCAUCUGGUCUCUACCACCAAAACAGAAGUGAUCCCACCUCUGGUUGAGAACAGGCAGUCCUGGUCAACUUGCAAGCCUC
UCUUCACUGGAAUGAACUACUGUACCACAGGAGCUUACUCCAACGCCAGCUCCACGGAGUCUGCCUCUUACUACCCACUGAC
AGGGGACACAAGGUAUGAGCUGGAGCUGAGGCCCACGGGAGAAGUGGAGCAGUAUUCUGCCACUGCAACCUAUGAACUCCU
AAAAGAGGACAAGUCUUUGGUUGACACAUUGAAGUUCCUAGUUCAAGCAGAAGGAGUGCAGCAGUCUGAAGCUACUGUACU
GUUCAAAUAUAAUCGGAGAAGCAGGACCUUAUCUAGUGAAGUCCUAAUUCCAGGGUUUGAUGUCAACUUCGGGACAAUACUA
AGAGUUAAUGAUGAAUCUGCUAAGGACAAAAACACUUACAAACUCAUCCUGGACAUUCAGAACAAGAAAAUCACUGAGGUCUC
UCUCGUGGGCCACUUGAGUUAUGAUAAAAAGGGAGAUGGCAAGAUCAAAGGUGUUGUUUCCAUACCACGUUUGCAAGCAGA
AGCCAGGAGUGAGGUCCACACCCACUGGUCCUCCACCAAACUGCUCUUCCAAAUGGACUCAUCUGCUACAGCUUACGGCUC
AACAAUUUCCAAGAGAGUGACAUGGCGUUACGAUAAUGAGAUAAUAGAAUUUGAUUGGAACACGGGAACCAAUGUGGAUACC
AAAAAAGUGGCCUCCAAUUUCCCUGUGGAUCUUUCCCAUUAUCCUAGAAUGUUGCAUGAGUAUGCCAAUGGUCUCCUGGAU
CACAGAGUCCCUCAAACAGAUGUGACUUUUCGGGACAUGGGUUCCAAAUUAAUUGUUGCAACAAACACAUGGCUUCAGAUGG
CAACCAGGGGUCUUCCUUACCCCCAAACUCUACAGGAUCACCUCAAUAGCCUCUCAGAGUUGAACCUCCUGAAAAUGGGACU
GUCUGACUUCCAUAUUCCAGACAACCUCUUCCUAAAGACUGAUGGCAGAGUCAAAUACACAAUGAACAGGAACAAAAUAAACA
UUGACAUCCCUUUGCCUUUGGGUGGCAAGUCUUCAAAAGACCUCAAGAUGCCAGAGAGUGUGAGGACACCAGCCCUCAACU
UCAAGUCUGUGGGAUUCCAUCUGCCAUCUCGAGAGGUCCAGGUCCCCACUUUUACAAUCCCCAAGACACAUCAGCUUCAAG
UGCCUCUCUUGGGUGUUCUAGACCUUUCCACAAAUGUCUACAGCAAUUUGUACAACUGGUCAGCCUCCUACACUGGUGGCA
ACACCAGCAGAGACCACUUCAGCCUUCAGGCUCAGUACCGCAUGAAGACUGACUCUGUGGUUGACCUGUUUUCCUACAGUG
UGCAAGGAUCUGGAGAAACAACAUAUGACAGCAAGAACACAUUUACAUUGUCCUGUGAUGGAUCUCUACACCAUAAAUUUCU
AGACUCAAAAUUCAAAGUCAGCCACGUAGAAAAAUUUGGAAACAGCCCAGUCUCAAAAGGUUUACUAACAUUUGAAACAUCUA
GUGCCUUGGGACCACAGAUGUCUGCUACUGUUCACCUAGACUCAAAAAAGAAACAACAUCUAUACGUCAAAGAUAUCAAGGU
UGAUGGACAGUUCAGAGCUUCUUCAUUUUAUGCUCAAGGCAAAUAUGGCCUGUCUUGUGAGAGAGAUGUUACAACUGGCCA
GCUGAGCGGCGAAUCCAACAUGAGAUUUAACUCCACCUACUUCCAGGGCACCAACCAGAUCGUGGGAAUGUACCAGGAUGG
AGCCCUGUCCAUCACCUCCACUUCUGACCUGCAAGAUGGCAUAUUCAAGAACACAGCUUCCUUGAAAUAUGAAAACUAUGAG
CUGACUCUGAAAUCUGAUAGCAGUGGGCAGUAUGAGAACUUCGCUGCUUCCAACAAGCUGGAUGUGACCUUCUCUACGCAA
AGUGCACUGCUGCGUUCUGAACACCAGGCCAAUUACAAGUCCCUGAGGCUUGUCACCCUUCUUUCAGGAUCCCUCACUUCC
CAGGGUGUAGAAUUAAAUGCUGACAUCUUGGGCACAGACAAAAUUAAUACUGGUGCUCACAAGGCAACACUAAAGAUUGCAC
GUGAUGGACUAUCAACCAGUGCGACCACCAACUUGAAGUACAGCCCCCUGCUGCUGGAGAAUGAGUUGAAUGCAGAGCUUG
GGCUCUCUGGGGCAUCCAUGAAAUUAUCAACAAACGGCCGCUUCAAAGAACACCAUGCAAAAUUCAGUCUUGAUGGGAGAGC
UGCCCUCACAGAGGUGUCACUGGGGAGCAUUUACCAGGCCAUGAUUCUGGGUGCAGACAGCAAAAACAUCUUCAACUUCAA
ACUCAGCCGAGAAGGGCUGAGGCUGUCCAAUGAUUUGAUGGGCUCCUAUGCUGAGAUGAAACUUGACCACACACACAGUCU
GAACAUUGCAGGUCUCUCACUGGACUUCUUCUCAAAAAUGGACAAUAUUUACAGUGGAGACAAGUUCUAUAAGCAGAAUUUU
AACUUACAGCUACAGCCCUAUUCUUUCAUAACUACUUUAAGCAACGACCUGAGAUAUGGUGCUCUAGAUUUGACCAACAAUG

FIG. 13B

SEQ ID NO:10 (CONTINUED)
GAAGGUUUCGGCUGGAGCCACUGAAGCUGAAUGUGGGUGGCAACUUUAAAGGAACCUAUCAAAAUAAUGAGCUGAAACAUAU
CUAUACCAUAUCUUAUACUGACCUGGUAGUAGCAAGUUACAGAGCAGACACUGUGGCUAAGGUUCAGGGUGUCGAAUUCAG
CCAUAGGCUAAAUGCAGACAUUGAAGGACUGACUUCCUCUGUUGAUGUCACUACCAGCUACAAUUCAGAUCCACUGCAUUUU
AACAAUGUUUUCCACUUUUCUCUGGCACCUUUUACCUUGGGCAUCGACACACAUACAAGUGGUGAUGGGAAACUGUCCUUC
UGGGGAGAACACACUGGGCAGCUAUAUAGUAAGUUUCUGUUGAAAGCAGAACCUCUGGCACUUAUUGUCUCUCAUGACUAC
AAAGGAUCCACAAGCCACAGUCUCCCGUACGAGAGCAGCAUCAGCACGGCUCUUGAACACACAGUCAGUGCCUUGCUGACG
CCAGCUGAGCAGACAAGCACCUGGAAAUUCAAGACCAAACUGAAUGACAAAGUAUACAGCCAGGACUUUGAAGCCUACAACA
CUAAAGACAAAAUCGGUGUUGAGCUUAGUGGACGGGCUGACCUCUCUGGGCUGUAUUCUCCAAUUAAACUACCGUUUUUCU
ACAGUGAGCCUGUCAAUGUCCUUAAUGGCUUAGAGGUAAAUGAUGCUGUUGACAAGCCCCAAGAAUUCACAAUUAUUGCUGU
GGUGAAGUACGAUAAGAACCAGGAUGUUCACACCAUCAACCUCCCAUUCUUCAAAAGCCUGCCAGACUAUUUGGAGAGAAAU
CGAAGAGGAAUGAUAAGUCUACUGGAAGCCAUGCGAGGGGAAUUGCAACGCCUCAGUGUUGAUCAGUUUGUGAGGAAAUAC
AGAGCGGCCCUGAGCAGACUUCCUCAGCAGAUUCAUCAUUAUCUGAAUGCAUCUGACUGGGAGAGACAAGUAGCUGGUGCC
AAGGAAAAAAUAACUUCUUUCAUGGAAAAUUAUAGAAUUACAGAUAAUGAUGUACUAAUUGCCAUAGAUAGUGCCAAAAUCAA
CUUCAAUGAAAAACUCUCUCAACUUGAGACAUACGCGAUACAAUUUGAUCAGUAUAUUAAAGAUAAUUAUGAUCCACAUGACU
UAAAAAGAACUAUUGCUGAGAUUAUUGAUCGAAUCAUUGAAAAGUUAAAAAUUCUUGAUGAACAGUAUCAUAUCCGUGUAAAU
CUAGCAAAAUCAAUCCAUAAUCUCUAUUUAUUUGUUGAAAACGUUGAUCUUAACCAAGUCAGUAGUAGUAACACCUCUUGGA
UCCAAAAUGUGGAUUCCAAUUAUCAAGUCAGAAUCCAAAUUCAAGAAAAACUACAGCAGCUCAGGACACAAAUUCAGAAUAUA
GACAUUCAGCAGCUUGCUGCAGAGGUAAAACGACAGAUGGACGCUAUUGAUGUCACAAUGCAUUUAGAUCAAUUGAGAACUG
CAAUUCUAUUCCAAAGAAUAAGUGACAUUAUUGACCGUGUCAAAUACUUUGUUAUGAAUCUUAUUGAAGAUUUUAAAGUAACU
GAGAAAAUCAAUACUUUUAGAGUUAUAGUCCGUGAGCUAAUUGAGAAAUAUGAAGUAGACCAACACAUCCAGGUUUUAAUGG
AUAAAUCAGUAGAGUUGGCCCACAGAUAUAGCCUGAGCGAGCCUCUUCAGAAACUCAGUAAUGUGCUACAGCGAAUUGAGAU
AAAAGAUUACUAUGAGAAAUUGGUUGGGUUUAUUGAUGAUACUGUUGAGUGGCUUAAAGCAUUGUCUUUCAAAAAUACCAUU
GAAGAACUAAAUAGAUUGACUGACAUGUUGGUGAAGAAGUUGAAAGCAUUUGAUUAUCACCAGUUUGUAGACAAAACCAACA
GCAAAAUCCGUGAGAUGACUCAGAGAAUCAAUGCUGAAAUCCAAGCUCUCAAACUUCCACAAAAAAUGGAAGCAUUAAAACUG
UUGGUAGAAGACUUCAAAACCACAGUCUCCAAUUCCCUGGAAAGACUCAAGGACACCAAAGUAACUGUGGUCAUUGAUUGGC
UGCAGGAUAUUUUGACUCAAAUGAAAGACCAUUUCCAAGAUACUCUGGAAGAUGUAAGAGACCGAAUUUAUCAAAUGGACAU
UCAGAGGGAACUGGAGCACUUCUUGUCUCUGGUAAACCAAGUUUACAGUACACUGGUCACCUAUAUGUCUGACUGGUGGAC
UCUGACUGCUAAAAACAUAACAGACUUUGCAGAGCAAUAUUCCAUCCAAAACUGGGCUGAGAGUAUAAAAGUACUGGUGGAA
CAAGGAUUCAUAGUUCCUGAAAUGCAAACAUUUCUGUGGACCAUGCCUGCUUUUGAGGUCAGUCUCCGUGCUCUCCAAGAA
GGUAACUUUCAGACCCCUGUCUUUAUAGUCCCCUUGACAGAUUUGAGGAUUCCAUCAAUUCGGAUAAACUUUAAAAUGUUAA
AGAAUAUAAAAAUCCCAUUGAGAUUUUCCACUCCAGAAUUCACUCUUCUCAACACCUUCCAUGUCCAUUCCUUUACAAUUGAC
UUGCUGGAAAUAAAAGCAAAGAUCAUUAGAACUAUCGACCAAAUUUUGAGCAGUGAGCUACAGUGGCCUCUUCCAGAAAUGU
AUUUGAGAGACCUGGAUGUAGUGAACAUUCCUCUUGCAAGACUGACUCUGCCAGACUUCCAUGUACCAGAAAUCACAAUUCC
AGAAUUCACAAUCCCAAAUGUCAAUCUCAAAGAUUUACACGUUCCUGAUCUUCACAUACCAGAAUUCCAACUUCCUCACCUCU

FIG. 13C

SEQ ID NO:10 (CONTINUED)
CACAUACAAUUGAAAUACCUGCUUUUGGCAAACUGCAUAGCAUCCUUAAGAUCCAAUCUCCUCUCUUUAUAUUAGAUGCUAA
UGCCAACAUACAGAAUGUAACAACUUCAGGGAACAAAGCAGAGAUUGUGGCUUCUGUCACUGCUAAAGGAGAGUCCCAAUUU
GAAGCUCUCAAUUUUGAUUUUCAAGCACAAGCUCAAUUCCUGGAGUUAAAUCCUCAUCCUCCAGUCCUGAAGGAAUCCAUGA
ACUUCUCCAGUAAGCAUGUGAGAAUGGAGCAUGAGGGUGAGAUAGUAUUUGAUGGAAAGGCCAUUGAGGGGAAAUCAGACA
CAGUCGCAAGUUUACACACAGAGAAAAAUGAAGUAGAGUUUAAUAAUGGUAUGACUGUCAAAGUAAACAAUCAGCUCACCCU
UGACAGUCACACAAAGUACUUCCACAAGUUGAGUGUUCCUAGGCUGGACUUCUCCAGUAAGGCUUCUCUUAAUAAUGAAAUC
AAGACACUAUUAGAAGCUGGACAUGUGGCAUUGACAUCUUCAGGGACAGGGUCAUGGAACUGGGCCUGUCCCAACUUCUCG
GAUGAAGGCAUACAUUCGUCCCAAAUUAGCUUUACUGUGGAUGGUCCCAUUGCUUUUGUUGGACUAUCCAAUAACAUAAAUG
GCAAACACUUACGGGUCAUCCAAAAACUGACUUAUGAAUCUGGCUUCCUCAACUAUUCUAAGUUUGAAGUUGAGUCAAAAGU
UGAAUCUCAGCACGUGGGCUCCAGCAUUCUAACAGCCAAUGGUCGGGCACUGCUCAAGGACGCAAAGGCAGAAAUGACUGG
UGAGCACAAUGCCAACUUAAAUGGAAAAGUUAUUGGAACUUUGAAAAAUUCUCUCUUCUUUUCAGCACAACCAUUUGAGAUU
ACUGCAUCCACAAAUAAUGAAGGAAAUUUGAAAGUGGGUUUUCCACUAAAGCUGACUGGGAAAAUAGACUUCCUGAAUAACU
AUGCAUUGUUUCUGAGUCCCCGUGCCCAACAAGCAAGCUGGCAAGCGAGUACCAGAUUCAAUCAGUACAAAUACAAUCAAAA
CUUUUCUGCUAUAAACAAUGAACACAACAUAGAAGCCAGUAUAGGAAUGAAUGGAGAUGCCAACCUGGAUUUCUUAAACAUA
CCUUUAACAAUUCCUGAAAUUAACUUGCCUUACACGGAGUUCAAAACUCCCUUACUGAAGGAUUUCUCCAUAUGGGAAGAAA
CAGGCUUGAAAGAAUUUUUGAAGACAACAAAGCAAUCAUUUGAUUUGAGUGUAAAGGCUCAAUAUAAAAAGAACAGUGACAAG
CAUUCCAUUGUUGUCCCUCUGGGUAUGUUUUAUGAAUUUAUUCUCAACAAUGUCAAUUCGUGGGACAGAAAAUUUGAGAAAG
UCAGAAACAAUGCUUUACAUUUUCUUACCACCUCCUAUAAUGAAGCAAAAAUUAAGGUUGAUAAGUACAAAACUGAAAAUUCC
CUUAAUCAGCCCUCUGGGACCUUUCAAAAUCAUGGCUACACUAUCCCAGUUGUCAACAUUGAAGUAUCUCCAUUUGCUGUAG
AGACACUGGCUUCCAGCCAUGUGAUCCCCACAGCAAUAAGCACCCCAAGUGUCACAAUCCCUGGUCCUAACAUCAUGGUGCC
UUCAUACAAGUUAGUGCUGCCACCCCUGGAGUUGCCAGUUUUCCAUGGUCCUGGGAAUCUAUUCAAGUUUUUCCUCCCAGA
UUUCAAGGGAUUCAACACUAUUGACAAUAUUUAUAUUCCAGCCAUGGGCAACUUUACCUAUGACUUUUCUUUUAAAUCAAGU
GUCAUCACACUGAAUACCAAUGCUGGACUUUAUAACCAAUCAGAUAUCGUUGCCCAUUUCCUUUCUUCCUCUUCAUUUGUCA
CUGACGCCCUGCAGUACAAAUUAGAGGGAACAUCACGUCUGAUGCGAAAAAGGGGAUUGAAACUAGCCACAGCUGUCUCUC
UAACUAACAAAUUUGUAAAGGGCAGUCAUGACAGCACCAUUAGUUUAACCAAGAAAAACAUGGAAGCAUCAGUGAGAACAACU
GCCAACCUCCAUGCUCCCAUAUUCUCAAUGAACUUCAAGCAGGAACUUAAUGGAAAUACCAAGUCAAAACCCACUGUUUCAU
CAUCCAUUGAACUAAACUAUGACUUCAAUUCCUCAAAGCUGCACUCUACUGCAACAGGAGGCAUUGAUCACAAGUUCAGCUU
AGAAAGUCUCACUUCCUACUUUUCCAUUGAGUCAUUCACCAAAGGAAAUAUCAAGAGUUCCUUCCUUUCUCAGGAAUAUUCA
GGAAGUGUUGCCAAUGAAGCCAAUGUAUAUCUGAAUUCCAAGGGUACUCGGUCUUCAGUGAGGCUACAAGGAGCUUCCAAA
GUUGAUGGUAUCUGGAACGUUGAAGUAGGAGAAAAUUUUGCUGGAGAAGCCACCCUCCAACGCAUCUACACCACAUGGGAG
CACAAUAUGAAAAACCAUUUGCAGGUAUAUAGCUACUUCUUCACAAAAGGAAAGCAAACAUGCAGAGCUACUUUGGAGCUCU
CCCCAUGGACCAUGUCAACCUUGCUACAGGUUCAUGUGAGUCAACUCAGUUCCCUCCUUGACCUCCAUCACUUUGACCAGG
AAGUGAUCCUAAAAGCUAACACUAAGAACCAGAAGAUCAGCUGGAAAGGUGGGGUCCAGGUUGAAUCACGGGUUCUUCAGCA
CAAUGCACAGUUCUCCAAUGACCAAGAAGAAAUACGGCUUGACCUUGCAGGAUCCUUAGACGGACAGCUGUGGGACCUUGA

FIG. 13D

SEQ ID NO:10 (CONTINUED)
AGCUAUCUUUUUACCAGUAUAUGGCAAGAGCUUGCAGGAACUCCUACAAAUGGAUGGAAAGCGACAGUAUCUUCAAGCUUCAACUU
CUCUUCUAUAUACCAAAAACCCUAAUGGCUAUCUCCUCUCACUCCCCGUGCAAGAACUGGCUGAUAGAUUUAUUAUACCAGGGAUA
AAACUAAAUGACUUCAGUGGAGUAAAAAUCUAUAAGAAGUUAAGUACUUCACCAUUUGCCCUCAACCUAACAAUGCUCCCCAAAGUA
AAAUUCCCUGGGAUUGAUCUGUUAACACAGUACUCUACACCAGAGGGCUCCUCUGUCCCUAUUUUUGAGGCAACUAUACCUGAAAU
UCAUUUAACUGUAUCCCAGUUUACACUUCCAAAGAGCCUUCCAGUUGGCAACACAGUCUUUGAUCUGAAUAAGUUGGCCAACAUGA
UUGCCGAUGUUGACCUGCCUAGUGUCACCCUGCCUGAGCAGACUAUUGUAAUCCCACCCUUGGAGUUCUCUGUACCUGCUGGGA
UUUUUAUUCCUUUCUUUGGAGAACUGACUGCACGUGCUGGGAUGGCUUCUCCCCUGUAUAAUGUCACUUGGAGCGCUGGUUGGA
AAACCAAAGCAGAUCAUGUUGAAACGUUCCUAGAUUCCAUGUGCACUUCAACCUUGCAGUUUCUGGAGUAUGCUUUAAAAGUUGUA
GAAACACACAAAAUUGAAGAAGAUCUGUUAACCUAUAAUAUCAAAGGAACACUUCAACACUGUGACUUCAAUGUGGAGUAUAAUGAA
GAUGGUCUAUUUAAAGGACUUUGGGACUGGCAGGGAGAGGCUCACCUGGACAUCACCAGCCCAGCACUGACUGACUUUCAUCUGU
ACUACAAAGAAGACAAGACAAGUCUGUCUGCCUCAGCAGCCUCCUCGACCAUCGGCACUGUGGGUCUGGAUUCGAGCACAGAUGA
CCAGAGUGUGGAGCUGAAUGUCUACUUCCACCCACAGUCCCCUCCAGAGAAGAAACUCAGCAUAUUCAAAACUGAGUGGAGGUACA
AGGAGUCUGAUGGUGAAAGGUACAUCAAAAUUAAUUGGGAAGAAGAGGCAGCUUCCAGAUUGCUAGGCUCCCUAAAAAGCAAUGU
GCCCAAGGCUUCUAAGGCUAUUUAUGAUUAUGCCAAUAAGUACCACCUGGAAUACGUUUCUUCAGAACUAAGAAAAAGUCUACAGG
UCAAUGCUGAACAUGCCAGAAGGAUGGUUGAUGAAAUGAACAUGAGUUUCCAGAGAGUAGCCCGUGAUACCUACCAGAAUCUCUAU
GAGGAGAUGUUGGCUCAGAAGAGCCUGAGCAUCCCUGAGAAUCUCAAGAAGAGGGUGUUAGACAGUAUAGUACAUGUUACUCAGA
AGUACCACAUGGCAGUCAUGUGGCUGAUGGACUCAUUCAUUCAUUUUCUGAAAUUCAAUAGAGUCCAGUUCCCAGGGUACGCUGG
AACAUAUACUGUGGACGAACUCUACACUAUAGUCAUGAAGGAAACCAAGAAGUCACUGUCUCAGCUGUUUAAUGGGUUAGGAAACC
UACUUUCCUACGUUCAAAACCAAGUAGAGAAAUCAAGAUUAAUCAAUGACAUAACAUUUAAAUGUCCUUUUUUCUCAAAACCUUGUA
AACUAAAAGAUCUCAUAUUGAUUUUCAGGGAGGAGUUAAACAUUUUAUCAAACAUAGGCCAACAGGAUAUCAAGUUUACAACAAUAC
UAAGUAGUCUUCAGGGCUUUUUGGAGAGAGUUUUAGACAUCAUAGAAGAACAAAUUAAAUGCCUAAAGGACAAUGAAUCUACUUGU
GUUGCUGACCAUAUCAACAUGGUUUUCAAAAUACAGGUCCCAUAUGCUUUUAAAUCCCUAAGAGAAGACAUAUACUUUGUCCUCGG
UGAGUUCAAUGACUUUCUUCAAUCCAUACUUCAGGAGGGGUCCUACAAGCUACAGCAGGUCCAUCAGUAUAUGAAGGCCCUUCGU
GAAGAGUAUUUUGAUCCGAGCAUGGUUGGGUGGACAGUGAAAUAUUAUGAAAUAGAAGAAAAUAUGGUUGAGCUGAUCAAGACCC
UUUUAGUUUCCUUUAGGGAUGUCUACUCUGAAUAUAGUGUGACAGCUGCUGAUUUUGCUUCCAAAAUGUCAACUCAAGUUGAACA
AUUUGUGUCCAGGGAUAUCAGAGAGUAUCUUAGCAUGCUUACUGAUAUAAAUGGAAAGUGGAUGGAAAAGAUUGCAGAGCUUUCU
AUUGUGGCAAAGGAAACAAUGAAAAGCUGGGUCACUGCCGUGGCCAAAAUAAUGUCUGAUUACCCCCAGCAGUUCCACUCCAAUCU
GCAGGAUUUUUCAGACCAACUCUCUAGCUACUAUGAAAAAUUUGUUGGUGAGUCCACAAGAUUGAUUGACCUGUCCAUUCAAAACU
ACCACGUGUUUCUCAGAUACAUCACCGAGUUACUGAGAAAGCUGCAGGUGGCCACAGCCAAUAAUGUGAGCCCCUAUAUAAAGCUU
GCUCAAGGAGAGCUGAUGAUCACCUUCUGAUUCAUCUACUAACAAAUUCAAAUUAAACCUUCACAUAGUAGGAGACUUUGUAGACU
ACUAUAAAGACCAUCCUGAGCCAGACCUGCAGUCAACAGCAAGAGCAAGAAGCACAUAGGAACUAUACCUGCAACCAAGCUGGCAU
AAGAACCAAGACCUUCAAAGCAGCCUGAACUCAAGAUGACAUAUUUUACAAGUUAGAGUAAAGUCAAGAGCUGAGUUGUUUUGUCC
AACUCAGGAUGGAGGGAGGGAGGGAAGGGGAAAUAAAUAAAUACUUCCUUAUUGUGCAGCAAAAAAAAAAAAAAAAAAAA

FIG. 13E

SEQ ID NO:1 >X04506 (Human ApoB)

UCCCACCGGGACCUGCGGGGCUGAGUGCCCUUCUCGGUUGCUGCCGCUGAGGAGCCCGCCCAGCCAGCCAGGGCCGCGAG
GCCGAGGCCAGGCCGCAGCCCAGGAGCCGCCCCACCGCAGCUGGCGAUGGACCCGCCGAGGCCCGCGCUGCUGGCGCUGC
UGGCGCUGCCUGCGCUGCUGCUGCUGCUGCUGGCGGGCGCCAGGGCCGAAGAGGAAAUGCUGGAAAAUGUCAGCCUGGUC
UGUCCAAAAGAUGCGACCCGAUUCAAGCACCUCCGGAAGUACACAUACAACUAUGAGGCUGAGAGUUCCAGUGGAGUCCCU
GGGACUGCUGAUUCAAGAAGUGCCACCAGGAUCAACUGCAAGGUUGAGCUGGAGGUUCCCCAGCUCUGCAGCUUCAUCCUG
AAGACCAGCCAGUGCACCCUGAAAGAGGUGUAUGGCUUCAACCCUGAGGGCAAAGCCUUGCUGAAGAAAACCAAGAACUCUG
AGGAGUUUGCUGCAGCCAUGUCCAGGUAUGAGCUCAAGCUGGCCAUUCCAGAAGGGAAGCAGGUUUUCCUUUACCCGGAGA
AAGAUGAACCUACUUACAUCCUGAACAUCAAGAGGGGCAUCAUUUCUGCCCUCCUGGUUCCCCCAGAGACAGAAGAAGCCAA
GCAAGUGUUGUUUCUGGAUACCGUGUAUGGAAACUGCUCCACUCACUUUACCGUCAAGACGAGGAAGGGCAAUGUGGCAAC
AGAAAUAUCCACUGAAAGAGACCUGGGGCAGUGUGAUCGCUUCAAGCCCAUCCGCACAGGCAUCAGCCCACUUGCUCUCAU
CAAAGGCAUGACCCGCCCCUUGUCAACUCUGAUCAGCAGCAGCCAGUCCUGUCAGUACACACUGGACGCUAAGAGGAAGCA
UGUGGCAGAAGCCAUCUGCAAGGAGCAACACCUCUUCCUGCCUUUCUCCUACAACAAUAAGUAUGGGAUGGUAGCACAAGU
GACACAGACUUUGAAACUUGAAGACACACCAAAGAUCAACAGCCGCUUCUUUGGUGAAGGUACUAAGAAGAUGGGCCUCGCA
UUUGAGAGCACCAAAUCCACAUCACCUCCAAAGCAGGCCGAAGCUGUUUUGAAGACUCUCCAGGAACUGAAAAAACUAACCA
UCUCUGAGCAAAAUAUCCAGAGAGCUAAUCUCUUCAAUAAGCUGGUUACUGAGCUGAGAGGCCUCAGUGAUGAAGCAGUCAC
AUCUCUCUUGCCACAGCUGAUUGAGGUGUCCAGCCCCAUCACUUUACAAGCCUUGGUUCAGUGUGGACAGCCUCAGUGCUC
CACUCACAUCCUCCAGUGGCUGAAACGUGUGCAUGCCAACCCCCUUCUGAUAGAUGUGGUCACCUACCUGGUGGCCCUGAU
CCCCGAGCCCUCAGCACAGCAGCUGCGAGAGAUCUUCAACAUGGCGAGGGAUCAGCGCAGCCGAGCCACCUUGUAUGCGCU
GAGCCACGCGGUCAACAACUAUCAUAAGACAAACCCUACAGGGACCCAGGAGCUGCUGGACAUUGCUAAUUACCUGAUGGAA
CAGAUUCAAGAUGACUGCACUGGGGAUGAAGAUUACACCUAUUUGAUUCUGCGGGUCAUUGGAAAUAUGGGCCAAACCAUG
GAGCAGUUAACUCCAGAACUCAAGUCUUCAAUCCUCAAAUGUGUCCAAAGUACAAAGCCAUCACUGAUGAUCCAGAAAGCUG
CCAUCCAGGCUCUGCGGAAAAUGGAGCCUAAAGACAAGGACCAGGAGGUUCUUCUUCAGACUUUCCUUGAUGAUGCUUCUC
CGGGAGAUAAGCGACUGGCUGCCUAUCUUAUGUUGAUGAGGAGUCCUUCACAGGCAGAUAUUAACAAAAUUGUCCAAAUUC
UACCAUGGGAACAGAAUGAGCAAGUGAAGAACUUUGUGGCUUCCCAUAUUGCCAAUAUCUUGAACUCAGAAGAAUUGGAUAU
CCAAGAUCUGAAAAAGUUAGUGAAAGAAGCUCUGAAAGAAUCUCAACUUCCAACUGUCAUGGACUUCAGAAAAUUCUCUCGG
AACUAUCAACUCUACAAAUCUGUUUCUCUUCCAUCACUUGACCCAGCCUCAGCCAAAAUAGAAGGGAAUCUUAUAUUUGAUC
CAAAUAACUACCUUCCUAAAGAAAGCAUGCUGAAAACUACCCUCACUGCCUUUGGAUUUGCUUCAGCUGACCUCAUCGAGAU
UGGCUUGGAAGGAAAAGGCUUUGAGCCAACAUUGGAAGCUCUUUUUGGGAAGCAAGGAUUUUUCCCAGACAGUGUCAACAA
AGCUUUGUACUGGGUUAAUGGUCAAGUUCCUGAUGGUGUCUCUAAGGUCUUAGUGGACCACUUUGGCUAUACCAAAGAUGA
UAAACAUGAGCAGGAUAUGGUAAAUGGAAUAAUGCUCAGUGUUGAGAAGCUGAUUAAAGAUUUGAAAUCCAAAGAAGUCCCG
GAAGCCAGAGCCUACCUCCGCAUCUUGGGAGAGGAGCUUGGUUUUGCCAGUCUCCAUGACCUCCAGCUCCUGGGAAAGCUG
CUUCUGAUGGGUGCCCGCACUCUGCAGGGGAUCCCCCAGAUGAUUGGAGAGGUCAUCAGGAAGGGCUCAAAGAAUGACUUU
UUUCUUCACUACAUCUUCAUGGAGAAUGCCUUUGAACUCCCCACUGGAGCUGGAUUACAGUUGCAAAUAUCUUCAUCUGGA
GUCAUUGCUCCCGGAGCCAAGGCUGGAGUAAAACUGGAAGUAGCCAACAUGCAGGCUGAACUGGUGGCAAAACCCUCCGUG

FIG. 14A

SEQ ID NO:1 (CONTINUED)

UCUGUGGAGUUUGUGACAAAUAUGGGCAUCAUCAUUCCGGACUUCGCUAGGAGUGGGGUCCAGAUGAACACCAACUUCUUC
CACGAGUCGGGUCUGGAGGCUCAUGUUGCCCUAAAAGCUGGGAAGCUGAAGUUUAUCAUUCCUUCCCCAAAGAGACCAGUC
AAGCUGCUCAGUGGAGGCAACACAUUACAUUUGGUCUCUACCACCAAAACGGAGGUGAUCCCACCUCUCAUUGAGAACAGGC
AGUCCUGGUCAGUUUGCAAGCAAGUCUUUCCUGGCCUGAAUUACUGCACCUCAGGCGCUUACUCCAACGCCAGCUCCACAG
ACUCCGCCUCCUACUAUCCGCUGACCGGGGACACCAGAUUAGAGCUGGAACUGAGGCCUACAGGAGAGAUUGAGCAGUAUU
CUGUCAGCGCAACCUAUGAGCUCCAGAGAGAGGACAGAGCCUUGGUGGAUACCCUGAAGUUUGUAACUCAAGCAGAAGGUG
CGAAGCAGACUGAGGCUACCAUGACAUUCAAAUAUAAUCGGCAGAGUAUGACCUUGUCCAGUGAAGUCCAAAUUCCGGAUUU
UGAUGUUGACCUCGGAACAAUCCUCAGAGUUAAUGAUGAAUCUACUGAGGGCAAAACGUCUUACAGACUCACCCUGGACAUU
CAGAACAAGAAAAUUACUGAGGUCGCCCUCAUGGGCCACCUAAGUUGUGACACAAAGGAAGAAAGAAAAAUCAAGGGUGUUA
UUUCCAUACCCCGUUUGCAAGCAGAAGCCAGAAGUGAGAUCCUCGCCCACUGGUCGCCUGCCAAACUGCUUCUCCAAAUGG
ACUCAUCUGCUACAGCUUAUGGCUCCACAGUUUCCAAGAGGGUGGCAUGGCAUUAUGAUGAAGAGAAGAUUGAAUUUGAAU
GGAACACAGGCACCAAUGUAGAUACCAAAAAAAUGACUUCCAAUUUCCCUGUGGAUCUCUCCGAUUAUCCUAAGAGCUUGCA
UAUGUAUGCUAAUAGACUCCUGGAUCACAGAGUCCCUGAAACAGACAUGACUUUCCGGCACGUGGGUUCCAAAUUAAUAGUU
GCAAUGAGCUCAUGGCUUCAGAAGGCAUCUGGGAGUCUUCCUUAUACCCAGACUUUGCAAGACCACCUCAAUAGCCUGAAG
GAGUUCAACCUCCAGAACAUGGGAUUGCCAGACUUCCACAUCCCAGAAAACCUCUUCUUAAAAAGCGAUGGCCGGGUCAAAU
AUACCUUGAACAAGAACAGUUUGAAAAUUGAGAUUCCUUUGCCUUUUGGUGGCAAAUCCUCCAGAGAUCUAAAGAUGUUAGA
GACUGUUAGGACACCAGCCCUCCACUUCAAGUCUGUGGGAUUCCAUCUGCCAUCUCGAGAGUUCCAAGUCCCUACUUUUAC
CAUUCCCAAGUUGUAUCAACUGCAAGUGCCUCUCCUGGGUGUUCUAGACCUCUCCACGAAUGUCUACAGCAACUUGUACAAC
UGGUCCGCCUCCUACAGUGGUGGCAACACCAGCACAGACCAUUUCAGCCUUCGGGCUCGUUACCACAUGAAGGCUGACUCU
GUGGUUGACCUGCUUUCCUACAAUGUGCAAGGAUCUGGAGAAACAACAUAUGACCACAAGAAUACGUUCACACUAUCAUGUG
AUGGGUCUCUACGCCACAAAUUUCUAGAUUCGAAUAUCAAAUUCAGUCAUGUAGAAAAACUUGGAAACAACCCAGUCUCAAAA
GGUUUACUAAUAUUCGAUGCAUCUAGUUCCUGGGGACCACAGAUGUCUGCUUCAGUUCAUUUGGACUCCAAAAAGAAACAGC
AUUUGUUUGUCAAAGAAGUCAAGAUUGAUGGGCAGUUCAGAGUCUCUUCGUUCUAUGCUAAAGGCACAUAUGCCUGUCUUG
UCAGAGGGAUCCUAACACUGGCCGGCUCAAUGGAGAGUCCAACCUGAGGUUUAACUCCUCCUACCUCCAAGGCACCAACCA
GAUAACAGGAAGAUAUGAAGAUGGAACCCUCUCCCUCACCUCCACCUCUGAUCUGCAAAGUGGCAUCAUUAAAAAUACUGCU
UCCCUAAAGUAUGAGAACUACGAGCUGACUUUAAAAUCUGACACCAAUGGGAAGUAUAAGAACUUUGCCACUUCUAACAAGA
UGGAUAUGACCUUCUCUAAGCAAAAUGCACUGCUGCGUUCUGAAUAUCAGGCUGAUUACGAGUCAUUGAGGUUCUUCAGCC
UGCUUUCUGGAUCACUAAAUUCCCAUGGUCUUGAGUUAAAUGCUGACAUCUUAGGCACUGACAAAAUUAAUAGUGGUGCUCA
CAAGGCGACACUAAGGAUUGGCCAAGAUGGAAUAUCUACCAGUGCAACGACCAACUUGAAGUGUAGUCUCCUGGUGCUGGA
GAAUGAGCUGAAUGCAGAGCUUGGCCUCUCUGGGGCAUCUAUGAAAUUAACAACAAAUGGCCGCUUCAGGGAACACAAUGC
AAAAUUCAGUCUGGAUGGGAAAGCCGCCCUCACAGAGCUAUCACUGGGAAGUGCUUAUCAGGCCAUGAUUCUGGGUGUCGA
CAGCAAAAACAUUUUCAACUUCAAGGUCAGUCAAGAAGGACUUAAGCUCUCAAAUGACAUGAUGGGCUCAUAUGCUGAAAUG
AAAUUUGACCACACAAACAGUCUGAACAUUGCAGGCUUAUCACUGGACUUCUCUUCAAAACUUGACAACAUUUACAGCUCUG
ACAAGUUUUAUAAGCAAACUGUUAAUUUACAGCUACAGCCCUAUUCUCUGGUAACUACUUUAAACAGUGACCUGAAAUACAAU

FIG. 14B

SEQ ID NO:1 (CONTINUED)
GCUCUGGAUCUCACCAACAAUGGGAAACUACGGCUAGAACCCCUGAAGCUGCAUGUGGCUGGUAACCUAAAAGGAGCCUAC
CAAAAUAAUGAAAUAAAACACAUCUAUGCCAUCUCUUCUGCUGCCUUAUCAGCAAGCUAUAAAGCAGACACUGUUGCUAAGG
UUCAGGGUGUGGAGUUUAGCCAUCGGCUCAACACAGACAUCGCUGGGCUGGCUUCAGCCAUUGACAUGAGCACAAACUAUA
AUUCAGACUCACUGCAUUUCAGCAAUGUCUUCCGUUCUGUAAUGGCCCCGUUUACCAUGACCAUCGAUGCACAUACAAAUGG
CAAUGGGAAACUCGCUCUCUGGGGAGAACAUACUGGGCAGCUGUAUAGCAAAUUCCUGUUGAAAGCAGAACCUCUGGCAUU
UACUUUCUCUCAUGAUUACAAAGGCUCCACAAGUCAUCAUCUCGUGUCUAGGAAAAGCAUCAGUGCAGCUCUUGAACACAAA
GUCAGUGCCCUGCUUACUCCAGCUGAGCAGACAGGCACCUGGAAACUCAAGACCCAAUUUAACAACAAUGAAUACAGCCAGG
ACUUGGAUGCUUACAACACUAAAGAUAAAAUUGGCGUGGAGCUUACUGGACGAACUCUGGCUGACCUAACUCUACUAGACUC
CCCAAUUAAAGUGCCACUUUUACUCAGUGAGCCCAUCAAUAUCAUUGAUGCUUUAGAGAUGAGAGAUGCCGUUGAGAAGCCC
CAAGAAUUUACAAUUGUUGCUUUUGUAAAGUAUGAUAAAAACCAAGAUGUUCACUCCAUUAACCUCCCAUUUUUUGAGACCU
UGCAAGAAUAUUUUGAGAGGAAUCGACAAACCAUUAUAGUUGUAGUGGAAAACGUACAGAGAAACCUGAAGCACAUCAAUAU
UGAUCAAUUUGUAAGAAAAUACAGAGCAGCCCUGGGAAAACUCCCACAGCAAGCUAAUGAUUAUCUGAAUUCAUUCAAUUGG
GAGAGACAAGUUUCACAUGCCAAGGAGAAACUGACUGCUCUCACAAAAAAGUAUAGAAUUACAGAAAAUGAUAUACAAAUUGC
AUUAGAUGAUGCCAAAAUCAACUUUAAUGAAAAACUAUCUCAACUGCAGACAUAUAUGAUACAAUUUGAUCAGUAUAUUAAAG
AUAGUUAUGAUUUACAUGAUUUGAAAAUAGCUAUUGCUAAUAUUAUUGAUGAAAUCAUUGAAAAAUUAAAAAGUCUUGAUGAG
CACUAUCAUAUCCGUGUAAAUUUAGUAAAAACAAUCCAUGAUCUACAUUUGUUUAUUGAAAAUAUUGAUUUUAACAAAAGUGG
AAGUAGUACUGCAUCCUGGAUUCAAAAUGUGGAUACUAAGUACCAAAUCAGAAUCCAGAUACAAGAAAAACUGCAGCAGCUUA
AGAGACACAUACAGAAUAUAGACAUCCAGCACCUAGCUGGAAAGUUAAAACAACACAUUGAGGCUAUUGAUGUUAGAGUGCU
UUUAGAUCAAUUGGGAACUACAAUUUCAUUUGAAAGAAUAAAUGAUGUUCUUGAGCAUGUCAAACACUUUGUUAUAAAUCUU
AUUGGGGAUUUUGAAGUAGCUGAGAAAAUCAAUGCCUUCAGAGCCAAAGUCCAUGAGUUAAUCGAGAGGUAUGAAGUAGACC
AACAAAUCCAGGUUUUAAUGGAUAAAUUAGUAGAGUUGACCCACCAAUACAAGUUGAAGGAGACUAUUCAGAAGCUAAGCAA
UGUCCUACAACAAGUUAAGAUAAAAGAUUACUUUGAGAAAUUGGUUGGAUUUAUUGAUGAUGCUGUGAAGAAGCUUAAUGAA
UUAUCUUUUAAAACAUUCAUUGAAGAUGUUAACAAAUUCCUUGACAUGUUGAUAAAGAAAUUAAAGUCAUUUGAUUACCACCA
GUUUGUAGAUGAAACCAAUGACAAAAUCCGUGAGGUGACUCAGAGACUCAAUGGUGAAAUUCAGGCUCUGGAACUACCACAA
AAAGCUGAAGCAUUAAAACUGUUUUUAGAGGAAACCAAGGCCACAGUUGCAGUGUAUCUGGAAAGCCUACAGGACACCAAAA
UAACCUUAAUCAUCAAUUGGUUACAGGAGGCUUUAAGUUCAGCAUCUUUGGCUCACAUGAAGGCCAAAUUCCGAGAGACUCU
AGAAGAUACACGAGACCGAAUGUAUCAAAUGGACAUUCAGCAGGAACUUCAACGAUACCUGUCUCUGGUAGGCCAGGUUUAU
AGCACACUUGUCACCUACAUUUCUGAUUGGUGGACUCUUGCUGCUAAGAACCUUACUGACUUUGCAGAGCAAUAUUCUAUCC
AAGAUUGGGCUAAACGUAUGAAAGCAUUGGUAGAGCAAGGGUUCACUGUUCCUGAAAUCAAGACCAUCCUUGGGACCAUGC
CUGCCUUUGAAGUCAGUCUUCAGGCUCUUCAGAAAGCUACCUUCCAGACACCUGAUUUUAUAGUCCCCCUAACAGAUUUGAG
GAUUCCAUCAGUUCAGAUAAACUUCAAAGACUUAAAAAAUAUAAAAAUCCCAUCCAGGUUUUCCACACCAGAAUUUACCAUCC
UUAACACCUUCCACAUUCCUUCCUUUACAAUUGACUUUGUCGAAAUGAAAGUAAAGAUCAUCAGAACCAUUGACCAGAUGCA
GAACAGUGAGCUGCAGUGGCCCGUUCCAGAUAUAUAUCUCAGGGAUCUGAAGGUGGAGGACAUUCCUCUAGCGAGAAUCAC
CCUGCCAGACUUCCGUUUACCAGAAAUCGCAAUUCCAGAAUUCAUAAUCCCAACUCUCAACCUUAAUGAUUUUCAAGUUCCU

FIG. 14C

SEQ ID NO:1 (CONTINUED)
GACCUUCACAUACCAGAAUUCCAGCUUCCCCACAUCUCACACACAAUUGAAGUACCUACUUUUGGCAAGCUAUACAGUAUUC
UGAAAAUCCAAUCUCCUCUUUUCACAUUAGAUGCAAAUGCUGACAUAGGGAAUGGAACCACCUCAGCAAACGAAGCAGGUAU
CGCAGCUUCCAUCACUGCCAAAGGAGAGUCCAAAUUAGAAGUUCUCAAUUUUGAUUUUCAAGCAAAUGCACAACUCUCAAAC
CCUAAGAUUAAUCCGCUGGCUCUGAAGGAGUCAGUGAAGUUCUCCAGCAAGUACCUGAGAACGGAGCAUGGGAGUGAAAUG
CUGUUUUUUGGAAAUGCUAUUGAGGGAAAAUCAAACACAGUGGCAAGUUUACACACAGAAAAAAAUACACUGGAGCUUAGUA
AUGGAGUGAUUGUCAAGAUAAACAAUCAGCUUACCCUGGAUAGCAACACUAAAUACUUCCACAAAUUGAACAUCCCCAAACUG
GACUUCUCUAGUCAGGCUGACCUGCGCAACGAGAUCAAGACACUGUUGAAAGCUGGCCACAUAGCAUGGACUUCUUCUGGA
AAAGGGUCAUGGAAAUGGGCCUGCCCCAGAUUCUCAGAUGAGGGAACACAUGAAUCACAAAUUAGUUUCACCAUAGAAGGAC
CCCUCACUUCCUUUGGACUGUCCAAUAAGAUCAAUAGCAAACACCUAAGAGUAAACCAAAACUUGGUUUAUGAAUCUGGCUC
CCUCAACUUUUCUAAACUUGAAAUUCAAUCACAAGUCGAUUCCCAGCAUGUGGGCCACAGUGUUCUAACUGCUAAAGGCAUG
GCACUGUUUGGAGAAGGGAAGGCAGAGUUUACUGGGAGGCAUGAUGCUCAUUUAAAUGGAAAGGUUAUUGGAACUUUGAAA
AAUUCUCUUUUCUUUUCAGCCCAGCCAUUUGAGAUCACGGCAUCCACAAACAAUGAAGGGAAUUUGAAAGUUCGUUUUCCAU
UAAGGUUAACAGGGAAGAUAGACUUCCUGAAUAACUAUGCACUGUUUCUGAGUCCCAGUGCCCAGCAAGCAAGUUGGCAAG
UAAGUGCUAGGUUCAAUCAGUAUAAGUACAACCAAAAUUUCUCUGCUGGAAACAACGAGAACAUUAUGGAGGCCCAUGUAGG
AAUAAAUGGAGAAGCAAAUCUGGAUUUCUUAAACAUUCCUUUAACAAUUCCUGAAAUGCGUCUACCUUACACAAUAAUCACAA
CUCCUCCACUGAAAGAUUUCUCUCUAUGGGAAAAAACAGGCUUGAAGGAAUUCUUGAAAACGACAAAGCAAUCAUUUGAUUU
AAGUGUAAAAGCUCAGUAUAAGAAAAACAAACACAGGCAUUCCAUCACAAAUCCUUUGGCUGUGCUUUGUGAGUUUAUCAGU
CAGAGCAUCAAAUCCUUUGACAGGCAUUUUGAAAAAAACAGAAACAAUGCAUUAGAUUUUGUCACCAAAUCCUAUAAUGAAAC
AAAAAUUAAGUUUGAUAAGUACAAAGCUGAAAAAUCUCACGACGAGCUCCCCAGGACCUUUCAAAUUCCUGGAUACACUGUU
CCAGUUGUCAAUGUUGAAGUGUCUCCAUUCACCAUAGAGAUGUCGGCAUUCGGCUAUGUGUUCCCAAAAGCAGUCAGCAUG
CCUAGUUUCUCCAUCCUAGGUUCUGACGUCCGUGUGCCUUCAUACACAUUAAUCCUGCCAUCAUUAGAGCUGCCAGUCCUU
CAUGUCCCUAGAAAUCUCAAGCUUUCUCUUCCACAUUUCAAGGAAUUGUGUACCAUAAGCCAUAUUUUUAUUCCUGCCAUGG
GCAAUAUUACCUAUGAUUUCUCCUUUAAAUCAAGUGUCAUCACACUGAAUACCAAUGCUGAACUUUUUAACCAGUCAGAUAU
UGUUGCUCAUCUCCUUUCUUCAUCUUCAUCUGUCAUUGAUGCACUGCAGUACAAAUUAGAGGGCACCACAAGAUUGACAAGA
AAAAGGGGAUUGAAGUUAGCCACAGCUCUGUCUCUGAGCAACAAAUUUGUGGAGGGUAGUCAUAACAGUACUGUGAGCUUA
ACCACGAAAAAUAUGGAAGUGUCAGUGGCAAAAACCACAAAAGCCGAAAUUCCAAUUUUGAGAAUGAAUUUCAAGCAAGAACU
UAAUGGAAAUACCAAGUCAAAACCUACUGUCUCUUCCUCCAUGGAAUUUAAGUAUGAUUUCAAUUCUUCAAUGCUGUACUCU
ACCGCUAAAGGAGCAGUUGACCACAAGCUUAGCUUGGAAAGCCUCACCUCUUACUUUUCCAUUGAGUCAUCUACCAAAGGAG
AUGUCAAGGGUUCGGUUCUUUCUCGGGAAUAUUCAGGAACUAUUGCUAGUGAGGCCAACACUUACUUGAAUUCCAAGAGCA
CACGGUCUUCAGUGAAGCUGCAGGGCACUUCCAAAAUUGAUGAUAUCUGGAACCUUGAAGUAAAAGAAAAUUUUGCUGGAGA
AGCCACACUCCAACGCAUAUAUUCCCUCUGGGAGCACAGUACGAAAAACCACUUACAGCUAGAGGGCCUCUUUUUCACCAAC
GGAGAACAUACAAGCAAAGCCACCCUGGAACUCUCUCCAUGGCAAAUGUCAGCUCUUGUUCAGGUCCAUGCAAGUCAGCCCA
GUUCCUUCCAUGAUUUCCCUGACCUUGGCCAGGAAGUGGCCCUGAAUGCUAACACUAAGAACCAGAAGAUCAGAUGGAAAAA
UGAAGUCCGGAUUCAUUCUGGGUCUUUCCAGAGCCAGGUCGAGCUUUCCAAUGACCAAGAAAAGGCACACCUUGACAUUGC

FIG. 14D

SEQ ID NO:1 (CONTINUED)
AGGAUCCUUAGAAGGACACCUAAGGUUCCUCAAAAAUAUCAUCCUACCAGUCUAUGACAAGAGCUUAUGGGAUUUCCUAAAGCUGG
AUGUAACCACCAGCAUUGGUAGGAGACAGCAUCUUCGUGUUUCAACUGCCUUUGUGUACACCAAAAACCCCAAUGGCUAUUCAUUC
UCCAUCCCUGUAAAAGUUUUGGCUGAUAAAUUCAUUACUCCUGGGCUGAAACUAAAUGAUCUAAAUUCAGUUCUUGUCAUGCCUAC
GUUCCAUGUCCCAUUUACAGAUCUUCAGGUUCCAUCGUGCAAACUUGACUUCAGAGAAAUACAAAUCUAUAAGAAGCUGAGAACUU
CAUCAUUUGCCCUCAACCUACCAACACUCCCCGAGGUAAAAUUCCCUGAAGUUGAUGUGUUAACAAAAUAUUCUCAACCAGAAGAC
UCCUUGAUUCCCUUUUUUGAGAUAACCGUGCCUGAAUCUCAGUUAACUGUGUCCCAGUUCACGCUUCCAAAAAGUGUUUCAGAUG
GCAUUGCUGCUUUGGAUCUAAAUGCAGUAGCCAACAAGAUCGCAGACUUUGAGUUGCCCACCAUCAUCGUGCCUGAGCAGACCAU
UGAGAUUCCCUCCAUUAAGUUCUCUGUACCUGCUGGAAUUGUCAUUCCUUCCUUUCAAGCACUGACUGCACGCUUUGAGGUAGAC
UCUCCCGUGUAUAAUGCCACUUGGAGUGCCAGUUUGAAAAACAAAGCAGAUUAUGUUGAAACAGUCCUGGAUUCCACAUGCAGCU
CAACCGUACAGUUCCUAGAAUAUGAACUAAAUGUUUUGGGAACACACAAAAUCGAAGAUGGUACGUUAGCCUCUAAGACUAAAGGA
ACACUUGCACACCGUGACUUCAGUGCAGAAUAUGAAGAAGAUGGCAAAUUUGAAGGACUUCAGGAAUGGGAAGGAAAAGCGCACCU
CAAUAUCAAAAGCCCAGCGUUCACCGAUCUCCAUCUGCGCUACCAGAAAGACAAGAAAGGCAUCUCCACCUCAGCAGCCUCCCCAG
CCGUAGGCACCGUGGGCAUGGAUAUGGAUGAAGAUGACGACUUUUCUAAAUGGAACUUCUACUACAGCCCUCAGUCCUCUCCAGA
UAAAAAACUCACCAUAUUCAAAACUGAGUUGAGGGUCCGGGAAUCUGAUGAGGAAACUCAGAUCAAAGUUAAUUGGGAAGAAGAGG
CAGCUUCUGGCUUGCUAACCUCUCUGAAAGACAACGUGCCCAAGGCCACAGGGGUCCUUUAUGAUUAUGUCAACAAGUACCACUG
GGAACACACAGGGCUCACCCUGAGAGAAGUGUCUUCAAAGCUGAGAAGAAAUCUGCAGAACAAUGCUGAGUGGGUUUAUCAAGGG
GCCAUUAGGCAAAUUGAUGAUAUCGACGUGAGGUUCCAGAAAGCAGCCAGUGGCACCACUGGGACCUACCAAGAGUGGAAGGACA
AGGCCCAGAAUCUGUACCAGGAACUGUUGACUCAGGAAGGCCAAGCCAGUUUCCAGGGACUCAAGGAUAACGUGUUUGAUGGCUU
GGUACGAGUUACUCAAAAAUUCCAUAUGAAAGUCAAGCAUCUGAUUGACUCACUCAUUGAUUUUCUGAACUUCCCCAGAUUCCAGU
UUCCGGGGAAACCUGGGAUAUACACUAGGGAGGAACUUUGCACUAUGUUCAUAAGGGAGGUAGGGACGGUACUGUCCCAGGUAUA
UUCGAAAGUCCAUAAUGGUUCAGAAAUACUGUUUUCCUAUUUCCAAGACCUAGUGAUUACACUUCCUUUCGAGUUAAGGAAACAUA
AACUAAUAGAUGUAAUCUCGAUGUAUAGGGAACUGUUGAAAGAUUUAUCAAAAGAAGCCCAAGAGGUAUUUAAAGCCAUUCAGUCU
CUCAAGACCACAGAGGUGCUACGUAAUCUUCAGGACCUUUUACAAUUCAUUUUCCAACUAAUAGAAGAUAACAUUAAACAGCUGAAA
GAGAUGAAAUUUACUUAUCUUAUUAAUUAUAUCCAAGAUGAGAUCAACACAAUCUUCAAUGAUUAUAUCCCAUAUGUUUUUAAAUUG
UUGAAAGAAAACCUAUGCCUUAAUCUUCAUAAGUUCAAUGAAUUUAUUCAAAACGAGCUUCAGGAAGCUUCUCAAGAGUUACAGCA
GAUCCAUCAAUACAUUAUGGCCCUUCGUGAAGAAUAUUUUGAUCCAAGUAUAGUUGGCUGGACAGUGAAAUAUUAUGAACUUGAAG
AAAAGAUAGUCAGUCUGAUCAAGAACCUGUUAGUUGCUCUUAAGGACUUCCAUUCUGAAUAUAUUGUCAGUGCCUCUAACUUUACU
UCCCAACUCUCAAGUCAAGUUGAGCAAUUUCUGCACAGAAAUAUUCAGGAAUAUCUUAGCAUCCUUACCGAUCCAGAUGGAAAAGG
GAAAGAGAAGAUUGCAGAGCUUUCUGCCACUGCUCAGGAAAUAAUUAAAAGCCAGGCCAUUGCGACGAAGAAAAUAAUUUCUGAUU
ACCACCAGCAGUUUAGAUAUAAACUGCAAGAUUUUUCAGACCAACUCUCUGAUUACUAUGAAAAAUUUAUUGCUGAAUCCAAAAGAU
UGAUUGACCUGUCCAUUCAAAACUACCACACAUUUCUGAUAUACAUCACGGAGUUACUGAAAAAGCUGCAAUCAACCACAGUCAUG
AACCCCUACAUGAAGCUUGCUCCAGGAGAACUUACUAUCAUCCUCUAAUUUUUUAAAAGAAAUCUUCAUUUAUUCUUCUUUUCCAA
UUGAACUUUCACAUAGCACAGAAAAAAUUCAAACUGCCUAUAUUGAUAAAACCAUACAGUGAGCCAGCCUUGCAGUAGGCAGUAGA
CUAUAAGCAGAAGCACAUAUGAACUGGACCUGCACCAAAGCUGGCACCAGGGCUCGGAAGGUCUCUGAACUCAGAAGGAUGGCAU
UUUUUGCAAGUUAAAGAAAAUCAGGAUCUGAGUUAUUUUGCUAAACUUGGGGGAGGAGGAACAAAUAAAUGGAGUCUUUAUUGUG
UAUCAUA

FIG. 14E

SEQUENCE LISTING

```
<160> NUMBER OF SEQ ID NOS: 232

<210> SEQ ID NO 1
<211> LENGTH: 14119
<212> TYPE: RNA
<213> ORGANISM: Homo sapiens

<400> SEQUENCE: 1

ucccaccggg accugcgggg cugagugccc uucucgguug cugccgcuga ggagcccgcc      60

cagccagcca gggccgcgag gccgaggcca ggccgcagcc caggagccgc cccaccgcag     120

cuggcgaugg acccgccgag gcccgcgcug cuggcgcugc uggcgcugcc ugcgcugcug     180

cugcugcugc uggcgggcgc cagggccgaa gaggaaaugc uggaaaaugu cagccugguc     240

uguccaaaag augcgacccg auucaagcac cuccggaagu acacauacaa cuaugaggcu     300

gagaguucca guggaguccc ugggacugcu gauucaagaa gugccaccag gaucaacugc     360

aagguugagc uggagguucc ccagcucugc agcuucaucc ugaagaccag ccagugcacc     420

cugaaagagg uguauggcuu caacccugag ggcaaagccu ugcugaagaa aaccaagaac     480

ucugaggagu uugcugcagc caugucccagg uaugagcuca agcuggccau uccagaaggg     540

aagcagguuu uccuuuaccc ggagaaagau gaaccuacuu acauccugaa caucaagagg     600

ggcaucauuu cugcccuccu gguuccccca gagacagaag aagccaagca aguguuguuu     660

cuggauaccg uguauggaaa cugcuccacu cacuuuaccg ucaagacgag gaagggcaau     720

guggcaacag aaauauccac ugaaagagac cuggggcagu gugaucgcuu caagcccauc     780

cgcacaggca ucagcccacu ugcucucauc aaaggcauga cccgccccuu gucaacucug     840

aucagcagca gccaguccug ucaguacaca cuggacgcua agaggaagca uguggcagaa     900

gccaucugca aggagcaaca ccucuuccug ccuuucuccu acaacaauaa guaugggaug     960

guagcacaag ugacacagac uuugaaacuu gaagacacac caaagaucaa cagccgcuuc    1020

uuuggugaag guacuaagaa gaugggccuc gcauuugaga gcaccaaauc cacaucaccu    1080

ccaaagcagg ccgaagcugu uuugaagacu cuccaggaac ugaaaaaacu aaccaucucu    1140

gagcaaaaua uccagagagc uaaucucuuc aauaagcugg uuacugagcu gagaggccuc    1200

agugaugaag cagucacauc ucucuugcca cagcugauug agguguccag ccccaucacu    1260
```

-continued uuacaagccu ugguucagug uggacagccu cagugcucca cucacauccu ccaguggcug 1320
aaacgugugc augccaaccc ccuucugaua gaugugguca ccuaccuggu ggcccugauc 1380
cccgagcccu cagcacagca gcugcgagag aucuucaaca uggcgaggga ucagcgcagc 1440
cgagccaccu uguaugcgcu gagccacgcg gucaacaacu aucauaagac aaacccuaca 1500
gggacccagg agcugcugga cauugcuaau uaccugaugg aacagauuca agaugacugc 1560
acuggggaug aagauuacac cuauuugauu cugcggguca uuggaaauau gggccaaacc 1620
auggagcagu uaacuccaga acucaagucu ucaauccuca aaugugucca aaguacaaag 1680
ccaucacuga ugauccagaa agcugccauc caggcucugc ggaaaaugga gccuaaagac 1740
aaggaccagg agguucuucu ucagacuuuc cuugaugaug cuucuccggg agauaagcga 1800
cuggcugccu aucuuauguu gaugaggagu ccuucacagg cagauauuaa caaaauuguc 1860
caaauucuac caugggaaca gaaugagcaa gugaagaacu uuguggcuuc ccauauugcc 1920
aauaucuuga acucagaaga auuggauauc caagaucuga aaaaguuagu gaaagaagcu 1980
cugaaagaau cucaacuucc aacugucaug gacuucagaa aauucucucg gaacuaucaa 2040
cucuacaaau cuguuucucu uccaucacuu gacccagccu cagccaaaau agaagggaau 2100
cuuauauuug auccaaauaa cuaccuuccu aaagaaagca ugcugaaaac uacccucacu 2160
gccuuuggau uugcuucagc ugaccucauc gagauuggcu uggaaggaaa aggcuuugag 2220
ccaacauugg aagcucuuuu ugggaagcaa ggauuuuucc cagacagugu caacaaagcu 2280
uuguacuggg uuaaugguca aguuccugau ggugucucua aggucuuagu ggaccacuuu 2340
ggcuauacca aagaugauaa acaugagcag gauaugguaa auggaauaau gcucaguguu 2400
gagaagcuga uuaaagauuu gaaauccaaa gaagucccgg aagccagagc cuaccuccgc 2460
aucuugggag aggagcuugg uuuugccagu cuccaugacc uccagcuccu gggaaagcug 2520
cuucugaugg gugcccgcac ucugcagggg aucccccaga ugauuggaga ggucaucagg 2580
aagggcucaa agaaugacuu uuuucuucac uacaucuuca uggagaaugc cuuugaacuc 2640
cccacuggag cuggauuaca guugcaaaua ucuucaucug gagucauugc ucccggagcc 2700
aaggcuggag uaaaacugga aguagccaac augcaggcug aacugguggc aaaacccucc 2760
gugucugugg aguuugugac aaauaugggc aucaucauuc cggacuucgc uaggagugg 2820
guccagauga acaccaacuu cuuccacgag ucgggucugg aggcucaugu ugcccuaaaa 2880
gcugggaagc ugaaguuuau cauuccuucc ccaaagagac cagucaagcu gcucagugga 2940
ggcaacacau uacauuuggu cucuaccacc aaaacggagg ugaucccacc ucucauugag 3000
aacaggcagu ccuggucagu uugcaagcaa gucuuuccug gccugaauua cugcaccuca 3060
ggcgcuuacu ccaacgccag cuccacagac uccgccuccu acuauccgcu gaccggggac 3120
accagauuag agcuggaacu gaggccuaca ggagagauug agcaguauuc ugucagcgca 3180
accuaugagc uccagagaga ggacagagcc uugguggaua cccugaaguu uguaacucaa 3240
gcagaaggug cgaagcagac ugaggcuacc augacauuca aauauaaucg gcagaguaug 3300
accuugucca gugaagucca aauuccggau uuugauguug accucggaac aauccucaga 3360
guuaaugaug aaucuacuga gggcaaaacg ucuuacagac ucacccugga cauucagaac 3420
aagaaaauua cugaggucgc ccucaugggc caccuaaguu gugacacaaa ggaagaaaga 3480
aaaaucaagg guguuauuuc cauaccccgu uugcaagcag aagccagaag ugagauccuc 3540
gcccacuggu cgccugccaa acugcuucuc caaauggacu caucugcuac agcuuauggc 3600
uccacaguuu ccaagagggu ggcauggcau uaugaugaag agaagauuga auuugaaugg 3660

-continued

```
aacacaggca ccaauguaga uaccaaaaaa augacuucca auuucccugu ggaucucucc   3720
gauuauccua agagcuugca uauguaugcu aauagacucc uggaucacag agucccugaa   3780
acagacauga cuuuccggca cgugggguucc aaauuaauag uugcaaugag cucauggcuu   3840
cagaaggcau cugggagucu uccuuauacc cagacuuugc aagaccaccu caauagccug   3900
aaggaguuca accuccagaa caugggauug ccagacuucc acaucccaga aaaccucuuc   3960
uuaaaaagcg auggccgggu caaauauacc uugaacaaga acaguuugaa aauugagauu   4020
ccuuugccuu uuggguggcaa auccuccaga gaucuaaaga uguuagagac uguuaggaca   4080
ccagcccucc acuucaaguc ugugggauuc caucugccau cucgagaguu ccaagucccu   4140
acuuuuacca uucccaaguu guaucaacug caagugccuc uccugggugu ucuagaccuc   4200
uccacgaaug ucuacagcaa cuuguacaac ugguccgccu ccuacagugg uggcaacacc   4260
agcacagacc auuucagccu ucgggcucgu uaccacauga aggcugacuc uguggguugac   4320
cugcuuuccu acaaugugca aggaucugga gaaacaacau augaccacaa gaauacguuc   4380
acacuaucau gugaugggguc ucuacgccac aaauuucuag auucgaauau caaauucagu   4440
cauguagaaa aacuuggaaa caacccaguc ucaaaagguu uacuaauauu cgaugcaucu   4500
aguuccuggg gaccacagau gucugcuuca guucauuugg acuccaaaaa gaaacagcau   4560
uuguuuguca aagaagucaa gauugauggg caguucagag ucucuucguu cuaugcuaaa   4620
ggcacauaug gccugucuug ucagagggau ccuaacacug gccggcucaa uggagagucc   4680
aaccugaggu uuaacuccuc cuaccuccaa ggcaccaacc agauaacagg aagauaugaa   4740
gauggaaccc ucucccucac cuccaccucu gaucugcaaa guggcaucau uaaaaauacu   4800
gcuucccuaa aguaugagaa cuacgagcug acuuuaaaau cugacaccaa ugggaaguau   4860
aagaacuuug ccacuucuaa caagauggau augaccuucu cuaagcaaaa ugcacugcug   4920
cguucugaau aucaggcuga uuacgaguca uugagguucu ucagccugcu uucuggauca   4980
cuaaauuccc auggucuuga guuaaaugcu gacaucuuag gcacugacaa aauuaauagu   5040
ggugcucaca aggcgacacu aaggauuggc caagauggaa uaucuaccag ugcaacgacc   5100
aacuugaagu guagucuccu ggugcuggag aaugagcuga augcagagcu uggccucucu   5160
ggggcaucua ugaaauuaac aacaaauggc cgcuucaggg aacacaaugc aaaauucagu   5220
cuggauggga aagccgcccu cacagagcua ucacugggaa gugcuuauca ggccaugauu   5280
cuggggugucg acagcaaaaa cauuuucaac uucaagguca gucaagaagg acuuaagcuc   5340
ucaaaugaca ugaugggcuc auaugcugaa augaaauuug accacacaaa cagucugaac   5400
auugcaggcu uaucacugga cuucucuuca aaacuugaca acauuuacag cucugacaag   5460
uuuuauaagc aaacuguuaa uuuacagcua cagcccuauu cucugguaac uacuuuaaac   5520
agugaccuga aauacaaugc ucuggaucuc accaacaaug ggaaacuacg gcuagaaccc   5580
cugaagcugc auguggcugg uaaccuaaaa ggagccuacc aaaauaauga aauaaaacac   5640
aucuaugcca ucucuucugc ugccuuauca gcaagcuaua aagcagacac uguugcuaag   5700
guucagggug uggaguuuag ccaucggcuc aacacagaca ucgcugggcu ggcuucagcc   5760
auugacauga gcacaaacua uaauucagac ucacugcauu ucagcaaugu cuuccguucu   5820
guaauggccc cguuuaccau gaccaucgau gcacauacaa auggcaaugg gaaacucgcu   5880
cucuggggag aacauacugg gcagcuguau agcaaauucc uguugaaagc agaaccucug   5940
gcauuuacuu ucucucauga uuacaaaggc uccacaaguc aucaucucgu gucuaggaaa   6000
```

-continued agcaucagug cagcucuuga acacaaaguc agugcccugc uuacuccagc ugagcagaca 6060
ggcaccugga aacucaagac ccaauuuaac aacaaugaau acagccagga cuuggaugcu 6120
uacaacacua aagauaaaau uggcguggag cuuacuggac gaacucuggc ugaccuaacu 6180
cuacuagacu ccccaauuaa agugccacuu uuacucagug agcccaucaa uaucauugau 6240
gcuuuagaga ugagagaugc cguugagaag ccccaagaau uuacaauugu ugcuuuugua 6300
aaguaugaua aaaaccaaga uguucacucc auuaaccucc cauuuuuuga gaccuugcaa 6360
gaauauuuug agaggaaucg acaaaccauu auaguuguag uggaaaacgu acagagaaac 6420
cugaagcaca ucaauauuga ucaauuugua agaaaauaca gagcagcccu gggaaaacuc 6480
ccacagcaag cuaaugauua ucugaauuca uucaauuggg agagacaagu uucacaugcc 6540
aaggagaaac ugacugcucu cacaaaaaag uauagaauua cagaaaauga uauacaaauu 6600
gcauuagaug augccaaaau caacuuuaau gaaaaacuau cucaacugca gacauauaug 6660
auacaauuug aucaguauau uaaagauagu uaugauuuac augauuugaa aauagcuauu 6720
gcuaauauua uugaugaaau cauugaaaaa uuaaaaaguc uugaugagca cuaucauauc 6780
cguguaaauu uaguaaaaac aauccaugau cuacauuugu uuauugaaaa uauugauuuu 6840
aacaaaagug gaaguaguac ugcauccugg auucaaaaug uggauacuaa guaccaaauc 6900
agaauccaga uacaagaaaa acugcagcag cuuaagagac acauacagaa uauagacauc 6960
cagcaccuag cuggaaaguu aaaacaacac auugaggcua uugauguuag agugcuuuua 7020
gaucaauugg gaacuacaau uucauuugaa agaauaaaug auguucuuga gcaugucaaa 7080
cacuuuguua uaaaucuuau uggggauuuu gaaguagcug agaaaaucaa ugccuucaga 7140
gccaaagucc augaguuaau cgagagguau gaaguagacc aacaaaucca gguuuuaaug 7200
gauaaauuag uagaguugac ccaccaauac aaguugaagg agacuauuca gaagcuaagc 7260
aauguccuac aacaaguuaa gauaaaagau uacuuugaga aauugguugg auuuauugau 7320
gaugcuguga agaagcuuaa ugaauuaucu uuuaaaacau ucauugaaga uguuaacaaa 7380
uuccuugaca uguugauaaa gaaauuaaag ucauuugauu accaccaguu uguagaugaa 7440
accaaugaca aaauccguga ggugacucag agacucaaug gugaaauuca ggcucuggaa 7500
cuaccacaaa aagcugaagc auuaaaacug uuuuuagagg aaaccaaggc cacaguugca 7560
guguaucugg aaagccuaca ggacaccaaa auaaccuuaa ucaucaauug guuacaggag 7620
gcuuuaaguu cagcaucuuu ggcucacaug aaggccaaau uccgagagac ucuagaagau 7680
acacgagacc gaauguauca aauggacauu cagcaggaac uucaacgaua ccugucucug 7740
guaggccagg uuuauagcac acuugucacc uacauuucug auuggugagac ucuugcugcu 7800 aagaaccuua cugacuuugc agagcaauau ucuauccaag auugggcuaa acguaugaaa 7860
gcauugguag agcaaggguu cacuguuccu gaaaucaaga ccauccuugg gaccaugccu 7920
gccuuugaag ucagucuuca ggcucuucag aaagcuaccu uccagacacc ugauuuuaua 7980 guccccuaa cagauuugag gauuccauca guucagauaa acuucaaaga cuuaaaaaau 8040
auaaaaaucc cauccagguu uuccacacca gaauuuacca uccuuaacac cuuccacauu 8100
ccuuccuuua caauugacuu ugucgaaaug aaaguaaaga ucaucagaac cauugaccag 8160
augcagaaca gugagcugca guggcccguu ccagauauau aucucaggga ucugaaggug 8220
gaggacauuc cucuagcgag aaucacccug ccagacuucc guuuaccaga aaucgcaauu 8280
ccagaauuca uaaucccaac ucucaaccuu aaugauuuuc aaguuccuga ccuucacaua 8340
ccagaauucc agcuucccca caucucacac acaauugaag uaccuacuuu uggcaagcua 8400

-continued

```
uacaguauuc ugaaaaucca aucuccucuu uucacauuag augcaaaugc ugacauaggg   8460
aauggaacca ccucagcaaa cgaagcaggu aucgcagcuu ccaucacugc caaaggagag   8520
uccaaauuag aaguucucaa uuuugauuuu caagcaaaug cacaacucuc aaacccuaag   8580
auuaauccgc uggcucugaa ggagucagug aaguucucca gcaaguaccu gagaacggag   8640
caugggagug aaaugcuguu uuuuggaaau gcuauugagg gaaaaucaaa cacaguggca   8700
aguuuacaca cagaaaaaaa uacacuggag cuuaguaaug gagugauugu caagauaaac   8760
aaucagcuua cccuggauag caacacuaaa uacuuccaca aauugaacau ccccaaacug   8820
gacuucucua gucaggcuga ccugcgcaac gagaucaaga cacuguugaa agcuggccac   8880
auagcaugga cuucuucugg aaaagggguca uggaaauggg ccugccccag auucucagau   8940
gagggaacac augaaucaca aauuaguuuc accauagaag gaccccucac uuccuuugga   9000
cuguccaaua agaucaauag caaacaccua agaguaaacc aaaacuuggu uuaugaaucu   9060
ggcuccccuca acuuuucuaa acuugaaauu caaucacaag ucgauuccca gcaugugggc   9120
cacaguguuc uaacugcuaa aggcauggca cuguuuggag aagggaaggc agaguuuacu   9180
gggaggcaug augcucauuu aaauggaaag guuauuggaa cuuugaaaaa uucucuuuuc   9240
uuuucagccc agccauuuga gaucacggca uccacaaaca augaagggaa uuugaaaguu   9300
cguuuuccau uaagguuaac agggaagaua gacuuccuga auaacuaugc acuguuucug   9360
agucccagug cccagcaagc aaguuggcaa guaagugcua gguucaauca guauaaguac   9420
aaccaaaauu ucucugcugg aaacaacgag aacauuaugg aggcccaugu aggaauaaau   9480
ggagaagcaa aucuggauuu cuuaaacauu ccuuuaacaa uuccugaaau gcgucuaccu   9540
uacacaauaa ucacaacucc uccacugaaa gauuucucuc uaugggaaaa aacaggcuug   9600
aaggaauucu ugaaaacgac aaagcaauca uuugauuuaa guguaaaagc ucaguauaag   9660
aaaaacaaac acaggcauuc caucacaaau ccuuuggcug ugcuuuguga guuuaucagu   9720
cagagcauca aauccuuuga caggcauuuu gaaaaaaaca gaaacaaugc auuagauuuu   9780
gucaccaaau ccuauaauga aacaaaaauu aaguuugaua aguacaaagc ugaaaaaucu   9840
cacgacgagc uccccaggac cuuucaaauu ccuggauaca cuguuccagu ugucaauguu   9900
gaagugucuc cauucaccau agagaugucg gcauucggcu auguguuccc aaaagcaguc   9960
agcaugccua guuucuccau ccuagguucu gacguccgug ugccuucaua cacauuaauc  10020
cugccaucau uagagcugcc aguccuucau gucccuagaa aucucaagcu uucucuucca  10080
cauuucaagg aauuguguac cauaagccau auuuuuauuc cugccauggg caauauuacc  10140
uaugauuucu ccuuuaaauc aagugucauc acacugaaua ccaaugcuga acuuuuuaac  10200
cagucagaua uuguugcuca ucuccuuucu ucaucuucau cugucauuga ugcacugcag  10260
uacaaauuag agggcaccac aagauugaca agaaaaaggg gauugaaguu agccacagcu  10320
cugucucuga gcaacaaauu uguggagggu agucauaaca guacugugag cuuaaccacg  10380
aaaaauaugg aagugucagu ggcaaaaacc acaaaagccg aaauuccaau uuugagaaug  10440
aauuucaagc aagaacuuaa uggaaauacc aagucaaaac cuacugucuc uuccuccaug  10500
gaauuuaagu augauuucaa uucuucaaug cuguacucua ccgcuaaagg agcaguugac  10560
cacaagcuua gcuuggaaag ccucaccucu uacuuuucca uugagucauc uaccaaagga  10620
gaugucaagg guucgguucu uucucgggaa uauucaggaa cuauugcuag ugaggccaac  10680
acuuacuuga auuccaagag cacacggucu ucagugaagc ugcagggcac uuccaaaauu  10740
```

-continued

```
gaugauaucu ggaaccuuga aguaaaagaa aauuuugcug gagaagccac acuccaacgc  10800
auauauuccc ucugggagca caguacgaaa aaccacuuac agcuagaggg ccucuuuuuc  10860
accaacggag aacauacaag caaagccacc cuggaacucu cuccauggca aaugucagcu  10920
cuuguucagg uccaugcaag ucagcccagu uccuuccaug auuucccuga ccuuggccag  10980
gaaguggccc ugaaugcuaa cacuaagaac cagaagauca gauggaaaaa ugaaguccgg  11040
auucauucug ggucuuucca gagccagguc gagcuuucca augaccaaga aaaggcacac  11100
cuugacauug caggauccuu agaaggacac cuaagguucc ucaaaaauau cauccuacca  11160
gucuaugaca agagcuuaug ggauuuccua aagcuggaug uaaccaccag cauugguagg  11220
agacagcauc uucguguuuc aacugccuuu guguacacca aaaaccccaa uggcuauuca  11280
uucuccaucc cuguaaaagu uuuggcugau aaauucauua cuccugggcu gaaacuaaau  11340
gaucuaaauu caguucuugu caugccuacg uuccaugucc cauuuacaga ucuucagguu  11400
ccaucgugca aacuugacuu cagagaaaua caaaucuaua agaagcugag aacuucauca  11460
uuugcccuca accuaccaac acucccccag guaaaauucc cugaaguuga uguguuaaca  11520
aaauauucuc aaccagaaga cuccuugauu cccuuuuuug agauaaccgu gccugaaucu  11580
caguuaacug ugucccaguu cacgcuucca aaaaguguuu cagauggcau ugcugcuuug  11640
gaucuaaaug caguagccaa caagaucgca gacuuugagu ugcccaccau caucgugccu  11700
gagcagacca uugagauucc cuccauuaag uucucuguac cugcuggaau ugucauuccu  11760
uccuuucaag cacugacugc acgcuuugag guagacucuc ccguguauaa ugccacuugg  11820
agugccaguu ugaaaaacaa agcagauuau guugaaacag uccuggauuc cacaugcagc  11880
ucaaccguac aguuccuaga auaugaacua aauguuuugg gaacacacaa aaucgaagau  11940
gguacguuag ccucuaagac uaaaggaaca cuugcacacc gugacuucag ugcagaauau  12000
gaagaagaug gcaaauuuga aggacuucag gaaugggaag gaaaagcgca ccucaauauc  12060
aaaagcccag cguucaccga ucuccaucug cgcuaccaga aagacaagaa aggcaucucc  12120
accucagcag ccuccccagc cguaggcacc gugggcaugg auauggauga agaugacgac  12180
uuuucuaaau ggaacuucua cuacagcccu caguccucuc cagauaaaaa acucaccaua  12240
uucaaaacug aguugagggu ccgggaaucu gaugaggaaa cucagaucaa aguuaauugg  12300
gaagaagagg cagcuucugg cuugcuaacc ucucugaaag acaacgugcc caaggccaca  12360
gggguccuuu augauuaugu caacaaguac cacugggaac acacagggcu cacccugaga  12420
gaagugucuu caaagcugag aagaaaucug cagaacaaug cugagugggu uuaucaaggg  12480
gccauuaggc aaauugauga uaucgacgug agguuccaga aagcagccag uggcaccacu  12540
gggaccuacc aagaguggaa ggacaaggcc cagaaucugu accaggaacu guugacucag  12600
gaaggccaag ccaguuucca gggacucaag gauaacgugu uugauggcuu gguacgaguu  12660
acucaaaaau uccauaugaa agucaagcau cugauugacu cacucauuga uuuucugaac  12720
uuccccagau uccaguuucc ggggaaaccu gggauauaca cuagggagga acuuugcacu  12780
auguucauaa gggagguagg gacgguacug ucccagguau auucgaaagu ccauaauggu  12840
ucagaaauac uguuuuccua uuuccaagac cuagugauua cacuuccuuu cgaguuaagg  12900
aaacauaaac uaauagaugu aaucucgaug uauagggaac uguugaaaga uuuaucaaaa  12960
gaagcccaag agguauuuaa agccauucag ucucucaaga ccacagaggu gcuacguaau  13020
cuucaggacc uuuuacaauu cauuuuccaa cuaauagaag auaacauuaa acagcugaaa  13080
gagaugaaau uuacuuaucu uauuaauuau auccaagaug agaucaacac aaucuucaau  13140
```

-continued

```
gauuauaucc cauauguuuu uaaauuguug aaagaaaacc uaugccuuaa ucuucauaag  13200

uucaaugaau uuauucaaaa cgagcuucag gaagcuucuc aagaguuaca gcagauccau  13260

caauacauua uggcccuucg ugaagaauau uuugauccaa guauaguugg cuggacagug  13320

aaauauuaug aacuugaaga aaagauaguc agucugauca agaaccuguu aguugcucuu  13380

aaggacuucc auucugaaua uauugucagu gccucuaacu uuacuuccca acucucaagu  13440

caaguugagc aauuucugca cagaaauauu caggaauauc uuagcauccu uaccgaucca  13500

gauggaaaag ggaaagagaa gauugcagag cuuucugcca cugcucagga aauaauuaaa  13560

agccaggcca uugcgacgaa gaaaauaauu ucugauuacc accagcaguu uagauauaaa  13620

cugcaagauu uuucagacca acucucugau uacuaugaaa aauuuauugc ugaauccaaa  13680

agauugauug accuguccau ucaaaacuac cacacauuuc ugauauacau cacggaguua  13740

cugaaaaagc ugcaaucaac cacagucaug aaccccuaca ugaagcuugc uccaggagaa  13800

cuuacuauca ucc ucuaauu uuuuaaaaga aaucuucauu uauucuucuu uuccaauuga  13860

acuuucacau agcacagaaa aaauucaaac ugccuauauu gauaaaacca uacagugagc  13920

cagccuugca guaggcagua gacuauaagc agaagcacau augaacugga ccugcaccaa  13980

agcuggcacc agggcucgga aggucucuga acucagaagg auggcauuuu uugcaaguua  14040

aagaaaauca ggaucugagu uauuuugcua aacuuggggg aggaggaaca aauaaaugga  14100

gucuuuauug uguaucaua                                               14119
```

<210> SEQ ID NO 2
<211> LENGTH: 1503
<212> TYPE: DNA
<213> ORGANISM: Human immunodeficiency virus

<400> SEQUENCE: 2

```
atgggtgcga gagcgtcagt attaagcggg ggagaattag atcgatggga aaaaattcgg     60

ttaaggccag ggggaaagaa aaaatataaa ttaaaacata tagtatgggc aagcagggag    120

ctagaacgat tcgcagttaa tcctggcctg ttagaaacat cagaaggctg tagacaaata    180

ctgggacagc tacaaccatc ccttcagaca ggatcagaag aacttagatc attatataat    240

acagtagcaa ccctctattg tgtgcatcaa aggatagaga taaaagacac caaggaagct    300

ttagacaaga tagaggaaga gcaaaacaaa agtaagaaaa aagcacagca agcagcagct    360

gacacaggac acagcaatca ggtcagccaa aattacccta tagtgcagaa catccagggg    420

caaatggtac atcaggccat atcacctaga actttaaatg catgggtaaa agtagtagaa    480

gagaaggctt tcagcccaga agtgataccc atgttttcag cattatcaga aggagccacc    540

ccacaagatt taaacaccat gctaaacaca gtgggggac atcaagcagc catgcaaatg     600

ttaaaagaga ccatcaatga ggaagctgca gaatgggata gagtgcatcc agtgcatgca    660

gggcctattg caccaggcca gatgagagaa ccaaggggaa gtgacatagc aggaactact    720

agtacccttc aggaacaaat aggatggatg acaaataatc cacctatccc agtaggagaa    780

atttataaaa gatggataat cctgggatta aataaaatag taagaatgta tagccctacc    840

agcattctgg acataagaca aggaccaaag gaacccttta gagactatgt agaccggttc    900

tataaaactc taagagccga gcaagcttca caggaggtaa aaaattggat gacagaaacc    960

ttgttggtcc aaaatgcgaa cccagattgt aagactattt taaaagcatt gggaccagcg   1020

gctacactag aagaaatgat gacagcatgt cagggagtag gaggacccgg ccataaggca   1080
```

-continued

```
agagttttgg ctgaagcaat gagccaagta acaaattcag ctaccataat gatgcagaga   1140

ggcaatttta ggaaccaaag aaagattgtt aagtgtttca attgtggcaa agaagggcac   1200

acagccagaa attgcagggc ccctaggaaa aagggctgtt ggaaatgtgg aaaggaagga   1260

caccaaatga aagattgtac tgagagacag gctaattttt tagggaagat ctggccttcc   1320

tacaagggaa ggccagggaa ttttcttcag agcagaccag agccaacagc cccaccagaa   1380

gagagcttca ggtctggggt agagacaaca actcccccctc agaagcagga gccgatagac   1440

aaggaactgt atcctttaac ttccctcagg tcactctttg gcaacgaccc ctcgtcacaa   1500

taa                                                                 1503
```

<210> SEQ ID NO 3
<211> LENGTH: 261
<212> TYPE: DNA
<213> ORGANISM: Human immunodeficiency virus

<400> SEQUENCE: 3

```
atggagccag tagatcctag actagagccc tggaagcatc caggaagtca gcctaaaact     60

gcttgtacca attgctattg taaaaagtgt tgctttcatt gccaagtttg tttcataaca    120

aaagccttag gcatctccta tggcaggaag aagcggagac agcgacgaag agctcatcag    180

aacagtcaga ctcatcaagc ttctctatca aagcaaccca cctcccaacc ccgaggggac    240

ccgacaggcc cgaaggaata g                                              261
```

<210> SEQ ID NO 4
<211> LENGTH: 2571
<212> TYPE: DNA
<213> ORGANISM: Human immunodeficiency virus

<400> SEQUENCE: 4

```
atgagagtga aggagaaata tcagcacttg tggagatggg ggtggagatg gggcaccatg     60

ctccttggga tgttgatgat ctgtagtgct acagaaaaat tgtgggtcac agtctattat    120

ggggtacctg tgtggaagga agcaaccacc actctatttt gtgcatcaga tgctaaagca    180

tatgatacag aggtacataa tgtttgggcc acacatgcct gtgtacccac agaccccaac    240

ccacaagaag tagtattggt aaatgtgaca gaaaatttta acatgtggaa aaatgacatg    300

gtagaacaga tgcatgagga tataatcagt ttatgggatc aaagcctaaa gccatgtgta    360

aaattaaccc cactctgtgt tagtttaaag tgcactgatt tgaagaatga tactaatacc    420

aatagtagta gcgggagaat gataatggag aaaggagaga taaaaaactg ctctttcaat    480

atcagcacaa gcataagagg taaggtgcag aaagaatatg catttttta taaacttgat    540

ataataccaa tagataatga tactaccagc tataagttga caagttgtaa cacctcagtc    600

attacacagg cctgtccaaa ggtatccttt gagccaattc ccatacatta ttgtgccccg    660

gctggttttg cgattctaaa atgtaataat aagacgttca atggaacagg accatgtaca    720

aatgtcagca cagtacaatg tacacatgga attaggccag tagtatcaac tcaactgctg    780

ttaaatggca gtctagcaga agaagaggta gtaattagat ctgtcaattt cacggacaat    840

gctaaaacca taatagtaca gctgaacaca tctgtagaaa ttaattgtac aagacccaac    900

aacaatacaa gaaaaagaat ccgtatccag agaggaccag ggagagcatt tgttacaata    960

ggaaaaatag gaaatatgag acaagcacat tgtaacatta gtagagcaaa atggaataac   1020

actttaaaac agatagctag caaattaaga gaacaatttg gaaataataa aacaataatc   1080

tttaagcaat cctcaggagg ggacccagaa attgtaacgc acagttttaa ttgtggaggg   1140
```

-continued

```
gaatttttct actgtaattc aacacaactg tttaatagta cttggtttaa tagtacttgg   1200

agtactgaag ggtcaaataa cactgaagga agtgacacaa tcaccctccc atgcagaata   1260

aaacaaatta taaacatgtg gcagaaagta ggaaaagcaa tgtatgcccc tcccatcagt   1320

ggacaaatta gatgttcatc aaatattaca gggctgctat taacaagaga tggtggtaat   1380

agcaacaatg agtccgagat cttcagacct ggaggaggag atatgaggga caattggaga   1440

agtgaattat ataaatataa agtagtaaaa attgaaccat taggagtagc acccaccaag   1500

gcaaagagaa gagtggtgca gagagaaaaa agagcagtgg gaataggagc tttgttcctt   1560

gggttcttgg gagcagcagg aagcactatg ggcgcagcct caatgacgct gacggtacag   1620

gccagacaat tattgtctgg tatagtgcag cagcagaaca atttgctgag ggctattgag   1680

gcgcaacagc atctgttgca actcacagtc tggggcatca agcagctcca ggcaagaatc   1740

ctggctgtgg aaagatacct aaaggatcaa cagctcctgg ggatttgggg ttgctctgga   1800

aaactcattt gcaccactgc tgtgccttgg aatgctagtt ggagtaataa atctctggaa   1860

cagatttgga atcacacgac ctggatggag tgggacagag aaattaacaa ttacacaagc   1920

ttaatacact ccttaattga agaatcgcaa aaccagcaag aaaagaatga acaagaatta   1980

ttggaattag ataaatgggc aagtttgtgg aattggttta acataacaaa ttggctgtgg   2040

tatataaaat tattcataat gatagtagga ggcttggtag gtttaagaat agtttttgct   2100

gtactttcta tagtgaatag agttaggcag ggatattcac cattatcgtt tcagacccac   2160

ctcccaaccc cgaggggacc cgacaggccc gaaggaatag aagaagaagg tggagagaga   2220

gacagagaca gatccattcg attagtgaac ggatccttgg cacttatctg ggacgatctg   2280

cggagcctgt gcctcttcag ctaccaccgc ttgagagact tactcttgat tgtaacgagg   2340

attgtggaac ttctgggacg cagggggtgg gaagccctca aatattggtg gaatctccta   2400

cagtattgga gtcaggaact aaagaatagt gctgttagct tgctcaatgc cacagccata   2460

gcagtagctg aggggacaga tagggttata gaagtagtac aaggagcttg tagagctatt   2520

cgccacatac ctagaagaat aagacagggc ttggaaagga ttttgctata a            2571
```

<210> SEQ ID NO 5
<211> LENGTH: 4308
<212> TYPE: DNA
<213> ORGANISM: Human immunodeficiency virus

<400> SEQUENCE: 5

```
atgggtgcga gagcgtcagt attaagcggg ggagaattag atcgatggga aaaaattcgg     60

ttaaggccag ggggaaagaa aaaatataaa ttaaaacata tagtatgggc aagcagggag    120

ctagaacgat tcgcagttaa tcctggcctg ttagaaacat cagaaggctg tagacaaata    180

ctgggacagc tacaaccatc ccttcagaca ggatcagaag aacttagatc attatataat    240

acagtagcaa ccctctattg tgtgcatcaa aggatagaga taaaagacac caaggaagct    300

ttagacaaga tagaggaaga gcaaaacaaa agtaagaaaa aagcacagca agcagcagct    360

gacacaggac acagcaatca ggtcagccaa aattacccta tagtgcagaa catccagggg    420

caaatggtac atcaggccat atcacctaga actttaaatg catgggtaaa agtagtagaa    480

gagaaggctt tcagcccaga agtgataccc atgttttcag cattatcaga aggagccacc    540

ccacaagatt taaacaccat gctaaacaca gtgggggac atcaagcagc catgcaaatg     600

ttaaaagaga ccatcaatga ggaagctgca gaatgggata gagtgcatcc agtgcatgca    660
```

-continued

```
gggcctattg caccaggcca gatgagagaa ccaaggggaa gtgacatagc aggaactact    720
agtacccttc aggaacaaat aggatggatg acaaataatc cacctatccc agtaggagaa    780
atttataaaa gatggataat cctgggatta aataaaatag taagaatgta tagccctacc    840
agcattctgg acataagaca aggaccaaag gaacccttta gagactatgt agaccggttc    900
tataaaactc taagagccga gcaagcttca caggaggtaa aaaattggat gacagaaacc    960
ttgttggtcc aaaatgcgaa cccagattgt aagactattt taaaagcatt gggaccagcg   1020
gctacactag aagaaatgat gacagcatgt cagggagtag gaggacccgg ccataaggca   1080
agagttttgg ctgaagcaat gagccaagta acaaattcag ctaccataat gatgcagaga   1140
ggcaatttta ggaaccaaag aaagattgtt aagtgtttca attgtggcaa agaagggcac   1200
acagccagaa attgcagggc ccctaggaaa aagggctgtt ggaaatgtgg aaaggaagga   1260
caccaaatga aagattgtac tgagagacag gctaattttt taagggaaga tctggccttc   1320
ctacaaggga aggccaggga atttcttca gagcagacca gagccaacag ccccaccaga    1380
agagagcttc aggtctgggg tagagacaac aactccccct cagaagcagg agccgataga   1440
caaggaactg tatcctttaa cttccctcag gtcactcttt ggcaacgacc cctcgtcaca   1500
ataaagatag gggggcaact aaaggaagct ctattagata caggagcaga tgatacagta   1560
ttagaagaaa tgagtttgcc aggaagatgg aaaccaaaaa tgatagggggg aattggaggt  1620
tttatcaaag taagacagta tgatcagata ctcatagaaa tctgtggaca taaagctata   1680
ggtacagtat tagtaggacc tacacctgtc aacataattg gaagaaatct gttgactcag   1740
attggttgca ctttaaattt tcccattagc cctattgaga ctgtaccagt aaaattaaag   1800
ccaggaatgg atggcccaaa agttaaacaa tggccattga cagaagaaaa aataaaagca   1860
ttagtagaaa tttgtacaga gatggaaaag gaagggaaaa tttcaaaaat tgggcctgaa   1920
aatccataca atactccagt atttgccata aagaaaaaag acagtactaa atggagaaaa   1980
ttagtagatt tcagagaact taataagaga actcaagact tctgggaagt tcaattagga   2040
ataccacatc ccgcagggtt aaaaaagaaa aaatcagtaa cagtactgga tgtgggtgat   2100
gcatattttt cagttccctt agatgaagac ttcaggaagt atactgcatt taccatacct   2160
agtataaaca atgagacacc agggattaga tatcagtaca atgtgcttcc acagggatgg   2220
aaaggatcac cagcaatatt ccaaagtagc atgacaaaaa tcttagagcc ttttagaaaa   2280
caaaatccag acatagttat ctatcaatac atggatgatt tgtatgtagg atctgactta   2340
gaaatagggc agcatagaac aaaaatagag gagctgagac aacatctgtt gaggtgggga   2400
cttaccacac cagacaaaaa acatcagaaa gaacctccat tcctttggat gggttatgaa   2460
ctccatcctg ataaatggac agtacagcct atagtgctgc cagaaaaaga cagctggact   2520
gtcaatgaca tacagaagtt agtggggaaa ttgaattggg caagtcagat ttacccaggg   2580
attaaagtaa ggcaattatg taaactcctt agaggaacca aagcactaac agaagtaata   2640
ccactaacag aagaagcaga gctagaactg gcagaaaaca gagagattct aaaagaacca   2700
gtacatggag tgtattatga cccatcaaaa gacttaatag cagaaataca gaagcagggg   2760
caaggccaat ggacatatca aatttatcaa gagccattta aaaatctgaa aacaggaaaa   2820
tatgcaagaa tgaggggtgc ccacactaat gatgtaaaac aattaacaga ggcagtgcaa   2880
aaaataacca cagaaagcat agtaatatgg ggaaagactc ctaaatttaa actgcccata   2940
caaaaggaaa catgggaaac atggtggaca gagtattggc aagccacctg gattcctgag   3000
tgggagtttg ttaatacccc tcccttagtg aaattatggt accagttaga gaaagaaccc   3060
```

```
atagtaggag cagaaacctt ctatgtagat ggggcagcta acagggagac taaattagga   3120

aaagcaggat atgttactaa tagaggaaga caaaaagttg tcaccctaac tgacacaaca   3180

aatcagaaga ctgagttaca agcaatttat ctagctttgc aggattcggg attagaagta   3240

aacatagtaa cagactcaca atatgcatta ggaatcattc aagcacaacc agatcaaagt   3300

gaatcagagt tagtcaatca aataatagag cagttaataa aaaaggaaaa ggtctatctg   3360

gcatgggtac cagcacacaa aggaattgga ggaaatgaac aagtagataa attagtcagt   3420

gctggaatca ggaaagtact atttttagat ggaatagata aggcccaaga tgaacatgag   3480

aaatatcaca gtaattggag agcaatggct agtgatttta acctgccacc tgtagtagca   3540

aaagaaatag tagccagctg tgataaatgt cagctaaaag gagaagccat gcatggacaa   3600

gtagactgta gtccaggaat atggcaacta gattgtacac atttagaagg aaaagttatc   3660

ctggtagcag ttcatgtagc cagtggatat atagaagcag aagttattcc agcagaaaca   3720

gggcaggaaa cagcatattt tcttttaaaa ttagcaggaa gatggccagt aaaaacaata   3780

catactgaca atggcagcaa tttcaccggt gctacggtta gggccgcctg ttggtgggcg   3840

ggaatcaagc aggaatttgg aattccctac aatccccaaa gtcaaggagt agtagaatct   3900

atgaataaag aattaaagaa aattatagga caggtaagag atcaggctga acatcttaag   3960

acagcagtac aaatggcagt attcatccac aattttaaaa gaaaaggggg gattgggggg   4020

tacagtgcag gggaaagaat agtagacata atagcaacag acatacaaac taaagaatta   4080

caaaaacaaa ttacaaaaat tcaaaatttt cgggtttatt acagggacag cagaaatcca   4140

ctttggaaag gaccagcaaa gctcctctgg aaaggtgaag gggcagtagt aatacaagat   4200

aatagtgaca taaaagtagt gccaagaaga aaagcaaaga tcattaggga ttatggaaaa   4260

cagatggcag gtgatgattg tgtggcaagt agacaggatg aggattag                4308
```

<210> SEQ ID NO 6
<211> LENGTH: 579
<212> TYPE: DNA
<213> ORGANISM: Human immunodeficiency virus

<400> SEQUENCE: 6

```
atggaaaaca gatggcaggt gatgattgtg tggcaagtag acaggatgag gattagaaca     60

tggaaaagtt tagtaaaaca ccatatgtat gtttcaggga aagctagggg atggttttat    120

agacatcact atgaaagccc tcatccaaga ataagttcag aagtacacat cccactaggg    180

gatgctagat tggtaataac aacatattgg ggtctgcata caggagaaag agactggcat    240

ttgggtcagg gagtctccat agaatggagg aaaaagagat atagcacaca agtagaccct    300

gaactagcag accaactaat tcatctgtat tactttgact gtttttcaga ctctgctata    360

agaaaggcct tattaggaca catagttagc cctaggtgtg aatatcaagc aggacataac    420

aaggtaggat ctctacaata cttggcacta gcagcattaa taacaccaaa aaagataaag    480

ccacctttgc ctagtgttac gaaactgaca gaggatagat ggaacaagcc ccagaagacc    540

aagggccaca gagggagcca cacaatgaat ggacactag                           579
```

<210> SEQ ID NO 7
<211> LENGTH: 621
<212> TYPE: DNA
<213> ORGANISM: Human immunodeficiency virus

<400> SEQUENCE: 7

-continued

```
atgggtggca agtggtcaaa aagtagtgtg attggatggc ctactgtaag ggaaagaatg      60

agacgagctg agccagcagc agatagggtg ggagcagcat ctcgagacct ggaaaaacat     120

ggagcaatca caagtagcaa tacagcagct accaatgctg cttgtgcctg gctagaagca     180

caagaggagg aggaggtggg ttttccagtc acacctcagg tacctttaag accaatgact     240

tacaaggcag ctgtagatct tagccacttt ttaaaagaaa aggggggact ggaagggcta     300

attcactccc aaagaagaca agatatcctt gatctgtgga tctaccacac acaaggctac     360

ttccctgatt agcagaacta cacaccaggg ccaggggtca gatatccact gacctttgga     420

tggtgctaca agctagtacc agttgagcca gataagatag aagaggccaa taaaggagag     480

aacaccagct tgttacaccc tgtgagcctg catgggatgg atgacccgga gagagaagtg     540

ttagagtgga ggtttgacag ccgcctagca tttcatcacg tggcccgaga gctgcatccg     600

gagtacttca agaactgctg a                                               621
```

<210> SEQ ID NO 8
<211> LENGTH: 721
<212> TYPE: RNA
<213> ORGANISM: Aequorea victoria

<400> SEQUENCE: 8

```
auggugagca agggcgagga gcuguucacc gggguggugc ccauccuggu cgagcuggac      60

ggcgacguaa acggccacaa guucagcgug uccggcgagg gcgagggcga ugccaccuac     120

ggcaagcuga cccugaaguu caucugcacc accggcaagc ugcccgugcc cuggcccacc     180

cucgugacca cccugaccua cggcgugcag ugcuucagcc gcuaccccga ccacaugaag     240

cagcacgacu ucuucaaguc cgccaugccc gaaggcuacg uccaggagcg caccaucuuc     300

uucaaggacg acggcaacua caagacccgc gccgagguga aguucgaggg cgacacccug     360

gugaaccgca ucgagcugaa gggcaucgac uucaaggagg acggcaacau ccuggggcac     420

aagcuggagu acaacuacaa cagccacaac gucuauauca uggccgacaa gcagaagaac     480

ggcaucaagg ugaacuucaa gauccgccac aacaucgagg acggcagcgu gcagcucgcc     540

gaccacuacc agcagaacac ccccaucggc gacggccccg ugcugcugcc cgacaaccac     600

uaccugagca cccaguccgc ccugagcaaa gaccccaacg agaagcgcga ucacaugguc     660

cugcuggagu ucgugaccgc cgccgggauc acucucggca uggacgagcu guacaaguaa     720

a                                                                     721
```

<210> SEQ ID NO 9
<211> LENGTH: 9262
<212> TYPE: RNA
<213> ORGANISM: Human immunodeficiency virus

<400> SEQUENCE: 9

```
gucucucugg uuagaccaga ucugagccug ggagcucucu ggcuaacuag ggaacccacu      60

gcuuaagccu caauaaagcu ugccuugagu gcuucaagua gugugugccc gucuguugug     120

ugacucuggu aacuagagau cccucagacc cuuuuaguca guguggaaaa ucucuagcag     180

uggcgcccga acagggacau gaaagcgaaa gggaaaccag aggagcucuc ucgacgcagg     240

acucggcuug cugaagcgcg cacggcaaga ggcgaggggc ggcgacuggu gaguacgcca     300

aaaauuuuga cuagcggagg cuagaaggag agagaugggu gcgagagcgu caguauuaag     360

cgggggaaaa uuagaucgau gggaaaaaau ucgguuaagg ccagggggaa agaaaaaaua     420

uaaauuaaaa cauauaguau gggcaagcag ggagcuagaa cgauucgcag uuaauccugg     480
```

-continued

```
ccuguuagaa acaucagaag gcuguagaca aauacuggga cagcuacaac caucccuuca    540
gacaggauca gaagaacgua gaucauuaua uaauacagua gcaacccucu auugugugca    600
ucaaaggaua gagauaaaag acaccaagga agcuuuagac aagauagagg aagagcaaaa    660
caaaaguaag aaaaaagcac agcaagcagc agcugacaca ggacacagca gccaggucag    720
ccaaaauuac ccuauagugc agaacaucca ggggcaaaug guacaucagg ccauaucacc    780
uagaacuuua aaugcauggg uaaaaguagu agaagagaag gcuuucagcc cagaagugau    840
acccauguuu ucagcauuau cagaaggagc caccccacaa gauuuaaaca ccaugcuaaa    900
cacagugggg ggacaucaag cagccaugca aauguuaaaa gagaccauca augaggaagc    960
ugcagaaugg gauagagugc auccagugca ugcagggccu auugcaccag gccagaugag   1020
agaaccaagg ggaagugaca uagcaggaac uacuaguacc cuucaggaac aaauaggaug   1080
gaugacacau aauccaccua ucccaguagg agaaaucuau aaaagaugga uaauccuggg   1140
auuaaauaaa auaguaagaa uguauagccc uaccagcauu cuggacauaa gacaaggacc   1200
aaaggaaccc uuuagagacu auguagaccg auucuauaaa acucuaagag ccgagcaagc   1260
uucacaagag guaaaaaauu ggaugacaga aaccuuguug guccaaaaug cgaacccaga   1320
uuguaagacu auuuuaaaag cauugggacc aggagcgaca cuagaagaaa ugaugacagc   1380
augucaggga guggggggac ccggccauaa agcaagaguu uuggcugaag caaugagcca   1440
aguaacaaau ccagcuacca uaaugauaca gaaaggcaau uuuaggaacc aaagaaagac   1500
uguuaagugu uucaauugug gcaaagaagg gcacauagcc aaaaauugca gggccccuag   1560
gaaaaagggc uguuggaaau guggaaagga aggacaccaa augaaagauu guacugagag   1620
acaggcuaau uuuuuaggga agaucuggcc uucccacaag ggaaggccag ggaauuuucu   1680
ucagagcaga ccagagccaa cagccccacc agaagagagc uucagguuug gggaagagac   1740
aacaacuccc ucucagaagc aggagccgau agacaaggaa cuguauccuu uagcuucccu   1800
cagaucacuc uuuggcagcg accccucguc acaauaaaga uagggggggca auuaaaggaa   1860
gcucuauuag auacaggagc agaugauaca guauuagaag aaaugaauuu gccaggaaga   1920
uggaaaccaa aaaugauagg gggaauugga gguuuuauca aaguaagaca guaugaucag   1980
auacucauag aaaucugcgg acauaaagcu auagguacag uauuaguagg accuacaccu   2040
gucaacauaa uuggaagaaa ucuguugacu cagauuggcu gcacuuuaaa uuuucccauu   2100
aguccuauug agacuguacc aguaaaauua aagccaggaa uggauggccc aaaaguuaaa   2160
caauggccau ugacagaaga aaaaauaaaa gcauuaguag aaauuuguac agaaauggaa   2220
aaggaaggaa aaauuucaaa aauugggccu gaaaauccau acaauacucc aguauuugcc   2280
auaaagaaaa aagacaguac uaaauggaga aaauuaguag auuucagaga acuuaauaag   2340
agaacucaag auuucuggga aguucaauua ggaauaccac auccugcagg guuaaaacag   2400
aaaaaaucag uaacaguacu ggaugugggc gaugcauauu uuucaguucc cuuagauaaa   2460
gacuucagga aguauacugc auuuaccaua ccuaguauaa acaaugagac accagggauu   2520
agauaucagu acaaugugcu uccacaggga uggaaaggau caccagcaau auuccagugu   2580
agcaugacaa aaaucuuaga gccuuuuaga aaacaaaauc cagacauagu caucuaucaa   2640
uacauggaug auuuguaugu aggaucugac uuagaaauag ggcagcauag aacaaaaaua   2700
gaggaacuga gacaacaucu guugaggugg ggauuuacca caccagacaa aaaacaucag   2760
aaagaaccuc cauuccuuug gauggguuau gaacuccauc cugauaaaug gacaguacag   2820
```

ccuauagugc ugccagaaaa ggacagcugg acugucaaug acauacagaa auuaguggga 2880
aaauugaauu gggcaaguca gauuuaugca gggauuaaag uaaggcaauu auguaaacuu 2940
cuuaggggaa ccaaagcacu aacagaagua guaccacuaa cagaagaagc agagcuagaa 3000
cuggcagaaa acagggagau ucuaaaagaa ccgguacaug gaguguauua ugacccauca 3060
aaagacuuaa uagcagaaau acagaagcag gggcaaggcc aauggacaua ucaaauuuau 3120
caagagccau uuaaaaaucu gaaaacagga aaguaugcaa gaaugaaggg ugcccacacu 3180
aaugauguga aacaauuaac agaggcagua caaaaaauag ccacagaaag cauaguaaua 3240
uggggaaaga cuccuaaauu uaaauuaccc auacaaaagg aaacauggga agcauggugg 3300
acagaguauu ggcaagccac cuggauuccu gagugggagu uugucaauac cccucccuua 3360
gugaaguuau gguaccaguu agagaaagaa cccauaauag gagcagaaac uuucuaugua 3420
gauggggcag ccaauaggga aacuaaauua ggaaaagcag gauauguaac ugacagagga 3480
agacaaaaag uuguccccu aacggacaca acaaaucaga agacugaguu acaagcaauu 3540
caucuagcuu ugcaggauuc gggauuagaa guaaacauag ugacagacuc acaauaugca 3600
uugggaauca uucaagcaca accagauaag agugaaucag aguuagucag ucaaauaaua 3660
gagcaguuaa uaaaaaagga aaaagucuac cuggcauggg uaccagcaca caaaggaauu 3720
ggaggaaaug aacaaguaga uaaauugguc agugcuggaa ucaggaaagu acuauuuuua 3780
gauggaauag auaaggccca agaagaacau gagaaauauc acaguaauug gagagcaaug 3840
gcuagugauu uuaaccuacc accuguagua gcaaaagaaa uaguagccag cugugauaaa 3900
ugucagcuaa aaggggaagc caugcaugga caaguagacu guagcccagg aauauggcag 3960
cuagauugua cacauuuaga aggaaaaguu aucuugguag caguucaugu agccagugga 4020
uauauagaag cagaaguaau uccagcagag acagggcaag aaacagcaua cuuccucuua 4080
aaauuagcag gaagauggcc aguaaaaaca guacauacag acaauggcag caauuucacc 4140
aguacuacag uuaaggccgc cuguuggugg gcggggauca agcaggaauu uggcauuccc 4200
uacaaucccc aaagucaagg aguaauagaa ucuaugaaua aagaauuaaa gaaaauuaua 4260
ggacagguaa gagaucaggc ugaacaucuu aagacagcag uacaaauggc aguauucauc 4320
cacaauuuua aaagaaaagg ggggauuggg ggguacagug caggggaaag aauaguagac 4380
auaauagcaa cagacauaca aacuaaagaa uuacaaaaac aaauuacaaa aauucaaaau 4440
uuucggguuu auuacaggga cagcagagau ccaguuugga aaggaccagc aaagcuccuc 4500
uggaaaggug aaggggcagu aguaauacaa gauaauagug acauaaaagu agugccaaga 4560
agaaaagcaa agaucaucag ggauuaugga aaacagaugg caggugauga uuguguggca 4620
aguagacagg augaggauua acacauggaa aagauuagua aaacaccaua uguauauuuc 4680
aaggaaagcu aaggacuggu uuuauagaca ucacuaugaa aguacuaauc caaaaauaag 4740
uucagaagua cacaucccac uaggggaugc uaaauuagua auaacaacau auuggggucu 4800
gcauacagga gaaagagacu ggcauuuggg ucagggaguc uccauagaau ggaggaaaaa 4860
gagauauagc acacaaguag acccugaccu agcagaccaa cuaauucauc ugcacuauuu 4920
ugauuguuuu ucagaaucug cuauaagaaa uaccauauua ggacguauag uuaguccuag 4980
gugugaauau caagcaggac auaacaaggu aggaucucua caguacuugg cacuagcagc 5040
auuaauaaaa ccaaaacaga uaaagccacc uuugccuagu guuaggaaac ugacagagga 5100
cagauggaac aagccccaga agaccaaggg ccacagaggg agccauacaa ugaauggaca 5160
cuagagcuuu uagaggaacu uaagagugaa gcuguuagac auuuuccuag gauauggcuc 5220

-continued

```
cauaacuuag gacaacauau cuaugaaacu uacggggaua cuugggcagg aguggaagcc   5280
auaauaagaa uucugcaaca acugcuguuu auccauuuca gaauugggug ucgacauagc   5340
agaauaggcg uuacucgaca gaggagagca agaaauggag ccaguagauc cuagacuaga   5400
gcccuggaag cauccaggaa gucagccuaa aacugcuugu accaauugcu auuguaaaaa   5460
guguugcuuu cauugccaag uuuguuucau aacaaaagcc uuaggcaucu ccuauggcag   5520
gaagaagcgg agacagcgac gaagaccucc ucaaggcagu cagacucauc aaguuucucu   5580
aucaaagcag uaaguaauac auguaaugca accuauacaa auagcaauag uagcauuagu   5640
aguagcaaua auaauagcaa uaguuguguq guccauagua aucauagaau auaggaaaau   5700
auuaagacaa agaaaaauag acagguuaau ugauagacua auagaaagag cagaagacag   5760
uggcaaugag agugaaggag aaauaucagc acuuguggag augggggugg agauggggca   5820
ccaugcuccu ugggauguug augaucugua gugcuacaga aaaauugugg gucacagucu   5880
auuauggggu accugugugg aaggaagcaa ccaccacucu auuuugugca ucagaugcua   5940
aagcauauga uacagaggua cauaauguuu gggccacaca ugccugugua cccacagacc   6000
ccaacccaca agaaguagua uugguaaaug ugacagaaaa uuuuaacaug uggaaaaaug   6060
acaugguaga acagaugcau gaggauauaa ucaguuuaug ggaucaaagc cuaaagccau   6120
guguaaaauu aaccccacuc uguguuaguu uaaagugcac ugauuugaag aaugauacua   6180
auaccaauag uaguagcggg agaaugauaa uggagaaagg agagauaaaa aacugcucuu   6240
ucaauaucag cacaagcaua agagguaagg ugcagaaaga auaugcauuu uuuuauaaac   6300
uugauauaau accaauagau aaugauacua ccagcuauac guugacaagu uguaacaccu   6360
cagucauuac acaggccugu ccaaagguau ccuuugagcc aauucccaua cauuauugug   6420
ccccggcugg uuuugcgauu cuaaaaugua auaauaagac guucaaugga acaggaccau   6480
guacaaaugu cagcacagua caauguacac auggaauuag gccaguagua ucaacucaac   6540
ugcuguuaaa uggcagucua gcagaagaag agguaguaau uagaucuguc aauuucacgg   6600
acaaugcuaa aaccauaaua guacagcuga acacaucugu agaaauuaau uguacaagac   6660
ccaacaacaa uacaagaaaa aaaauccgua uccagagggg accagggaga gcauuuguua   6720
caauaggaaa aauaggaaau augagacaag cacauuguaa cauuaguaga gcaaaaugga   6780
augccacuuu aaaacagaua gcuagcaaau uaagagaaca auuuggaaau aauaaaacaa   6840
uaaucuuuaa gcaauccuca ggaggggacc cagaaauugu aacgcacagu uuuaauugug   6900
gaggggaauu uuucuacugu aauucaacac aacuguuuaa uaguacuugg uuuaauagua   6960
cuuggaguac ugaaggguca aauaacacug aaggaaguga cacaaucaca cucccaugca   7020
gaauaaaaca auuuauaaac augugggcagg aaguaggaaa agcaauguau gccccuccca   7080
ucagcggaca aauuagaugu ucaucaaaua uuacagggcu gcuauuaaca agagauggug   7140
guaauaacaa caaugggucc gagaucuuca gaccuggagg aggagauaug agggacaauu   7200
ggagaaguga auuauauaaa uauaaaguag uaaaaauuga accauuagga guagcaccca   7260
ccaaggcaaa gagaagagug gugcagagag aaaaaagagc agugggaaua ggagcuuugu   7320
uccuuggguu cuugggagca gcaggaagca cuaugggcgc agcgucaaug acgcugacgg   7380
uacaggccag acaauuauug ucugguauag ugcagcagca gaacaauuug cugagggcua   7440
uugaggcgca acagcaucug uugcaacuca cagucugggg caucaagcag cuccaggcaa   7500
gaauccuggc uguggaaaga uaccuaaagg aucaacagcu ccuggggauu uggggguugcu   7560
```

cuggaaaacu cauuugcacc acugcugugc cuuggaaugc uaguuggagu aauaaaucuc 7620
uggaacagau uuggaaucac acgaccugga uggaguggga cagagaaauu aacaauuaca 7680
caagcuuaau acacuccuua auugaagaau cgcaaaacca gcaagaaaag aaugaacaag 7740
aauuauugga auuagauaaa ugggcaaguu uguggaauug guuuaacaua acaaauuggc 7800
ugugguauau aaaauuauuc auaaugauag uaggaggcuu gguagguuua agaauaguuu 7860
uugcuguacu uucuguagug aauagaguua ggcagggaua uucaccauua ucguuucaga 7920
cccaccuccc aaucccgagg ggacccgaca ggcccgaagg aauagaagaa gaaggugggag 7980 agagagacag agacagaucc auucgauuag ugaacggauc cuuagcacuu aucugggacg 8040
aucugcggag ccugugccuc uucagcuacc accgcuugag agacuuacuc uugauuguaa 8100
cgaggauugu ggaacuucug ggacgcaggg ggugggaagc ccucaaauau ugguggaauc 8160
uccuacaaua uuggagucag gagcuaaaga auagugcugu uagcuugcuc aaugccacag 8220
cuauagcagu agcugagggg acagauaggg uuauagaagu aguacaagaa gcuuauagag 8280
cuauucgcca cauaccuaga agaauaggac agggcuugga aaggauuuug cuauaagaug 8340
gguggcaagu ggucaaaaag uaguguggguu ggauggccug cuguaaggga aagaaugaga 8400
cgagcugagc cagcagcaga uggggugggga gcagcaucuc gagaccuaga aaaacaugga 8460
gcaaucacaa guagcaacac agcagcuaac aaugcugcuu gugccuggcu agaagcacaa 8520
gaggaggaga agguggguuu uccagucaca ccucagguac cuuuaagacc aaugacuuac 8580
aaggcagcug uagaucuuag ccacuuuuua aaagaaaagg ggggacugga agggcuaauu 8640
cacucccaac gaagacaaga uauccuugau cuguggaucu accacacaca aggcuacuuc 8700
ccugauuggc agaacuacac accaggacca gggaucagau auccacugac cuuuggaugg 8760
cgcuacaagc uaguaccagu ugagccagag aaguuagaag aagccaacaa aggagagaac 8820
accagcuugu uacacccugu gagccugcau ggaauggaug acccggagag agaaguguua 8880
gaguggaggu uugacagccg ccuagcauuu caucacgugg cccgagagcu gcauccggag 8940
uacuucaaga acugcugaua ucgagcuugc uacaagggac uuuccgcugg ggacuuucca 9000
gggaggcgug gccugggcgg gacuggggag uggcgagccc ucagauccug cauauaagca 9060
gcugcuuuuu gccuguacug ggucucucug guuagaccag aucugagccu gggagcucuc 9120
uggcuaacua gggaacccac ugcuuaagcc ucaauaaagc uugccuugag ugcuucaagu 9180
agugugugcc cgucuguugu gugacucugg uaacuagaga ucccucagac ccuuuuaguc 9240
aguguggaaa aucucuagca gu 9262

<210> SEQ ID NO 10
<211> LENGTH: 13931
<212> TYPE: RNA
<213> ORGANISM: Mus musculus

<400> SEQUENCE: 10
uaccugccug agcuccgccu ccgaagaccc uguagagcaa gcagcagggg cuaggcccgu 60
ggccaggcca cagccaggaa gccaccccac cauccauccg ccaugggccc acgaaagccu 120
gcccugcgga cgccguuacu gcugcuguuc cugcuacugu ucuuggacac cagcgucugg 180
gcucaagaug aaguccugga aaacuuaagc uucagcuguc caaaagaugc aacucgauuc 240
aagcaccucc gaaaguacgu guacaacuau gaagcugaaa guuccagcgg uguccagggc 300
acagcugacu ccagaagcgc caccaagauc aacuguaagg uagagcugga gguccccccaa 360 aucugugguu ucaucaugag gaccaaccag uguacccuua aagaggugua uggcuucaac 420

-continued

```
ccugagggca aggccuugau gaagaaaacc aagaacucug aagaguuugc agcugccaug    480
uccagguacg aacucaagcu ggccauuccu gaagggaaac aaauuguucu uuacccugac    540
aaggaugaac cuaaauauau ccugaacauc aagaggggca ucaucucugc ucuucugguu    600
cccccagaga cagaagagga ccaacaagag uuguuccugg auaccgugua uggaaacugc    660
ucaacucagg uuaccgugaa uucaagaaag ggaaccguac caacagaaau guccacagag    720
agaaaccugc agcaauguga cggcuuccag cccaucagua caagugucag cccucucgcu    780
cucaucaaag gccugguccca ccccuuguca acucuuauca gcagcagcca aacuugccag    840
uacacccugg auccuaagag gaagcaugug ucugaagcug ucugugauga gcagcaucuu    900
uuccugccuu ucuccuacaa gaauaaguau gggaucauga cacguguuac acagaaacug    960
agucuugaag acacaccuaa gaucaacagu cgcuucuuca gugaagguac caaccggaug   1020
ggucuggccu uugagagcac caaguccacg ucaucccccaa agcaggcuga ugcuguuuug   1080
aagacccuuc aagaacugaa aaaauugucc aucucagagc agaaugcuca gagagcaaau   1140
cucuucaaua aacugguuac ugagcugaga ggccucacug gugaagcaau cacaucccuc   1200
uugccacagc ugauugaagu guccagcccc aucacuuuac aagccuuggu ucagugugga   1260
cagccacagu gcuauacuca cauccuccag uggcugaaaa cugagaaggc ucacccccuc   1320
cugguugaca uugucaccua ccugauggcu cugaucccaa aucccucaac acagaggcug   1380
caggaaaucu uuaauacugc caaggagcag cagagccgag ccacucugua ugcacugagc   1440
cacgcaguua acagcuauuu ugauguggac cauucaagga gcccaguucu gcaggauauc   1500
gcugguuacc uguugaaaca gaucgacaau gaaugcacgg gcaaugaaga ccacaccuuc   1560
uugauucuga gggucauugg aaauauggga agaaccaugg aacaaguaau gccagcccuc   1620
aaguccucag uccugagcug uguacgaagu acaaaaccau cucugcugau ucagaaagcu   1680
gcucuccagg cccugaggaa gauggaacug gaagaugagg uccggacgau ccuuuuugau   1740
acauuuguaa auggugucgc ucccguggag aagagacugg cugccuaucu cuugcugaug   1800
aagaacccuu ccucaucaga uauuaacaaa auugcccaac uucuccaaug ggaacagagu   1860
gagcagguga agaacuucgu ggcaucucac auugccaaca ucuugaacuc ggaagaacug   1920
uauguccaag aucugaaagu uuugaucaaa aaugcucugg agaauucuca auuuccaacg   1980
aucauggacu ucagaaaauu uucccgaaac uaucagauuu ccaaaucugc uucucuccca   2040
auguucgacc cagucucagu caaaauagaa gggaaucuua uauuugaucc aagcaguuau   2100
cuucccagag aaagcuugcu gaaaacaacc cucacagucu uuggacuugc uucacuugau   2160
cucuuugaga uugguuuaga aggaaaaggg uuugagccaa cacuagaagc ucuuuuuggu   2220
aagcaaggau ucuucccaga cagugucaac aaggcuuugu auugggucaa uggccgaguu   2280
ccagauggug ucuccaaggu cuugguggac cacuuuggcu auacuacaga uggcaagcau   2340
gaacaggaca uggugaaugg aaucaugccc auuguggaca aguugaucaa agaucugaaa   2400
ucuaaagaaa uuccugaagc cagggccuau cuccgcaucc uaggaaaaga gcuaagcuuu   2460
gucagacucc aagaccucca aguccugggg aagcuguugc ugaguggugc acaaacuuug   2520
cagggaaucc cccagauggu uguacaggcc aucagagaag ggucaaagaa ugacuuguuu   2580
cuccacuaca ucuucaugga caaugccuuu gagcuccccca cuggagcagg guuacagcug   2640
caaguguccu cgucuggagu cuucaccccc gggaucaagg cuggugaag acuggaauua   2700
gccaacauac aggcagagcu aguggcaaag cccucugugu ccuuggaguu ugugacaaau   2760
```

augggcauca ucaucccaga cuucgcuaag agcagugucc agaugaacac caacuucuuc 2820
cacgagucag gccuggaggc gcgaguggcc cugaaggcug ggcagcugaa ggucaucauu 2880
ccuucuccaa agaggccagu caagcuguuc aguggcagca acacacugca ucuggucucu 2940
accaccaaaa cagaagugau cccaccucug guugagaaca ggcaguccug gucaacuugc 3000
aagccucucu ucacuggaau gaacuacugu accacaggag cuuacuccaa cgccagcucc 3060
acggagucug ccucuuacua cccacugaca ggggacacaa gguaugagcu ggagcugagg 3120
cccacgggag aaguggagca guauucugcc acugcaaccu augaacuccu aaaagaggac 3180
aagucuuugg uugacacauu gaaguuccua guucaagcag aaggagugca gcagucugaa 3240
gcuacuguac uguucaaaua uaaucggaga agcaggaccu uaucuaguga aguccuaauu 3300
ccaggguuug augucaacuu cgggacaaua cuaagaguua augaugaauc ugcuaaggac 3360
aaaaacacuu acaaacucau ccuggacauu cagaacaaga aaaucacuga ggucucucuc 3420 guggccacu ugaguuauga uaaaaaggga gauggcaaga ucaaaggugu uguuuccaua 3480
ccacguuugc aagcagaagc caggagugag guccacaccc acugguccuc caccaaacug 3540
cucuuccaaa uggacucauc ugcuacagcu uacggcucaa caauuuccaa gagagugaca 3600
uggcguuacg auaaugagau aauagaauuu gauuggaaca cgggaaccaa uguggauacc 3660
aaaaaagugg ccuccaauuu cccuguggau cuuucccauu auccuagaau guugcaugag 3720
uaugccaaug gucuccugga ucacagaguc ccucaaacag augugacuuu ucgggacaug 3780
gguuccaaau uaauuguugc aacaaacaca uggcuucaga uggcaaccag gggucuuccu 3840
uacccccaaa cucuacagga ucaccucaau agccucucag aguugaaccu ccugaaaaug 3900
ggacugucug acuuccauau uccagacaac cucuuccuaa agacugaugg cagagucaaa 3960
uacacaauga acaggaacaa aauaaacauu gacaucccuu ugccuuuggg uggcaagucu 4020
ucaaaagacc ucaagaugcc agagagugug aggacaccag cccucaacuu caagucugug 4080
ggauuccauc ugccaucucg agagguccag guccccacuu uuacaauccc caagacacau 4140
cagcuucaag ugccucucuu ggguguucua gaccuuucca caaaugucua cagcaauuug 4200
uacaacuggu cagccuccua cacugguggc aacaccagca gagaccacuu cagccuucag 4260
gcucaguacc gcaugaagac ugacucugug guugaccugu uuuccuacag ugugcaagga 4320
ucuggagaaa caacauauga cagcaagaac acauuuacau uguccuguga uggaucucua 4380
caccauaaau uucuagacuc aaaauucaaa gucagccacg uagaaaaauu uggaaacagc 4440
ccagucucaa aagguuuacu aacauuugaa acaucuagug ccuugggacc acagaugucu 4500
gcuacuguuc accuagacuc aaaaaagaaa caacaucuau acgucaaaga uaucaagguu 4560
gauggacagu ucagagcuuc uucauuuuau gcucaaggca aauauggccu gucuugugag 4620
agagauguua caacuggcca gcugagcggc gaauccaaca ugagauuuaa cuccaccuac 4680
uuccagggca ccaaccagau cgugggaaug uaccaggaug gagcccuguc caucaccucc 4740
acuucugacc ugcaagaugg cauauucaag aacacagcuu ccuugaaaua ugaaaacuau 4800
gagcugacuc ugaaaucuga uagcaguggg caguaugaga acuucgcugc uuccaacaag 4860
cuggauguga ccuucucuac gcaaagugca cugcugcguu cugaacacca ggccaauuac 4920
aagucccuga ggcuugucac ccuucuuuca ggaucccuca cuucccaggg uguagaauua 4980
aaugcugaca ucuugggcac agacaaaauu aauacuggug cucacaaggc aacacuaaag 5040
auugcacgug auggacuauc aaccagugcg accaccaacu ugaaguacag cccccugcug 5100
cuggagaaug aguugaaugc agagcuuggg cucucugggg cauccaugaa auuaucaaca 5160

-continued

```
aacggccgcu ucaaagaaca ccaugcaaaa uucagucuug augggagagc ugcccucaca   5220
gaggugucac uggggagcau uuaccaggcc augauucugg gugcagacag caaaaacauc   5280
uucaacuuca aacucagccg agaagggcug aggcugucca augauuugau gggcuccuau   5340
gcugagauga aacuugacca cacacacagu cugaacauug caggucucuc acuggacuuc   5400
uucucaaaaa uggacaauau uuacagugga gacaaguucu auaagcagaa uuuuaacuua   5460
cagcuacagc ccuauucuuu cauaacuacu uuaagcaacg accugagaua uggugcucua   5520
gauuugacca acaauggaag guuucggcug gagccacuga agcugaaugu ggguggcaac   5580
uuuaaaggaa ccuaucaaaa uaaugagcug aaacauaucu auaccauauc uuauacugac   5640
cugguaguag caaguuacag agcagacacu guggcuaagg uucagggugu cgaauucagc   5700
cauaggcuaa augcagacau ugaaggacug acuuccucug uugaugucac uaccagcuac   5760
aauucagauc cacugcauuu uaacaauguu uuccacuuuu cucuggcacc uuuuaccuug   5820
ggcaucgaca cacauacaag uggugauggg aaacuguccu ucuggggaga acacacuggg   5880
cagcuauaua guaaguuucu guugaaagca gaaccucugg cacuuauugu cucucaugac   5940
uacaaaggau ccacaagcca cagucucccg uacgagagca gcaucagcac ggcucuugaa   6000
cacacaguca gugccuugcu gacgccagcu gagcagacaa gcaccuggaa auucaagacc   6060
aaacugaaug acaaaguaua cagccaggac uuugaagccu acaacacuaa agacaaaauc   6120
gguguugagc uuaguggacg ggcugaccuc ucugggcugu auucuccaau uaaacuaccg   6180
uuuuucuaca gugagccugu caauguccuu aauggcuuag agguaaauga ugcuguugac   6240
aagccccaag aauucacaau uauugcugug gugaaguacg auaagaacca ggauguucac   6300
accaucaacc ucccauucuu caaaagccug ccagacuauu uggagagaaa ucgaagagga   6360
augauaaguc uacuggaagc caugcgaggg gaauugcaac gccucagugu ugaucaguuu   6420
gugaggaaau acagagcggc ccugagcaga cuuccucagc agauucauca uuaucugaau   6480
gcaucugacu gggagagaca aguagcuggu gccaaggaaa aaauaacuuc uuucauggaa   6540
aauuauagaa uuacagauaa ugauguacua auugccauag auagugccaa aaucaacuuc   6600
aaugaaaaac ucucucaacu ugagacauac gcgauacaau uugaucagua uauuaaagau   6660
aauuaugauc cacaugacuu aaaaagaacu auugcugaga uuauugaucg aaucauugaa   6720
aaguuaaaaa uucuugauga acaguaucau auccguguaa aucuagcaaa aucaauccau   6780
aaucucuauu uauuuguuga aaacguugau cuuaaccaag ucaguaguag uaacaccucu   6840
uggauccaaa auguggauuc caauuaucaa gucagaaucc aaauucaaga aaaacuacag   6900
cagcucagga cacaaauuca gaauauagac auucagcagc uugcugcaga gguaaaacga   6960
cagauggacg cuauugaugu cacaaugcau uuagaucaau ugagaacugc aauucuauuc   7020
caaagaauaa gugacauuau ugaccguguc aaauacuuug uuaugaaucu uauugaagau   7080
uuuaaaguaa cugagaaaau caauacuuuu agaguuauag uccgugagcu aauugagaaa   7140
uaugaaguag accaacacau ccagguuuua auggauaaau caguagaguu ggcccacaga   7200
uauagccuga gcgagccucu ucagaaacuc aguaaugugc uacagcgaau ugagauaaaa   7260
gauuacuaug agaaauuggu ugggguuuauu gaugauacug uugaguggcu uaaagcauug   7320
ucuuucaaaa auaccauuga agaacuaaau agauugacug acauguuggu gaagaaguug   7380
aaagcauuug auuaucacca guuuguagac aaaaccaaca gcaaaauccg ugagaugacu   7440
cagagaauca augcugaaau ccaagcucuc aaacuuccac aaaaaaugga agcauuaaaa   7500
```

-continued

```
cuguugguag aagacuucaa aaccacaguc uccaauuccc uggaaagacu caaggacacc   7560
aaaguaacug uggucauuga uuggcugcag gauauuuuga cucaaaugaa agaccauuuc   7620
caagauacuc uggaagaugu aagagaccga auuuaucaaa uggacauuca gagggaacug   7680
gagcacuucu ugucucuggu aaaccaaguu uacaguacac uggucaccua uaugucugac   7740
ugguggacuc ugacugcuaa aaacauaaca gacuuugcag agcaauauuc cauccaaaac   7800
ugggcugaga guauaaaagu acugguggaa caaggauuca uaguuccuga aaugcaaaca   7860
uuucugugga ccaugccugc uuuugagguc agucuccgug cucuccaaga agguaacuuu   7920
cagaccccug ucuuuauagu ccccuugaca gauuugagga uuccaucaau ucggauaaac   7980
uuuaaaaugu uaaagaauau aaaaauccca uugagauuuu ccacuccaga auucacucuu   8040
cucaacaccu uccaugucca uuccuuuaca auugacuugc uggaaauaaa agcaaagauc   8100
auuagaacua ucgaccaaau uuugagcagu gagcuacagu ggccucuucc agaaauguau   8160
uugagagacc uggauguagu gaacauuccu cuugcaagac ugacucugcc agacuuccau   8220
guaccagaaa ucacaauucc agaauucaca aucccaaaug ucaaucucaa agauuuacac   8280
guuccugauc uucacauacc agaauuccaa cuuccucacc ucucacauac aauugaaaua   8340
ccugcuuuug gcaaacugca uagcauccuu aagauccaau cuccucucuu uauauuagau   8400
gcuaaugcca acauacagaa uguaacaacu ucagggaaca aagcagagau uguggcuucu   8460
gucacugcua aaggagaguc ccaauuugaa gcucucaauu uugauuuuca agcacaagcu   8520
caauuccugg aguuaaaucc ucauccucca guccugaagg aauccaugaa cuucuccagu   8580
aagcauguga gaauggagca ugagggugag auaguauuug auggaaaggc cauugagggg   8640
aaaucagaca cagucgcaag uuuacacaca gagaaaaaug aaguagaguu uaauaauggu   8700
augacuguca aaguaaacaa ucagcucacc cuugacaguc acacaaagua cuuccacaag   8760
uugaguguuc cuaggcugga cuucuccagu aaggcuucuc uuaauaauga aaucaagaca   8820
cuauuagaag cuggacaugu ggcauugaca ucuucaggga cagggucaug gaacugggcc   8880
ugucccaacu ucucggauga aggcauacau ucgucccaaa uuagcuuuac uguggauggu   8940
cccauugcuu uuguuggacu auccaauaac auaaauggca aacacuuacg ggucauccaa   9000
aaacugacuu augaaucugg cuuccucaac uauucuaagu uugaaguuga gucaaaaguu   9060
gaaucucagc acgugggcuc cagcauucua acagccaaug gucgggcacu gcucaaggac   9120
gcaaaggcag aaaugacugg ugagcacaau gccaacuuaa auggaaaagu uauuggaacu   9180
uugaaaaauu cucucuucuu uucagcacaa ccauuugaga uuacugcauc cacaaauaau   9240
gaaggaaauu ugaaaguggg uuuuccacua aagcugacug ggaaaauaga cuuccugaau   9300
aacuaugcau uguuucugag uccccgugcc caacaagcaa gcuggcaagc gaguaccaga   9360
uucaaucagu acaaauacaa ucaaaacuuu ucugcuauaa acaaugaaca caacauagaa   9420
gccaguauag gaaugaaugg agaugccaac cuggauuucu uaaacauacc uuuaacaauu   9480
ccugaaauua acuugccuua cacggaguuc aaaacucccu uacugaagga uuucuccaua   9540
ugggaagaaa caggcuugaa agaauuuuug aagacaacaa agcaaucauu ugauuugagu   9600
guaaaggcuc aauauaaaaa gaacagugac aagcauucca uuguuguccc ucuggguaug   9660
uuuuaugaau uuauucucaa caaugucaau ucgugggaca gaaaauuuga gaaagucaga   9720
aacaaugcuu uacauuuucu uaccaccucc uauaaugaag caaaaauuaa gguugauaag   9780
uacaaaacug aaaauucccu uaaucagccc ucugggaccu uucaaaauca uggcuacacu   9840
aucccaguug ucaacauuga aguaucucca uuugcuguag agacacuggc uuccagccau   9900
```

-continued

```
gugaucccca cagcaauaag caccccaagu gucacaaucc cugguccuaa caucauggug   9960
ccuucauaca aguuagugcu gccaccccug gaguugccag uuuuccaugg uccugggaau  10020
cuauucaagu uuuuccuccc agauuucaag ggauucaaca cuauugacaa uauuuauauu  10080
ccagccaugg gcaacuuuac cuaugacuuu ucuuuuaaau caagugucau cacacugaau  10140
accaaugcug gacuuuauaa ccaaucagau aucguugccc auuuccuuuc uuccucuuca  10200
uuugucacug acgcccugca guacaaauua gagggaacau cacgucugau gcgaaaaagg  10260
ggauugaaac uagccacagc ugucucucua acuaacaaau uuguaaaggg cagucaugac  10320
agcaccauua guuuaaccaa gaaaaacaug gaagcaucag ugagaacaac ugccaaccuc  10380
caugcuccca uauucucaau gaacuucaag caggaacuua auggaaauac caagucaaaa  10440
cccacuguuu caucauccau ugaacuaaac uaugacuuca auuccucaaa gcugcacucu  10500
acugcaacag gaggcauuga ucacaaguuc agcuuagaaa gucucacuuc cuacuuuucc  10560
auugagucau ucaccaaagg aaauaucaag aguuccuucc uuucucagga auauucagga  10620
aguguugcca augaagccaa uguauaucug aauuccaagg guacucgguc uucagugagg  10680
cuacaaggag cuuccaaagu ugaugguauc uggaacguug aaguaggaga aaauuuugcu  10740
ggagaagcca cccuccaacg caucuacacc acaugggagc acaauaugaa aaaccauuug  10800
cagguauaua gcuacuucuu cacaaaagga aagcaaacau gcagagcuac uuuggagcuc  10860
uccccaugga ccaugucaac cuugcuacag guucauguga gucaacucag uucccuccuu  10920
gaccuccauc acuuugacca ggaagugauc cuaaaagcua acacuaagaa ccagaagauc  10980
agcuggaaag guggggucca gguugaauca cggguucuuc agcacaaugc acaguucucc  11040
aaugaccaag aagaaauacg gcuugaccuu gcaggauccu uagacggaca gcugugggac  11100
cuugaagcua ucuuuuuacc aguauauggc aagagcuugc aggaacuccu acaaauggau  11160
ggaaagcgac aguaucuuca agcuucaacu ucucuucuau auaccaaaaa cccuaauggc  11220
uaucuccucu cacuccccgu gcaagaacug gcugauagau uuauuauacc agggauaaaa  11280
cuaaaugacu ucaguggagu aaaaaucuau aagaaguuaa guacuucacc auuugcccuc  11340
aaccuaacaa ugcuccccaa aguaaaauuc ccugggauug aucuguuaac acaguacucu  11400
acaccagagg gcuccucugu cccuauuuuu gaggcaacua uaccugaaau ucauuuaacu  11460
guaucccagu uuacacuucc aaagagccuu ccaguuggca acacagucuu ugaucugaau  11520
aaguuggcca acaugauugc cgauguugac cugccuagug ucacccugcc ugagcagacu  11580
auuguaaucc cacccuugga guucucugua ccugcuggga uuuuuauucc uuucuuugga  11640
gaacugacug cacgugcugg gauggcuucu ccccuguaua augucacuug gagcgcuggu  11700
uggaaaacca aagcagauca uguugaaacg uuccuagauu ccaugugcac uucaaccuug  11760
caguuucugg aguaugcuuu aaaaguugua gaaacacaca aaauugaaga agaucuguua  11820
accuauaaua ucaaaggaac acuucaacac ugugacuuca auguggagua uaaugaagau  11880
ggucuauuua aaggacuuug ggacuggcag ggagaggcuc accuggacau caccagccca  11940
gcacugacug acuuucaucu guacuacaaa gaagacaaga caagucuguc ugccucagca  12000
gccuccucga ccaucggcac ugugggucug gauucgagca cagaugacca gaguguggag  12060
cugaaugucu acuuccaccc acaguccccu ccagagaaga aacucagcau auucaaaacu  12120
gaguggaggu acaaggaguc ugauggugaa agguacauca aaauuaauug ggaagaagag  12180
gcagcuucca gauugcuagg cucccuaaaa agcaaugugc ccaaggcuuc uaaggcuauu  12240
```

-continued uaugauuaug ccaauaagua ccaccuggaa uacguuucuu cagaacuaag aaaaagucua 12300
caggucaaug cugaacaugc cagaaggaug guugaugaaa ugaacaugag uuuccagaga 12360
guagcccgug auaccuacca gaaucucuau gaggagaugu uggcucagaa gagccugagc 12420
aucccugaga aucucaagaa gagggguuua gacaguauag uacauguuac ucagaaguac 12480
cacauggcag ucauguggcu gauggacuca uucauucauu uucugaaauu caauagaguc 12540
caguucccag gguacgcugg aacauauacu guggacgaac ucuacacuau agucaugaag 12600
gaaaccaaga agucacuguc ucagcuguuu aaugggguuag gaaaccuacu uuccuacguu 12660
caaaaccaag uagagaaauc aagauuaauc aaugacauaa cauuuaaaug uccuuuuuuc 12720
ucaaaaccuu guaaacuaaa agaucucaua uugauuuuca gggaggaguu aaacauuuua 12780
ucaaacauag gccaacagga uaucaaguuu acaacaauac uaaguagucu ucagggcuuu 12840
uuggagagag uuuuagacau cauagaagaa caaauuaaau gccuaaagga caaugaaucu 12900
acuuguguug cugaccauau caacaugguu uucaaaauac aggucccaua ugcuuuuaaa 12960
ucccuaagag aagacauaua cuuuguccuc ggugaguuca augacuuucu ucaauccaua 13020
cuucaggagg gguccuacaa gcuacagcag guccaucagu auaugaaggc ccuucgugaa 13080
gaguauuuug auccgagcau gguugggugg acagugaaau auuaugaaau agaagaaaau 13140
augguugagc ugaucaagac ccuuuuaguu uccuuuaggg augucuacuc ugaauauagu 13200
gugacagcug cugauuuugc uuccaaaaug ucaacucaag uugaacaauu uguguccagg 13260
gauaucagag aguaucuuag caugcuuacu gauauaaaug gaaaguggau ggaaaagauu 13320
gcagagcuuu cuauuguggc aaaggaaaca augaaaagcu gggucacugc cguggccaaa 13380 auaaaugucug auuaccccca gcaguuccac uccaaucugc aggauuuuuc agaccaacuc 13440
ucuagcuacu augaaaaauu uguuggugag uccacaagau ugauugaccu guccauucaa 13500
aacuaccacg uguuucucag auacaucacc gaguuacuga gaaagcugca gguggccaca 13560
gccaauaaug ugagccccua uauaaagcuu gcucaaggag agcugaugau caccuucuga 13620
uucaucuacu aacaaauuca aauuaaaccu ucacauagua ggagacuuug uagacuacua 13680
uaaagaccau ccugagccag accugcaguc aacagcaaga gcaagaagca cauaggaacu 13740
auaccugcaa ccaagcuggc auaagaacca agaccuucaa agcagccuga acucaagaug 13800
acauauuuua caaguuagag uaaagucaag agcugaguug uuuuguccaa cucaggaugg 13860
agggagggag ggaaggggaa auaaauaaau acuuccuuau ugugcagcaa aaaaaaaaaa 13920
aaaaaaaaaa a 13931

<210> SEQ ID NO 11
<211> LENGTH: 21
<212> TYPE: RNA
<213> ORGANISM: Aequorea victoria

<400> SEQUENCE: 11
gggcagcuug ccggugguguu u 21

<210> SEQ ID NO 12
<211> LENGTH: 21
<212> TYPE: RNA
<213> ORGANISM: Aequorea victoria

<400> SEQUENCE: 12
caccaccccg gugaacagcu u 21

<210> SEQ ID NO 13
<211> LENGTH: 21
<212> TYPE: RNA
<213> ORGANISM: Aequorea victoria

<400> SEQUENCE: 13
gcuguucacg ucgcugcccu u 21

<210> SEQ ID NO 14
<211> LENGTH: 19
<212> TYPE: DNA
<213> ORGANISM: Aequorea victoria

<400> SEQUENCE: 14
gctgttcacg tcgctgccc 19

<210> SEQ ID NO 15
<211> LENGTH: 80
<212> TYPE: DNA
<213> ORGANISM: Artificial Sequence
<220> FEATURE:
<223> OTHER INFORMATION: Oligo for MV-siRNA expressing clones

<400> SEQUENCE: 15
gatcccccac caccccggtg aacagcgtta gctgttcacg tcgctgcccg ttagggcagc 60
ttgccggtgg tgttttttta 80

<210> SEQ ID NO 16
<211> LENGTH: 75
<212> TYPE: DNA
<213> ORGANISM: Artificial Sequence
<220> FEATURE:
<223> OTHER INFORMATION: Oligo for MV-siRNA expressing clones

<400> SEQUENCE: 16
agcttaacac caccggcaag ctgccctaac gggcagcgac gtgaacagct aacgctgttc 60
accggggtgg tgggg 75

<210> SEQ ID NO 17
<211> LENGTH: 144
<212> TYPE: DNA
<213> ORGANISM: Artificial Sequence
<220> FEATURE:
<223> OTHER INFORMATION: Oligo for MV-siRNA expressing clones

<400> SEQUENCE: 17
gatcccccac caccccggtg aacagcttgt aggtggcatc gcagaagcga tgccacctac 60
aagctgttca cgtcgctgcc cttgtaggtg gcatcgcaga agcgatgcca cctacaaggg 120
cagcttgccg gtggtgtttt ttta 144

<210> SEQ ID NO 18
<211> LENGTH: 139
<212> TYPE: DNA
<213> ORGANISM: Artificial Sequence
<220> FEATURE:
<223> OTHER INFORMATION: Oligo for MV-siRNA expressing clones

<400> SEQUENCE: 18
agcttaacac caccggcaag ctgcccttgt aggtggcatc gcttctgcga tgccacctac 60
aagggcagcg acgtgaacag cttgtaggtg gcatcgcttc tgcgatgcca cctacaagct 120
gttcaccggg gtggtgggg 139

-continued

<210> SEQ ID NO 19
<211> LENGTH: 89
<212> TYPE: DNA
<213> ORGANISM: Artificial Sequence
<220> FEATURE:
<223> OTHER INFORMATION: Oligo for MV-siRNA expressing clones

<400> SEQUENCE: 19
gatcccccgt gctgcttcat gtggtcgttg ttacgaccac aatggcgaca accttgttag 60
gttgtcgggc agcagcacgt tttttttta 89

<210> SEQ ID NO 20
<211> LENGTH: 84
<212> TYPE: DNA
<213> ORGANISM: Artificial Sequence
<220> FEATURE:
<223> OTHER INFORMATION: Oligo for MV-siRNA expressing clones

<400> SEQUENCE: 20
agcttaaaac gtgctgctgc ccgacaacct aacaaggttg tcgccattgt ggtcgtaaca 60
acgaccacat gaagcagcac gggg 84

<210> SEQ ID NO 21
<211> LENGTH: 147
<212> TYPE: DNA
<213> ORGANISM: Artificial Sequence
<220> FEATURE:
<223> OTHER INFORMATION: Oligo for MV-siRNA expressing clones

<400> SEQUENCE: 21
gatcccccgt gctgcttcat gtggtcgttg taggtggcat cgcagaagcg atgccaccta 60
caacgaccac aatggcgaca accttgtagg tggcatcgca gaagcgatgc cacctacaag 120
gttgtcgggc agcagcacgt tttttta 147

<210> SEQ ID NO 22
<211> LENGTH: 142
<212> TYPE: DNA
<213> ORGANISM: Artificial Sequence
<220> FEATURE:
<223> OTHER INFORMATION: Oligo for MV-siRNA expressing clones

<400> SEQUENCE: 22
agcttaacgt gctgctgccc gacaaccttg taggtggcat cgcttctgcg atgccaccta 60
caaggttgtc gccattgtgg tcgttgtagg tggcatcgct tctgcgatgc cacctacaac 120
gaccacatga agcagcacgg gg 142

<210> SEQ ID NO 23
<211> LENGTH: 62
<212> TYPE: DNA
<213> ORGANISM: Artificial Sequence
<220> FEATURE:
<223> OTHER INFORMATION: Oligo for MV-siRNA expressing clones

<400> SEQUENCE: 23
gatccccgca agctgaccct gaagttcttc aagagagaac ttcagggtca gcttgctttt 60
ta 62

<210> SEQ ID NO 24
<211> LENGTH: 62
<212> TYPE: DNA
<213> ORGANISM: Artificial Sequence -continued
<220> FEATURE:
<223> OTHER INFORMATION: Oligo for MV-siRNA expressing clones

<400> SEQUENCE: 24
agcttaaaaa gcaagctgac cctgaagttc tctcttgaag aacttcaggg tcagcttgcg 60
gg 62

<210> SEQ ID NO 25
<211> LENGTH: 21
<212> TYPE: RNA
<213> ORGANISM: Artificial Sequence
<220> FEATURE:
<223> OTHER INFORMATION: synthetic siRNA

<400> SEQUENCE: 25
cugcugguag uggucggcgu u 21

<210> SEQ ID NO 26
<211> LENGTH: 21
<212> TYPE: RNA
<213> ORGANISM: Artificial Sequence
<220> FEATURE:
<223> OTHER INFORMATION: synthetic siRNA

<400> SEQUENCE: 26
cgccgacuuc gugacgugcu u 21

<210> SEQ ID NO 27
<211> LENGTH: 21
<212> TYPE: RNA
<213> ORGANISM: Artificial Sequence
<220> FEATURE:
<223> OTHER INFORMATION: synthetic siRNA

<400> SEQUENCE: 27
gcacgucgcc guccagcagu u 21

<210> SEQ ID NO 28
<211> LENGTH: 21
<212> TYPE: RNA
<213> ORGANISM: Artificial Sequence
<220> FEATURE:
<223> OTHER INFORMATION: synthetic siRNA

<400> SEQUENCE: 28
guugccgucg uccuugaagu u 21

<210> SEQ ID NO 29
<211> LENGTH: 21
<212> TYPE: RNA
<213> ORGANISM: Artificial Sequence
<220> FEATURE:
<223> OTHER INFORMATION: synthetic siRNA

<400> SEQUENCE: 29
cuucaagugg aacuacggcu u 21

<210> SEQ ID NO 30
<211> LENGTH: 21
<212> TYPE: RNA
<213> ORGANISM: Artificial Sequence
<220> FEATURE:
<223> OTHER INFORMATION: synthetic siRNA

<400> SEQUENCE: 30
gccguaggua ggcggcaacu u 21

<210> SEQ ID NO 31
<211> LENGTH: 67
<212> TYPE: RNA
<213> ORGANISM: Artificial Sequence
<220> FEATURE:
<223> OTHER INFORMATION: multivalent-siRNA clones

<400> SEQUENCE: 31
cgccgacuuc gugacgugcu ugugcacguc gccguccagc aguugucugc ugguaguggu 60
cggcguu 67

<210> SEQ ID NO 32
<211> LENGTH: 80
<212> TYPE: DNA
<213> ORGANISM: Artificial Sequence
<220> FEATURE:
<223> OTHER INFORMATION: multivalent-siRNA clones

<400> SEQUENCE: 32
gatcccccgc cgacttcgtg acgtgcttgt gcacgtcgcc gtccagcagt tgtctgctgg 60
tagtggtcgg cgttttttta 80

<210> SEQ ID NO 33
<211> LENGTH: 80
<212> TYPE: DNA
<213> ORGANISM: Artificial Sequence
<220> FEATURE:
<223> OTHER INFORMATION: multivalent-siRNA clones

<400> SEQUENCE: 33
agcttaaaaa aacgccgacc actaccagca gacaactgct ggacggcgac gtgcacaagc 60
acgtcacgaa gtcggcgggg 80

<210> SEQ ID NO 34
<211> LENGTH: 131
<212> TYPE: RNA
<213> ORGANISM: Artificial Sequence
<220> FEATURE:
<223> OTHER INFORMATION: multivalent-siRNA clones

<400> SEQUENCE: 34
cgccgacuuc gugacgugcu uguagguggc aucgcagaag cgaugccacc uacaagcacg 60
ucgccgucca gcaguuguag guggcaucgc agaagcgaug ccaccuacaa cugcugguag 120
uggucggcgu u 131

<210> SEQ ID NO 35
<211> LENGTH: 142
<212> TYPE: DNA
<213> ORGANISM: Artificial Sequence
<220> FEATURE:
<223> OTHER INFORMATION: multivalent-siRNA clones

<400> SEQUENCE: 35
gatcccccgc cgacttcgtg acgtgcttgt aggtggcatc gcagaagcga tgccacctac 60
aagcacgtcg ccgtccagca gttgtaggtg gcatcgcaga agcgatgcca cctacaactg 120
ctggtagtgg tcggcgtttt ta 142

<210> SEQ ID NO 36
<211> LENGTH: 142

```
<212> TYPE: DNA
<213> ORGANISM: Artificial Sequence
<220> FEATURE:
<223> OTHER INFORMATION: multivalent-siRNA clones

<400> SEQUENCE: 36

agcttaaaaa cgccgaccac taccagcagt tgtaggtggc atcgcttctg cgatgccacc    60

tacaactgct ggacggcgac gtgcttgtag gtggcatcgc ttctgcgatg ccacctacaa   120

gcacgtcacg aagtcggcgg gg                                            142

<210> SEQ ID NO 37
<211> LENGTH: 67
<212> TYPE: RNA
<213> ORGANISM: Artificial Sequence
<220> FEATURE:
<223> OTHER INFORMATION: multivalent-siRNA clones

<400> SEQUENCE: 37

cuucaagugg aacuacggcu ugugccguag guaggcggca acuuguuug ccgucguccu    60

ugaaguu                                                              67

<210> SEQ ID NO 38
<211> LENGTH: 60
<212> TYPE: DNA
<213> ORGANISM: Artificial Sequence
<220> FEATURE:
<223> OTHER INFORMATION: multivalent-siRNA clones

<400> SEQUENCE: 38

gatccccgga tccgacatcc acgttcttca agagagaacg tggatgtcgg atccttttta   60

<210> SEQ ID NO 39
<211> LENGTH: 60
<212> TYPE: DNA
<213> ORGANISM: Artificial Sequence
<220> FEATURE:
<223> OTHER INFORMATION: multivalent-siRNA clones

<400> SEQUENCE: 39

agcttaaaaa ggatccgaca tccacgttct ctcttgaaga acgtggatgt cggatccggg   60

<210> SEQ ID NO 40
<211> LENGTH: 131
<212> TYPE: RNA
<213> ORGANISM: Artificial Sequence
<220> FEATURE:
<223> OTHER INFORMATION: multivalent-siRNA clones

<400> SEQUENCE: 40

cuucaagugg aacuacggcu uguagguggc aucgcagaag cgaugccacc uacaagccgu    60

agguaggcgg caacuuguag guggcaucgc agaagcgaug ccaccuacaa guugccgucg   120

uccuugaagu u                                                         131

<210> SEQ ID NO 41
<211> LENGTH: 142
<212> TYPE: DNA
<213> ORGANISM: Artificial Sequence
<220> FEATURE:
<223> OTHER INFORMATION: multivalent-siRNA clones

<400> SEQUENCE: 41

gatccccctt caagtggaac tacggcttgt aggtggcatc gcagaagcga tgccacctac   60
```

-continued

```
aagccgtagg taggcggcaa cttgtaggtg gcatcgcaga agcgatgcca cctacaagtt    120

gccgtcgtcc ttgaagtttt ta                                              142


<210> SEQ ID NO 42
<211> LENGTH: 142
<212> TYPE: DNA
<213> ORGANISM: Artificial Sequence
<220> FEATURE:
<223> OTHER INFORMATION: multivalent-siRNA clones

<400> SEQUENCE: 42

agcttaaaaa cttcaaggac gacggcaact tgtaggtggc atcgcttctg cgatgccacc     60

tacaagttgc cgcctaccta cggcttgtag gtggcatcgc ttctgcgatg ccacctacaa    120

gccgtagttc cacttgaagg gg                                              142


<210> SEQ ID NO 43
<211> LENGTH: 77
<212> TYPE: DNA
<213> ORGANISM: Artificial Sequence
<220> FEATURE:
<223> OTHER INFORMATION: Anti-HIV MV-siRNA oligo

<400> SEQUENCE: 43

gatccccgtg aaggggaacc aagagattga tctcttgtta atatcagctt gagctgatat     60

ttctccttca cttttta                                                     77


<210> SEQ ID NO 44
<211> LENGTH: 77
<212> TYPE: DNA
<213> ORGANISM: Artificial Sequence
<220> FEATURE:
<223> OTHER INFORMATION: Anti-HIV MV-siRNA oligo

<400> SEQUENCE: 44

agcttaaaaa gtgaaggaga aatatcagct caagctgata ttaacaagag atcaatctct     60

tggttcccct tcacggg                                                     77


<210> SEQ ID NO 45
<211> LENGTH: 80
<212> TYPE: DNA
<213> ORGANISM: Artificial Sequence
<220> FEATURE:
<223> OTHER INFORMATION: Anti-HIV MV-siRNA oligo

<400> SEQUENCE: 45

gatcccccaa gcagttttag gctgacgtta gtcagcctca ttgacacagg ttactgtgtc     60

agctgctgct tgttttttta                                                  80


<210> SEQ ID NO 46
<211> LENGTH: 80
<212> TYPE: DNA
<213> ORGANISM: Artificial Sequence
<220> FEATURE:
<223> OTHER INFORMATION: Anti-HIV MV-siRNA oligo

<400> SEQUENCE: 46

agcttaaaaa aacaagcagc agctgacaca gtaacctgtg tcaatgaggc tgactaacgt     60

cagcctaaaa ctgcttgggg                                                  80


<210> SEQ ID NO 47
<211> LENGTH: 21
```

<212> TYPE: RNA
<213> ORGANISM: Artificial Sequence
<220> FEATURE:
<223> OTHER INFORMATION: Trivalent MV-siRNA oligo sequences

<400> SEQUENCE: 47
gccuucccuu gugggaaggu u 21

<210> SEQ ID NO 48
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 48
ccuucccuug ugggaaggcu u 21

<210> SEQ ID NO 49
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 49
gccuuccuug ugggaaggcu u 21

<210> SEQ ID NO 50
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 50
uucugcaccu uaccucuuau u 21

<210> SEQ ID NO 51
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 51
uaagaggaag uaugcuguuu u 21

<210> SEQ ID NO 52
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 52
aacagcaguu guugcagaau u 21

<210> SEQ ID NO 53
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 53
ccagacaaua auugucuggu u 21

<210> SEQ ID NO 54
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 54
cucccaggcu cagaucuggu u 21

<210> SEQ ID NO 55
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 55
ccagaucuuc ccuaaaaaau u 21

<210> SEQ ID NO 56
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 56
uuuuuuaucu gccugggagu u 21

<210> SEQ ID NO 57
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 57
uggguucccu aguuagccau u 21

<210> SEQ ID NO 58
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 58
uggcuaagau cuacagcugu u 21

<210> SEQ ID NO 59
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 59
cagcuguccc aagaacccau u 21

<210> SEQ ID NO 60
<211> LENGTH: 21
<212> TYPE: RNA
<213> ORGANISM: Artificial Sequence

```
<220> FEATURE:
<223> OTHER INFORMATION: Trivalent MV-siRNA oligo sequences

<400> SEQUENCE: 60

auccuuugau gcacacaauu u                                          21


<210> SEQ ID NO 61
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 61

auugugucac uuccuucagu u                                          21


<210> SEQ ID NO 62
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 62

cugaaggaag cuaaaggauu u                                          21


<210> SEQ ID NO 63
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 63

uccuguguca gcugcugcuu u                                          21


<210> SEQ ID NO 64
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 64

agcagcauug uuagcugcuu u                                          21


<210> SEQ ID NO 65
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 65

agcagcuuua uacacaggau u                                          21


<210> SEQ ID NO 66
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 66

accaacaagg uuucugucau u                                          21
```

<210> SEQ ID NO 67
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 67
ugacagaucu aauuacuacu u 21

<210> SEQ ID NO 68
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 68
guaguaauua ucuguugguu u 21

<210> SEQ ID NO 69
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 69
cugagggaag cuaaaggauu u 21

<210> SEQ ID NO 70
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 70
caaagcuaga ugaauugcuu u 21

<210> SEQ ID NO 71
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 71
agcaauuggu acaagcaguu u 21

<210> SEQ ID NO 72
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 72
acugcuuguu agagcuuugu u 21

<210> SEQ ID NO 73
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 73
aggucagggu cuacuugugu u 21

<210> SEQ ID NO 74
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 74
cacaagugcu gauauuucuu u 21

<210> SEQ ID NO 75
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 75
agaaauaauu gucugaccuu u 21

<210> SEQ ID NO 76
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 76
cuaaguuaug gagccauauu u 21

<210> SEQ ID NO 77
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 77
auauggccug auguaccauu u 21

<210> SEQ ID NO 78
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 78
augguacuuc ugaacuuagu u 21

<210> SEQ ID NO 79
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 79
uggcuccauu ucuugcucuu u 21

<210> SEQ ID NO 80

<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 80
agagcaaccc caaauccccu u 21

<210> SEQ ID NO 81
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 81
ggggauuuag ggggagccau u 21

<210> SEQ ID NO 82
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 82
aucuccacaa gugcugauau u 21

<210> SEQ ID NO 83
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 83
uaucagcagu ucuugaaguu u 21

<210> SEQ ID NO 84
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 84
acuucaaauu guuggagauu u 21

<210> SEQ ID NO 85
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 85
agacugugac ccacaauuuu u 21

<210> SEQ ID NO 86
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 86
aaauugugga ugaauacugu u 21

<210> SEQ ID NO 87
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 87
caguauuugu cuacagucuu u 21

<210> SEQ ID NO 88
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 88
acaggccugu guaaugacuu u 21

<210> SEQ ID NO 89
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 89
agucauuggu cuuaaagguu u 21

<210> SEQ ID NO 90
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 90
accuuuagga caggccuguu u 21

<210> SEQ ID NO 91
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 91
ucaguguuau uugacccuuu u 21

<210> SEQ ID NO 92
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 92
aagggucuga gggaucucuu u 21

<210> SEQ ID NO 93
<211> LENGTH: 21
<212> TYPE: RNA

<213> ORGANISM: Artificial Sequence
<220> FEATURE:
<223> OTHER INFORMATION: Trivalent MV-siRNA oligo sequences

<400> SEQUENCE: 93
agagaucuuu ccacacugau u 21

<210> SEQ ID NO 94
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 94
cauagugcuu ccugcugcuu u 21

<210> SEQ ID NO 95
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 95
agcagcauug uuagcugcuu u 21

<210> SEQ ID NO 96
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 96
agcagcuaac agcacuaugu u 21

<210> SEQ ID NO 97
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 97
gcugcuuaua ugcaggaucu u 21

<210> SEQ ID NO 98
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 98
gauccugucu gaagggaugu u 21

<210> SEQ ID NO 99
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 99
caucccuguu aaaagcagcu u 21

-continued

<210> SEQ ID NO 100
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 100
uggucuaacc agagagaccu u 21

<210> SEQ ID NO 101
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 101
ggucucuuuu aacauuugcu u 21

<210> SEQ ID NO 102
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 102
gcaaauguuu ucuagaccau u 21

<210> SEQ ID NO 103
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 103
cucccaggcu cagaucuggu u 21

<210> SEQ ID NO 104
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 104
uggguucccu aguuagccau u 21

<210> SEQ ID NO 105
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 105
uggaacuuuc agcuucauau u 21

<210> SEQ ID NO 106
<211> LENGTH: 21
<212> TYPE: RNA
<213> ORGANISM: Artificial Sequence
<220> FEATURE:

-continued

<223> OTHER INFORMATION: Trivalent MV-siRNA to ApoB

<400> SEQUENCE: 106
uaugaaggca ccaugauguu u 21

<210> SEQ ID NO 107
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 107
acaucaucuu ccaguuccau u 21

<210> SEQ ID NO 108
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 108
acucuucaga guucuugguu u 21

<210> SEQ ID NO 109
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 109
accaagaccu uggagacacu u 21

<210> SEQ ID NO 110
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 110
gugucucagu uggaagaguu u 21

<210> SEQ ID NO 111
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 111
accuggacau ggcagcugcu u 21

<210> SEQ ID NO 112
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 112
gcagcugcaa acucuucagu u 21

<210> SEQ ID NO 113
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 113
cugaagacgu auuccagguu u 21

<210> SEQ ID NO 114
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 114
caggguaaag aacaauuugu u 21

<210> SEQ ID NO 115
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 115
caaauugcug uagacauuuu u 21

<210> SEQ ID NO 116
<211> LENGTH: 21
<212> TYPE: RNA
<213> ORGANISM: Artificial Sequence
<220> FEATURE:
<223> OTHER INFORMATION: Trivalent MV-siRNA to ApoB

<400> SEQUENCE: 116
aaauguccag cguacccugu u 21

<210> SEQ ID NO 117
<211> LENGTH: 23
<212> TYPE: RNA
<213> ORGANISM: Artificial Sequence
<220> FEATURE:
<223> OTHER INFORMATION: Trivalent MV-siRNA to ApoB

<400> SEQUENCE: 117
cccuggacac cgcuggaacu uuu 23

<210> SEQ ID NO 118
<211> LENGTH: 23
<212> TYPE: RNA
<213> ORGANISM: Artificial Sequence
<220> FEATURE:
<223> OTHER INFORMATION: Trivalent MV-siRNA to ApoB

<400> SEQUENCE: 118
aaguuccaau aacuuuucca uuu 23

<210> SEQ ID NO 119
<211> LENGTH: 23
<212> TYPE: RNA
<213> ORGANISM: Artificial Sequence
<220> FEATURE:
<223> OTHER INFORMATION: Trivalent MV-siRNA to ApoB

<400> SEQUENCE: 119
auggaaaagg caaguccagg guu 23

<210> SEQ ID NO 120
<211> LENGTH: 24
<212> TYPE: RNA
<213> ORGANISM: Artificial Sequence
<220> FEATURE:
<223> OTHER INFORMATION: Trivalent MV-siRNA to ApoB

<400> SEQUENCE: 120
cccuggacac cgcuggaacu uuuu 24

<210> SEQ ID NO 121
<211> LENGTH: 24
<212> TYPE: RNA
<213> ORGANISM: Artificial Sequence
<220> FEATURE:
<223> OTHER INFORMATION: Trivalent MV-siRNA to ApoB

<400> SEQUENCE: 121
aaaguuccaa uaacuuuucc auuu 24

<210> SEQ ID NO 122
<211> LENGTH: 24
<212> TYPE: RNA
<213> ORGANISM: Artificial Sequence
<220> FEATURE:
<223> OTHER INFORMATION: Trivalent MV-siRNA to ApoB

<400> SEQUENCE: 122
auggaaaaug gcaaguccag gguu 24

<210> SEQ ID NO 123
<211> LENGTH: 21
<212> TYPE: RNA
<213> ORGANISM: Artificial Sequence
<220> FEATURE:
<223> OTHER INFORMATION: Bivalent MV-siRNA oligo to ApoB

<400> SEQUENCE: 123
ugaaucgagu ugcaucuuuu u 21

<210> SEQ ID NO 124
<211> LENGTH: 21
<212> TYPE: RNA
<213> ORGANISM: Artificial Sequence
<220> FEATURE:
<223> OTHER INFORMATION: Bivalent MV-siRNA oligo to ApoB

<400> SEQUENCE: 124
aaagaugcug cucaucacau u 21

<210> SEQ ID NO 125
<211> LENGTH: 21
<212> TYPE: RNA
<213> ORGANISM: Artificial Sequence
<220> FEATURE:
<223> OTHER INFORMATION: Bivalent MV-siRNA oligo to ApoB

<400> SEQUENCE: 125
ugugaugaca cucgauucau u 21

<210> SEQ ID NO 126
<211> LENGTH: 23

<212> TYPE: RNA
<213> ORGANISM: Artificial Sequence
<220> FEATURE:
<223> OTHER INFORMATION: Bivalent MV-siRNA oligo to ApoB
<220> FEATURE:
<221> NAME/KEY: modified_base
<222> LOCATION: 2,7
<223> OTHER INFORMATION: n = any base, universal base, rSpacer, linker
phosphoramidite, 5-nitrodole, PC Spacer, or abasic
base

<400> SEQUENCE: 126
unguganuga cacucgauuc auu 23

<210> SEQ ID NO 127
<211> LENGTH: 19
<212> TYPE: DNA
<213> ORGANISM: Artificial Sequence
<220> FEATURE:
<223> OTHER INFORMATION: Bivalent MV-siRNA oligo to ApoB

<400> SEQUENCE: 127
tgtgatgaca ctcgattca 19

<210> SEQ ID NO 128
<211> LENGTH: 21
<212> TYPE: RNA
<213> ORGANISM: Artificial Sequence
<220> FEATURE:
<223> OTHER INFORMATION: Bivalent MV-siRNA oligo to ApoB

<400> SEQUENCE: 128
cagcuugagu ucguaccugu u 21

<210> SEQ ID NO 129
<211> LENGTH: 21
<212> TYPE: RNA
<213> ORGANISM: Artificial Sequence
<220> FEATURE:
<223> OTHER INFORMATION: Bivalent MV-siRNA oligo to ApoB

<400> SEQUENCE: 129
cagguacaga gaacuccaau u 21

<210> SEQ ID NO 130
<211> LENGTH: 21
<212> TYPE: RNA
<213> ORGANISM: Artificial Sequence
<220> FEATURE:
<223> OTHER INFORMATION: Bivalent MV-siRNA oligo to ApoB

<400> SEQUENCE: 130
uuggagucug accaagcugu u 21

<210> SEQ ID NO 131
<211> LENGTH: 21
<212> TYPE: RNA
<213> ORGANISM: Artificial Sequence
<220> FEATURE:
<223> OTHER INFORMATION: Bivalent MV-siRNA oligo to ApoB
<220> FEATURE:
<221> NAME/KEY: modified_base
<222> LOCATION: 13, 19
<223> OTHER INFORMATION: n = any base, universal base, rSpacer, linker
phosphoramidite, 5-nitrodole, PC Spacer, or abasic
base

<400> SEQUENCE: 131

-continued

```
uuggagucug acnaagcunu u                                          21


<210> SEQ ID NO 132
<211> LENGTH: 19
<212> TYPE: DNA
<213> ORGANISM: Artificial Sequence
<220> FEATURE:
<223> OTHER INFORMATION: Bivalent MV-siRNA oligo to ApoB

<400> SEQUENCE: 132

ttggagtctg accaagctg                                             19


<210> SEQ ID NO 133
<211> LENGTH: 21
<212> TYPE: RNA
<213> ORGANISM: Artificial Sequence
<220> FEATURE:
<223> OTHER INFORMATION: Trivalent MV-siRNA oligonucleotide to ApoB

<400> SEQUENCE: 133

ucagggccgc ucuguauuuu u                                          21


<210> SEQ ID NO 134
<211> LENGTH: 21
<212> TYPE: RNA
<213> ORGANISM: Artificial Sequence
<220> FEATURE:
<223> OTHER INFORMATION: Trivalent MV-siRNA oligonucleotide to ApoB

<400> SEQUENCE: 134

aaauacauuu cuggaagagu u                                          21


<210> SEQ ID NO 135
<211> LENGTH: 21
<212> TYPE: RNA
<213> ORGANISM: Artificial Sequence
<220> FEATURE:
<223> OTHER INFORMATION: Trivalent MV-siRNA oligonucleotide to ApoB

<400> SEQUENCE: 135

cucuuccaaa aagcccugau u                                          21


<210> SEQ ID NO 136
<211> LENGTH: 65
<212> TYPE: RNA
<213> ORGANISM: Artificial Sequence
<220> FEATURE:
<223> OTHER INFORMATION: Trivalent MV-siRNA oligonucleotide to ApoB
<220> FEATURE:
<221> NAME/KEY: modified_base
<222> LOCATION: 22, 44
<223> OTHER INFORMATION: n = any base, universal base, rSpacer, linker
      phosphoramidite, 5-nitrodole, PC Spacer, or abasic
      base

<400> SEQUENCE: 136

aaauacauuu cuggaagagu uncucuucca aaaagcccug auunucaggg ccgcucugua    60

uuuuu                                                            65


<210> SEQ ID NO 137
<211> LENGTH: 21
<212> TYPE: RNA
<213> ORGANISM: Artificial Sequence
<220> FEATURE:
<223> OTHER INFORMATION: multivalent-siRNA oligonucleotide targeted to
      ApoB
```

-continued

<400> SEQUENCE: 137
aacccacuuu caaauuuccu u 21

<210> SEQ ID NO 138
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB

<400> SEQUENCE: 138
ggaaauugag aauucuccau u 21

<210> SEQ ID NO 139
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB

<400> SEQUENCE: 139
uggagaaucu caguggguuu u 21

<210> SEQ ID NO 140
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB
<220> FEATURE:
<221> NAME/KEY: modified_base
<222> LOCATION: 5,13,18
<223> OTHER INFORMATION: n = any base, universal base, rSpacer, linker phosphoramidite, 5-nitrodole, PC Spacer, or abasic base
<220> FEATURE:
<221> NAME/KEY: misc_feature
<222> LOCATION: 1,2,3,7,8,9,10,11,12,15,16,17,20,21
<223> OTHER INFORMATION: Bases have an rSpace linkage
<220> FEATURE:
<221> NAME/KEY: modified_base
<222> LOCATION: 4,6,14,19
<223> OTHER INFORMATION: Bases have a 2'-fluoro modification

<400> SEQUENCE: 140
ugganaaucu canugggnuu u 21

<210> SEQ ID NO 141
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB

<400> SEQUENCE: 141
gaugaugaaa caguggguuu u 21

<210> SEQ ID NO 142
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB

<400> SEQUENCE: 142
ggaaauugga gacaucaucu u 21

<210> SEQ ID NO 143
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB
<220> FEATURE:
<221> NAME/KEY: modified_base
<222> LOCATION: 1,15
<223> OTHER INFORMATION: n = any base, universal base, rSpacer, linker phosphoramidite, 5-nitrodole, PC Spacer, or abasic base
<220> FEATURE:
<221> NAME/KEY: misc_feature
<222> LOCATION: 2,6,7,8,9,10,11,12,13,16,18,19,20,21
<223> OTHER INFORMATION: Bases have an rSpace linkage
<220> FEATURE:
<221> NAME/KEY: modified_base
<222> LOCATION: 3,4,5,14,17
<223> OTHER INFORMATION: Bases have a 2'-fluoro modification

<400> SEQUENCE: 143
ngaaauugga gacancaucu u 21

<210> SEQ ID NO 144
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB

<400> SEQUENCE: 144
gcaaacucuu cagaguucuu u 21

<210> SEQ ID NO 145
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB

<400> SEQUENCE: 145
agaacuccaa gggugggauu u 21

<210> SEQ ID NO 146
<211> LENGTH: 21
<212> TYPE: RNA
<213> ORGANISM: Artificial Sequence
<220> FEATURE:
<223> OTHER INFORMATION: multivalent-siRNA oligonucleotide targeted to ApoB

<400> SEQUENCE: 146
aucccacuuu caaguuugcu u 21

<210> SEQ ID NO 147
<211> LENGTH: 19
<212> TYPE: RNA
<213> ORGANISM: Artificial Sequence
<220> FEATURE:
<223> OTHER INFORMATION: multivalent-siRNA oligonucleotide targeted to ApoB
<220> FEATURE:

-continued

<221> NAME/KEY: modified_base
<222> LOCATION: 2,14,18
<223> OTHER INFORMATION: n = any base, universal base, rSpacer, linker
      phosphoramidite, 5-nitrodole, PC Spacer, or abasic
      base
<220> FEATURE:
<221> NAME/KEY: misc_feature
<222> LOCATION: 3,4,5,6,7,8,9,10,11,12,16,17,19
<223> OTHER INFORMATION: Bases have an rSpace linkage
<220> FEATURE:
<221> NAME/KEY: modified_base
<222> LOCATION: 1,13,15
<223> OTHER INFORMATION: Bases have a 2'-fluoro modification

<400> SEQUENCE: 147
ancccacuuu caanuuunc 19

<210> SEQ ID NO 148
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 148
cuucaucacu gaggccucuu u 21

<210> SEQ ID NO 149
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 149
agaggccaag cucugcauuu u 21

<210> SEQ ID NO 150
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 150
aaugcagaug aagaugaaga a 21

<210> SEQ ID NO 151
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 151
uucagccugc auguuggcuu u 21

<210> SEQ ID NO 152
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

```
<400> SEQUENCE: 152

agccaacuau acuuggaucu u                                              21

<210> SEQ ID NO 153
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 153

gauccaaaag caggcugaag a                                              21

<210> SEQ ID NO 154
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 154

cccucaucug agaaucuggu u                                              21

<210> SEQ ID NO 155
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 155

ccagauucau aaaccaaguu u                                              21

<210> SEQ ID NO 156
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 156

acuugguggc ccaugagggu u                                              21

<210> SEQ ID NO 157
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 157

ucaagaauuc cuucaagccu u                                              21

<210> SEQ ID NO 158
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 158
```

ggcuugaagc gaucacacuu u 21

<210> SEQ ID NO 159
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 159
agugugaacg uauucuugau u 21

<210> SEQ ID NO 160
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 160
uugcaguuga uccugguggu u 21

<210> SEQ ID NO 161
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 161
ccaccaggua ggugaccacu u 21

<210> SEQ ID NO 162
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 162
guggucagga gaacugcaau u 21

<210> SEQ ID NO 163
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 163
ccuccagcuc aaccuugcau u 21

<210> SEQ ID NO 164
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 164
ugcaaggucu caaaaaaugu u 21

<210> SEQ ID NO 165
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 165
cauuuuugau cucuggaggu u 21

<210> SEQ ID NO 166
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 166
caggauguaa guagguucau u 21

<210> SEQ ID NO 167
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 167
ugaaccuuag caacaguguu u 21

<210> SEQ ID NO 168
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 168
acacugugcc cacauccugu u 21

<210> SEQ ID NO 169
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 169
ggcuugaagc gaucacacuu u 21

<210> SEQ ID NO 170
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 170
agugugaacg uauucuuguu u 21

<210> SEQ ID NO 171
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 171
acaagaauuc cuucaagccu u 21

<210> SEQ ID NO 172
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 172
ugaagagauu agcucucugu u 21

<210> SEQ ID NO 173
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 173
cagagaggcc aagcucugcu u 21

<210> SEQ ID NO 174
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 174
gcagagcugg cucucuucau u 21

<210> SEQ ID NO 175
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 175
cucaguaacc agcuuauugu u 21

<210> SEQ ID NO 176
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 176
caauaagauu uauaacaaau u 21

<210> SEQ ID NO 177
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 177
uuuguuaucu uauacugagu u 21

<210> SEQ ID NO 178
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 178
gaaccaaggc uuguaaaguu u 21

<210> SEQ ID NO 179
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 179
acuuuacaaa agcaacaauu u 21

<210> SEQ ID NO 180
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 180
auuguuguua aauugguucu u 21

<210> SEQ ID NO 181
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 181
cagguaggug accacaucuu u 21

<210> SEQ ID NO 182
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 182
agaugugacu gcuucaucau u 21

<210> SEQ ID NO 183
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 183
ugaugaacug cgcuaccugu u 21

<210> SEQ ID NO 184
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 184
ccagucgcuu aucucccggu u 21

<210> SEQ ID NO 185
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 185
ccgggagcaa ugacuccagu u 21

<210> SEQ ID NO 186
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 186
cuggagucau ggcgacuggu u 21

<210> SEQ ID NO 187
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 187
uggaagagaa acagauuugu u 21

<210> SEQ ID NO 188
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 188
caaaucuuua aucagcuucu u 21

<210> SEQ ID NO 189

<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 189
gaagcugccu cuucuuccau u 21

<210> SEQ ID NO 190
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 190
auccaaaggc agugaggguu u 21

<210> SEQ ID NO 191
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 191
acccucaacu caguuuugau u 21

<210> SEQ ID NO 192
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 192
ucaaaaccgg aauuuggauu u 21

<210> SEQ ID NO 193
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 193
uagagacacc aucaggaacu u 21

<210> SEQ ID NO 194
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 194
guuccuggag agucuucaau u 21

<210> SEQ ID NO 195
<211> LENGTH: 21

```
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 195

uugaagaauu aggucucuau u                                              21


<210> SEQ ID NO 196
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 196

gcucauguuu aucaucuuuu u                                              21


<210> SEQ ID NO 197
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 197

aaagaugcug aacuuaaagu u                                              21


<210> SEQ ID NO 198
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 198

cuuuaagggc aacaugagcu u                                              21


<210> SEQ ID NO 199
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 199

ggagcaauga cuccagaugu u                                              21


<210> SEQ ID NO 200
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 200

caucuggggg auccccugcu u                                              21


<210> SEQ ID NO 201
<211> LENGTH: 21
<212> TYPE: RNA
```

<213> ORGANISM: Artificial Sequence
<220> FEATURE:
<223> OTHER INFORMATION: Multivalent-siRNA Oligonucleotide Targeted to
Human ApoB

<400> SEQUENCE: 201
gcaggggagg uguugcuccu u 21

<210> SEQ ID NO 202
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 202
ucacaaacuc cacagacacu u 21

<210> SEQ ID NO 203
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 203
gugucugcuu uauagcuugu u 21

<210> SEQ ID NO 204
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 204
caagcuaaag gauuugugau u 21

<210> SEQ ID NO 205
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 205
gcagcuugac uggucucuuu u 21

<210> SEQ ID NO 206
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 206
aagagacucu gaacugcccu u 21

<210> SEQ ID NO 207
<211> LENGTH: 21
<212> TYPE: RNA
<213> ORGANISM: Artificial Sequence -continued
<220> FEATURE:
<223> OTHER INFORMATION: Multivalent-siRNA Oligonucleotide Targeted to
      Human ApoB

<400> SEQUENCE: 207
gggcagugau ggaagcugcu u 21

<210> SEQ ID NO 208
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 208
caggacugcc uguucucaau u 21

<210> SEQ ID NO 209
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 209
uugagaacuu cuaauuuggu u 21

<210> SEQ ID NO 210
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 210
ccaaauuuga aaaguccugu u 21

<210> SEQ ID NO 211
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 211
uguaggccuc aguuccagcu u 21

<210> SEQ ID NO 212
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 212
gcuggaauuc ugguaugugu u 21

<210> SEQ ID NO 213
<211> LENGTH: 21
<212> TYPE: RNA
<213> ORGANISM: Artificial Sequence
<220> FEATURE:

```
<223> OTHER INFORMATION: Multivalent-siRNA Oligonucleotide Targeted to
      Human ApoB

<400> SEQUENCE: 213

cacauaccga augccuacau u                                              21

<210> SEQ ID NO 214
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 214

gacuucacug gacaaggucu u                                              21

<210> SEQ ID NO 215
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 215

gaccuugaag uugaaaaugu u                                              21

<210> SEQ ID NO 216
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 216

cauuuucugc acugaagucu u                                              21

<210> SEQ ID NO 217
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 217

aagcaguuug gcaggcgacu u                                              21

<210> SEQ ID NO 218
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
      Human ApoB

<400> SEQUENCE: 218

gucgccuugu gagcaccacu u                                              21

<210> SEQ ID NO 219
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
```

Human ApoB

<400> SEQUENCE: 219
guggugccac ugacugcuuu u 21

<210> SEQ ID NO 220
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 220
cagaugaguc cauuuggagu u 21

<210> SEQ ID NO 221
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 221
cuccaaacag ugccaugccu u 21

<210> SEQ ID NO 222
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 222
ggcauggagc cuucaucugu u 21

<210> SEQ ID NO 223
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 223
cacagacuug aaguggaggu u 21

<210> SEQ ID NO 224
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB

<400> SEQUENCE: 224
ccuccacuga gcagcuugau u 21

<210> SEQ ID NO 225
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to
Human ApoB -continued

<400> SEQUENCE: 225
ucaagcuuca aagucugugu u 21

<210> SEQ ID NO 226
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 226
auggcagaug gaaucccacu u 21

<210> SEQ ID NO 227
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 227
gugggaucac cuccguuuuu u 21

<210> SEQ ID NO 228
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 228
aaaacgguuu cucugccauu u 21

<210> SEQ ID NO 229
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 229
ugauacaacu ugggaauggu u 21

<210> SEQ ID NO 230
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB

<400> SEQUENCE: 230
ccauucccua ugucagcauu u 21

<210> SEQ ID NO 231
<211> LENGTH: 21
<212> TYPE: RNA
<213> ORGANISM: Artificial Sequence
<220> FEATURE:
<223> OTHER INFORMATION: Multivalent-siRNA Oligonucleotide Targeted to Human ApoB -continued

```
<400> SEQUENCE: 231

augcugacaa auuguaucau u                                              21


<210> SEQ ID NO 232
<211> LENGTH: 21
<212> TYPE: RNA
<213> ORGANISM: Artificial Sequence
<220> FEATURE:
<223> OTHER INFORMATION: Trivalent MV-siRNA oligo sequences

<400> SEQUENCE: 232

auugugucac uucccucagu u                                              21
```

POLYNUCLEOTIDES FOR MULTIVALENT RNA INTERFERENCE, COMPOSITIONS AND METHODS OF USE THEREOF

CROSS-REFERENCE TO RELATED APPLICATION(S)

This application claims the benefit under 35 U.S.C. § 119(e) of U.S. Provisional Patent Application No. 61/183,011, filed Jun. 1, 2009, which is incorporated by reference in its entirety.

STATEMENT REGARDING FEDERALLY SPONSORED RESEARCH

The Sequence Listing associated with this application is provided in text format in lieu of a paper copy, and is hereby incorporated by reference into the specification. The name of the text file containing the Sequence Listing is 270038_405PC_SEQUENCE_LISTING.txt. The text file is 106 KB, was created Jun. 1, 2010, and is being submitted electronically via EFS-Web.

BACKGROUND

Technical Field

The present invention relates generally to precisely structured polynucleotide molecules, and methods of using the same for multivalent RNA interference and the treatment of disease.

Description of the Related Art

The phenomenon of gene silencing, or inhibiting the expression of a gene, holds significant promise for therapeutic and diagnostic purposes, as well as for the study of gene function itself. Examples of this phenomenon include antisense technology and dsRNA forms of posttranscriptional gene silencing (PTGS) which has become popular in the form of RNA interference (RNAi).

Antisense strategies for gene silencing have attracted much attention in recent years. The underlying concept is simple yet, in principle, effective: antisense nucleic acids (NA) base pair with a target RNA resulting in inactivation of the targeted RNA. Target RNA recognition by antisense RNA or DNA can be considered a hybridization reaction. Since the target is bound through sequence complementarity, this implies that an appropriate choice of antisense NA should ensure high specificity. Inactivation of the targeted RNA can occur via different pathways, dependent on the nature of the antisense NA (either modified or unmodified DNA or RNA, or a hybrid thereof) and on the properties of the biological system in which inhibition is to occur.

RNAi based gene suppression is a widely accepted method in which a sense and an antisense RNA form double-stranded RNA (dsRNA), e.g., as a long RNA duplex, a 19-24 nucleotide duplex, or as a short-hairpin dsRNA duplex (shRNA), which is involved in gene modulation by involving enzyme and/or protein complex machinery. The long RNA duplex and the shRNA duplex are pre-cursors that are processed into small interfering RNA (siRNA) by the endoribonuclease described as Dicer. The processed siRNA or directly introduced siRNA is believed to join the protein complex RISC for guidance to a complementary gene, which is cleaved by the RISC/siRNA complex.

However, many problems persist in the development of effective antisense and RNAi technologies. For example, DNA antisense oligonucleotides exhibit only short-term effectiveness and are usually toxic at the doses required; similarly, the use of antisense RNAs has also proved ineffective due to stability problems. Also, the siRNA used in RNAi has proven to result in significant off-target suppression due to either strand guiding cleaving complexes potential involvement in endogenous regulatory pathways. Various methods have been employed in attempts to improve antisense stability by reducing nuclease sensitivity and chemical modifications to siRNA have been utilized. These include modifying the normal phosphodiester backbone, e.g., using phosphorothioates or methyl phosphonates, incorporating 2'-OMe-nucleotides, using peptide nucleic acids (PNAs and using 3'-terminal caps, such as 3'-aminopropyl modifications or 3'-3' terminal linkages. However, these methods can be expensive and require additional steps. In addition, the use of non-naturally occurring nucleotides and modifications precludes the ability to express the antisense or siRNA sequences in vivo, thereby requiring them to be synthesized and administered afterwards. Additionally, the siRNA duplex exhibits primary efficacy to a single gene and off-target to a secondary gene. This unintended effect is negative and is not a reliable RNAi multivalence.

Consequently, there remains a need for effective and sustained methods and compositions for the targeted, direct inhibition of gene function in vitro and in vivo, particularly in cells of higher vertebrates, including a single-molecule complex capable of multivalent gene inhibition.

BRIEF SUMMARY

The present invention provides novel compositions and methods, which include precisely structured oligonucleotides that are useful in specifically regulating gene expression of one or more genes simultaneously when the nucleotide target site sequence of each is not identical to the other.

In certain embodiments, the present invention includes an isolated precisely structured three-stranded polynucleotide complex comprising a region having a sequence complementary to a target gene or sequence at multiple sites or complementary to multiple genes at single sites.

In certain embodiments, the present invention includes an isolated precisely structured the polynucleotide comprising a region having a sequence complementary to a target gene or sequence at multiple sites or complementary to multiple genes at single sites; each having partially self-complementary regions. In particular embodiments. the oligonucleotide comprises two or more self-complementary regions. In certain embodiments, the polynucleotides of the present invention comprise RNA, DNA, or peptide nucleic acids.

Certain embodiments relate to polynucleotide complexes of at least three separate polynucleotides, comprising (a) a first polynucleotide comprising a target-specific region that is complementary to a first target sequence, a 5' region, and a 3' region; (b) a second polynucleotide comprising a target-specific region that is complementary to a second target sequence, a region, and a 3' region; and (c) a third polynucleotide comprising a null region or a target-specific region that is complementary to a third target specific, a 5' region, and a 3' region, wherein each of the target-specific regions of the first, second, and third polynucleotides are complementary to a different target sequence, wherein the 5' region of the first polynucleotide is complementary to the 3' region of the third polynucleotide, wherein the 3' region of the first polynucleotide is complementary to the 5' region of the second polynucleotide, and wherein the 3' region of the second polynucleotide is complementary to the 5' region of the third polynucleotide, and wherein the three separate polynucleotides hybridize via their complementary 3' and 5' regions to form a polynucleotide complex with a first, second, and third-single stranded region, and a first, second, and third self-complementary region.

In certain embodiments, the first, second, and/or third polynucleotide comprises about 15-30 nucleotides. In certain embodiments, the first, second, and/or third polynucleotide comprises about 17-25 nucleotides. In certain embodiments, one or more of the self-complementary regions comprises about 5-10 nucleotide pairs. In certain embodiments, one or more of the self-complementary regions comprises about 7-8 nucleotide pairs.

In certain embodiments, each of said first, second, and third target sequences are present in the same gene, cDNA, mRNA, or microRNA. In certain embodiments, at least two of said first, second, and third target sequences are present in different genes, cDNAs, mRNAs, or microRNAs.

In certain embodiments, all or a portion of the 5' and/or 3' region of each polynucleotide is also complementary to the target sequence for that polynucleotide. In certain embodiments, one or more of the self-complementary regions comprises a 3' overhang.

Certain embodiments relate to self-hybridizing polynucleotide molecules, comprising (a) a first nucleotide sequence comprising a target-specific region that is complementary to a first target sequence, a 5' region, and a 3' region, (b) a second nucleotide sequence comprising a target-specific region that is complementary to a second target sequence, a 5' region, and a 3' region; and (c) a third nucleotide sequence comprising a null region or a target-specific region that is complementary to a third target sequence, a 5' region, and a 3' region, wherein the target-specific regions of each of the first, second, and third nucleotide sequences are complementary to a different target sequence, wherein the 5' region of the first nucleotide sequence is complementary to the 3' region of the third nucleotide sequence, wherein the 3' region of the first nucleotide sequence is complementary to the 5' region of the second nucleotide sequence, and wherein the 3' region of the second nucleotide sequence is complementary to the 5' region of the third nucleotide sequence, and wherein each of the 5' regions hybridizes to their complementary 3' regions to form a self-hybridizing polynucleotide molecule with a first, second, and third single-stranded region, and a first, second, and third self-complementary region.

In certain embodiments, the first, second, or third polynucleotide sequences comprise about 15-60 nucleotides. In certain embodiments, the target-specific region comprises about 15-30 nucleotides. In certain embodiments, one or more of the self-complementary regions comprises about 10-54 nucleotides. In certain embodiments, one or more of the self-complementary regions comprises a 3' overhang. In certain embodiments, one or more of the self-complementary regions forms a stem-loop structure. In certain embodiments, one or more of the self-complementary regions comprises a proximal box of dinucleotides AG/UU that is outside of the target specific region. In certain embodiments, one or more of the self-complementary regions comprises a distal box of 4 nucleotides that is outside of the target-specific region, wherein the third nucleotide of the distal box is not a G. Also included are vectors that encode a self-hybridizing polynucleotide molecule, as described herein.

In certain embodiments, each of said first, second, and third target sequences are present in the same gene, cDNA, mRNA, or microRNA. In certain embodiments, at least two of said first, second, and third target sequences are present in different genes, cDNAs, mRNAs, or microRNAs.

In certain embodiments, a self-complementary region comprises a stem-loop structure composed of a bi-loop, tetraloop or larger loop. In certain embodiments, the sequence complementary to a target gene sequence comprises at least 17 nucleotides, or 17 to 30 nucleotides, including all integers in between.

In certain embodiments, the self-complementary region (or double-stranded region) comprises at least 5 nucleotides, at least 6 nucleotides, at least 24 nucleotides, or 12 to 54 or 60 nucleotides, including all integers in between.

In certain embodiments, a loop region of a stem-loop structure comprises at least 1 nucleotide. In certain embodiments, the loop region comprises at least 2, at least 3, at least 4, at least 5, at least 6, at least 7, or at least 8 nucleotides.

In further embodiments, a loop region of a stem-loop structure is comprised of a specific tetra-loop sequence NGNN or AAGU or UUUU or UUGA or GUUA, where these sequences are 5' to 3'.

In a further embodiment, the present invention includes an expression vector capable of expressing a polynucleotide of the present invention. In various embodiments, the expression vector is a constitutive or an inducible vector.

The present invention further includes a composition comprising a physiologically acceptable carrier and a polynucleotide of the present invention.

In other embodiments, the present invention provides a method for reducing the expression of a gene, comprising introducing a polynucleotide complex or molecule of the present invention into a cell. In various embodiments, the cell is plant, animal, protozoan, viral, bacterial, or fungal. In one embodiment, the cell is mammalian.

In some embodiments, the polynucleotide complex or molecule is introduced directly into the cell, while in other embodiments, the polynucleotide complex or molecule is introduced extracellularly by a means sufficient to deliver the isolated polynucleotide into the cell.

In another embodiment, the present invention includes a method for treating a disease, comprising introducing a polynucleotide complex or molecule of the present invention into a cell, wherein overexpression of the targeted gene is associated with the disease. In one embodiment, the disease is a cancer.

The present invention further provides a method of treating an infection in a patient, comprising introducing into the patient a polynucleotide complex or molecule of the present invention, wherein the isolated polynucleotide mediates entry, replication, integration, transmission, or maintenance of an infective agent.

In yet another related embodiment, the present invention provides a method for identifying a function of a gene, comprising introducing into a cell a polynucleotide complex or molecule of the present invention, wherein the polynucleotide complex or molecule inhibits expression of the gene, and determining the effect of the introduction of the polynucleotide complex or molecule on a characteristic of the cell, thereby determining the function of the targeted gene. In one embodiment, the method is performed using high throughput screening.

In a further embodiment, the present invention provides a method of designing a polynucleotide sequence comprising two or more self-complementary regions for the regulation of expression of a target gene, comprising: (a) selecting the first three guide sequences 17 to 25 nucleotides in length and complementary to a target gene or multiple target genes; (b) selecting one or more additional sequences 4 to 54 nucleotides in length, which comprises self-complementary regions and which are not fully-complementary to the first sequence; and optionally (c) defining the sequence motif in (b) to be complementary, non-complementary, or replicate a gene sequence which are non-complementary to the sequence selected in step (a).

In another embodiment, the mutated gene is a gene expressed from a gene encoding a mutant p53 polypeptide. In another embodiment, the gene is viral, and may include one or more different viral genes. In specific embodiments, the gene is an HIV gene, such as gag, pol, env, or tat, among others described herein and known in the art. In other embodiments, the gene is ApoB.

BRIEF DESCRIPTION OF THE DRAWINGS

FIG. 1 shows a polynucleotide complex of three separate polynucleotide molecules. (A) indicates the region comprising sequence complementary to a site on a target gene (hatched); (B) indicates the region comprising sequence complementary to a second site on the target gene or a site on a different gene (cross-hatched); (C) indicates the region comprising sequence complementary to a third site on the target gene or a site on a different gene (filled in black). The numbers 1, 2, and 3 indicate the 3' end of each oligonucleotide that guides gene silencing; (A) loads in the direction of 1, (B) in the direction 2, and (C) in the direction 3. The 3' and 5' regions of each molecule, which hybridize to each other to form their respective self-complementary or double-stranded regions, are indicated by connecting bars. Each polynucleotide comprises a two nucleotide 3' overhang.

FIG. 2 shows a single, self-hybridizing polynucleotide of the invention, having three single-stranded regions and three self-complementary regions, which is a precursor for processing into a core molecule. The target specific regions are darkened. (D) indicates a self-complementary stem-loop region (filled in white) capped with a tetraloop of four nucleotides; (D) also indicates a stem-loop region having a 14/16 nucleotide cleavage site within the stem-loop structure; cleavage may occur by RNase III to remove the stem loop nucleotides shown in white); (E) indicates a distal box wherein the third nucleotide as determined 5' to 3' is not a G, since it is believed that the presence of a G would block RNase III cleavage required for removal of the stem-loop region; (F) indicates a proximal box of dinucleotides AG/UU, which is an in vivo determinante of RNase III recognition and binding of RNase III (Nichols 2000); (G) indicates a tetraloop. The polynucleotide molecule shown in FIG. 2 is a longer transcript RNA that is 'pre-processed' in the cell by RNase III. The resulting RNA structure is identical to the structure depicted in FIG. 1.

FIG. 3 depicts a self-forming single-stranded oligonucleotide with tetraloop formats. (H) indicates a tetraloop; (I) indicates a tri-loop connecting two core strands when the leading strand incorporates a 2 nucleotide overhang. In this structure, tetraloops are used to mimic what would be a 3' hydroxyl/5' phosphate of the overhangs in the structure shown in FIG. 1 and function more directly than those of the structure shown in FIG. 2. As demonstrated in Example 2, this short tetraloop format guides silencing directly without pre-processing. It is believed that the GUUA loop twists the nucleotides in the loop and expose the hydrogens (see, e.g., Nucleic Acids Research, 2003, Vol. 31 No. 3, FIG. 6, page 1094). This structure is compatible with PAZ or RISC.

FIG. 4 depicts a self-forming single stranded oligonucleotide for divalent use. (J) indicates a larger loop connecting two core strands; (K) indicates the key strand as completing the complex formation but "null" to a target gene, i.e., not-specific for a target gene. The two target specific regions are shaded. This structure is a composition for 'divalent' use when working with RNA transcripts. Since chemical modifications are not possible, the structure determines asymmetrically of loading and silencing activity. The first 19 nucleotides of the molecule is the PRIMARY strand, (K) indicates a KEY strand that is deactivated, and the SECONDARY strand is the last 21 nucleotides of the molecule. The first priority of loading into RISC and functioning is the SECONDARY strand by exposed 5'/3' ends. The next priority is the PRIMARY strand, which is exposed after RNase III pre-processing in the cell. The 3' end of the nullified KEY strand is not functional, since the large loop is not processed nor is compatible with loading into RISC itself.

FIG. 5 depicts a polynucleotide complex of the present invention having modified RNA bases. (L), (M), and (N) illustrate regions (defined by hashed lines) in which the Tm can be incrementally increased by the use of modified RNA (e.g., 2'-O-methyl RNA or 2'-fluoro RNA instead of 2'-OH RNA) to preference the annealing and/or the silencing order of ends 1, 2 or 3.

FIG. 6 depicts two embodiments of oligonucleotide complexes of the present invention. (O) illustrates a blunt-ended DNA strand that deactivates the silencing function of this strand; and (P) illustrates an end that can be utilized for conjugation of a delivery chemistry, ligand, antibody, or other payload or targeting molecule.

FIG. 7A shows increased suppression of GFP by MV clone long I (108%) and MV clone long II (119%), relative to shRNA control (set at 100%). FIG. 7B shows increased suppression of GFP expression by synthetic MV-siRNA GFP I (127%), relative to shRNA control (set at 100%), which is slightly reduced when one of the strands of the synthetic MV-siRNA complex is replaced by a DNA strand (MF-siRNA GFP I DNA (116%)).

FIGS. 8A, 8B and 8C show exemplary targeting regions (underlined) for the GFP coding sequence (SEQ ID NO:8). FIG. 8A shows the regions that were targeted by the MV-siRNA molecules of Tables 1 and 2 in Example 1. FIGS. 8B and 8C show additional exemplary targeting regions.

FIGS. 10A, 10B, 10C and 10D show the nucleotide sequence of an exemplary HIV genome (SEQ ID NO:9), which can be targeted according to the MV-siRNA molecules of the present invention. This sequence extends from FIG. 10A through FIG. 10D.

FIG. 11 shows the nucleotide sequence of the env gene (SEQ ID NO:4), derived from the HIV genomic sequence of FIG. 10.

FIGS. 12A and 12B provide additional HIV sequences. FIG. 12A shows the nucleotide sequence of the gag gene (SEQ ID NO:2), and FIG. 12B shows the nucleotide sequence of the tat gene (SEQ ID NO:3), both of which are derived from the HIV genomic sequence of FIG. 10.

FIGS. 13A, 13B, 13C, 13D and 13E show the coding sequence of murine apolipoprotein B (ApoB) (SEQ ID NO:10), which can be targeted using certain MV-siRNAs provided herein. This sequence extends from FIG. 13A through FIG. 13E.

FIGS. 14A, 14B, 14C, 14D and 14E show the mRNA sequence of human apolipoprotein B (apoB) (SEQ ID NO:1), which can be targeted using certain MV-siRNAs provided herein. This sequence extends from FIG. 14A through FIG. 14E.

DETAILED DESCRIPTION

Figure 1:
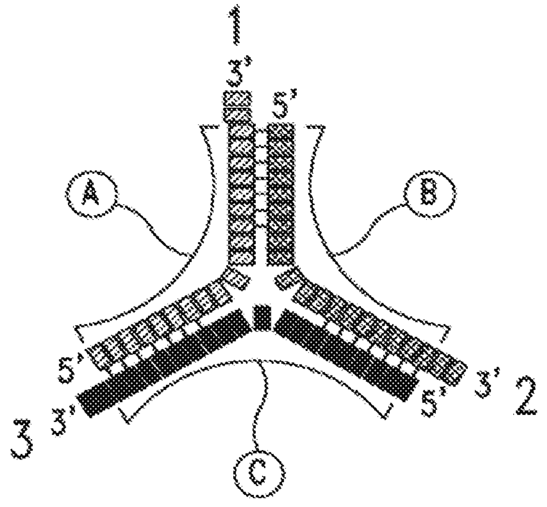
FIGS. 1 through 6 illustrate exemplary polynucleotide structures of the present invention.

The present invention provides novel compositions and methods for inhibiting the expression of a gene at multiple target sites, or for inhibiting the expression of multiple genes at one or more target sites, which sites are not of equivalent nucleotide sequences, in eukaryotes in vivo and in vitro. In particular, the present invention provides polynucleotide complexes and polynucleotide molecules comprising two, three, or more regions having sequences complementary to regions of one or more target genes, which are capable of targeting and reducing expression of the target genes. In various embodiments, the compositions and methods of the present invention may be used to inhibit the expression of a single target gene by targeting multiple sites within the target gene or its expressed RNA. Alternatively, they may be used to target two or more different genes by targeting sites within two or more different genes or their expressed RNAs.

The present invention offers significant advantages over traditional siRNA molecules. First, when polynucleotide complexes or molecules of the present invention target two or more regions within a single target, gene, they are capable of achieving greater inhibition of gene expression from the target gene, as compared to an RNAi agent that targets only one region within a target gene. In addition, polynucleotide complexes or molecules of the present invention that target two or more different target genes may be used to inhibit the expression of multiple target genes associated with a disease or disorder using a single polynucleotide complex or molecule. Furthermore, polynucleotide complexes and molecules of the present invention do not require the additional non-targeting strand present in conventional double-stranded RNAi agents, so they do not have off-target effects caused by the non-targeting strand. Accordingly, the polynucleotide complexes and molecules of the present invention offer surprising advantages over polynucleotide inhibitors of the prior art, including antisense RNA and RNA interference molecules, including increased potency and increased effectiveness against one or more target genes.

The present invention is also based upon the recognition of the polynucleotide structure guiding a protein complex for cleavage using only one, two, or three of the guide strands, which are complementary to one, two, or three distinct nucleic sequences of the target genes. This multivalent function results in a markedly broader and potent inhibition of a target gene or group of target genes than that of dsRNA, while utilizing many of the same endogenous mechanisms.

Certain embodiments of the present invention are also based upon the recognition of the polynucleotide structure directionally by presentation of the 3' overhangs and 5' phosphate resulting in a sense strand free complex, which contributes to greater specificity than that of dsRNA-based siRNA.

Given their effectiveness, the compositions of the present invention may be delivered to a cell or subject with an accompanying guarantee of specificity predicted by the single guide strand complementary to the target gene or multiple target genes.

Multivalent siRNAs

The present invention includes polynucleotide complexes and molecules that comprise two or more targeting regions complementary to regions of one or more target genes. The polynucleotide complexes and molecules of the present invention may be referred to as multivalent siRNAs (mv-siRNAs), since they comprise at least two targeting regions complementary to regions of one or more target genes. Accordingly, the compositions and methods of the present invention may be used to inhibit or reduce expression of one or more target genes, either by targeting two or more regions within a single target gene, or by targeting one or more regions within two or more target genes.

In certain embodiments, polynucleotide complexes of the present invention comprise three or more separate oligonucleotides, each having a 5' and 3' end, with two or more of the oligonucleotides comprising a targeting region, which oligonucleotides hybridize to each other as described herein to form a complex. Each of the strands is referred to herein as a "guide strand." In other embodiments, polynucleotide molecules of the present invention are a single polynucleotide that comprises three or more guide strands, with two or more of the guide strands comprising a targeting region, which polynucleotide hybridizes to itself through self-complementary regions to form a structure described herein. The resulting structure may then be processed, e.g., intracellularly, to remove loop structures connecting the various guide strands. Each guide strand, which may be present in different oligonucleotides or within a single polynucleotide, comprises regions complementary to other guide strands.

In certain embodiments, the present invention provides polynucleotide complexes and molecules that comprise at least three guide strands, at least two of which comprise regions that are complementary to different sequences within one or more target genes. In various embodiments, the polynucleotide complexes of the present invention comprise two, three or more separate polynucleotides each comprising one or more guide strands, which can hybridize to each other to form a complex. In other embodiments, the polynucleotide molecules of the present invention comprise a single polynucleotide that comprises three or more guide strands within different regions of the single polynucleotide.

Certain embodiments of the present invention are directed to polynucleotide complexes or molecules having at least three guide strands, two or more of which are partially or fully complementary to one or more target genes; and each having about 4 to about 12, about 5 to about 10, or preferably about 7 to about 8, nucleotides on either end that are complementary to each other (i.e., complementary to a region of another guide strand), allowing the formation of a polynucleotide complex (see, e.g., FIG. 1). For example, each end of a guide strand may comprise nucleotides that are complementary to nucleotides at one end of another of the guide strands of the polynucleotide complex or molecule. Certain embodiments may include polynucleotide complexes that comprise 4, 5, 6 or more individual polynucleotide molecules or guide strands.

In certain embodiments, a polynucleotide complex of the present invention comprises at least three separate polynucleotides, which include: (1) a first polynucleotide comprising a target-specific region that is complementary to a first target sequence, a 5' region, and a 3' region; (2) a second polynucleotide comprising a target-specific region that is complementary to a second target sequence, a 5' region, and a 3' region; and (3) a third polynucleotide comprising either a null region or a target-specific region that is complementary to a third target specific, a 5' region, and a 3' region, wherein each of the target-specific regions of the first, second, and third polynucleotides are complementary to a different target sequence, wherein the 5' region of the first polynucleotide is complementary to the 3' region of the third polynucleotide, wherein the 3' region of the first polynucleotide is complementary to the 5' region of the second polynucleotide, and wherein the 3' region of the second polynucleotide is complementary to the 5' region of the third polynucleotide, and wherein the three separate polynucleotides hybridize via their complementary 3' and 5' regions to form a polynucleotide complex with a first, second, and third single-stranded region, and a first, second, and third self-complementary region.

As described above, in particular embodiments, a polynucleotide complex of the present invention comprises at least three separate oligonucleotides, each having a 5' end and a 3' end. As depicted in FIG. 1, a region at the 5' end of the first oligonucleotide anneals to a region at the 3' end of the third oligonucleotide; a region at the 5' end of the third oligonucleotide anneals to a region at the 3' end of the second oligonucleotide; and a region at the 5' end of the second oligonucleotide anneals to a region at the 3' end of the first oligonucleotide. If additional oligonucleotides are present in the complex, then they anneal to other oligonucleotides of the complex in a similar manner. The regions at the ends of the oligonucleotides that anneal to each other may include the ultimate nucleotides at either or both the 5' and/or 3' ends. Where the regions of both the hybridizing 3' and 5' ends include the ultimate nucleotides of the oligonucleotides, the resulting double-stranded region is blunt-ended. In particular embodiments, the region at the 3' end that anneals does not include the ultimate and/or penultimate nucleotides, resulting in a double-stranded region having a one or two nucleotide 3' overhang.

Figure 2:
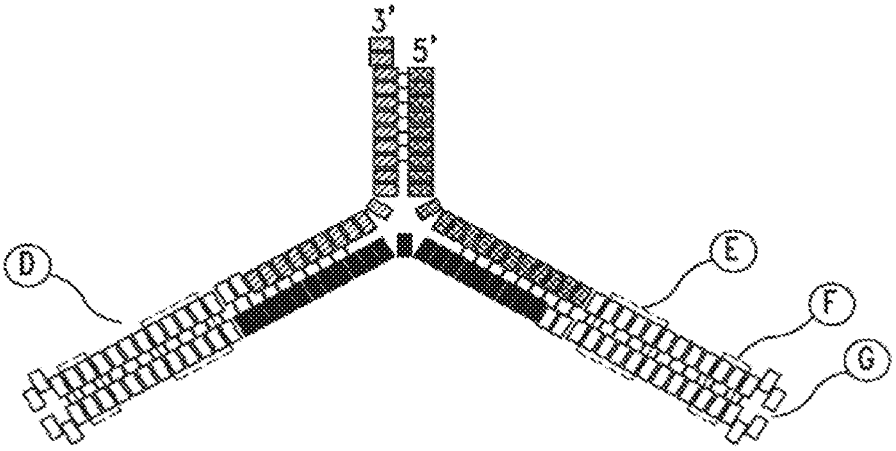
Figure 3:
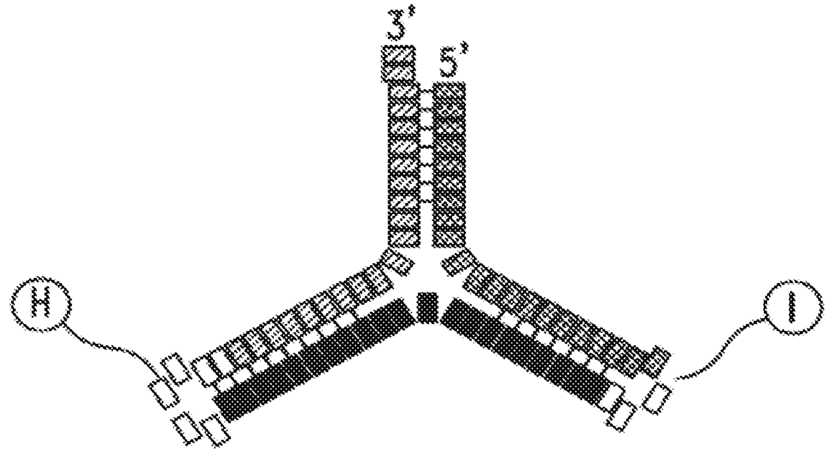
Figure 4:
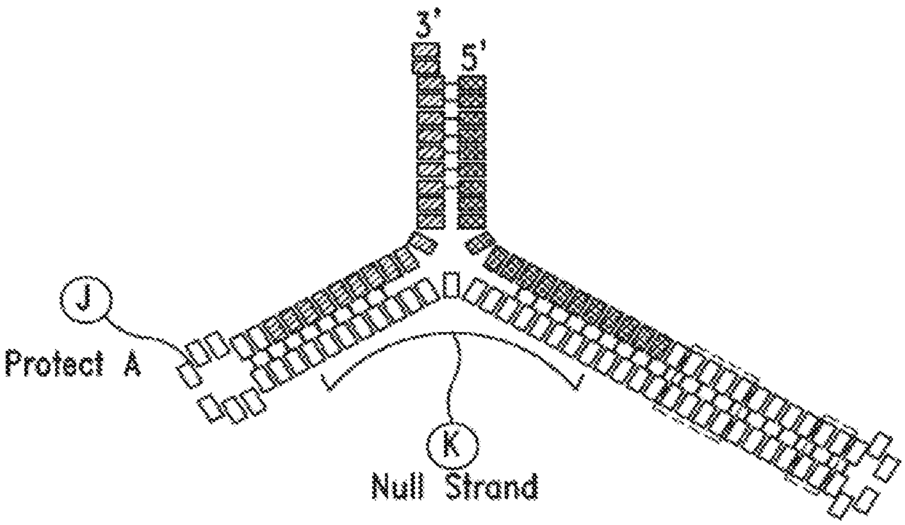
Figure 5:
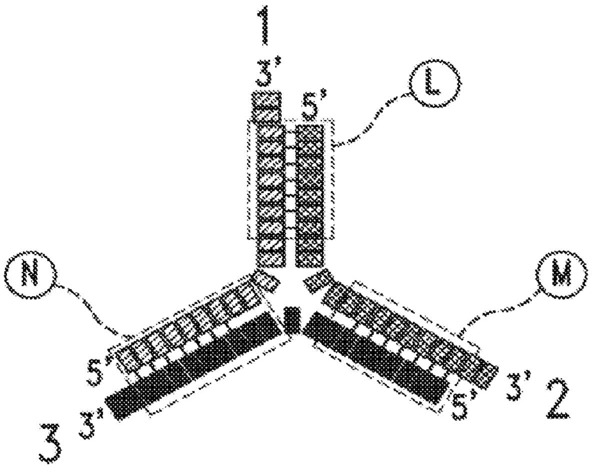
Figure 6:
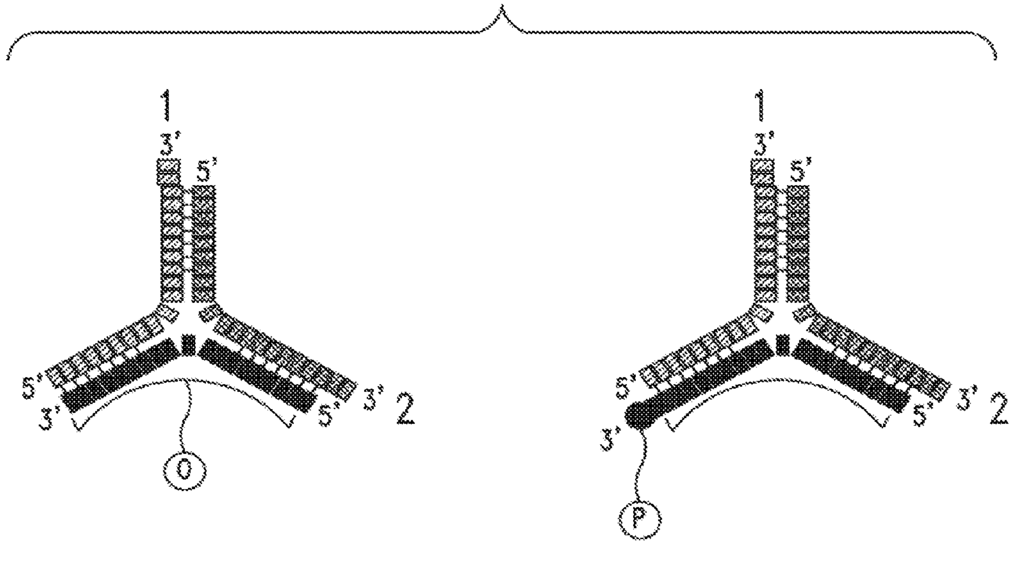

In certain embodiments, the guide strands are present in a single polynucleotide molecule, and hybridize to form a single, self-hybridizing polynucleotide with three single-stranded regions and three self-complementary regions (or double-stranded regions), and at least two target-specific regions (see, e.g., FIG. 2). In related embodiments, a single molecule may comprise at least 3, at least 4, at least 5 or at least 6 guide strands, and forms a single, self-hybridizing polynucleotide with at least 3, at least 4, at least 5, or at least 6 self-complementary regions (or double-stranded regions), and at least 2, at least 3, at least 4, or at least 5 target-specific regions, respectively. In particular embodiments, this single, self-hybridizing polynucleotide is a precursor molecule that may be processed by the cell to remove the loop regions and, optionally, an amount of proximal double-stranded region, resulting in an active mv-siRNA molecule (see, e.g., FIG. 2).

Thus, in particular embodiments, the present invention includes a self-hybridizing polynucleotide molecule, comprising: (1) a first nucleotide sequence comprising a target-specific region that is complementary to a first target sequence, a 5' region, and a 3' region, (2) a second nucleotide sequence comprising a target-specific region that is complementary to a second target sequence, a 5' region, and a 3' region; and (3) a third nucleotide sequence comprising a null region of a target-specific region that is complementary to a third target sequence, a 5' region, and a 3' region, wherein the target-specific regions of each of the first, second, and third nucleotide sequences are complementary to a different target sequence, wherein the 5' region of the first nucleotide sequence is complementary to the 3' region of the third nucleotide sequence, wherein the 3' region of the first nucleotide sequence is complementary to the 5' region of the second nucleotide sequence, and wherein the 3' region of the second nucleotide sequence is complementary to the 5' region of the third nucleotide sequence, and wherein each of the 5' regions hybridizes to their complementary 3' regions to form a self-hybridizing polynucleotide molecule with a first, second, and third single-stranded region, and a first, second, and third self-complementary region.

In particular embodiments, a single, self-hybridizing polynucleotide of the present invention may comprise one or more cleavable nucleotides in the single-stranded loops that form when the polynucleotide is annealed to itself. Once the single, self-hybridizing polynucleotide is annealed to itself, the cleavable nucleotides may be cleaved to result in a polynucleotide complex comprising three or more separate oligonucleotides. Examples of cleavable nucleotides that may be used according to the present invention include, but are not limited to, photocleavable nucleotides, such as pcSpacer (Glen Research Products, Sterling, Va., USA), or phosphoramadite nucleotides.

As used herein, polynucleotides complexes and molecules of the present invention include isolated polynucleotides comprising three single-stranded regions, at least two of which are complementary to two or more target sequences, each target sequence located within one or more target genes, and comprising at least two or three self-complementary regions interconnecting the 5' or 3' ends of the single-stranded regions, by forming a double-stranded region, such as a stem-loop structure. The polynucleotides may also be referred to herein as the oligonucleotides.

In certain embodiments, the polynucleotide complexes and molecules of the present invention comprise two or more regions of sequence complementary to a target gene. In particular embodiments, these regions are complementary to the same target genes or genes, while in other embodiments, they are complementary to two or more different target genes or genes.

Accordingly, the present invention includes one or more self-complementary polynucleotides that comprise a series of sequences complementary to one or more target genes or genes. In particular embodiments, these sequences are separated by regions of sequence that are non-complementary or semi-complementary to a target gene sequence and non-complementary to a self-complementary region. In other embodiments of the polynucleotide comprising multiple sequences that are complementary to target genes or genes, the polynucleotide comprises a self-complementary region at the 5' end, 3 end', or both ends of one or more regions of sequence complementary to a target gene. In a particular embodiment, a polynucleotide comprises two or more regions of sequence complementary to one or more target genes, with self-complementary regions located at the 5' and 3' end of each guide strand that is complementary to a target gene. In certain embodiments, all or a portion of these 3' and 5' regions may be complementary to the target sequence, in addition to being complementary to their corresponding 3' or 5' regions.

The term "complementary" refers to nucleotide sequences that are fully or partially complementary to each other, according to standard base pairing rules. The term "partially complementary" refers to sequences that have less than full complementarity, but still have a sufficient number of complementary nucleotide pairs to support binding or hybridization within the stretch of nucleotides under physiological conditions.

In particular embodiments, the region of a guide strand complementary to a target gene (i.e., the targeting region) may comprise one or more nucleotide mismatches as compared to the target gene. Optionally, the mismatched nucleotide(s) in the guide strand may be substituted with an unlocked (UNA) nucleic acid or a phosphoramidite nucleic acid (e.g., rSpacer, Glen Research, Sterling, Va., USA), to allow base-pairing, e.g., Watson-Crick base pairing, of the mismatched nucleotide(s) to the target gene.

As used herein, the term "self-complementary" or "self-complementary region" may refer to a region of a polynucleotide molecule of the invention that binds or hybridizes to another region of the same molecule to form A-T(U) and G-C hybridization pairs, thereby forming a double stranded region; and/or it may refer to a region of a first nucleotide molecule that binds to a region of a second or third nucleotide molecule to form a polynucleotide complex of the invention (i.e., an RNAi polynucleotide complex), wherein the complex is capable of RNAi interference activity against two or more target sites. The two regions that bind to each other to form the self-complementary region may be contiguous or may be separated by other nucleotides. Also, as in an RNAi polynucleotide complex, the two regions may be on separate nucleotide molecules.

In certain embodiments, a "self complementary region" comprises a "3' region" of a first defined nucleotide sequence that is bound or hybridized to a "5' region" of a second or third defined nucleotide sequence, wherein the second or third defined sequence is within the same molecule—to form a self-hybridizing polynucleotide molecule. In certain embodiments, a "self complementary region" comprises a "3' region" of a first polynucleotide molecule that is bound or hybridized to a "5' region" of a separate polynucleotide molecule, to form a polynucleotide complex. These 3' and 5' regions are typically defined in relation to their respective target-specific region, in that the 5' regions are on the 5' end of the target-specific region and the 3' regions are on the 3' end of the target specific region. In certain embodiments, one or both of these 3' and 5' regions not only hybridize to their corresponding 3' or 5' regions to form a self-complementary region, but may be designed to also contain full or partial complementarily their respective target sequence, thereby forming part of the target-specific region. In these embodiments, the target-specific region contains both a single-stranded region and self-complementary (i.e., double-stranded) region.

In certain embodiments, these "self-complementary regions" comprise about 5-12 nucleotide pairs, preferably 5-10 or 7-8 nucleotide pairs, including all integers in between. Likewise, in certain embodiments, each 3' region or 5' region comprises about 5-12 nucleotides, preferably 5-10 or 7-8 nucleotides, including all integers in between.

The term "non-complementary" indicates that in a particular stretch of nucleotides, there are no nucleotides within that align with a target to form A-T(U) or G-C hybridizations. The term "semi-complementary" indicates that in a stretch of nucleotides, there is at least one nucleotide pair that aligns with a target to form an A-T(U) or G-C hybridizations, but there are not a sufficient number of complementary nucleotide pairs to support binding within the stretch of nucleotides under physiological conditions.

The term "isolated" refers to a material that is at least partially free from components that normally accompany the material in the material's native state. Isolation connotes a degree of separation from an original source or surroundings. Isolated, as used herein, e.g., related to DNA, refers to a polynucleotide that is substantially away from other coding or non-coding sequences, and that the DNA molecule can contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

In various embodiments, a polynucleotide complex or molecule of the present invention comprises RNA, DNA, or peptide nucleic acids, or a combination of any or all of these types of molecules. In addition, a polynucleotide may comprise modified nucleic acids, or derivatives or analogs of nucleic acids. General examples of nucleic acid modifications include, but are not limited to, biotin labeling, fluorescent labeling, amino modifiers introducing a primary amine into the polynucleotide, phosphate groups, deoxyuridine, halogenated nucleosides, phosphorothioates, 2'-O-Methyl RNA analogs, chimeric RNA analogs, wobble groups, universal bases, and deoxyinosine.

A "subunit" of a polynucleotide or oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage). A given synthetic MV-siRNA may utilize one or more different types of subunits and/or intersubunit linkages, mainly to alter its stability, Tm, RNase sensitivity, or other characteristics, as desired. For instance, certain embodiments may employ RNA subunits with one or more 2'-O-methyl RNA subunits.

The cyclic subunits of a polynucleotide or an oligonucleotide may be based on ribose or another pentose sugar or, in certain embodiments, alternate or modified groups. Examples of modified oligonucleotide backbones include, without limitation, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Also contemplated are peptide nucleic acids (PNAs), locked nucleic acids (LNAs), 2'-O-methyl oligonucleotides (2'-OMe), 2'-methoxyethoxy oligonucleotides (MOE), among other oligonucleotides known in the art.

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses or chemistries of the oligomers, Ts and Us are interchangeable. For instance, with other antisense chemistries such as 2'-O-methyl antisense oligonucleotides that are more RNA-like, the T bases may be shown as U.

As noted above, certain polynucleotides or oligonucleotides provided herein include one or more peptide nucleic acid (PNAs) subunits. Peptide nucleic acids (PNAs) are analogs of DNA in which the backbone is structurally homomorphous with a deoxyribose backbone, consisting of N-(2-aminoethyl)glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). A backbone made entirely of PNAs is uncharged, resulting in PNA/DNA or PNA/RNA duplexes that exhibit greater than normal thermal stability. PNAs are not recognized by nucleases or proteases.

PNAs may be produced synthetically using any technique known in the art. PNA is a DNA analog in which a polyamide backbone replaces the traditional phosphate ribose ring of DNA. Despite a radical structural change to the natural structure, PNA is capable of sequence-specific binding in a helix form to DNA or RNA. Characteristics of PNA include a high binding affinity to complementary DNA or RNA, a destabilizing effect caused by single-base mismatch, resistance to nucleases and proteases, hybridization with DNA or RNA independent of salt concentration and triplex formation with homopurine DNA. Panagene™ has developed its proprietary Bts PNA monomers (Bts; benzothiazole-2-sulfonyl group) and proprietary oligomerisation process. The PNA oligomerisation using Bts PNA monomers is composed of repetitive cycles of deprotection, coupling and capping. Panagene's patents to this technology include U.S. Pat. No. 6,969,766, U.S. Pat. No. 7,211,668, U.S. Pat. No. 7,022,851, U.S. Pat. No. 7,125,994, U.S. Pat. No. 7,145,006 and U.S. Pat. No. 7,179,896. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al. Science, 1991, 254, 1497.

Also included are "locked nucleic acid" subunits (LNAs). The structures of LNAs are known in the art: for example, Wengel, et al., Chemical Communications (1998) 455; Tetrahedron (1998) 54, 3607, and Accounts of Chem. Research (1999) 32, 301); Obika, et al., Tetrahedron Letters (1997) 38, 8735; (1998) 39, 5401, and Bioorganic Medicinal Chemistry (2008)16, 9230.

Polynucleotides and oligonucleotides may incorporate one or more LNAs; in some cases, the compounds may be entirely composed of LNAs. Methods for the synthesis of individual LNA nucleoside subunits and their incorporation into oligonucleotides are known in the art: U.S. Pat. Nos. 7,572,582; 7,569,575; 7,084,125; 7,060,809; 7,053,207; 7,034,133; 6,794,499; and 6,670,461. Typical intersubunit linkers include phosphodiester and phosphorothioate moieties; alternatively, non-phosphorous containing linkers may be employed. One embodiment includes an LNA containing compound where each LNA subunit is separated by a RNA or a DNA subunit (i.e., a deoxyribose nucleotide). Further exemplary compounds may be composed of alternating LNA and RNA or DNA subunits where the intersubunit linker is phosphorothioate.

Certain polynucleotides or oligonucleotides may comprise morpholino-based subunits bearing base-pairing moieties, joined by uncharged or substantially uncharged linkages. The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine or an equivalent base-pairing moiety effective to bind, by base specific hydrogen bonding, to a base in a polynucleotide.

Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, and PCT Appn. Nos. PCT/US07/11435 (cationic linkages) and U.S. Ser. No. 08/012,804 (improved synthesis), all of which are incorporated herein by reference.

In one aspect of the invention, MV-siRNA comprise at least one ligand tethered to an altered or non-natural nucleobase. Included are payload molecules and targeting molecules. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described herein. In certain embodiments, the non-natural nucleobase is difluorotolyl, nitropyrrolyl, or nitroimidazolyl. In certain embodiments, the non-natural nucleobase is difluorotolyl.

A wide variety ligands are known in the art and are amenable to the present invention. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the ligand is a steroid or aromatic compound. In certain instances, the ligand is cholesteryl.

In other embodiments, the polynucleotide or oligonucleotide is tethered to a ligand for the purposes of improving cellular targeting and uptake. For example, an MV-siRNA agent may be tethered to an antibody, or antigen binding fragment thereof. As an additional example, an MV-siRNA agent may be tethered to a specific ligand binding molecule, such as a polypeptide or polypeptide fragment that specifically binds a particular cell-surface receptor, or that more generally enhances cellular uptake, such as an arginine-rich peptide.

The term "analog" as used herein refers to a molecule, compound or composition that retains the same structure and/or function (e.g., binding to a target) as a polynucleotide herein. Examples of analogs include peptidomimetic and small and large organic or inorganic compounds.

The term "derivative" or "variant" as used herein refers to a polynucleotide that differs from a naturally occurring polynucleotide (e.g., target gene sequence) by one or more nucleic acid deletions, additions, substitutions or side-chain modifications. In certain embodiments, variants have at least 70%, at least 80% at least 90%, at least 95%, or at least 99% sequence identity to a region of a target gene sequence. Thus, for example, in certain embodiments, an oligonucleotide of the present invention comprises a region that is complementary to a variant of a target gene sequence.

Polynucleotide complexes and molecules of the present invention comprise a sequence region, or two or more sequence regions, each of which is complementary, and in particular embodiments completely complementary, to a region of a target gene or polynucleotide sequences (or a variant thereof). In particular embodiments, a target gene is a mammalian gene, e.g., a human gene, or a gene of a microorganism infecting a mammal, such as a virus. In certain embodiments, a target gene is a therapeutic target. For example, a target gene may be a gene whose expression or overexpression is associated with a human disease or disorder. This may be a mutant gene or a wild type or normal gene. A variety of therapeutic target genes have been identified, and any of these may be targeted by polynucleotide complexes and molecules of the present invention. Therapeutic target genes include, but are not limited to, oncogenes, growth factor genes, translocations associated with disease such as leukemias, inflammatory protein genes, transcription factor genes, growth factor receptor genes, anti-apoptotic genes, interleukins, sodium channel genes, potassium channel genes, such as, but not limited to the following genes or genes encoding the following proteins: apolipoprotein B (ApoB), apolipoprotein B-100 (ApoB-100), bcl family members, including bcl-2 and bcl-x, MLL-AF4, Huntington gene, AML-MT68 fusion gene, IKK-B, Aha1, PCSK9, Eg5, transforming growth factor beta (TGF-beta), Nav1.8, RhoA, HIF-1alpha, Nogo-L, Nogo-R, toll-like receptor 9 (TLR9), vascular endothelial growth factor (VEGF), SNCA, beta-catenin, CCR5, c-myc, p53, interleukin-1, interleukin 2, interleukin-12, interleukin-6, interleukin-17a (IL-17a), interleukin-17f (IL-17f), Osteopontin (OPN) gene, psoriasis gene, and tumor necrosis factor gene.

In particular embodiments, polynucleotide complexes or molecules of the present invention comprise guide strands or target-specific regions targeting two or more genes, e.g., two or more genes associated with a particular disease or disorder. For example, they may include guide strands complementary to interleukin-1 gene or mRNA and tumor necrosis factor gene or mRNA; complementary to interleukin-1 gene or mRNA and interleukin-12 gene or mRNA; or complementary to interleukin-1 gene or mRNA, interleukin-12 gene or mRNA and tumor necrosis factor gene or mRNA, for treatment of rheumatoid arthritis. In one embodiment, they include guide strands complementary to osteopontin gene or mRNA and TNF gene or mRNA.

Other examples of therapeutic target genes include genes and mRNAs encoding viral proteins, such as human immunodeficiency virus (HIV) proteins, HTLV virus proteins, hepatitis C virus (HCV) proteins, Ebola virus proteins, JC virus proteins, herpes virus proteins, human polyoma virus proteins, influenza virus proteins, and Rous sarcoma virus proteins. In particular embodiments, polynucleotide complexes or molecules of the present invention include guide strands complementary to two or more genes or mRNAs expressed by a particular virus, e.g., two or more HIV protein genes or two or more herpes virus protein genes. In other embodiments, they include guide strands having complementary to two or more herpes simplex virus genes or mRNAs, e.g., the UL29 gene or mRNA and the Nectin-1 gene or mRNA of HSV-2, to reduce HSV-2 expression, replication or activity. In one embodiment, the polynucleotide complexes or molecules having regions targeting two or more HSV-2 genes or mRNAs are present in a formulation for topical delivery.

In particular embodiments, polynucleotide complexes and molecules of the present invention comprise one, two, three or more guide strands or target-specific regions that target an apolipoprotein B (ApoB) gene or mRNA, e.g., the human ApoB gene or mRNA or the mouse ApoB gene or mRNA. Accordingly, in particular embodiments, they comprise one, two, three or more regions comprising a region complementary to a region of the human ApoB sequence set forth in SEQ ID NO:1. In other embodiments, they comprise one, two, three or more regions comprising a region complementary to a region of the mouse ApoB sequence set forth in SEQ ID NO:10. In particular embodiments, they comprise two or more guide sequences having the specific sequences set forth in the accompanying Examples.

In certain embodiments, polynucleotide complexes and molecules of the present invention comprise one, two, three or more guide strands or regions that target HIV genes. In particular embodiments, they target one, two, three or more HIV genes or mRNAs encoding one or more proteins selected from HIV gag, HIV tat, HIV env, HIV gag-pol, HIV vif, and HIV nef proteins. Accordingly, in particular embodiments, they comprise one, two, three or more regions complementary to a region of the HIV gag sequence set forth in SEQ ID NO:2; one, two, three or more regions complementary to a region of the HIV tat sequence set forth in SEQ ID NO:3, one, two, three or more regions complementary to a region of the HIV env sequence set forth in SEQ ID NO:4, one, two, three or more regions complementary to a region of the HIV gag-pol sequence set forth in SEQ ID NO:5, one, two, three or more regions comprising a region complementary to a region of the HIV vif sequence set forth in SEQ ID NO:6, one, two, three or more regions comprising a region complementary to a region of the HIV nef sequence set forth in SEQ ID NO:7. In particular embodiments, they comprise two or more guide sequences having the specific HIV sequences set forth in the accompanying Examples.

In certain embodiments, selection of a sequence region complementary to a target gene (or gene) is based upon analysis of the chosen target sequence and determination of secondary structure, $T_m$, binding energy, and relative stability and cell specificity. Such sequences may be selected based upon their relative inability to form dimers, hairpins, or other secondary structures that would reduce structural integrity of the polynucleotide or prohibit specific binding to the target gene in a host cell.

Preferred target regions of the target gene or mRNA may include those regions at or near the AUG translation initiation codon and those sequences that are substantially complementary to 5' regions of the gene or mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402) or Oligoengine Workstation 2.0.

In one embodiment, target sites are preferentially not located within the 5' and 3' untranslated regions (UTRs) or regions near the start codon (within approximately 75 bases), since proteins that bind regulatory regions may interfere with the binding of the polynucleotide In addition, potential target sites may be compared to an appropriate genome database, such as BLASTN 2.0.5, available on the NCBI server at www.ncbi.nlm, and potential target sequences with significant homology to other coding sequences eliminated.

In another embodiment, the target sites are located within the 5' or 3' untranslated region (UTRs). In addition, the self-complementary region of the polynucleotide may be composed of a particular sequence found in the gene of the target.

The target gene may be of any species, including, for example, plant, animal (e.g. mammalian), protozoan, viral (e.g., HIV), bacterial or fungal. In certain embodiments, the polynucleotides of the present invention may comprise or be complementary to the GFP sequences in Example 1, the HIV sequences in Example 2, or the ApoB sequences in Example 3.

As noted above, the target gene sequence and the complementary region of the polynucleotide may be complete complements of each other, or they may be less than completely complementary, as long as the strands hybridize to each other under physiological conditions.

The polynucleotide complexes and molecules of the present invention comprise at least one, two, or three regions complementary to one or more target genes, as well as one or more self-complementary regions and/or interconnecting loops" Typically, the region complementary to a target gene is 15 to 17 to 24 nucleotides in length, including integer values within these ranges. This region may be at least 16 nucleotides in length, at least 17 nucleotides in length, at least 20 nucleotides in length, at least 24 nucleotides in length, between 15 and 24 nucleotides in length, between 16 and 24 nucleotides in length, or between 17 and 24 nucleotides in length, inclusive of the end values, including any integer value within these ranges.

The self-complementary region is typically between 2 and 54 nucleotides in length, at least 2 nucleotides in length, at least 16 nucleotides in length, or at least 20 nucleotides in length, including any integer value within any of these ranges. Hence, in one embodiment, a self-complementary region may comprise about 1-26 nucleotide pairs. A single-stranded region can be about 3-15 nucleotides, including all integers in between. A null region refers to a region that is not-specific for any target gene, at least by design. A null region or strand may be used in place of a target-specific region, such as in the design of a bi-valent polynucleotide complex or molecule of the invention (see, e.g., Figure IV(K)).

In certain embodiments, a self-complementary region is long enough to form a double-stranded structure. In certain embodiments, a 3' region and a 5' region may hybridize to for a self-complementary region (i.e., a double-stranded region) comprising a stem-loop structure. Accordingly, in one embodiment, the primary sequence of a self-complementary region comprises two stretches of sequence complementary to each other separated by additional sequence that is not complementary or is semi-complementary. While less optimal, the additional sequence can be complementary in certain embodiments. The additional sequence forms the loop of the stem-loop structure and, therefore, must be long enough to facilitate the folding necessary to allow the two complementary stretches to bind each other. In particular embodiments, the loop sequence comprises at least 3, at least 4, at least 5 or at least 6 bases. In one embodiment, the loop sequence comprises 4 bases. The two stretches of sequence complementary to each other (within the self-complementary region; i.e., the stem regions) are of sufficient length to specifically hybridize to each other under physiological conditions. In certain embodiments, each stretch comprises 4 to 12 nucleotides; in other embodiments, each stretch comprises at least 4, at least 5, at least 6, at least 8, or at least 10 nucleotides, or any integer value within these ranges. In a particular embodiment, a self-complementary region comprises two stretches of at least 4 complementary nucleotides separated by a loop sequence of at least 4 nucleotides. In certain embodiments, all or a portion of a self-complementary region may or may not be complementary to the region of the polynucleotide that is complementary to the target gene or gene.

In particular embodiments, self-complementary regions possess thermodynamic parameters appropriate for binding of self-complementary regions, e.g., to form a stem-loop structure.

In one embodiment, self-complementary regions are dynamically calculated by use of RNA via free-energy analysis and then compared to the energy contained within the remaining "non self-complementary region" or loop region to ensure that the energy composition is adequate to form a desired structure, e.g., a stem-loop structure. In general, different nucleotide sequences of the gene targeting region are considered in determining the compositions of the stem-loop structures to ensure the formation of such. The free-energy analysis formula may again be altered to account for the type of nucleotide or pH of the environment in which it is used. Many different secondary structure prediction programs are available in the art, and each may be used according to the invention. Thermodynamic parameters for RNA and DNA bases are also publicly available in combination with target sequence selection algorithms, of which several are available in the art.

In one embodiment, the polynucleotide complex or molecule comprises or consists of (a) three oligonucleotides comprising 17 to 24 nucleotides in length (including any integer value in-between), which is complementary to and capable of hybridizing under physiological conditions to at least a portion of an gene molecule, flanked optionally by (b) self-complementary sequences comprising 16 to 54 nucleotides in length (including any integer value in-between) or (c) 2 to 12 nucleotides capable of forming a loop. In one embodiment, each self-complementary sequence is capable of forming a stem-loop structure, one of which is located at the 5' end and one of which is located at the 3' end of the secondary guide strands.

In certain embodiments, the self-complementary region functions as a structure to recruit enzymatic cleavage of itself and/or bind to particular regions of proteins involved in the catalytic process of gene modulation, In addition, the loop may be of a certain 4-nucleotide (e.g., tetraloop NGNN, AAGU, UUGA, or GUUA) structure to promote the cleavage of the self-complementary region by an RNase such as RNase III. In addition, the self-complementary region can be cleaved by RNase III 11/13 or 14/16 nucleotides into the duplex region leaving a 2 nucleotide 3' end. In certain embodiments, the tetraloop has the sequence GNRA or GNYA, where N indicates any nucleotide or nucleoside, R indicates a purine nucleotide or nucleoside; and Y indicates a pyrimidine nucleotide or nucleoside.

In certain embodiments, the self-complementary polynucleotide that has been enzymatically cleaved as described above will load onto the protein region of RISC complexes. In certain embodiments, the self-complementary region containing a loop greater than 4 nucleotides can prevent the cleavage of the self-complementary region by RNase such as RNase III. In preferred embodiments, the polynucleotide of the present invention binds to and reduces expression of a target gene. A target gene may be a known gene target, or, alternatively, a target gene may be not known, i.e., a random sequence may be used. In certain embodiments, target gene levels are reduced at least 10%, at least 20%, at least 30%, at least 40%, at least 50%, at least 60%, at least 70%, at least 75%, at least 80%, at least 90%, or at least 95%.

In one embodiment of the invention, the level of inhibition of target gene expression (i.e., gene expression) is at least 90%, at least 95%, at least 98%, and at least 99% or is almost 100%, and hence the cell or organism will in effect have the phenotype equivalent to a so-called "knock out" of a gene. However, in some embodiments, it may be preferred to achieve only partial inhibition so that the phenotype is equivalent to a so-called "knockdown" of the gene. This method of knocking down gene expression can be used therapeutically or for research (e.g., to generate models of disease states, to examine the function of a gene, to assess whether an agent acts on a gene, to validate targets for drug discovery).

The polynucleotide complexes and molecules of the invention can be used to target and reduce or inhibit expression of genes (inclusive of coding and non-coding sequences), cDNAs, mRNAs, or microRNAs. In particular embodiments, their guide strands or targeting regions bind to mRNAs or microRNAs.

The invention further provides arrays of the polynucleotide of the invention, including microarrays. Microarrays are miniaturized devices typically with dimensions in the micrometer to millimeter range for performing chemical and biochemical reactions and are particularly suited for embodiments of the invention. Arrays may be constructed via microelectronic and/or microfabrication using essentially any and all techniques known and available in the semiconductor industry and/or in the biochemistry industry, provided that such techniques are amenable to and compatible with the deposition and/or screening of polynucleotide sequences.

Microarrays of the invention are particularly desirable for high throughput analysis of multiple polynucleotides. A microarray typically is constructed with discrete region or spots that comprise the polynucleotide of the present invention, each spot comprising one or more the polynucleotide, preferably at positionally addressable locations on the array surface. Arrays of the invention may be prepared by any method available in the art. For example, the light-directed chemical synthesis process developed by Affymetrix (see, U.S. Pat. Nos. 5,445,934 and 5,856,174) may be used to synthesize biomolecules on chip surfaces by combining solid-phase photochemical synthesis with photolithographic fabrication techniques. The chemical deposition approach developed by Incyte Pharmaceutical uses pre-synthesized cDNA probes for directed deposition onto chip surfaces (see, e.g., U.S. Pat. No. 5,874,554).

In certain embodiments, a polynucleotide molecule of the present invention is chemically synthesized using techniques widely available in the art, and annealed as a three stranded complex. In a related embodiment, the three or more guide strands of a polynucleotide complex of the present invention may be individually chemically synthesized and annealed to produce the polynucleotide complex.

In other embodiments, it is expressed in vitro or in vivo using appropriate and widely known techniques, such as vectors or plasmid constructs. Accordingly, in certain embodiments, the present invention includes in vitro and in vivo expression vectors comprising the sequence of a polynucleotide of the present invention interconnected by either stem-loop or loop forming nucleotide sequences. Methods well known to those skilled in the art may be used to construct expression vectors containing sequences encoding a polynucleotide, as well as appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A vector or nucleic acid construct system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector or nucleic acid construct is preferably one which is operably functional in a mammalian cell. The vector can also include a selection marker such as an antibiotic or drug resistance gene, or a reporter gene (i.e., green fluorescent protein, luciferase), that can be used for selection or identification of suitable transformants or transfectants. Exemplary delivery systems may include viral vector systems (i.e., viral-mediated transduction) including, but not limited to, retroviral (e.g., lentiviral) vectors, adenoviral vectors, adeno-associated viral vectors, and herpes viral vectors, among others known in the art.

As noted above, certain embodiments employ retroviral vectors such as lentiviral vectors. The term "lentivirus" refers to a genus of complex retroviruses that are capable of infecting both dividing and non-dividing cells. Examples of lentiviruses include HIV (human immunodeficiency virus; including HIV type 1, and HIV type 2), visna-maedi, the caprine arthritis-encephalitis virus, equine infectious anemia virus, feline immunodeficiency virus (FIV), bovine immune deficiency virus (BIV), and simian immunodeficiency virus (SIV). Lentiviral vectors can be derived from any one or more of these lentiviruses (see, e.g., Evans et al., *Hum Gene Ther.* 10:1479-1489, 1999; Case et al., *PNAS USA* 96:2988-2993, 1999; Uchida et al., *PNAS USA* 95:11939-11944, 1998; Miyoshi et al., *Science* 283:682-686, 1999; Sutton et al., *J Virol* 72:5781-5788, 1998; and Frecha et al., *Blood.* 112:4843-52, 2008, each of which is incorporated by reference in its entirety).

In certain embodiments the retroviral vector comprises certain minimal sequences from a lentivirus genome, such as the HIV genome or the SIV genome. The genome of a lentivirus is typically organized into a 5' long terminal repeat (LTR) region, the gag gene, the pol gene, the env gene, the accessory genes (e.g., nef, vif, vpr, vpu, tat, rev) and a 3' LTR region. The viral LTR is divided into three regions referred to as U3, R (repeat) and U5. The U3 region contains the enhancer and promoter elements, the U5 region contains the polyadenylation signals, and the R region separates the U3 and U5 regions. The transcribed sequences of the R region appear at both the 5' and 3' ends of the viral RNA (see, e.g., "RNA Viruses: A Practical Approach" (Alan J. Cann, Ed., Oxford University Press, 2000); O Narayan, *J. Gen. Virology.* 70:1617-1639, 1989; Fields et al., Fundamental Virology Raven Press., 1990; Miyoshi et al., *J Virol.* 72:8150-7, 1998; and U.S. Pat. No. 6,013,516, each of which is incorporated by reference in its entirety). Lentiviral vectors may comprise any one or more of these elements of the lentiviral genome, to regulate the activity of the vector as desired, or, they may contain deletions, insertions, substitutions, or mutations in one or more of these elements, such as to reduce the pathological effects of lentiviral replication, or to limit the lentiviral vector to a single round of infection.

Typically, a minimal retroviral vector comprises certain 5'LTR and 3'LTR sequences, one or more genes of interest (to be expressed in the target cell), one or more promoters, and a cis-acting sequence for packaging of the RNA. Other regulatory sequences can be included, as described herein and known in the art. The viral vector is typically cloned into a plasmid that may be transfected into a packaging cell line, such as a eukaryotic cell (e.g., 293-HEK), and also typically comprises sequences useful for replication of the plasmid in bacteria.

In certain embodiments, the viral vector comprises sequences from the 5' and/or the 3' LTRs of a retrovirus such as a lentivirus. The LTR sequences may be LTR sequences from any lentivirus from any species. For example, they may be LTR sequences from HIV, SIV, FIV or BIV. Preferably the LTR sequences are HIV LTR sequences.

In certain embodiments, the viral vector comprises the R and U5 sequences from the 5' LTR of a lentivirus and an inactivated or "self-inactivating" 3' LTR from a lentivirus. A "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. Self-inactivating 3' LTRs are described, for example, in Zufferey et al., *J Virol.* 72:9873-9880, 1998; Miyoshi et al., *J Virol.* 72:8150-8157, 1998; and Iwakuma et al., *Virology* 261:120-132, 1999, each of which is incorporated by reference in its entirety. Self-inactivating 3' LTRs may be generated by any method known in the art. In certain embodiments, the U3 element of the 3' LTR contains a deletion of its enhancer sequence, preferably the TATA box, Spl and/or NF-kappa B sites. As a result of the self-inactivating 3' LTR, the provirus that is integrated into the host cell genome will comprise an inactivated 5' LTR.

Expression vectors typically include regulatory sequences, which regulate expression of the polynucleotide. Regulatory sequences present in an expression vector include those non-translated regions of the vector, e.g., enhancers, promoters, 5' and 3' untranslated regions, which interact with host cellular proteins to carry out transcription and translation. Such elements may vary in their strength and specificity. Depending on the vector system and cell utilized, any number of suitable transcription and translation elements, including constitutive and inducible promoters, may be used. In addition, tissue- or -cell specific promoters may also be used.

For expression in mammalian cells, promoters from mammalian genes or from mammalian viruses are generally preferred. In addition, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Certain embodiments may employ the one or more of the RNA polymerase II and III promoters. A suitable selection of RNA polymerase III promoters can be found, for example, in Paule and White. *Nucleic Acids Research.*, Vol 28, pp 1283-1298, 2000, which is incorporated by reference in its entirety. RNA polymerase II and III promoters also include any synthetic or engineered DNA fragments that can direct RNA polymerase II or III, respectively, to transcribe its downstream RNA coding sequences. Further, the RNA polymerase II or III (Pol II or III) promoter or promoters used as part of the viral vector can be inducible. Any suitable inducible Pol II or III promoter can be used with the methods of the invention. Exemplary Pol II or III promoters include the tetracycline responsive promoters provided in Ohkawa and Taira, *Human Gene Therapy*, Vol. 11, pp 577-585, 2000; and Meissner et al., *Nucleic Acids Research*, Vol. 29, pp 1672-1682, 2001, each of which is incorporated by reference in its entirety.

Non-limiting examples of constitutive promoters that may be used include the promoter for ubiquitin, the CMV promoter (see, e.g., Karasuyama et al., *J. Exp. Med.* 169:13, 1989), the β-actin (see, e.g., Gunning et al., *PNAS USA* 84:4831-4835, 1987), and the pgk promoter (see, e.g., Adra et al., *Gene* 60:65-74, 1987); Singer-Sam et al., *Gene* 32:409-417, 1984; and Dobson et al., *Nucleic Acids Res.* 10:2635-2637, 1982, each of which is incorporated by reference). Non-limiting examples of tissue specific promoters include the Ick promoter (see, e.g., Garvin et al., *Mol. Cell Biol.* 8:3058-3064, 1988; and Takadera et al., *Mol. Cell Biol.* 9:2173-2180, 1989), the myogenin promoter (Yee et al., *Genes and Development* 7:1277-1289, 1993), and the thy1 (see, e.g., Gundersen et al., *Gene* 113:207-214, 1992).

Additional examples of promoters include the ubiquitin-C promoter, the human p heavy chain promoter or the Ig heavy chain promoter (e.g., MH-b12), and the human K light chain promoter or the Ig light chain promoter (e.g., EEK-b12), which are functional in B-lymphocytes. The MH-b12 promoter contains the human p heavy chain promoter preceded by the iEμ enhancer flanked by matrix association regions, and the EEK-b12 promoter contains the κ light chain promoter preceded an intronic enhancer (iEκ), a matrix associated region, and a 3' enhancer (3'Eκ) (see, e.g., Luo et al., *Blood.* 113:1422-1431, 2009, herein incorporated by reference). Accordingly, certain embodiments may employ one or more of these promoter or enhancer elements.

In certain embodiments, the invention provides for the conditional expression of a polynucleotide. A variety of conditional expression systems are known and available in the art for use in both cells and animals, and the invention contemplates the use of any such conditional expression system to regulate the expression or activity of a polynucleotide. In one embodiment of the invention, for example, inducible expression is achieved using the REV-TET system. Components of this system and methods of using the system to control the expression of a gene are well documented in the literature, and vectors expressing the tetracycline-controlled transactivator (tTA) or the reverse tTA (rtTA) are commercially available (e.g., pTet-Off, pTet-On and ptTA-2/3/4 vectors, Clontech, Palo Alto, Calif.). Such systems are described, for example, in U.S. Pat. No. 5,650, 298, No. 6,271,348, No. 5,922,927, and related patents, which are incorporated by reference in their entirety.

In certain embodiments, the viral vectors (e.g., retroviral, lentiviral) provided herein are "pseudo-typed" with one or more selected viral glycoproteins or envelope proteins, mainly to target selected cell types. Pseudo-typing refers to generally to the incorporation of one or more heterologous viral glycoproteins onto the cell-surface virus particle, often allowing the virus particle to infect a selected cell that differs from its normal target cells. A "heterologous" element is derived from a virus other than the virus from which the RNA genome of the viral vector is derived. Typically, the glycoprotein-coding regions of the viral vector have been genetically altered such as by deletion to prevent expression of its own glycoprotein. Merely by way of illustration, the envelope glycoproteins gp41 and/or gp120 from an HIV-derived lentiviral vector are typically deleted prior to pseudo-typing with a heterologous viral glycoprotein.

Generation of viral vectors can be accomplished using any suitable genetic engineering techniques known in the art, including, without limitation, the standard techniques of restriction endonuclease digestion, ligation, transformation, plasmid purification, PCR amplification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

Any variety of methods known in the art may be used to produce suitable retroviral particles whose genome comprises an RNA copy of the viral vector. As one method, the viral vector may be introduced into a packaging cell line that packages the viral genomic RNA based on the viral vector into viral particles with a desired target cell specificity. The packaging cell line typically provides in trans the viral proteins that are required for packaging the viral genomic RNA into viral particles and infecting the target cell, including the structural gag proteins, the enzymatic pol proteins, and the envelope glycoproteins.

In certain embodiments, the packaging cell line may stably express certain of the necessary or desired viral proteins (e.g., gag, pol) (see, e.g., U.S. Pat. No. 6,218,181, herein incorporated by reference). In certain embodiments, the packaging cell line may be transiently transfected with plasmids that encode certain of the necessary or desired viral proteins (e.g., gag, pol, glycoprotein), including the measles virus glycoprotein sequences described herein. In one exemplary embodiment, the packaging cell line stably expresses the gag and pol sequences, and the cell line is then transfected with a plasmid encoding the viral vector and a plasmid encoding the glycoprotein. Following introduction of the desired plasmids, viral particles are collected and processed accordingly, such as by ultracentrifugation to achieve a concentrated stock of viral particles. Exemplary packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430) cell lines.

In one particular embodiment, the polynucleotides are expressed using a vector system comprising a pSUPER vector backbone and additional sequences corresponding to the polynucleotide to be expressed. The pSUPER vectors system has been shown useful in expressing shRNA reagents and downregulating gene expression (Brummelkamp, T. T. et al., Science 296:550 (2002) and Brummelkamp, T. R. et al., Cancer Cell, published online Aug. 22, 2002). PSUPER vectors are commercially available from OligoEngine, Seattle, Wash.

Methods of Regulating Gene Expression

The polynucleotides of the invention may be used for a variety of purposes, all generally related to their ability to inhibit or reduce expression of one or more target genes. Accordingly, the invention provides methods of reducing expression of one or more target genes comprising introducing a polynucleotide complex or molecule of the present invention into a cell comprising said one or more target genes. In particular embodiments, the polynucleotide complex or molecule comprises one or more guide strands that collectively target the one or more target genes. In one embodiment, a polynucleotide of the invention is introduced into a cell that contains a target gene or a homolog, variant or ortholog thereof, targeted by either one, two, or three of the guide strands or targeting regions.

In addition, the polynucleotides of the present invention may be used to reduce expression indirectly. For example, a polynucleotide complex or molecule of the present invention may be used to reduce expression of a transactivator that drives expression of a second gene (i.e., the target gene), thereby reducing expression of the second gene. Similarly, a polynucleotide may be used to increase expression indirectly. For example, a polynucleotide complex or molecule of the present invention may be used to reduce expression of a transcriptional repressor that inhibits expression of a second gene, thereby increasing expression of the second gene.

In various embodiments, a target gene is a gene derived from the cell into which a polynucleotide is to be introduced, an endogenous gene, an exogenous gene, a transgene, or a gene of a pathogen that is present in the cell after transfection thereof. Depending on the particular target gene and the amount of the polynucleotide delivered into the cell, the method of this invention may cause partial or complete inhibition of the expression of the target gene. The cell containing the target gene may be derived from or contained in any organism (e.g., plant, animal, protozoan, virus, bacterium, or fungus). As used herein, "target genes" include genes, mRNAs, and microRNAs.

Inhibition of the expression of the target gene can be verified by means including, but not limited to, observing or detecting an absence or observable decrease in the level of protein encoded by a target gene, an absence or observable decrease in the level of a gene product expressed from a target gene (e.g., mRNAO, and/or a phenotype associated with expression of the gene, using techniques known to a person skilled in the field of the present invention.

Examples of cell characteristics that may be examined to determine the effect caused by introduction of a polynucleotide complex or molecule of the present invention include, cell growth, apoptosis, cell cycle characteristics, cellular differentiation, and morphology.

A polynucleotide complex or molecule of the present invention may be directly introduced to the cell (i.e., intracellularly), or introduced extracellularly into a cavity or interstitial space of an organism, e.g., a mammal, into the circulation of an organism, introduced orally, introduced by bathing an organism in a solution containing the polynucleotide, or by some other means sufficient to deliver the polynucleotide into the cell.

In addition, a vector engineered to express a polynucleotide may be introduced into a cell, wherein the vector expresses the polynucleotide, thereby introducing it into the cell. Methods of transferring an expression vector into a cell are widely known and available in the art, including, e.g., transfection, lipofection, scrape-loading, electroporation, microinjection, infection, gene gun, and retrotransposition. Generally, a suitable method of introducing a vector into a cell is readily determined by one of skill in the art based upon the type of vector and the type of cell, and teachings widely available in the art. Infective agents may be introduced by a variety of means readily available in the art, including, e.g., nasal inhalation.

Methods of inhibiting gene expression using the oligonucleotides of the invention may be combined with other knockdown and knockout methods, e.g., gene targeting, antisense RNA, ribozymes, double-stranded RNA (e.g., shRNA and siRNA) to further reduce expression of a target gene.

In different embodiments, target cells of the invention are primary cells, cell lines, immortalized cells, or transformed cells. A target cell may be a somatic cell or a germ cell. The target cell may be a non-dividing cell, such as a neuron, or it may be capable of proliferating in vitro in suitable cell culture conditions. Target cells may be normal cells, or they may be diseased cells, including those containing a known genetic mutation. Eukaryotic target cells of the invention include mammalian cells, such as, for example, a human cell, a murine cell, a rodent cell, and a primate cell. In one embodiment, a target cell of the invention is a stem cell, which includes, for example, an embryonic stem cell, such as a murine embryonic stem cell.

The polynucleotide complexes, molecules, and methods of the present invention may be used to treat any of a wide variety of diseases or disorders, including, but not limited to, inflammatory diseases, cardiovascular diseases, nervous system diseases, tumors, demyelinating diseases, digestive system diseases, endocrine system diseases, reproductive system diseases, hemic and lymphatic diseases, immunological diseases, mental disorders, muscoloskeletal diseases, neurological diseases, neuromuscular diseases, metabolic diseases, sexually transmitted diseases, skin and connective tissue diseases, urological diseases, and infections.

In certain embodiments, the methods are practiced on an animal, in particular embodiments, a mammal, and in certain embodiments, a human.

Accordingly, in one embodiment, the present invention includes methods of using a polynucleotide complex or molecule of the present invention for the treatment or prevention of a disease associated with gene deregulation, overexpression, or mutation. For example, a polynucleotide complex or molecule of the present invention may be introduced into a cancerous cell or tumor and thereby inhibit expression of a gene required for or associated with maintenance of the carcinogenic/tumorigenic phenotype. To prevent a disease or other pathology, a target gene may be selected that is, e.g., required for initiation or maintenance of a disease/pathology. Treatment may include amelioration of any symptom associated with the disease or clinical indication associated with the pathology.

In addition, the polynucleotides of the present invention are used to treat diseases or disorders associated with gene mutation. In one embodiment, a polynucleotide is used to modulate expression of a mutated gene or allele. In such embodiments, the mutated gene is a target of the polynucleotide complex or molecule, which will comprise a region complementary to a region of the mutated gene. This region may include the mutation, but it is not required, as another region of the gene may also be targeted, resulting in decreased expression of the mutant gene or gene. In certain embodiments, this region comprises the mutation, and, in related embodiments, the polynucleotide complex or molecule specifically inhibits expression of the mutant gene or gene but not the wild type gene or gene. Such a polynucleotide is particularly useful in situations, e.g., where one allele is mutated but another is not. However, in other embodiments, this sequence would not necessarily comprise the mutation and may, therefore, comprise only wild-type sequence. Such a polynucleotide is particularly useful in situations, e.g., where all alleles are mutated. A variety of diseases and disorders are known in the art to be associated with or caused by gene mutation, and the invention encompasses the treatment of any such disease or disorder with a the polynucleotide.

In certain embodiments, a gene of a pathogen is targeted for inhibition. For example, the gene could cause immunosuppression of the host directly or be essential for replication of the pathogen, transmission of the pathogen, or maintenance of the infection. In addition, the target gene may be a pathogen gene or host gene responsible for entry of a pathogen into its host, drug metabolism by the pathogen or host, replication or integration of the pathogen's genome, establishment or spread of an infection in the host, or assembly of the next generation of pathogen. Methods of prophylaxis (i.e., prevention or decreased risk of infection), as well as reduction in the frequency or severity of symptoms associated with infection, are included in the present invention. For example, cells at risk for infection by a pathogen or already infected cells, particularly human immunodeficiency virus (HIV) infections, may be targeted for treatment by introduction of a the polynucleotide according to the invention (see Examples 1 and 2 for targeting sequences). Thus, in one embodiment, polynucleotide complexes or molecules of the present invention that target one or more HIV proteins are used to treat or inhibit HIV infection or acquired immune deficiency syndrome (AIDS).

In other specific embodiments, the present invention is used for the treatment or development of treatments for cancers of any type. Examples of tumors that can be treated using the methods described herein include, but are not limited to, neuroblastomas, myelomas, prostate cancers, small cell lung cancer, colon cancer, ovarian cancer, non-small cell lung cancer, brain tumors, breast cancer, leukemias, lymphomas, and others.

In one embodiment, polynucleotide complexes or molecules of the present invention that target apolipoprotein B (apoB) are used to treat, reduce, or inhibit atherosclerosis or heart disease. ApoB is the primary apolipoprotein of low-density lipoproteins (LDLs), which is responsible for carrying cholesterol to tissues. ApoB on the LDL particle acts as a ligand for LDL receptors, and high levels of ApoB can lead to plaques that cause vascular disease (atherosclerosis), leading to heart disease.

The polynucleotide complexes, molecules and expression vectors (including viral vectors and viruses) may be introduced into cells in vitro or ex vivo and then subsequently placed into an animal to affect therapy, or they may be directly introduced to a patient by in vivo administration. Thus, the invention provides methods of gene therapy, in certain embodiments. Compositions of the invention may be administered to a patient in any of a number of ways, including parenteral, intravenous, systemic, local, topical, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection.

Compositions of the invention may be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The amount of the oligonucleotides administered to a patient can be readily determined by a physician based upon a variety of factors, including, e.g., the disease and the level of the oligonucleotides expressed from the vector being used (in cases where a vector is administered). The amount administered per dose is typically selected to be above the minimal therapeutic dose but below a toxic dose. The choice of amount per dose will depend on a number of factors, such as the medical history of the patient, the use of other therapies, and the nature of the disease. In addition, the amount administered may be adjusted throughout treatment, depending on the patient's response to treatment and the presence or severity of any treatment-associated side effects.

Methods of Determining Gene Function

The invention further includes a method of identifying gene function in an organism comprising the use of a polynucleotide complex or molecule of the present invention to inhibit the activity of a target gene of previously unknown function. Instead of the time consuming and laborious isolation of mutants by traditional genetic screening, functional genomics envisions determining the function of uncharacterized genes by employing the invention to reduce the amount and/or alter the timing of target gene activity. The invention may be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for the yeast, *D. melanogaster*, and *C. elegans* genomes, can be coupled with the invention to determine gene function in an organism (e.g., nematode). The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

In one embodiment, a polynucleotide of the present invention is used to inhibit gene expression based upon a partial sequence available from an expressed sequence tag (EST), e.g., in order to determine the gene's function or biological activity. Functional alterations in growth, development, metabolism, disease resistance, or other biological processes would be indicative of the normal role of the EST's gene product.

The ease with which a polynucleotide can be introduced into an intact cell/organism containing the target gene allows the present invention to be used in high throughput screening (HTS). For example, solutions containing the polynucleotide that are capable of inhibiting different expressed genes can be placed into individual wells positioned on a microtiter plate as an ordered array, and intact cells/organisms in each well can be assayed for any changes or modifications in behavior or development due to inhibition of target gene activity. The function of the target gene can be assayed from the effects it has on the cell/organism when gene activity is inhibited. In one embodiment, the polynucleotides of the invention are used for chemocogenomic screening, i.e., testing compounds for their ability to reverse a disease modeled by the reduction of gene expression using a polynucleotide of the invention.

If a characteristic of an organism is determined to be genetically linked to a polymorphism through RFLP or QTL analysis, the present invention can be used to gain insight regarding whether that genetic polymorphism might be directly responsible for the characteristic. For example, a fragment defining the genetic polymorphism or sequences in the vicinity of such a genetic polymorphism can be amplified to produce an RNA, a polynucleotide can be introduced to the organism, and whether an alteration in the characteristic is correlated with inhibition can be determined.

The present invention is also useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of a the polynucleotide at specific times of development and locations in the organism without introducing permanent mutations into the target genome. Similarly, the invention contemplates the use of inducible or conditional vectors that express a the polynucleotide only when desired.

The present invention also relates to a method of validating whether a gene product is a target for drug discovery or development. A the polynucleotide that targets the gene that corresponds to the gene for degradation is introduced into a cell or organism. The cell or organism is maintained under conditions in which degradation of the gene occurs, resulting in decreased expression of the gene. Whether decreased expression of the gene has an effect on the cell or organism is determined. If decreased expression of the gene has an effect, then the gene product is a target for drug discovery or development.

Methods of Designing and Producing Polynucleotide Complexes and Molecules

The polynucleotide complexes and molecules of the present invention comprise a novel and unique set of functional sequences, arranged in a manner so as to adopt a secondary structure containing one or more double-stranded regions (sometimes adjoined by stem-loop or loop structures), which imparts the advantages of the polynucleotide. Accordingly, in certain embodiments, the present invention includes methods of designing the polynucleotide complexes and molecules of the present invention. Such methods typically involve appropriate selection of the various sequence components of the polynucleotide complexes and molecules. The terms "primary strand", "secondary strand", and "key strand" refer to the various guide strands present within a polynucleotide complex or molecule of the present invention.

In one embodiment, the basic design of the polynucleotide complex is as follows:

Design Motifs:

(primary strand)(UU)(secondary strand)(UU)(key strand)(UU)

Accordingly, in a related embodiment, a the polynucleotide is designed as follows:

II. (secondary strand)(UU)(UU)(key strand)(UU)(primary strand)

III. (secondary strand)(UU)(loop or stem-loop)(key strand)(UU)(loop or stem-loop)(primary strand)(UU)

Set Parameters

Set seed size for self complementarity at approx 38-43%. For a 19 nucleotide targets, a range or 7 or 8 nucleotides is preferred as SEED_SIZE.

For each gene, define a PRIMARY and SECONDARY target gene.

Define Primary Strands

Start with one or more target gene sequences. For each gene, build a list of PRIMARY target sequences 17-24 nucleotide motifs that meet criteria of G/C content, specificity, and poly-A or poly-G free. For each, find also a SECONDARY and KEY strand.

Find Secondary and Key Strands d. For each target sequence on each gene, clustal align base 1 through SEED_SIZE the reverse of each sequence to the SECONDARY gene Record sequence with a perfect alignment. The target sequence on the SECONDARY gene is the alignment start, minus the length of the motif, plus SEED_SIZE to alignment start, plus SEED_SIZE. The SECONDARY strand is the reverse compliment.

To find each KEY strand, define SEED_A as base 1 through SEED_SIZE of the PRIMARY strand, define SEED_B as bases at motif length minus SEED_SIZE to motif length of the SECONDARY strand. Set a MID_SECTION as characters "I" repeated of length motif sequence length minus SEED_A length plus SEED_B length. Set key alignment sequence as SEED_A, MID_SECTION, SEED_B. Clustal align to the target gene for the key segment. Record KEY target sequence as bases at alignment hit on key target gene to bases alignment hit plus motif length. The KEY strand is the reverse compliment.

Construct Optional Polynucleotide g. Build candidate Stem A & B with (4-24) nucleotides that have melting temperature dominant to equal length region of target. Stem strands have A-T, G-C complementarity to each other. Length and composition depend upon which endoribonuclease is chosen for pre-processing of the stem-loop structure.

h. Build candidate Stem C & D with (4-24) nucleotides that have melting temperature dominant to equal length region of target. Stem strands have A-T, G-C complementarity to each other, but no complementarity to Stem A & B. Length and composition depend upon which endoribonuclease is chosen for pre-processing of the stem-loop structure.

i. Build loop candidates with (4-12) A-T rich nucleotides into loop A & B. Length and composition depend upon which endoribonuclease is chosen for pre-processing of the stem-loop structure. Tetraloops as described are suggested for longer stems processed by RNase III or Pac1 RNase III endoribonucleases as drawn in (Fig. A.). Larger loops are suggested for preventing RNase III or Pac1 processing and placed onto shorter stems as drawn in (Fig. C, Fig. D.).

j. Form a contiguous sequence for each motif candidate.

k. Fold candidate sequence using software with desired parameters.

l. From output, locate structures with single stranded target regions which are flanked at either one or both ends with a desired stem/loop structure.

In one embodiment, a method of designing a polynucleotide sequence comprising one or more self-complementary regions for the regulation of expression of a target gene (i.e., a the polynucleotide), includes: (a) selecting a first sequence 17 to 30 nucleotides in length and complementary to a target gene; and (b) selecting one or more additional sequences 12 to 54 nucleotides in length, which comprises self-complementary regions and which are non-complementary to the first sequence.

These methods, in certain embodiments, include determining or predicting the secondary structure adopted by the sequences selected in step (b), e.g., in order to determine that they are capable of adopting a stem-loop structure.

Similarly, these methods can include a verification step, which comprises testing the designed polynucleotide sequence for its ability to inhibit expression of a target gene, e.g., in an in vivo or in vitro test system.

The invention further contemplates the use of a computer program to select sequences of a polynucleotide, based upon the complementarity characteristics described herein. The invention, thus, provides computer software programs, and computer readable media comprising said software programs, to be used to select the polynucleotide sequences, as well as computers containing one of the programs of the present invention.

In certain embodiments, a user provides a computer with information regarding the sequence, location or name of a target gene. The computer uses this input in a program of the present invention to identify one or more appropriate regions of the target gene to target, and outputs or provides complementary sequences to use in the polynucleotide of the invention. The computer program then uses this sequence information to select sequences of the one or more self-complementary regions of the polynucleotide. Typically, the program will select a sequence that is not complementary to a genomic sequence, including the target gene, or the region of the polynucleotide that is complementary to the target gene. Furthermore, the program will select sequences of self-complementary regions that are not complementary to each other. When desired, the program also provides sequences of gap regions. Upon selection of appropriate sequences, the computer program outputs or provides this information to the user.

The programs of the present invention may further use input regarding the genomic sequence of the organism containing the target gene, e.g., public or private databases, as well as additional programs that predict secondary structure and/or hybridization characteristics of particular sequences, in order to ensure that the polynucleotide adopts the correct secondary structure and does not hybridize to non-target genes.

The present invention is based, in part, upon the surprising discovery that the polynucleotide, as described herein, is extremely effective in reducing target gene expression of one or more genes. The polynucleotide offer significant advantages over previously described antisense RNAs, including increased potency, and increased effectiveness to multiple target genes. Furthermore, the polynucleotide of the invention offer additional advantages over traditional dsRNA molecules used for siRNA, since the use of the polynucleotide substantially eliminates the off-target suppression associated with dsRNA molecules and offers multivalent RNAi.

It is understood that the compositions and methods of the present invention may be used to target a variety of different target genes. The term "target gene" may refer to a gene, an mRNA, or a microRNA. Accordingly, target sequences provided herein may be depicted as either DNA sequences or RNA sequences. One of skill the art will appreciate that the compositions of the present invention may include regions complementary to either the DNA or RNA sequences provided herein. Thus, where either a DNA or RNA target sequence is provided, it is understood that the corresponding RNA or DNA target sequence, respectively, may also be targeted.

The practice of the present invention will employ a variety of conventional techniques of cell biology, molecular biology, microbiology, and recombinant DNA, which are within the skill of the art. Such techniques are fully described in the literature. See, for example, Molecular Cloning: A Laboratory Manual, 2$^{nd}$ Ed., ed. by Sambrook, Fritsch, and Maniatis (Cold Spring Harbor Laboratory Press, 1989); and DNA Cloning, Volumes I and II (D. N. Glover ed. 1985).

All of the patents, patent applications, and non-patent references referred to herein are incorporated by reference in their entirety, as if each one was individually incorporated by reference.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

Trivoid Anti-GFP

Multivalent siRNA were designed against a single gene, the green fluorescent protein (GFP). A multivalent synthetic RNA MV-siRNA complex directed against GFP was tested to compare suppression activity in relation to that of a single shRNA clone. Also, to test the effect of deactivating one of the strands of the synthetic MV-siRNA complex, one strand was replaced with DNA (T1-19_C_dna); as shown below. This replacement resulted in a relative drop in suppression by –30%. Additionally, 'short' and 'long' forms of the MV-siRNA self-complementary clones described herein were tested and compared to the suppression of GFP expression in relation to that of a published shRNA clone.

Oligomer sequences for the synthetic MV-siRNA, and the DNA replacement strand, are shown below in Table 1. The targeted regions of the GFP coding sequence are illustrated in FIG. 8A.

TABLE 1

Oligos for Synthetic MV-siRNA:

| Name | Sequence | SEQ ID NO: |
|---|---|---|
| TI-19/7_A | GGGCAGCUUGCCGGUGGUGUU | 11 |
| TI-19/7_B | CACCACCCCGGUGAACAGCUU | 12 |
| TI-19/7_C | GCUGUUCACGUCGCUGCCCUU | 13 |
| TI-19/7_C_dna | GCTGTTCACGTCGCTGCCC | 14 |

To prepare the synthetic multivalent-siRNAs (MV-siRNAs), each tube of the individual oligos above was resuspended in RNase-free water to obtain a final concentration of 50 μM (50 pmoles/μL). The individual oligos were then combined as (a) TI-19/7_A, TI-19/7_B, and TI-19/7_C (MV-siRNA GFP I), or as (b) TI-19/7_A, TI-19/7_B, and TI-19/7_C_dna (MV-siRNA GFP I DNA), and annealed as follows. 30 μL of each one of the resupended oligos were combined with 10 μL of 10× annealing buffer (100 mM Tris-HCl pH7.5, 1M NaCl, 10 mM EDTA), vortexed, heated for 5 minutes at 94° C., and step cooled to 70° C. over 30 minutes. The final concentration of the annealed MV-siRNA was about 15 μM.

To prepare the multivalent-siRNA clones and shRNA control, the sequences in Table 2 below were cloned into the pSUPER vector, according to the pSUPER manual. The first sequence for each named clone (e.g., TI, T1_long, TII) represents the sequence of the self-complementary multivalent siRNA that was expressed in the cell as an RNA transcript (comparable to the sequence of the synthetic MV-siRNAs in Table 1), and the sequence referred to as "_as" is part of the coding sequence for that molecule.

TABLE 2

Oligos for MV-siRNA expressing clones:

| Name | Sequence | SEQ ID NO: |
|---|---|---|
| TI | GATCCCCCACCACCCCGGTGAACAGCgttaGCTGTTCACGTCGCTGCCCgttaGGGCAGCTTGCCGGTGGTGttTTTTTA | 15 |

TABLE 2-continued

| Oligos for MV-siRNA expressing clones: | | |
|---|---|---|
| Name | Sequence | SEQ ID NO: |
| TI_as | AGCTTAACACCACCGGCAAGCTGCCCTAACGGGCAGCGACGTG AACAGCTAACGCTGTTCACCGGGGTGGTGGGG | 16 |
| T1_long | GATCCCCCACCACCCCGGTGAACAGCTTGTAGGTGGCATCGCA GAAGCGATGCCACCTACAAGCTGTTCACGTCGCTGCCCTTGTAG GTGGCATCGCAGAAGCGATGCCACCTACAAGGGCAGCTTGCCG GTGGTGttTTTTTA | 17 |
| T1_long_as | AGCTTAACACCACCGGCAAGCTGCCCTTGTAGGTGGCATCGCTT CTGCGATGCCACCTACAAGGGCAGCGACGTGAACAGCTTGTAG GTGGCATCGCTTCTGCGATGCCACCTACAAGCTGTTCACCGGG GTGGTGGGG | 18 |
| TII | GATCCCCCGTGCTGCTTCATGTGGTCGTTgttaCGACCACAATGG CGACAACCTTgttaGGTTGTCGGGCAGCAGCACGTTttTTTTTA | 19 |
| TII_as | AGCTTAAAACGTGCTGCTGCCCGACAACCTAACAAGGTTGTCGC CATTGTGGTCGTAACAACGACCACATGAAGCAGCACGGGG | 20 |
| TII_long | GATCCCCCGTGCTGCTTCATGTGGTCGTTGTAGGTGGCATCGCA GAAGCGATGCCACCTACAACGACCACAATGGCGACAACCTTGTA GGTGGCATCGCAGAAGCGATGCCACCTACAAGGTTGTCGGGCA GCAGCACGttTTTTTA | 21 |
| TII_long_as | AGCTTAACGTGCTGCTGCCCGACAACCTTGTAGGTGGCATCGCT TCTGCGATGCCACCTACAAGGTTGTCGCCATTGTGGTCGTTGTA GGTGGCATCGCTTCTGCGATGCCACCTACAACGACCACATGAA GCAGCACGGGG | 22 |
| shRNA | GATCCCCGCAAGCTGACCCTGAAGTTCTTCAAGAGAGAACTTCA GGGTCAGCTTGCTTTTTA | 23 |
| shRNA_as | AGCTTAAAAAGCAAGCTGACCCTGAAGTTCTCTCTTGAAGAACTT CAGGGTCAGCTTGCGGG | 24 |

To test the effects on GFP-expression, the annealed MV-siRNA molecules (at a final concentration of 7.5 nM per well) and pSUPER vectors containing the MV-siRNA clones or shRNA control were transfected with Lipofectamine 2000 into 293 cells that constitutively express GFP. GFP fluorescence was measure by flow cytometry 24 hour after transfection.

Figure 7A:
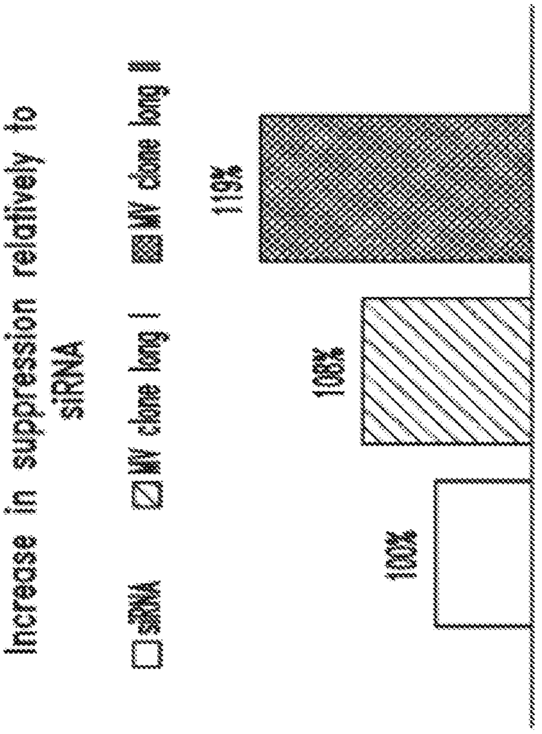
FIGS. 7A and 7B show the results of suppression of GFP expression by multivalent-siRNA molecules of the invention, as compared to standard shRNA molecules (see Example 1).

The results for one experiment are shown in Table 3 below, and summarized in FIG. 7A. In FIG. 7A, the MV-siRNA long I and long II clones demonstrate significantly increased suppression of GFP activity compared to the shRNA control (referred to in that Figure as "siRNA").

TABLE 3

| Well | Transfected: | Mean Fluorescence | % GFP |
|---|---|---|---|
| Positive shRNA | shRNA | 330 | 66% |
| | shRNA | 302 | 60% |
| Synthetic: | MV-siRNA | 305 | 61% |
| Clone: | MV-siRNA short TI | 360 | 72% |
| | MV-siRNA long TI | 218 | 43% |
| | MV-siRNA long TII | 245 | 49% |
| Negative | Blank | 502 | 100% |
| | non-GFP 293 cells | 0.5 | 0% |

Figure 7B:
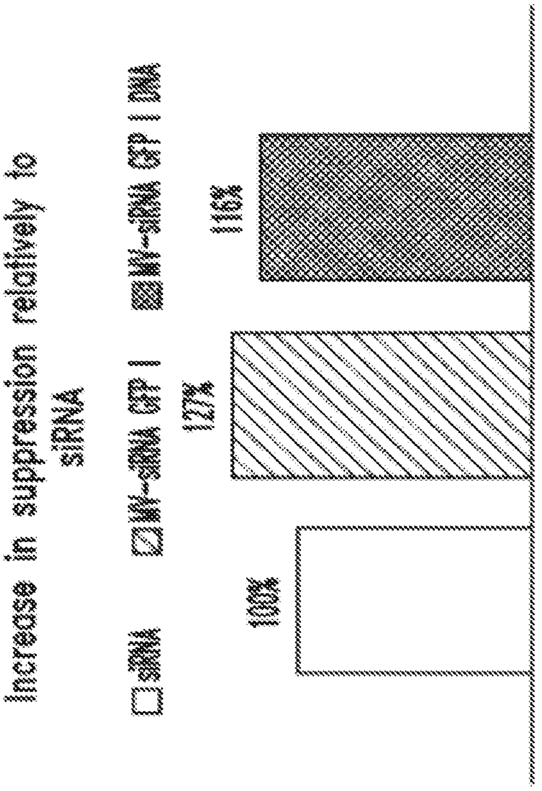

FIG. 7B shows the results of an experiment in which the synthetic MV-siRNA GFP I complex demonstrated increased suppression of GFP activity compared to the shRNA clone (referred to in that Figure as "siRNA"). However, the suppression activity for the MV-siRNA GFP I complex was slightly reduced when one strand was replaced with DNA, as shown for the synthetic MV-siRNA GFP I DNA complex.

Exemplary synthetic MV-siRNAs directed to GFP can also be designed as in Table 4 below, in which the 3 oligos of T1.A-C can be annealed as described above. Similarly, the 3 oligos of T2.A-C can be annealed as described above.

TABLE 4

| Exemplary synthetic siRNA sets T1 and T2. | | |
|---|---|---|
| Name | Sequence | SEQ ID NO: |
| T1.A | CUGCUGGUAGUGGUCGGCGUU | 25 |
| T1.B | CGCCGACUUCGUGACGUGCUU | 26 |
| T1.C | GCACGUCGCCGUCCAGCAGUU | 27 |
| T2.A | GUUGCCGUCGUCCUUGAAGUU | 28 |
| T2.B | CUUCAAGUGGAACUACGGCUU | 29 |
| T2.C | GCCGUAGGUAGGCGGCAACUU | 30 |

MV-siRNA clones directed to GFP can also be designed as in Table 5 below. As illustrated above, these sequences can be cloned into the pSuper vector, or any other vector system.

TABLE 5

| Exemplary MV-siRNA clones | | |
|---|---|---|
| Name | Sequence | SEQ ID NO: |
| T1_transcript | CGCCGACUUCGUGACGUGCUUGUGCACGUCGCCGUCCAGC AGUUGUCUGCUGGUAGUGGUCGGCGUU | 31 |
| T1 | GATCCCCCGCCGACTTCGTGACGTGCTTGTGCACGTCGCCGT CCAGCAGTTGTCTGCTGGTAGTGGTCGGCGTTTTTTTA | 32 |
| T1_as | AGCTTAAAAAAACGCCGACCACTACCAGCAGACAACTGCTGG ACGGCGACGTGCACAAGCACGTCACGAAGTCGGCGGGG | 33 |
| T1_long transcript | CGCCGACUUCGUGACGUGCUUGUAGGUGGCAUCGCAGAAG CGAUGCCACCUACAAGCACGUCGCCGUCCAGCAGUUGUAGG UGGCAUCGCAGAAGCGAUGCCACCUACAACUGCUGGUAGUG GUCGGCGUU | 34 |
| T1_long | GATCCCCCGCCGACTTCGTGACGTGCTTGTAGGTGGCATCGC AGAAGCGATGCCACCTACAAGCACGTCGCCGTCCAGCAGTTG TAGGTGGCATCGCAGAAGCGATGCCACCTACAACTGCTGGTA GTGGTCGGCGTTTTTA | 35 |
| T1_long_as | AGCTTAAAAACGCCGACCACTACCAGCAGTTGTAGGTGGCAT CGCTTCTGCGATGCCACCTACAACTGCTGGACGGCGACGTGC TTGTAGGTGGCATCGCTTCTGCGATGCCACCTACAAGCACGT CACGAAGTCGGCGGGG | 36 |
| T2_transcript | CUUCAAGUGGAACUACGGCUUGUGCCGUAGGUAGGCGGCAA CUUGUGUUGCCGUCGUCCUUGAAGUU | 37 |
| T2 | GATCCCCGGATCCGACATCCACGTTCTTCAAGAGAGAACGTG GATGTCGGATCCTTTTTA | 38 |
| T2_as | AGCTTAAAAAGGATCCGACATCCACGTTCTCTCTTGAAGAACG TGGATGTCGGATCCGGG | 39 |
| T2_long transcript | CUUCAAGUGGAACUACGGCUUGUAGGUGGCAUCGCAGAAGC GAUGCCACCUACAAGCCGUAGGUAGGCGGCAACUUGUAGGU GGCAUCGCAGAAGCGAUGCCACCUACAAGUUGCCGUCGUCC UUGAAGUU | 40 |
| T2_long | GATCCCCCTTCAAGTGGAACTACGGCTTGTAGGTGGCATCGC AGAAGCGATGCCACCTACAAGCCGTAGGTAGGCGGCAACTTG TAGGTGGCATCGCAGAAGCGATGCCACCTACAAGTTGCCGTC GTCCTTGAAGTTTTTA | 41 |
| T2_long_as | AGCTTAAAAACTTCAAGGACGACGGCAACTTGTAGGTGGCATC GCTTCTGCGATGCCACCTACAAGTTGCCGCCTACCTACGGCTT GTAGGTGGCATCGCTTCTGCGATGCCACCTACAAGCCGTAGT TCCACTTGAAGGGG | 42 |

Example 2

Trivoid Anti-HIV

Multivalent-siRNA can be designed against multiple genes at unrelated sites. In this example, a cloned MV-siRNA was tested against HIV. These results show that a di-valent MV-siRNA molecule against HIV's Gag and Tat (hv_sB) genes was significantly more efficient in inhibiting HIV replication than an siRNA directed against Gag alone (hv_s).

The oligos shown in Table 6 were cloned into pSUPER-.neo+gfp vector according to manufacturers guidelines. The hv_s is targeted to Gag only, and the hv_sB is targeted to both Gag and Tat.

TABLE 6

| Anti-HIV MV-siRNA clones | | |
|---|---|---|
| Name | Sequence | SEQ ID NO: |
| hv_s | GATCCCCGTGAAGGGGAACCAAGAGATTgaTCTCTTGTTAATATCAG CTTgaGCTGATATTTCTCCTTCACTTTTTA | 43 |
| hv_s_as | AGCTTAAAAAGTGAAGGAGAAATATCAGCTCAAGCTGATATTAACAA GAGATCAATCTCTTGGTTCCCCTTCACGGG | 44 |

TABLE 6-continued

| Anti-HIV MV-siRNA clones | | |
|---|---|---|
| Name | Sequence | SEQ ID NO: |
| hv_sB | GATCCCCCAAGCAGTTTTAGGCTGACgTTaGTCAGCCTCATTGACAC AGgTTaCTGTGTCAGCTGCTGCTTGTTTTTTA | 45 |
| hv_sB_As | AGCTTAAAAAAACAAGCAGCAGCTGACACAGTAACCTGTGTCAATGA GGCTGACTAACGTCAGCCTAAAACTGCTTGGGG | 46 |

Figure 9:
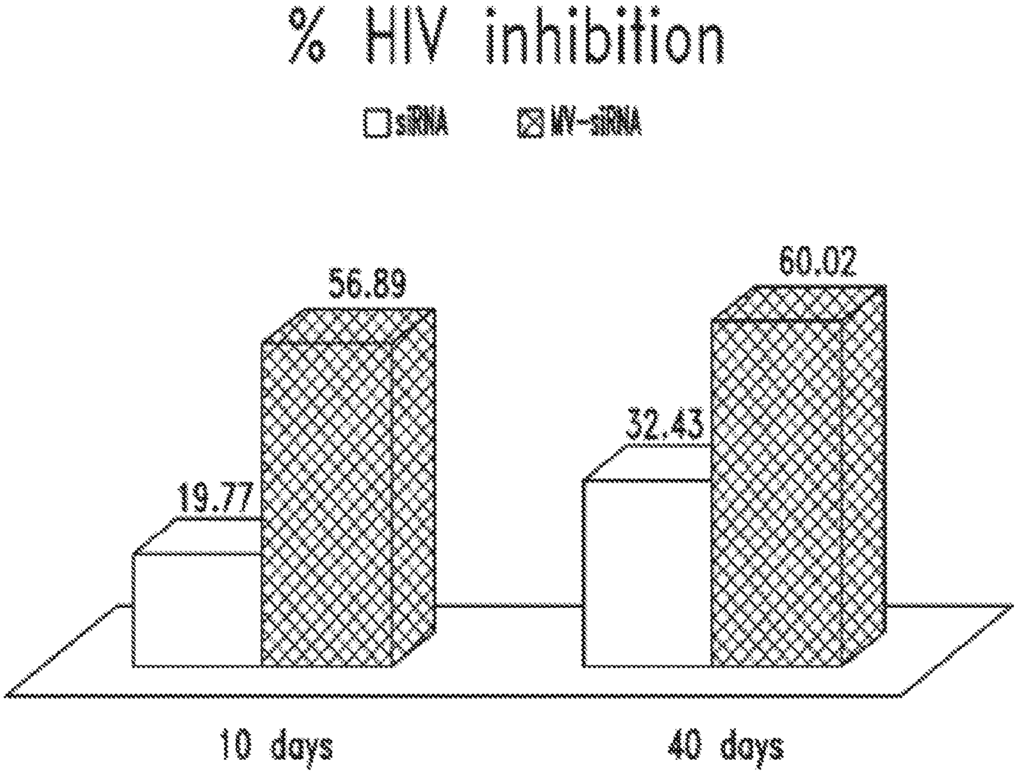
FIG. 9 shows the inhibitory effects of MV-siRNA molecules on HIV replication, in which a di-valent MV-siRNA targeted to both gag and tat has a significantly greater inhibitory effect on HIV replication than an siRNA targeted to gag only. The di-valent MV-siRNA exhibited 56.89% inhibition at 10 days and 60.02% inhibition at 40 days, as compared to the siRNA targeted to gag alone, which exhibited 19.77% inhibition at 10 days and 32.43% inhibition at 40 days.

The vector constructs encoding the MV-siRNA clones were transfected into cells, and the analyses were carried out on days 10 and 40 post infection with HIV-1 (pNL4.3 strain) with an MOI of 1.0. FIG. 9 shows that at 10 days post transfection, inhibition of HIV replication by the MV-siRNA targeted to both Gag and Tat was about 3 times greater than inhibition by the siRNA molecule targeted only to Gag.

Multivalent-siRNA can be designed to target 1, 2, or 3 different genes of HIV. The sequence of an exemplary HIV genome is provided in FIGS. 10A-D. A sequence of an env gene is provided in FIG. 11, a gag gene in FIG. 12A, and a tat gene in FIG. 12B. The various genes or regions of HIV can be generally defined and targeted by their range of nucleotide sequence as follows: 5' LTR: 1-181; GAG: 336-1838; POL: 1631-4642; VIF: 4587/4662-5165; VPR: 5105-5395 (including mutations at 5157, 5266, and 5297); TAT: 5376-7966; REV: 5515-8195; VPU: 5607-5852; ENV: 5767-8337; NEF: 8339-8959; and 3' LTR: 8628-9263. Based on these target genes, exemplary MV-RNA oligo sequences for HIV are provided in Table 7 below.

TABLE 7

| Exemplary Trivalent MV-siRNA Sequences | | | |
|---|---|---|---|
| No. | Sequence | Target Gene | SEQ ID NO: |
| 1 | GCCUUCCCUUGUGGGAAGGUU | 1649 | 47 |
| 2 | CCUUCCCUUGUGGGAAGGCUU | 1648 | 48 |
| 3 | GCCUUCCUUGUGGGAAGGCUU | 1648 | 49 |
| 4 | UUCUGCACCUUACCUCUUAUU | 6259 | 50 |
| 5 | UAAGAGGAAGUAUGCUGUUUU | 4062 | 51 |
| 6 | AACAGCAGUUGUUGCAGAAUU | 5291 | 52 |
| 7 | CCAGACAAUAAUUGUCUGGUU | 7387 | 53 |
| 8 | CCAGACAAUAAUUGUCUGGUU | 7387 | 53 |
| 9 | CCAGACAAUAAUUGUCUGGUU | 7387 | 53 |
| 10 | CUCCCAGGCUCAGAUCUGGUU | 16 | 54 |
| 11 | CCAGAUCUUCCCUAAAAAAUU | 1630 | 55 |
| 12 | UUUUUUAUCUGCCUGGGAGUU | 7011 | 56 |
| 13 | UGGGUUCCCUAGUUAGCCAUU | 40 | 57 |
| 14 | UGGCUAAGAUCUACAGCUGUU | 8585 | 58 |
| 15 | CAGCUGUCCCAAGAACCCAUU | 7325 | 59 |

TABLE 7-continued

| Exemplary Trivalent MV-siRNA Sequences | | | |
|---|---|---|---|
| No. | Sequence | Target Gene | SEQ ID NO: |
| 16 | AUCCUUUGAUGCACACAAUUU | 591 | 60 |
| 17 | AUUGUGUCACUUCCUUCAGUU | 6988 | 61 |
| 18 | CUGAAGGAAGCUAAAGGAUUU | 1785 | 62 |
| 19 | UCCUGUGUCAGCUGCUGCUUU | 685 | 63 |
| 20 | AGCAGCAUUGUUAGCUGCUUU | 8481 | 64 |
| 21 | AGCAGCUUUAUACACAGGAUU | 9046 | 65 |
| 22 | ACCAACAAGGUUUCUGUCAUU | 1284 | 66 |
| 23 | UGACAGAUCUAAUUACUACUU | 6573 | 67 |
| 24 | GUAGUAAUUAUCUGUUGGUUU | 6311 | 68 |
| 25 | CUGAGGGAAGCUAAAGGAUUU | 1785 | 69 |
| 26 | AUCCUUUGAUGCACACAAUUU | 591 | 60 |
| 27 | AUUGUGUCACUUCCCUCAGUU | 6988 | 61 |
| 28 | CAAAGCUAGAUGAAUUGCUUU | 3534 | 70 |
| 29 | AGCAAUUGGUACAAGCAGUUU | 5432 | 71 |
| 30 | ACUGCUUGUUAGAGCUUUGUU | 2952 | 72 |
| 31 | AGGUCAGGGUCUACUUGUGUU | 4872 | 73 |
| 32 | CACAAGUGCUGAUAUUUCUUU | 5779 | 74 |
| 33 | AGAAAUAAUUGUCUGACCUUU | 7384 | 75 |
| 34 | CUAAGUUAUGGAGCCAUAUUU | 5212 | 76 |
| 35 | AUAUGGCCUGAUGUACCAUUU | 758 | 77 |
| 36 | AUGGUACUUCUGAACUUAGUU | 4736 | 78 |
| 37 | UGGCUCCAUUUCUUGCUCUUU | 5365 | 79 |
| 38 | AGAGCAACCCCAAAUCCCCUU | 7544 | 80 |
| 39 | GGGGAUUUAGGGGGAGCCAUU | 4191 | 81 |
| 40 | AUCUCCACAAGUGCUGAUAUU | 5784 | 82 |
| 41 | UAUCAGCAGUUCUUGAAGUUU | 8942 | 83 |
| 42 | ACUUCAAAUUGUUGGAGAUUU | 8158 | 84 |

TABLE 7-continued

| Exemplary Trivalent MV-siRNA Sequences | | | |
|---|---|---|---|
| No. | Sequence | Target Gene | SEQ ID NO: |
| 43 | AGACUGUGACCCACAAUUUUU | 5862 | 85 |
| 44 | AAAUUGUGGAUGAAUACUGUU | 4310 | 86 |
| 45 | CAGUAUUUGUCUACAGUCUUU | 499 | 87 |
| 46 | ACAGGCCUGUGUAAUGACUUU | 6362 | 88 |
| 47 | AGUCAUUGGUCUUAAAGGUUU | 8559 | 89 |
| 48 | ACCUUUAGGACAGGCCUGUUU | 6371 | 90 |
| 49 | UCAGUGUUAUUUGACCCUUUU | 6973 | 91 |
| 50 | AAGGGUCUGAGGGAUCUCUUU | 135 | 92 |
| 51 | AGAGAUCUUUCCACACUGAUU | 158 | 93 |
| 52 | CAUAGUGCUUCCUGCUGCUUU | 7337 | 94 |
| 53 | AGCAGCAUUGUUAGCUGCUUU | 8481 | 95 |
| 54 | AGCAGCUAACAGCACUAUGUU | 8190 | 96 |
| 55 | GCUGCUUAUAUGCAGGAUCUU | 9044 | 97 |
| 56 | GAUCCUGUCUGAAGGGAUGUU | 531 | 98 |
| 57 | CAUCCCUGUUAAAAGCAGCUU | 7118 | 99 |
| 58 | UGGUCUAACCAGAGAGACCUU | 9081 | 100 |
| 59 | GGUCUCUUUUAACAUUUGCUU | 928 | 101 |
| 60 | GCAAAUGUUUUCUAGACCAUU | 7557 | 102 |
| 61 | CUCCCAGGCUCAGAUCUGGUU | 9097 | 103 |
| 62 | CCAGAUCUUCCCUAAAAAAUU | 1630 | 55 |
| 63 | UUUUUUAUCUGCCUGGGAGUU | 7011 | 56 |
| 64 | UGGGUUCCCUAGUUAGCCAUU | 9121 | 104 |
| 65 | UGGCUAAGAUCUACAGCUGUU | 8585 | 58 |
| 66 | CAGCUGUCCCAAGAACCCAUU | 7325 | 59 |

To Make MV-siRNA complexes targeted to HIV from the sequences in Table 7 above, the individual oligos can be combined and annealed as follows.

1) MV-siRNA_1649/1648/1648; Anneal sequences 1 & 2, and 3.
2) MV-siRNA_6259/4062/5291; Anneal sequences 4 & 5, and 6.
3) MV-siRNA_7387/7387/7387; Anneal sequences 7 & 8, and 9.
4) MV-siRNA_16/1630/7011; Anneal sequences 10 & 11, and 12.
5) MV-siRNA_40/8585/7325; Anneal sequences 13 & 14, and 15.
6) MV-siRNA_591/6988/1785; Anneal sequences 16 & 17, and 18.
7) MV-siRNA_685/8481/9046; Anneal sequences 19 & 20, and 21.
8) MV-siRNA_1284/6573/6311; Anneal sequences 21 & 22, and 23.
9) MV-siRNA_1785/591/6988; Anneal sequences 24 & 25, and 26.
10) MV-siRNA_3534/5432/2952; Anneal sequences 27 & 28, and 29.
11) MV-siRNA_4872/5779/7384; Anneal sequences 30 & 31, and 32.
12) MV-siRNA_5212/758/4736; Anneal sequences 33 & 34, and 35.
13) MV-siRNA_5365/7544/4191; Anneal sequences 36 & 37, and 38.
14) MV-siRNA_5784/8942/8158; Anneal sequences 39 & 40, and 41.
15) MV-siRNA_5862/4310/499; Anneal sequences 42 & 43, and 44.
16) MV-siRNA_6362/8559/6371; Anneal sequences 45 & 46, and 47.
17) MV-siRNA_6973/135/158; Anneal sequences 48 & 49, and 50.
18) MV-siRNA_7337/8481/8190; Anneal sequences 51 & 52, and 53.
19) MV-siRNA_9044/531/7118; Anneal sequences 54 & 55, and 56.
20) MV-siRNA_9081/928/7557; Anneal sequences 57 & 58, and 59.
21) MV-siRNA_9097/1630/7011; Anneal sequences 60 & 61, and 62.
22) MV-siRNA.sub_9121/8585/7325; Anneal sequences 63 & 64, and 65.

Example 3

Trivoid Anti-ApoB

Multivalent siRNA can be designed to suppress large genes by targeting in 2-3 locations on a single gene. The MV-siRNA can also employ alternative RNA chemistries to enhance the Tm during annealing. In this example, as shown in Table 8 below, a series of MV-siRNA are designed to target the apolipoprotein B (ApoB) gene, and the presence of optional 2'-O methyl RNA subunits is indicated within parenthesis.

TABLE 8

| Trivalent MV-siRNA to ApoB | | | |
|---|---|---|---|
| No. | Sequence | Target Gene | SEQ ID NO: |
| 1 | (UGGAACU)UUCAGCUUCAUAUU | ApoB @ 268 | 105 |
| 2 | (UAUGAAG)GCACCAUGAUGUUU | ApoB @ 9905 | 106 |
| 3 | (ACAUCAU)CUUCC(AGUUCCA)UU | ApoB @ 1703 | 107 |
| 4 | (ACUCUUC)AGAGUUCUUGGUUU | ApoB @ 448 | 108 |
| 5 | (ACCAAGA)CCUUGGAGACACUU | ApoB @ 2288 | 109 |
| 6 | (GUGUCUC)AGUUG(GAAGAGU)UU | ApoB @ 6609 | 110 |
| 7 | (ACCUGGA)CAUGGCAGCUGCUU | ApoB @ 469 | 111 |
| 8 | (GCAGCUG)CAAACUCUUCAGUU | ApoB @ 458 | 112 |
| 9 | (CUGAAGA)CGUAU(UCCAGGU)UU | ApoB @ 12263 | 113 |
| 10 | (CAGGGUA)AAGAACAAUUUGUU | ApoB @ 520 | 114 |
| 11 | (CAAAUUG)CUGUAGACAUUUUU | ApoB @ 4182 | 115 |
| 12 | (AAAUGUC)CAGCG(UACCCUG)UU | ApoB @ 12548 | 116 |

TABLE 8-continued

Trivalent MV-siRNA to ApoB

| No. | Sequence | Target Gene | SEQ ID NO: |
|---|---|---|---|
| 13 | (CCCUGGA) CACCGCUGGAACUUUU | ApoB @ 279 | 117 |
| 14 | (AAGUUCC) AAUAACUUUUCCAUUU | ApoB @ 9161 | 118 |
| 15 | (AUGGAAA) AGGCAAG (UCCAGGG) UU | ApoB @ 9968 | 119 |
| 16 | (CCCUGGA) CACCGCUGGAACUUUUU | ApoB @ 278 | 120 |
| 17 | (AAAGUUC) CAAUAACUUUUCCAUUU | ApoB @ 9161 | 121 |
| 18 | (AUGGAAA) AUGGCAAG (UCCAGGG) UU | ApoB @ 9968 | 122 |

To make synthetic MV-siRNA trivalent complexes from the sequences in Table 8 above, the individual oligos can be combined and annealed as follows.

1) MV-siRNA_268/9950/1703; Anneal sequences 1 & 2, and then 3.
2) MV-siRNA_448/2288/6609; Anneal sequences 4 & 5, and then 6.
3) MV-siRNA_469/458/12263; Anneal sequences 7 & 8, and then 9.
4) MV-siRNA_520/4182/12548; Anneal sequences 10 & 11, and then 12.
5) MV-siRNA_279/9161/9986; Anneal sequences 13 & 14, and then 15.
6) MV-siRNA_278/9161/9986; Anneal sequences 16 & 17, and then 18.

Multivalent siRNA that are designed with potent primary and secondary strands can also employ wobble or universal bases to complete target complimentarity, or blunt ended DNA to deactivate the strand from silencing any target. Exemplary oligos directed to ApoB are shown in Table 9 below, in which (*) indicates an optional wobble or universal base.

TABLE 9

Exemplary Bivalent MV-siRNA to ApoB

| No. | Sequence | Target Gene | SEQ ID NO: |
|---|---|---|---|
| 19 | UGAAUCGAGUUGCAUCUUUUU | ApoB @ 223 | 123 |
| 20 | AAAGAUGCUGCUCAUCACAUU | ApoB @ 883 | 124 |
| 21 | UGUGAUGACACUCGAUUCAUU | ApoB @ 10116 (G/A pairs) | 125 |
| 22 | U*UGAU*ACACUCGAUUCAUU | ApoB @ 10116 (univ. base) | 126 |
| 23 | TGTGATGACACTCGATTCA | null @ 10116 | 127 |
| 24 | CAGCUUGAGUUCGUACCUGUU | ApoB @ 483 | 128 |
| 25 | CAGGUACAGAGAACUCCAAUU | ApoB @ 11596 | 129 |
| 26 | UUGGAGUCUGACCAAGCUGUU | ApoB @ 2454 | 130 |
| 27 | UUGGAGUCUGAC*AAGCU*UU | ApoB @ 2454 | 131 |
| 28 | TTGGAGTCTGACCAAGCTG | null @ 2454 | 132 |

To make synthetic MV-siRNA bivalent complexes from the sequences in Table 9 above, the individual oligos can be combined and annealed as follows.

7a) MV-siRNA_223/883/10116); Anneal sequences 19, 20, and 21.
7b) MV-siRNA_223/883/10116*); Anneal sequences 19, 20, and 22.
7c) MV-siRNA_223/883/null); Anneal sequences 19, 20, and 23.
8a) MV-siRNA_483/11596/2454); Anneal sequences 24, 25, and 26.
8b) MV-siRNA_483/11596/2454*); Anneal sequences 24, 25, and 26.
8c) MV-siRNA_483/11596/null); Anneal sequences 24, 25, and 26.

Multivalent-siRNAs can also be designed to suppress large genes by targeting 2-3 locations on a single gene. As noted, above, certain embodiments of the instant MV-siRNAs can also employ alternative RNA chemistries to enhance the Tm during annealing. In Table 10 below, optional 2'-O methyl RNA 2'-fluoro bases are indicated within parenthesis. Among other examples of alternate bases, 5-methyl can also increase Tm of MV-siRNA structure, if desired.

TABLE 10

Exemplary Trivalent MV-siRNA to ApoB

| No. | Sequence | Target Gene | SEQ ID NO: |
|---|---|---|---|
| 1 | UGG (AA) CUUUCAGCUUCAUAUU | ApoB @ 268 | 105 |
| 2 | U (AU) GAAGGCACCAUGAUGUUU | ApoB @ 9905 | 106 |
| 3 | (ACAUCAU) CUUCCAGUUCCAUU | ApoB @ 1703 | 107 |
| 4 | AC (U) CUUCAGAGUUCUUGGUUU | ApoB @ 448 | 108 |
| 5 | (ACCAAGA) CCUUGGAGACACUU | ApoB @ 2288 | 109 |
| 6 | G (U) GUCUCAGUUGGAAGAGUUU | ApoB @ 6609 | 110 |
| 7 | (ACCUGGA) CAUGGCAGCUGCUU | ApoB @ 469 | 111 |
| 8 | GC (A) GCUGCAAACUCUUCAGUU | ApoB @ 458 | 112 |
| 9 | (CUGAAGA) CGUAU (UCCAGGU) UU | ApoB @ 12263 | 113 |
| 10 | (CAGGGUA) AAGAACAAUUUGUU | ApoB @ 520 | 114 |
| 11 | (CAAAUU) GCUGUAGACA (UUU) UU | ApoB @ 4182 | 115 |
| 12 | (AAAUGUC) CAGCGUACCCUGUU | ApoB @ 12548 | 116 |
| 13 | (CCCUGGA) CACCGCUGGAACUUUU | ApoB @ 279 | 117 |
| 14 | (AAGUUCC) AAUAACUUUUCCAUUU | ApoB @ 9161 | 118 |
| 15 | (AU) GGAAAAGGCAAG (UCCAGGG) UU | ApoB @ 9968 | 119 |
| 16 | CCC (U) GGACACCGCUGG (AACUUU) UU | ApoB @ 278 | 120 |
| 17 | (AAA) GUUCCAAUAACUU (UU) CC (AU) UU | ApoB @ 9161 | 121 |
| 18 | (AUGGAAA) AUGGCAAG (UCCAGGG) UU | ApoB @ 9968 | 122 |
| 19 | UCAGGGCCGCUCUGUAUUUUU | ApoB @ 6427 | 133 |
| 20 | AAAUACAUUUCUGGAAGAGUU | ApoB @ 8144 | 134 |
| 21 | CUCUUCCAAAAAGCCCUGAUU | ApoB @ 12831 | 135 |

TABLE 10-continued

Exemplary Trivalent MV-siRNA to ApoB

| No. | Sequence | Target Gene | SEQ ID NO: |
|---|---|---|---|
| 22 | AAAUACAUUUCUGGAAGAGuu & CUCUUCCAAAAAGCCCUGAuu & UCAGGGCCGCUCUGUAUUUuu | Linker construct for cleavage after annealing. "&" = PC Spacer, or linkage phosphoramidite | 136 |

To make synthetic MV-siRNA bivalent complexes from the sequences in Table 10 above, the individual oligos can be combined and annealed as follows.

1) MV-siRNA_268/9950/1703; Anneal sequences 1 & 2, and then 3.
2) MV-siRNA_448/2288/6609; Anneal sequences 4 & 5, and then 6.
3) MV-siRNA_469/458/12263; Anneal sequences 7 & 8, and then 9.
4) MV-siRNA_520/4182/12548; Anneal sequences 10 & 11, and then 12.
5) MV-siRNA_279/9161/9986; Anneal sequences 13 & 14, and then 15.
6) MV-siRNA_278/9161/9986; Anneal sequences 16 & 17, and then 18.
7) MV-siRNA_6427/8144/12831; Anneal sequences 19 & 20, and then 21.
7b) MV-siRNA_6427/8144/12831; Anneal strand 22, then cleave linkage phosphate with ammonium hydroxide. 7b) MV-siRNA_6427/8144/12831; Anneal strand 22, then cleave PC Spacer with UV light in the 300-350 nm spectral range.

In certain embodiments, multivalent-siRNA that are designed with potent primary and secondary strands can employ wobble, spacer, or abasic base types (examples are indicated by (*) in Table 11 below) to complete target compliments, or blunt ended DNA to deactivate the strand from silencing any target. In some embodiments, UNA, linker phosphoramidites, rSpacer, 5-nitroindole can act as effective abasic bases in place of mismatched nucleotides. If desired, the use of abasic bases can result in weakened Tm, and/or pyrimidines surrounding an abasic site can utilize 2'-fluoro bases to increase Tm by about 2 degrees for every 2'-fluoro base.

TABLE 11

Exemplary MV-siRNA Targeted to ApoB

| No. | Sequence | Target Gene | SEQ ID NO: |
|---|---|---|---|
| 23 | UGAAUCGAGUUGCAUCUUUUU | ApoB @ 223 | 123 |
| 24 | AAAGAUGCUGCUCAUCACAUU | ApoB @ 883 | 124 |
| 25 | UGUGAUGACACUCGAUUCAUU | ApoB @ 10116 (G/A pairs) | 125 |
| 26 | U*UGAU*ACACUCGAUUCAUU | ApoB @ 10116 (* rSPACER base) | 126 |
| 27 | TGTGATGACACTCGATTCA | null @ 10116 | 127 |
| 28 | CAGCUUGAGUUCGUACCUGUU | ApoB @ 483 | 128 |
| 29 | CAGGUACAGAGAACUCCAAUU | ApoB @ 11596 | 129 |
| 30 | UUGGAGUCUGACCAAGCUGUU | ApoB @ 2454 | 130 |
| 31 | UUGGAGUCUGAC*AAGCU*UU | ApoB @ 2454 (* abasic base) | 131 |
| 32 | TTGGAGTCTGACCAAGCTG | null @ 2454 | 132 |
| 33 | AACCCACUUUCAAAUUUCCUU | ApoB @ 9244 | 137 |
| 34 | GGAAAUUGAGAAUUCUCCAUU | ApoB @ 1958 | 138 |
| 35 | UGGAGAAUCUCAGUGGGUUUU | ApoB @ 8005 | 139 |
| 36 | rUrGrGfA-fArArUrCrUrCrA-fUrGrGrG-fUrUrU | ApoB @ 8005 | 140 |
| 37 | GAUGAUGAAACAGUGGGUUUU | ApoB @ 10439 | 141 |
| 38 | AACCCACUUUCAAAUUUCCUU | ApoB @ 9244 | 137 |
| 39 | GGAAAUUGGAGACAUCAUCUU | ApoB @ 2284 | 142 |
| 40 | -rGfAfAfArUrUrGrGrArGrArCfA-rCfArUrCrUrU | ApoB @ 2284 | 143 |
| 41 | GCAAACUCUUCAGAGUUCUUU | ApoB @ 452 | 144 |
| 42 | AGAACUCCAAGGGUGGGAUUU | ApoB @ 11588 | 145 |
| 43 | AUCCCACUUUCAAGUUUGCUU | ApoB @ 9244 | 146 |
| 44 | fA-rCrCrCrArCrUrUrUrCrAfA-fUrUrU-rC | ApoB @ 9244 | 147 |

To make synthetic MV-siRNA bivalent complexes from the sequences in Table 11 above, the individual oligos can be combined and annealed as follows.

7a) MV-siRNA_223/883/10116); Anneal sequences 23, 24, and 25.
7b) MV-siRNA_223/883/10116*); Anneal sequences 23, 24, and 26.
7c) MV-siRNA_223/883/null); Anneal sequences 23, 24, and 27.
8a) MV-siRNA_483/11596/2454); Anneal sequences 28, 29, and 30.
8b) MV-siRNA_483/11596/2454*); Anneal sequences 28, 29, and 31.
8c) MV-siRNA_483/11596/null); Anneal sequences 28, 29, and 32.
9) MV-siRNA_9244/1958/8005); Anneal sequences 33, 34, and 35.
9b) MV-siRNA_9244/1958/8005); Anneal sequences 33, 34, and 36.
10) MV-siRNA_10439/9244/2284); Anneal sequences 37, 38, and 39.
10b) MV-siRNA_10439/9244/2284); Anneal sequences 37, 38, and 40.
11) MV-siRNA_452/11588/9244); Anneal sequences 41, 42, and 43.

11b) MV-siRNA_452/11588/9244); Anneal sequences 41, 42, and 44.

As exemplified in Table 12 below, multivalent siRNA can be targeted against human ApoB. Bivalent MV-siRNA can function with various tolerances to structure and target complementarity of each strand

TABLE 12

Exemplary Multivalent-siRNA Targeted to Human ApoB

| No. | Sequence | ApoB Gene site | SEQ ID NO: |
|---|---|---|---|
| 1 | CUUCAUCACUGAGGCCUCUUU | 1192 | 148 |
| 2 | AGAGGCCAAGCUCUGCAUUUU | 5140 | 149 |
| 3 | AAUGCAGAUGAAGAUGAAGAA | 10229 | 150 |
| 4 | UUCAGCCUGCAUGUUGGCUUU | 2724 | 151 |
| 5 | AGCCAACUAUACUUGGAUCUU | 13294 | 152 |
| 6 | GAUCCAAAAGCAGGCUGAAGA | 4960 | 153 |
| 7 | CCCUCAUCUGAGAAUCUGGUU | 8927 | 154 |
| 8 | CCAGAUUCAUAAACCAAGUUU | 9044 | 155 |
| 9 | ACUUGGUGGCCCAUGAGGGUU | 3440 | 156 |
| 10 | UCAAGAAUUCCUUCAAGCCUU | 9595 | 157 |
| 11 | GGCUUGAAGCGAUCACACUUU | 758 | 158 |
| 12 | AGUGUGAACGUAUUCUUGAUU | 4367 | 159 |
| 13 | UUGCAGUUGAUCCUGGUGGUU | 344 | 160 |
| 14 | CCACCAGGUAGGUGACCACUU | 1354 | 161 |
| 15 | GUGGUCAGGAGAACUGCAAUU | 2483 | 162 |
| 16 | CCUCCAGCUCAACCUUGCAUU | 358 | 163 |
| 17 | UGCAAGGUCUCAAAAAAUGUU | 6341 | 164 |
| 18 | CAUUUUUGAUCUCUGGAGGUU | 4043 | 165 |
| 19 | CAGGAUGUAAGUAGGUUCAUU | 570 | 166 |
| 20 | UGAACCUUAGCAACAGUGUUU | 5687 | 167 |
| 21 | ACACUGUGCCCACAUCCUGUU | 9109 | 168 |
| 22 | GGCUUGAAGCGAUCACACUUU | 758 | 169 |
| 23 | AGUGUGAACGUAUUCUUGUUU | 4367 | 170 |
| 24 | ACAAGAAUUCCUUCAAGCCUU | 9595 | 171 |
| 25 | UGAAGAGAUUAGCUCUCUGUU | 1153 | 172 |
| 26 | CAGAGAGGCCAAGCUCUGCUU | 5143 | 173 |
| 27 | GCAGAGCUGGCUCUCUUCAUU | 10304 | 174 |
| 28 | CUCAGUAACCAGCUUAUUGUU | 1170 | 175 |
| 29 | CAAUAAGAUUUAUAACAAAUU | 7084 | 176 |
| 30 | UUUGUUAUCUUAUACUGAGUU | 9650 | 177 |
| 31 | GAACCAAGGCUUGUAAAGUUU | 1258 | 178 |
| 32 | ACUUUACAAAAGCAACAAUUU | 6286 | 179 |
| 33 | AUUGUUGUUAAAUUGGUUCUU | 6078 | 180 |
| 34 | CAGGUAGGUGACCACAUCUUU | 1350 | 181 |
| 35 | AGAUGUGACUGCUUCAUCAUU | 1203 | 182 |
| 36 | UGAUGAACUGCGCUACCUGUU | 8486 | 183 |
| 37 | CCAGUCGCUUAUCUCCCGGUU | 1786 | 184 |
| 38 | CCGGGAGCAAUGACUCCAGUU | 2678 | 185 |
| 39 | CUGGAGUCAUGGCGACUGGUU | 2486 | 186 |
| 40 | UGGAAGAGAAACAGAUUUGUU | 2046 | 187 |
| 41 | CAAAUCUUUAAUCAGCUUCUU | 2403 | 188 |
| 42 | GAAGCUGCCUCUUCUUCCAUU | 12299 | 189 |
| 43 | AUCCAAAGGCAGUGAGGGUUU | 2152 | 190 |
| 44 | ACCCUCAACUCAGUUUUGAUU | 12242 | 191 |
| 45 | UCAAAACCGGAAUUUGGAUUU | 3316 | 192 |
| 46 | UAGAGACACCAUCAGGAACUU | 2302 | 193 |
| 47 | GUUCCUGGAGAGUCUUCAAUU | 1102 | 194 |
| 48 | UUGAAGAAUUAGGUCUCUAUU | 1153 | 195 |
| 49 | GCUCAUGUUUAUCAUCUUUUU | 2350 | 196 |
| 50 | AAAGAUGCUGAACUUAAAGUU | 7622 | 197 |
| 51 | CUUUAAGGGCAACAUGAGCUU | 2863 | 198 |
| 52 | GGAGCAAUGACUCCAGAUGUU | 2675 | 199 |
| 53 | CAUCUGGGGGAUCCCCUGCUU | 2544 | 200 |
| 54 | GCAGGGGAGGUGUUGCUCCUU | 912 | 201 |
| 55 | UCACAAACUCCACAGACACUU | 2761 | 202 |
| 56 | GUGUCUGCUUUAUAGCUUGUU | 5672 | 203 |
| 57 | CAAGCUAAAGGAUUUGUGAUU | 9683 | 204 |
| 58 | GCAGCUUGACUGGUCUCUUUU | 2914 | 205 |
| 59 | AAGAGACUCUGAACUGCCCUU | 4588 | 206 |
| 60 | GGGCAGUGAUGGAAGCUGCUU | 8494 | 207 |
| 61 | CAGGACUGCCUGUUCUCAAUU | 2996 | 208 |
| 62 | UUGAGAACUUCUAAUUUGGUU | 8522 | 209 |
| 63 | CCAAAUUUGAAAAGUCCUGUU | 9855 | 210 |
| 64 | UGUAGGCCUCAGUUCCAGCUU | 3132 | 211 |
| 65 | GCUGGAAUUCUGGUAUGUGUU | 8335 | 212 |
| 66 | CACAUACCGAAUGCCUACAUU | 9926 | 213 |
| 67 | GACUUCACUGGACAAGGUCUU | 3300 | 214 |
| 68 | GACCUUGAAGUUGAAAAUGUU | 5301 | 215 |
| 69 | CAUUUUCUGCACUGAAGUCUU | 11983 | 216 |

TABLE 12-continued

Exemplary Multivalent-siRNA Targeted to Human ApoB

| No. | Sequence | ApoB Gene site | SEQ ID NO: |
|---|---|---|---|
| 70 | AAGCAGUUUGGCAGGCGACUU | 3549 | 217 |
| 71 | GUCGCCUUGUGAGCACCACUU | 5039 | 218 |
| 72 | GUGGUGCCACUGACUGCUUUU | 12521 | 219 |
| 73 | CAGAUGAGUCCAUUUGGAGUU | 3568 | 220 |
| 74 | CUCCAAACAGUGCCAUGCCUU | 9142 | 221 |
| 75 | GGCAUGGAGCCUUCAUCUGUU | 3256 | 222 |
| 76 | CACAGACUUGAAGUGGAGGUU | 4086 | 223 |
| 77 | CCUCCACUGAGCAGCUUGAUU | 2924 | 224 |
| 78 | UCAAGCUUCAAAGUCUGUGUU | 974 | 225 |
| 79 | AUGGCAGAUGGAAUCCCACUU | 4102 | 226 |
| 80 | GUGGGAUCACCUCCGUUUUUU | 2971 | 227 |
| 81 | AAAACGGUUUCUCUGCCAUUU | 12836 | 228 |
| 82 | UGAUACAACUUGGGAAUGGUU | 4148 | 229 |
| 83 | CCAUUCCCUAUGUCAGCAUUU | 2971 | 230 |
| 84 | AUGCUGACAAAUUGUAUCAUU | 12836 | 231 |

To make synthetic MV-siRNA bivalent complexes from the sequences in Table 12 above, the individual oligos can be combined and annealed as follows. MV-siRNA; Anneal sequences 1, 2, and 3. MV-siRNA; Anneal sequences 4, 5, and 6. MV-siRNA; Anneal sequences 7, 8, and 9. MV-siRNA; Anneal sequences 10, 11, and 12. MV-siRNA; Anneal sequences 13, 14, and 15. MV-siRNA; Anneal sequences 16, 17, and 18. MV-siRNA; Anneal sequences 19, 20, and 21. MV-siRNA; Anneal sequences 22, 23, and 24. MV-siRNA; Anneal sequences 25, 26, and 27. MV-siRNA; Anneal sequences 28, 29, and 30. MV-siRNA; Anneal sequences 31, 32, and 33. MV-siRNA; Anneal sequences 34, 35, and 36. MV-siRNA; Anneal sequences 37, 38, and 39. MV-siRNA; Anneal sequences 40, 41, and 42. MV-siRNA; Anneal sequences 43, 44, and 45. MV-siRNA; Anneal sequences 46, 47, and 48. MV-siRNA; Anneal sequences 49, 50, and 51. MV-siRNA; Anneal sequences 52, 53, and 54. MV-siRNA; Anneal sequences 55, 56, and 57. MV-siRNA; Anneal sequences 58, 59, and 60. MV-siRNA; Anneal sequences 61, 62, and 63. MV-siRNA; Anneal sequences 64, 65 and 66. MV-siRNA; Anneal sequences 67, 68, and 69. MV-siRNA; Anneal sequences 70, 71, and 72. MV-siRNA; Anneal sequences 73, 74, and 75. MV-siRNA; Anneal sequences 76, 77, and 78. MV-siRNA; Anneal sequences 79, 80, and 81. MV-siRNA; Anneal sequences 82, 83, and 84.

MV-siRNA directed to ApoB can be used to treat or manage a wide variety of diseases or conditions associated with the expression of that target protein, as described herein and known in the art.

REFERENCES

1. Fire, A., Xu, S., Montgomery, M. K., Kostas, S. A., Driver, S. E., and Mello, C. C. (1998) Potent and specific genetic interference by double stranded RNA in *Caenorhabditis elegans*. Nature. 408, 325-330.
2. Kennerdell, J. R., and Carthew, R. W. (1998) Use of dsRNA-mediated genetic interference to demonstrate that frizzled and frizzled 2 act in the wingless pathway. Cell. 95, 1017-1026.
3. Misquitta, L., and Paterson, B. M. (1999) Targeted disruption of gene function in *Drosophila* by RNA interference (RNA-i): a role for nautilus in embryonic somatic muscle formation. Proc. Natl. Acad. Sci. USA. 96, 1451-1456.
4. Hammond, S. M., Bernstein, E., Beach, D., and Hannon, G. J. (2000) An RNA-directed nuclease mediates post transcriptional gene silencing in *Drosophila* cells. Nature. 404, 293-296.
5. Lohmann, J. U., Endl, I., and Bosch, T. C. (1999) Silencing of developmental genes in Hydra. Dev. Biol. 214, 211-214.
6. Wargelius, A., Ellingsen, S., and Fjose, A. (1999) Double stranded RNA induces specific developmental defects in zebrafish embyos. Biochem. Biophys. Res. Commun. 263, 156-161.
7. Ngo, H., Tschudi, C., Gull, K., and Ullu, E. (1998) Double stranded RNA induces gene degradation in *Trypanosoma brucei*. Proc. Natl. Acad. Sci. USA. 95, 14687-14692.
8. Montgomery, M. K., Xu, S., Fire, A. (1998) RNA as a target of double stranded RNA mediated genetic interference in *Caenorhabiditis elegans*. Proc. Natl. Acad. Sci. USA. 95, 15502-15507.
9. Bosher, J. M., Dufourcq, P., Sookhareea, S., Labouesse, M. (1999) RNA interference can target pre-gene. Consequences for gene expression in *Caenorhabiditis elegans* operon. Genetics. 153, 1245-1256.
10. Fire, A. (1999) RNA-triggered gene silencing. Trends Genet. 15, 358-363.
11. Sharp, P. A. (1999) RNAi and double-stranded RNA. Genes Dev. 13, 139-141.
12. Ketting, R. F., Harerkamp, T. H., van Luenen, H. G., and Plasterk, R. H. (1999) Mut-7 of *C. elegans*, required for transposon silencing and RNA interference, is a homolog of Werner syndrome helicase and RNase I. Cell. 99, 133-141.
13. Tabara, H., Sarkissian, M., Kelly, W. G., Fleenor, J., Grishok, A., Timmons, L., Fire, A., and Mello, C. C. (1999) The rde-1 gene, RNA interference, and transposon silencing in *C. elegans*. Cell. 99, 123-132.
14. Zamore, P. D., Tuschl, T., Sharp, P. A., and Bartel, D. P. (2000) RNAi: Double stranded RNA directs the ATP dependent cleavage of gene at 21 to 23 nucleotide intervals. Cell. 101, 25-33.
15. Bernstein, E., Caudy, A. A., Hammond, S. M., and Hannon, G. J. (2001) Role for a bidentate ribonuclease in the initiation step of RNA interference. Nature. 409, 363-366.
16. Elbashir, S., Lendeckel, W., and Tuschl, T. (2001) RNA interference is mediated by 21 and 22 nucleotide RNAs. Genes and Dev. 15, 188-200.
17. Sharp, P. A. (2001) RNA interference 2001. Genes and Dev. 15, 485-490.
18. Hunter, T., Hunt, T., and Jackson, R. J. (1975) The characteristics of inhibition of protein synthesis by double-stranded ribonucleic acid in reticulocyte lysates. J. Biol. Chem. 250, 409-417.
19. Bass, B. L. (2001) The short answer. Nature. 411, 428-429.
20. Elbashir, S. M., Harborth, J., Lendeckel, W., Yalcin, A., Weber, K., and Tuschl, T. (2001) Duplexes of 21-nucleotide RNAs mediate RNA interference in cultured mammalian cells. Nature. 411, 494-498.

21. Carson, P. E. and Frischer, H. (1966) Glucose-6-Phosphate dehydrogenase deficiency and related disorders of the pentose phosphate pathway. Am J Med. 41, 744-764.
22. Stamato, T. D., Mackenzie, L., Pagani, J. M., and Weinstein, R. (1982) Mutagen treatment of single Chinese Hamster Ovary cells produce colonies mosaic for Glucose-6-phosphate dehydrogenase activity. Somatic Cell Genetics. 8, 643-651.
23. Genetic characterization of methicillin-resistant Staphylococcus aureus Vaccine. 2004, Dec. 6; 22 Suppl 1:S5-8. [Hiramatsu K, Watanabe S, Takeuchi F, Ito T, and Baba T].
24. A novel family of RNA tetraloop structure forms the recognition site for Saccharomyces cerevisiae RNase III. [EMBO J. 2001].
25. Solution structure of conserved AGNN tetraloops: insights into RNase IIIp RNA processing. [EMBO J. 2001].
26. Review The RNase III family: a conserved structure and expanding functions in eukaryotic dsRNA metabolism. [Curr Issues Mol Biol. 2001]
27. Sequence dependence of substrate recognition and cleavage by yeast RNase III. [J Mol Biol. 2003]
28. Noncatalytic assembly of ribonuclease III with double-stranded RNA. [Structure. 2004]
29. Intermediate states of ribonuclease III in complex with double-stranded RNA. [Structure. 2005]
30. Review Structural basis for non-catalytic and catalytic activities of ribonuclease III. [Acta Crystallogr D Biol Crystallogr. 2006]
31. Review Ribonuclease revisited: structural insights into ribonuclease III family enzymes. [Curr Opin Struct Biol. 2007]
32. Short RNA guides cleavage by eukaryotic RNase III. [PLoS ONE. 2007 May 30; 2(5):e472.]
33. A stepwise model for double-stranded RNA processing by ribonuclease III. [Mol Microbiol. 2008]
34. Review: The mechanism of RNase III action: how dicer dices. [Curr Top Microbiol Immunol. 2008]

The invention claimed is:

1. A method of reducing expression of one or more target genes, comprising introducing a polynucleotide complex into a cell, the cell comprising the one or more target genes, wherein the polynucleotide complex consists of:

a first polynucleotide that is fully or partially complementary to a first target sequence, wherein the first target sequence is a region of the one or more target genes, and wherein the first polynucleotide is approximately 15-30 nucleotides in length;

a second polynucleotide that is fully or partially complementary to a second target sequence, wherein the second target sequence is a region of the one or more target genes, and wherein the second polynucleotide is approximately 15-30 nucleotides in length; and a third polynucleotide that is either (a) fully or partially complementary to a third target sequence, wherein the third target sequence is a region of the one or more target genes, or (b) not specific to any target sequence, and wherein the third polynucleotide is approximately 15-30 nucleotides in length;

wherein a 3' region of the first polynucleotide is complementary to a 5' region of the second polynucleotide, where a 3' region of the second polynucleotide is complementary to a 5' region of the third polynucleotide, and wherein a 3' region of the third polynucleotide is complementary to a 5' region of the first polynucleotide; and wherein the first, second, and third polynucleotides hybridize via the complementary 3' and 5' regions to form a polynucleotide complex with a first, second, and third stem region and wherein the introduction of the polynucleotide complex to the cell results in a reduction in expression of the one or more target genes.

2. The method of claim 1, wherein the polynucleotide complex is introduced to the cell using a method selected from transfection, lipofection, scrape-loading, electroporation, microinjection, infection, gene gun, and retrotransposition.

3. The method of claim 1, wherein the cell is a plant cell, an animal cell, a protozoan cell, a bacterial cell, or a fungal cell.

4. The method of claim 3, wherein the animal cell is a mammalian cell selected from a human cell, a murine cell, a rodent cell, and a primate cell.

5. The method of claim 1, wherein the cell is a cancer cell, a virally infected cell, a mutated cell, or a normal cell.

6. The method of claim 1, wherein the cell is derived from primary cells, a cell line, immortalized cells, or transformed cells.

7. The method of claim 1, wherein the one or more target genes comprise a gene, an mRNA, a microRNA, or a combination thereof.

8. The method of claim 1, wherein the one or more target genes comprise an oncogene, a mutated gene, an mRNA transcript of a viral gene, or an mRNA transcript of a human apolipoprotein B (ApoB) gene.

9. A method of reducing gene expression of one or more target genes comprising introducing a self-hybridizing polynucleotide into a cell, the cell comprising the one or more target genes, wherein the self-hybridizing polynucleotide consists of a single polynucleotide molecule comprising:

a first target-specific region that is fully or partially complementary to a first target sequence, wherein the first target sequence is a region of the one or more target genes, and wherein the first target-specific region is approximately 15-30 nucleotides in length;

a second target-specific region that is fully or partially complementary to a second target sequence, wherein the second target sequence is a region of the one or more target genes, and wherein the second target-specific region is approximately 15-30 nucleotides in length; and a third target-specific region that is either (a) fully or partially complementary to a third target sequence wherein the third target sequence is a region of the one or more target genes, or (b) not specific to any target sequence, and wherein the third target-specific region is approximately 15-30 nucleotides in length;

wherein a 3' region of the first target-specific region is complementary to a 5' region of the second target-specific region within the single polynucleotide molecule, where a 3' region of the second target-specific region is complementary to a 5' region of the third target-specific region within the single polynucleotide molecule, and wherein a 3' region of the third target-specific region is complementary to a 5' region of the first target-specific region within the single polynucleotide molecule; and wherein at least one of the first, second or third target-specific region binds or hybridizes to another target-specific region of the same single polynucleotide molecule via the complementary 3' and 5' regions to form at least one stem region and at least one loop or stem loop and wherein the introduction of the polynucleotide complex to the cell results in a reduction in the expression of the one or more target genes.

10. The method of claim 9, wherein the self-hybridizing polynucleotide is encoded by a vector.

11. The method of claim 9, wherein the vector is introduced to the cell using a method selected from transfection, lipofection, scrape-loading, electroporation, microinjection, infection, gene gun, and retrotransposition.

12. The method of claim 9, wherein the cell is a plant cell, an animal cell, a protozoan cell, a bacterial cell, or a fungal cell.

13. The method of claim 12, wherein the animal cell is a mammalian cell selected from a human cell, a murine cell, a rodent cell, and a primate cell.

14. The method of claim 9, wherein the cell is a cancer cell, a virally infected cell, a mutated cell, or a normal cell.

15. The method of claim 9, wherein the cell is derived from primary cells, a cell line, immortalized cells, or transformed cells.

16. The method of claim 9, wherein the one or more target genes comprise a gene, an mRNA, a microRNA, or a combination thereof.

17. The method of claim 9, wherein the one or more target genes comprise an oncogene, a mutated gene, an mRNA transcript of a viral gene, or an mRNA transcript of a human apolipoprotein B (ApoB) gene.

* * * * *